(12) United States Patent
Shair et al.

(10) Patent No.: US 10,273,240 B2
(45) Date of Patent: Apr. 30, 2019

(54) CORTISTATIN ANALOGUES, SYNTHESES, AND USES THEREOF

(71) Applicant: President and Fellows of Harvard College, Cambridge, MA (US)

(72) Inventors: Matthew D. Shair, Lexington, MA (US); Henry Efrem Pelish, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/807,301

(22) Filed: Nov. 8, 2017

(65) Prior Publication Data

US 2018/0134725 A1 May 17, 2018

Related U.S. Application Data

(63) Continuation of application No. PCT/US2016/031279, filed on May 6, 2016.

(60) Provisional application No. 62/187,656, filed on Jul. 1, 2015, provisional application No. 62/187,669, filed on Jul. 1, 2015, provisional application No. 62/158,936, filed on May 8, 2015, provisional application No. 62/158,982, filed on May 8, 2015.

(51) Int. Cl.

| A61K 31/4355 | (2006.01) |
|---|---|
| A61K 31/4725 | (2006.01) |
| A61K 31/55 | (2006.01) |
| C07D 405/04 | (2006.01) |
| C07D 471/08 | (2006.01) |
| C07D 489/08 | (2006.01) |
| C07D 491/08 | (2006.01) |
| C07D 491/18 | (2006.01) |
| C07D 493/08 | (2006.01) |
| A61P 35/02 | (2006.01) |

(52) U.S. Cl.
CPC ............ *C07D 491/18* (2013.01); *A61P 35/02* (2018.01); *C07D 493/08* (2013.01)

(58) Field of Classification Search
CPC ............ A61K 31/4355; A61K 31/4725; A61K 31/55; C07D 405/04; C07D 471/08; C07D 489/08; C07D 491/08
USPC .......... 514/212.06, 215, 282, 307, 308, 309; 540/520, 581; 546/44, 45, 46, 139, 141, 546/143

See application file for complete search history.

(56) References Cited

U.S. PATENT DOCUMENTS

| 2,886,589 A | 5/1959 | Novello et al. |
|---|---|---|
| 4,853,224 A | 8/1989 | Wong |
| 4,863,457 A | 9/1989 | Lee |
| 4,997,652 A | 3/1991 | Wong |
| 5,098,443 A | 3/1992 | Parel et al. |
| 5,185,152 A | 2/1993 | Peyman |
| 5,378,475 A | 1/1995 | Smith et al. |
| 5,410,016 A | 4/1995 | Hubbell et al. |
| 5,443,505 A | 8/1995 | Wong et al. |
| 5,554,187 A | 9/1996 | Rizzo, III |
| 5,710,182 A | 1/1998 | Reunamaki et al. |
| 5,725,493 A | 3/1998 | Avery et al. |
| 6,177,095 B1 | 1/2001 | Sawhney et al. |
| 6,632,457 B1 | 10/2003 | Sawhney |
| 6,803,031 B2 | 10/2004 | Rabinowitz et al. |
| 8,642,766 B2 | 2/2014 | Shenvi et al. |
| 8,791,263 B2 | 7/2014 | Kobayashi et al. |
| 9,127,019 B2 | 9/2015 | Flyer et al. |
| 2003/0060425 A1 | 3/2003 | Ahlem et al. |
| 2003/0149287 A1 | 8/2003 | Zasloff et al. |
| 2004/0220161 A1 | 11/2004 | Ahlem et al. |
| 2005/0014737 A1 | 1/2005 | Agoston et al. |
| 2006/0014727 A1 | 1/2006 | Karsan et al. |
| 2006/0094696 A1 | 5/2006 | Leese et al. |
| 2007/0004689 A1 | 1/2007 | Agoston et al. |
| 2007/0225256 A1 | 9/2007 | Leese et al. |
| 2009/0023666 A1 | 1/2009 | Gardiner et al. |
| 2010/0168141 A1 | 7/2010 | Evans et al. |
| 2011/0190323 A1 | 8/2011 | Flyer et al. |
| 2012/0083484 A1 | 4/2012 | Castro et al. |
| 2012/0190659 A1 | 7/2012 | Corey et al. |
| 2014/0038958 A1 | 2/2014 | Ronnison et al. |
| 2014/0155376 A1 | 6/2014 | Hendricks et al. |
| 2016/0016971 A1 | 1/2016 | Valente et al. |

FOREIGN PATENT DOCUMENTS

| EP | 0562849 A2 | 9/1993 |
|---|---|---|
| WO | WO 1997/043417 A1 | 11/1997 |
| WO | WO 1998/029438 A2 | 7/1998 |
| WO | WO 2000/041545 A2 | 7/2000 |
| WO | WO 2000/066611 A1 | 11/2000 |
| WO | WO 2001/023405 A2 | 4/2001 |

(Continued)

OTHER PUBLICATIONS

US, 2017/0029435, A1, U.S. Appl. No. 15/192,629, Shair et al., Aug. 3, 2017.

(Continued)

*Primary Examiner* — Brenda L Coleman

(74) *Attorney, Agent, or Firm* — Knowles Intellectual Property Strategies, LLC

(57) ABSTRACT

New cortistatin compounds and pharmaceutically acceptable salts and pharmaceutically acceptable compositions thereof are provided. These compounds can be used to treat a disorder mediated by CDK8 and/or CDK19 kinase or by the Mediator Complex generally. In particular, the compounds can be used, for example, to treat a disorder such as a tumor, cancer, or a disorder associated with angiogenesis.

23 Claims, 30 Drawing Sheets

Specification includes a Sequence Listing.

(56) References Cited

FOREIGN PATENT DOCUMENTS

| WO | WO 2001/027135 A2 | 4/2001 |
|---|---|---|
| WO | WO 2001/030802 A2 | 5/2001 |
| WO | WO 2003/004518 A2 | 1/2003 |
| WO | WO 3063791 A2 | 8/2003 |
| WO | WO 2006/093993 A1 | 9/2006 |
| WO | WO 2007/082980 A1 | 7/2007 |
| WO | WO 2007/103162 A2 | 9/2007 |
| WO | WO 2008/064425 A1 | 6/2008 |
| WO | WO 2010/024930 A2 | 4/2010 |
| WO | WO 2010/123545 A2 | 10/2010 |
| WO | WO 2012/096934 A2 | 7/2012 |
| WO | WO 2013/122609 A1 | 8/2013 |
| WO | WO 2014/123900 A1 | 8/2014 |
| WO | WO 2014/134169 A1 | 9/2014 |
| WO | WO 2014/199377 A1 | 12/2014 |
| WO | WO 2015/040089 A1 | 3/2015 |
| WO | WO 2015/100420 A1 | 7/2015 |

OTHER PUBLICATIONS

US, 2017/0320886, A1, U.S. Appl. No. 15/658,201 Flyer et al. Nov. 9, 2017.

U.S. Pat. No. 9,127,019, B2, U.S. Appl. No. 14/293,743, Flyer et al., Sep. 8, 2015.

U.S. Pat. No. 9,714,255, B2, U.S. Appl. No. 14/848,086, Flyer et al., Jul. 25, 2017.

Abushanab et al., 9(10 leads to 19)abeo steriods. Total synthesis of abeo-estradiol, abeo-estradiol 3-methyl ether, and 17 alpha-ethynyl abeo-estradiol-3-methyl ether. JOC Apr. 30, 1976;41(9):1601-3.

Aguayo et al. Angiogenesis in acute and chronic leukemias and myelodysplastic syndromes. Blood. Sep. 15, 2000;96(6):2240-5.

Aoki et al., Cortistatins A, B, C, and D, anti-angiogenic steroidal alkaloids, from the marine sponge *Corticum simplex*. JACS Mar. 15, 2006;128(10):3148-9.

Aoki et al., Cortistatins J, K, L, novel abeo-0(10-19)-androstane-type steroidal alkaloids with isoquinoline unit, from marine sponge *Carticium simplex*. Tetrahedron Lett. 2007;48(26)4485-88.

Aoki et al., Structure-activity relationship and biological property of cortistatins, anti-angiogenic spongean steoidal alkaloids. Bioorg. Med. Chem. Nov. 1, 2007;15(21):6758-62. Epub Aug. 21, 2007.

*Arefolov v. Presidents and Fellows of Harvard College and Matthew Shair*, Case No. 1:17-cv-10785 (D. Mass.).

Atta et al., New Steroidal Alkaloids from the Roots of Buxus sempervirens. J. Nat. Prod. 1999; 62(5):665-69.

Berge et al., Pharmaceutical salts. J. Pharm. Sci. Jan. 1977;66(1):1-19.

Boeckman et al., The Dess-Martin Periodinane: 1,1,1-Triacetoxy-1,1-Dihydro-1,2-Benziodoxol-3(1H)-One. J. Org. Synth. 2000 77:141-52.

Brown et al., 1986, Caplus an 1986:627117.

Brown, The Pomeranz-Fritsch Reaction, Isoquinoline vs Oxazoles. J. Org. Chem. 1977;42:3208-09.

Cassoni et al., Ghrelin and cortistatin in lung cancer: expression of peptides and related receptors in human primary tumors and in vitro effect on the H345 small cell carcinoma cell line. J. Endocrinol. Invest. Oct. 2006; 29(9):781-90—Abstract.

Chen et al., Eryhtropoietin deficiency decreases vascular stability in mice. J. Clin. Invest. Feb. 2008.p118(2):526-33.

Cheson et al., National Cancer Institute-sponsored Working Group guidelines for chronic lymphocytic leukemia:revised guidelines for diagnosis and treatment. Blood. Jun. 15, 1996;87(12):4990-7.

Czako et al. "Discovery of Potent and Practical Antiangiogenic Agents Inspired by Cortistatin A", J. Am. Chem. Soc. vol. 131, No. 25, Apr. 1, 2009.

De Marino et al.,A new steroidal alkaloid from a marine sponge *Corticium* sp. Tetrahedron Lett. 1998;39(41):7611-14.

Du Bois et al. Nitrogen Transfer from Nitrodomanganese (v) Complex: Amination of Silyl Enol Ethers. JACS 1996;118(4)915-16.

Duboudin et al., Evidence for [2+2] and [4+2] cycloadditions of allylic Grignard-reagents to benzyne. J. Chem. Soc-Chem Commun. 1977;13:454-55.

Evans et al., New silicon-phosphorous reagents in organic synthesis-carbonyl and conjugate addition-reactions of silicon phosphate esters and related systems. JACS 1978;100(11):3467-77.

Extended European Search Report for EP 09810384.9, dated Mar. 30, 2012.

Ferrara, Vascular endothelial growth factor as a target for anticancer therapy. Oncologist. 2004;9 Suppl 1:2-10.

Folkman, Angiogenesis: an organizing principle for drug discovery? Nat. Rev. Drug Discov. Apr. 2007;6(4):273-86.

Folkman, Antiangiogenesis in cancer therapy—endostatin and its mechanisms of action. Exp. Cell Res. Mar. 10, 2006;312(5):594-607. Epub Dec. 22, 2005.

Folkman, Tumor angiogenesis: therapeutic implications. N. Engl. J. Med. Nov. 18, 1971;285(21):1182-6.

Furrow et al., Practical procedures for the preperation of N-tert-butyldimethylsilylhydrazones and their use in modified Wolff-Kishner reductions and in the synthesis of vinyl halides and gem-dihalides. JACS May 5, 2004;126(17):5436.

Gerber et al., The role of VEGF in normal and neoplastic hematopoiesis. J. Mol. Med. Jan. 2003;81(1):20-31. Epub Dec. 14, 2002.

Grant et al., Matrigel induces thymosin beta 4 gene in differentiating endothelial cells. J. Cell Sci. Dec. 1995;108(Pt 12):3685-94.

Hajos et al., Synthesis and Conversion of 2-Methyl-2-(30oxobutyl)-1,3-cyclopentanedione to the Isomeric Racemic Ketols of the [3.2.1]Bicyclooctane and of the Perhydroindan Series. J. Org. Chem. 1974;39:1612-15.

Hajos et al., Total Synthesis of (+−)-17B-Hydroxy-d9(10)-des-A-Androsten-5-one-[(+−)-2,3,4a,4,5,7,8,9,9aB,9ba-Decahydro-3B-hydroxy-3aB,6-dimethyl-1H-benz[e]inden=7-one]. J. Org. Chem. 1967;32:3008-10.

Hanahan et al., Patterns and emerging mechanisms of the angiogenic switch during tumorigenesis. Cell. Aug. 9, 1996;86(3):353-64.

Huang et al., Control of cyclin D1, p27(Kip1), and cell cycle progression in human capillary endothelial cells by cell shape and cytoskeletal tension. Mol. Biol. Cell. Nov. 1998, 9(11):3179-93.

Hurwitz et al., Bevacizumab plus irinotecan, fluorouracil, and leucoviorin for metastatic colorectal cancer. N. Engl. J. Med. Jun. 3, 2004;350(23):2335-42.

Hussong et al., Evidence of increased angiogenesis in patients with acute myeloid leukemia. Blood. Jan. 1, 2000;95(1):309-13.

International Preliminary Report on Patentability for PCT/US2009/04911, dated Nov. 3, 2011.

International Search Report and Written Opinion for PCT/IS2016/40482, dated Sep. 26, 2016.

International Search Report and Written Opinion for PCT/US16/68125 dated Mar. 16, 2017.

International Search Report and Written Opinion for PCT/US16/68137 dated Mar. 16, 2017.

International Search Report and Written Opinion for PCT/US16/68143 dated Mar. 23, 2017.

International Search Report and Written Opinion for PCT/US2009/04911, dated May 4, 2010.

International Search Report and Written Opinion for PCT/US2014/072365 dated May 19, 2015.

International Search Report and Written Opinion for PCT/US2016/31188, dated Aug. 18, 2016.

International Search Report and Written Opinion for PCT/US2016/31279, dated Aug. 25, 2016.

Isaacs et al., Synthesis of an Enantiomerically Pure Intermediate Containing the CD Substructure of Taxol. J. Org. Chem. 1993;58:3938-41.

Jain, Normalizing tumor vaculature with anti-angiogenic therapy:a new paradigm for combination therapy. Nat. Med. Sep. 2001;7(9):987-9.

Kerbel et al., Clinical translation of angiogenesis inhibitors. Nat. Rev. Cancer. Oct. 2002;2(10):727-39.

(56) References Cited

OTHER PUBLICATIONS

Khurana et al., Angiogenesis-dependent and independent phases of intimal hyperplasia. Circulation. Oct. 19, 2004;110(16):2436-43. Epub Oct. 11, 2004.
Klagsbrun et al., Molecular angiogenesis. Chem. Biol. Aug. 1999;6(8):R127-24.
Kohen et al., Solvolysis of 19-substituted androstane derivaties. J. Org. Chem. Jul. 1970;35(7):2272-5.
Kolb et al., Catalytic Asymmetric Dihydroxylation. J. Chem. Rev. 1994;94:2483-547.
Kolonin et al., Reversal of obesity by targeted ablation of adipose tissue. Nat. Med. Jun. 2004;10(6);625-32. Epub May 9, 2004.
Kotoku et al., "Synthetic Stufies of Cortistatin A Analogue from the CD-Ring Fragment of Vitamin D2", Chem. Pharm. Bull. 61(1) 1024-1029, May 13, 2013.
Kozikowiski et al., Phosphoniosilyation—an efficient and practical method for the beta-functionalization of enones. J. Org. Chem. 1986;51(17):3400-02.
Kunding, Low temperature Grignard reactions with pure Mg slurries. Trapping of cyclopropylmethyl and benzocyclobutenylmethyl Grignard reagents with CO2. Helvetica Chimica Acta. 1981;64(8):2606-13.
Kupchan et al., Buxus alkaloids. 13. A synthetic approach to the 9(10-19) abeo-pregnane system. JACS. Nov. 22, 1967;89(24):6327-32.
Lee et al., Entantioselective synthesis of (+)-cortistatin A, a potent and selective inhibitor of endothelial cell proliferation. JACS Dec. 17, 2008;130(50):16864-6.
Liu et al., 5-(Trimethylstannyl)-2H-pyran-2-one and 3-(Trimethylstannyl)-2H-pyran-2-one: New 2H-Pyran-2-one Synthons. JOC Sep. 20, 1996;61(19):6693-6699.
Magnus et al., Oxidative addition of azide anion to triisopropylsilyl enol ethers: Synthesis of [alpha]-azido ketones and 2-amino(methoxycarbonyl)alk-2-en-1-ones. Tetrahedron 1995;51(41):11075-86.
Mammoto et al., A mechanosensitivie transcriptional mechanism that controls angiogenesis. Nature. Feb. 26, 2009;457(7233)1103-8.
Mayer, Two steps forward in the treatment of colorectal cancer. N. Engl. J. Med. Jun. 3, 2004;350(23):2406-8.
Molica et al., Prognostic value of enhanced bone marrow angiogenesis in early B-cell chronic lymphocytic leukemia. Blood. Nov. 1, 2002;100(9):3344-51.
Moses, The regulation of neovascularization of matrix metalloproteinases and their inhibitors. Stem Cells. 1997;15(3):180-9.
Moulton et al., Angiogenesis inhibitors endostatin or TNP-470 reduce intimal neovascularization and plaque growth in apolipoprotein E-deficient mice. Circulation. Apr. 6, 1999;99(13):1726-32.
Mousseau et al., An analog of the natural steroidal alkaloid Cortistatin A potently suppresses Tat dependent HIV transcription, Cell Host Microbe. Jul. 19, 2012; 12 (1): 97-108. doi:10.1016/j.chom.2012.05.016.
Neef et al., A radical approach to the synthesis of 9(10-19)abeosteroids. Tetrahedron. 1993;49(4):833-40.
Neef et al., New steroids by Simmons-Smith methylenation and subsequent rearrangement. J. Org. Chem. 1987;52(18):4143-46.
Nicolaou et al., Total synthesis of (+)-cortistatin A. (Supportive Information) Angew. Chem. Int. Ed. Engl. 2008;47(38):1-57.
Ohtani et al., Blockade of vascular endothelial growth factor suppresses experimental restenosis after intraluminal injury by inhibiting recruitment of monocye lineage cells. Circulation. Oct. 19, 2004;110(16):2444-52. Epub Oct. 11, 2004.
Ottow et al., Highly diastereoselective synthesis of 11 beta, 17 beta-diaryl-18a-homo-19-nor steroids. Journal Fur Praktishche Chemie-Chemiker-Zeitung. 1997;339(4):365-70.
Peacock et al., Angiogenesis inhibition suppresses collagen arthritis. J. Exp. Med. Apr. 1, 1992;175(4):1135-8.
Pelish et al. Mediator Kinase Inhibition Further Activates Super-Enhancer Associated Genes in AML. Nature. Oct. 8, 2015; 526(7572): 273-276.
Perez-Atayde et al., Spectrum of tumor angiogenesis in the bone marrow of children with acute lymphoblastic leukemia. Am. J. Pathol. Mar. 1997;150(3):815-21.
Puckett et al., The structure of buxenine-G. Tetrahedron Lett. 1966;7(32):3815-18.
Rastinejad et al., Regulation of the activity of a new inhibitor of angiogenesis by a cancer suppressor gene. Cell. Feb. 10, 1989;56(3):345-55.
Rigby et al., A general approach to the synthesis of C8-Oxygenated Guaianolides. JOC. 1987;52:34-44.
Shenvi et al., Synthesis of (+)-cortistatin A (Supporting Information). JACS Jun. 11, 2008; 130(23):SI-1-SI-22. Epub May 14, 2008.
Shenvi et al., Synthesis of (+)-cortistatin A JACS Jun. 11, 2008; 130(23):7241-3. Epub May 14, 2008.
Shih et al., Selective stimulation of VEGFR-1 prevents oxygen-induced retinal vascular degeneration in retinopathy of prematurity. J. Clin. Invest. Jul. 2003;112(1):50-7.
Shimizu et al., ABL2/ARG tyrosine kinase mediates SEMA3F-induced RhoA inactivation and cytoskeleton collapse in human glioma cells. J. Biol. Chem. Oct. 3, 2008;283(40):27230-8. Epub Jul. 25, 2008.
Shojima et al., The role of vascular endothelial growth factor in restenosis: the controversy continues. Circulation. Oct. 19, 2004;110(16):2283-6.
Smith et al., Organometallic reagents in synthesis: A new protocol for construction of the indole nucleus. Tetrahedron. 1986;42:2957.
Still et al., Rapid Chromatographic Technique for Perparative Seperations with Moderate Resolution. J. Org. Chem. 1978;43:2923-25.
Street et al., Vascular endothelial growth factor stimulates bone repair by promoting angiogenesis and bone turnover. Proc. Natl. Acad. Sci. USA. Jul. 23, 2002;99(15):9656-61. Epub Jul. 12, 2002.
Tamao et al., (Diisopropoxymethylsilyl)methyl Grignard Reagent: A New, Practically Useful Nucleophilic Hydroxymethylating Agent. J. Org. Chem. 1983;48:2120-22.
Teicher et al., Antiangiogenic agents can increase tumor oxygenation and response to radiation therapy. Radiat. Oncol. Investig. 1994; 2(6):269-276.
Vacca et al., Bone marrow angiogenesis and progression in multiple myeloma. Br. J. Haematol. Jul. 1994;87(3):503-8.
Wang et al., Marine-Derived Angiogenesis Inhibitors for Cancer Therapy. Mar. 15, 2013; 11(3): 903-933.
Watanabe et al., Cortistatins E, F, G, and H, four novel steroidal alkaloids from marine sponge *Corticium simplex*. Tetrahedron. 2007;63(19):4074-79.
Williams et al., Isocyanide addition to pyridinium salts. Efficient entry into substituted nicotinonitrile derivatives. Org. Lett. Dec. 7, 2006;8(25):5789-92.
Yamashita et al., A concise synthesis of the pentacyclic framework of Cortistatins. Org. Lett., Jul. 17, 2008; 10(16): 3413-3415.

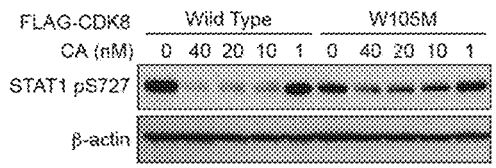
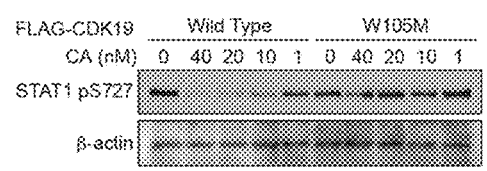
FIG. 11A
FIG. 11B
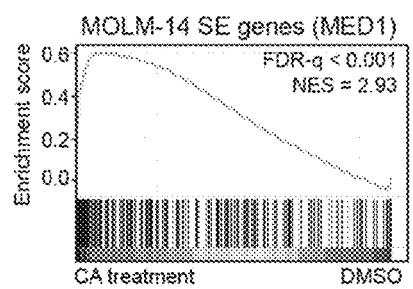
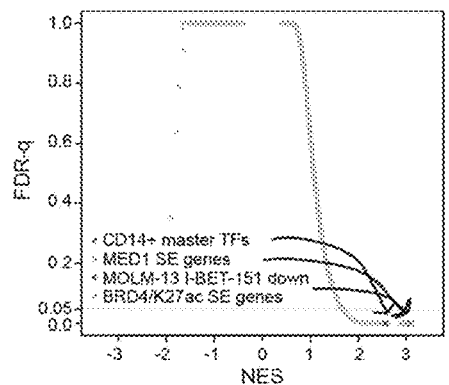
FIG. 12
FIG. 13
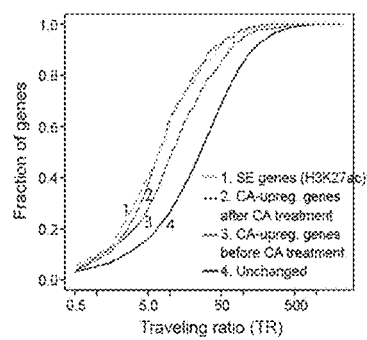
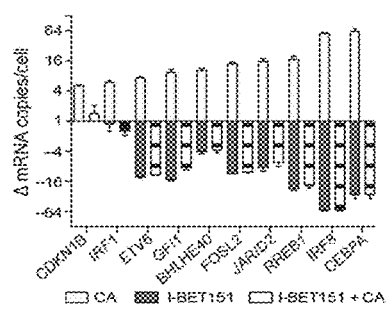
FIG. 14
FIG. 15

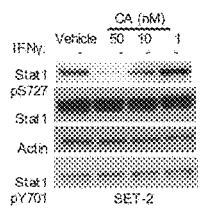
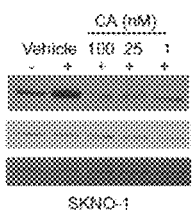
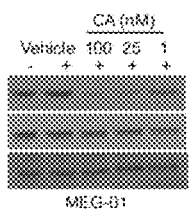
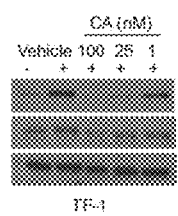
FIG. 37A　　FIG. 37B　　FIG. 37C　　FIG. 37D
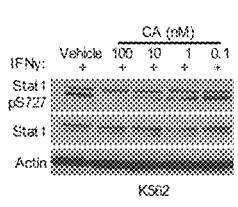
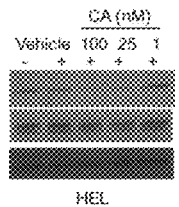
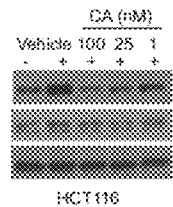
FIG. 37E　　FIG. 37F　　FIG. 37G
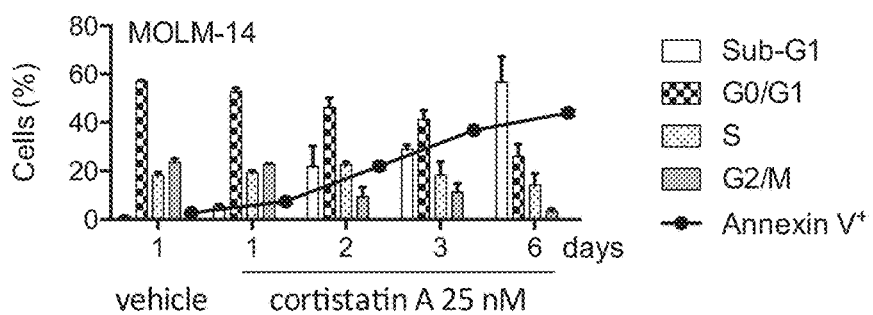
FIG. 38A
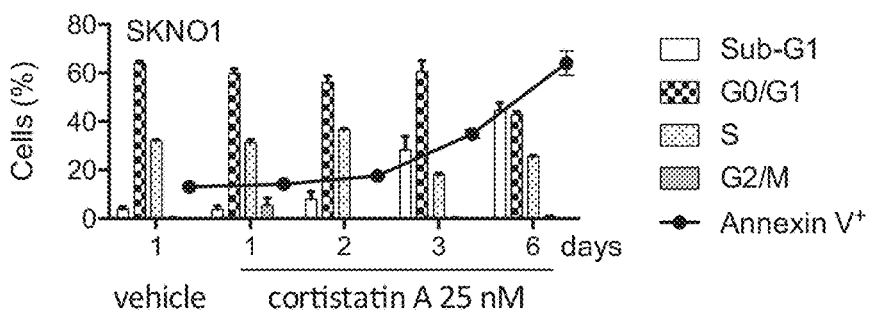
FIG. 38B

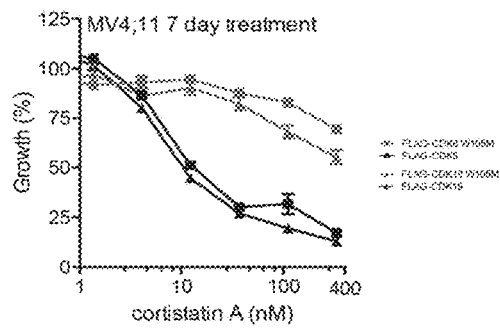 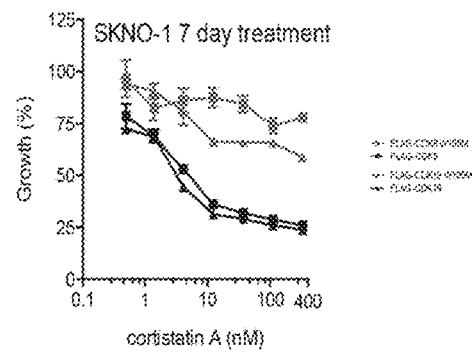
FIG. 48A  FIG. 48B
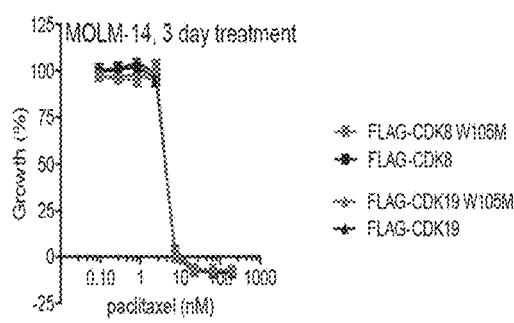 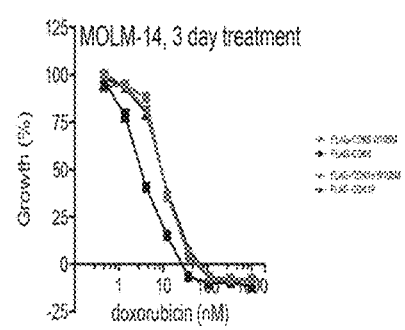
FIG. 49A  FIG. 49B
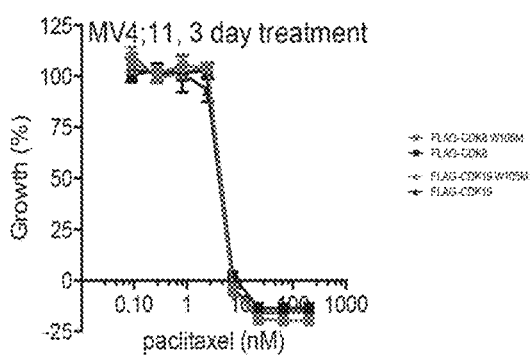 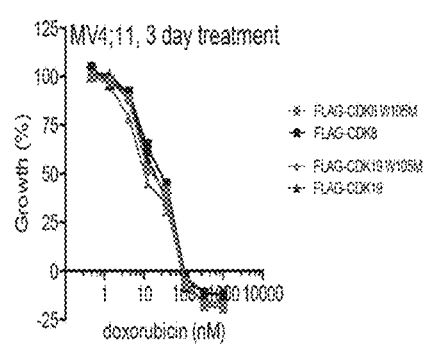
FIG. 50A  FIG. 50B

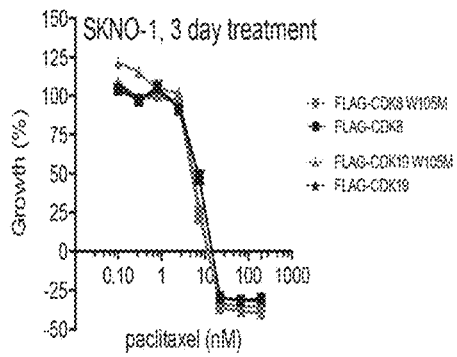
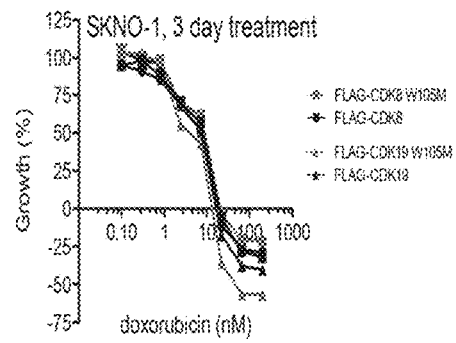

FIG. 51A   FIG. 51B

| CDK1 | 76 | LYLIFEFLSMDLKKYLDSIP------ | SEQ ID NO. 1 |
| CDK2 | 76 | LYLVFEFLHQDLKKFMDASA------ | SEQ ID NO. 2 |
| CDK3 | 76 | LYLVFEFLSQDLKKYMDSTP------ | SEQ ID NO. 3 |
| CDK4 | 89 | VTLVFEHVDQDLRTYLDKAP------ | SEQ ID NO. 4 |
| CDK5 | 76 | LILVFEFCDQDLKKYFDSCN------ | SEQ ID NO. 5 |
| CDK6 | 94 | LILVFEHVDQDLTTYLDKVP------ | SEQ ID NO. 6 |
| CDK7 | 87 | ISLVFDFMETDLEVIIKDNS------ | SEQ ID NO. 7 |
| CDK8 | 93 | VWLLFDYAEHDLWHIIKFHRASKANK | SEQ ID NO. 8 |
| CDK9 | 99 | IYLVFDFCEHDLAGLLSNVL------ | SEQ ID NO. 9 |
| CDK10 | 113 | IFLVMGYCEQDLASLLENMP------ | SEQ ID NO. 10 |
| CDK11A | 500 | IYIVMNYVEHDLKSLMETMK------ | SEQ ID NO. 11 |
| CDK11B | 512 | IYIVMNYVEHDLKSLMETMK------ | SEQ ID NO. 12 |
| CDK12 | 809 | FYLVFEYMDHDLMGLLESGL------ | SEQ ID NO. 13 |
| CDK13 | 787 | FYLVFEYMDHDLMGLLESGL------ | SEQ ID NO. 14 |
| CDK14 | 206 | LILVFEYVHTDLCQYMDKHP------ | SEQ ID NO. 15 |
| CDK15 | 174 | LIFVFEYMHTDLAQYMSQHP------ | SEQ ID NO. 16 |
| CDK16 | 236 | LILVFEYLDKDLKQYLDDCG------ | SEQ ID NO. 17 |
| CDK17 | 263 | LILVFEYLDKDLKQYMDDCG------ | SEQ ID NO. 18 |
| CDK18 | 213 | LILVFEYLDSDLKQYLDHCG------ | SEQ ID NO. 19 |
| CDK19 | 93 | VWLLFDYAEHDLWHIIKFHRASKANK | SEQ ID NO. 20 |
| CDK20 | 77 | FVLAFEFMLSDLAEVVRHAQ------ | SEQ ID NO. 21 |

FIG. 52

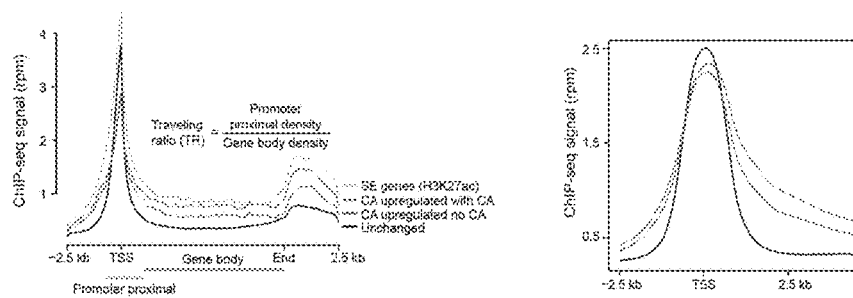
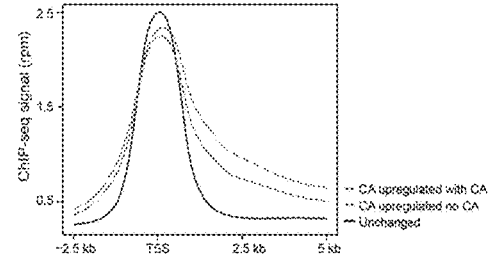
FIG. 54
FIG. 55
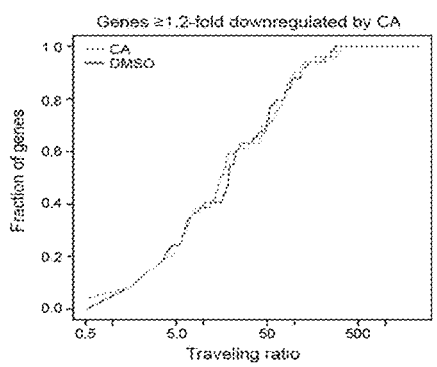
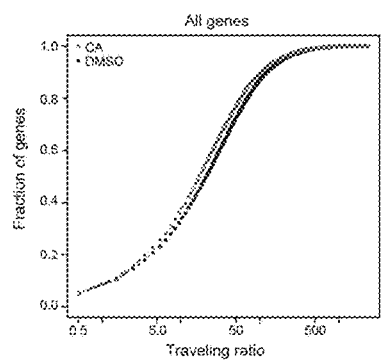
FIG. 56A
FIG. 56B
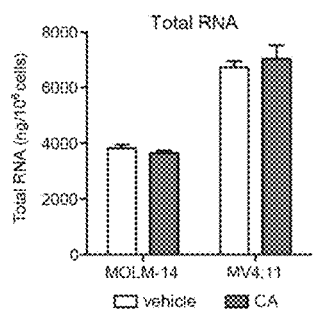
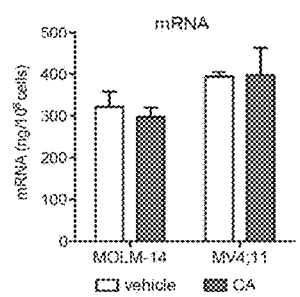
FIG. 57A
FIG. 57B

```
                           SEQUENCE LISTING

<160> NUMBER OF SEQ ID NOS: 21

<210> SEQ ID NO 1
<211> LENGTH: 20
<212> TYPE: PRT
<213> ORGANISM: Artificial Sequence
<220> FEATURE:
<223> OTHER INFORMATION: CDK1 Aligned Sequence Fragment

<400> SEQUENCE: 1

Leu Tyr Leu Ile Phe Glu Phe Leu Ser Met Asp Leu Lys Lys Tyr Leu
1               5                   10                  15

Asp Ser Ile Pro
            20

<210> SEQ ID NO 2
<211> LENGTH: 20
<212> TYPE: PRT
<213> ORGANISM: Artificial Sequence
<220> FEATURE:
<223> OTHER INFORMATION: CDK2 Aligned Sequence Fragment

<400> SEQUENCE: 2

Leu Tyr Leu Val Phe Glu Phe Leu His Gln Asp Leu Lys Lys Phe Met
1               5                   10                  15

Asp Ala Ser Ala
            20

<210> SEQ ID NO 3
<211> LENGTH: 20
<212> TYPE: PRT
<213> ORGANISM: Artificial Sequence
<220> FEATURE:
<223> OTHER INFORMATION: CDK3 Aligned Sequence Fragment

<400> SEQUENCE: 3

Leu Tyr Leu Val Phe Glu Phe Leu Ser Gln Asp Leu Lys Lys Tyr Met
1               5                   10                  15

Asp Ser Thr Pro
            20

<210> SEQ ID NO 4
<211> LENGTH: 20
<212> TYPE: PRT
<213> ORGANISM: Artificial Sequence
```

```
<220> FEATURE:
<223> OTHER INFORMATION: CDK4 Aligned Sequence Fragment

<400> SEQUENCE: 4

Val Thr Leu Val Phe Glu His Val Asp Gln Asp Leu Arg Thr Tyr Leu
1               5                   10                  15

Asp Lys Ala Pro
            20

<210> SEQ ID NO 5
<211> LENGTH: 20
<212> TYPE: PRT
<213> ORGANISM: Artificial Sequence
<220> FEATURE:
<223> OTHER INFORMATION: CDK5 Aligned Sequence Fragment

<400> SEQUENCE: 5

Leu Thr Leu Val Phe Glu Phe Cys Asp Gln Asp Leu Lys Lys Tyr Phe
1               5                   10                  15

Asp Ser Cys Asn
            20

<210> SEQ ID NO 6
<211> LENGTH: 20
<212> TYPE: PRT
<213> ORGANISM: Artificial Sequence
<220> FEATURE:
<223> OTHER INFORMATION: CDK6 Aligned Sequence Fragment

<400> SEQUENCE: 6

Leu Thr Leu Val Phe Glu His Val Asp Gln Asp Leu Thr Thr Tyr Leu
1               5                   10                  15

Asp Lys Val Pro
            20

<210> SEQ ID NO 7
<211> LENGTH: 20
<212> TYPE: PRT
<213> ORGANISM: Artificial Sequence
<220> FEATURE:
<223> OTHER INFORMATION: CDK7 Aligned Sequence Fragment

<400> SEQUENCE: 7

Ile Ser Leu Val Phe Asp Phe Met Glu Thr Asp Leu Glu Val Ile Ile
1               5                   10                  15

Lys Asp Asn Ser
            20

<210> SEQ ID NO 8
<211> LENGTH: 26
<212> TYPE: PRT
<213> ORGANISM: Artificial Sequence
<220> FEATURE:
<223> OTHER INFORMATION: CDK8 Aligned Sequence Fragment

<400> SEQUENCE: 8

Val Trp Leu Leu Phe Asp Tyr Ala Glu His Asp Leu Trp His Ile Ile
1               5                   10                  15

Lys Phe His Arg Ala Ser Lys Ala Asn Lys
            20                  25
```

```
<210> SEQ ID NO 9
<211> LENGTH: 20
<212> TYPE: PRT
<213> ORGANISM: Artificial Sequence
<220> FEATURE:
<223> OTHER INFORMATION: CDK9 Aligned Sequence Fragment

<400> SEQUENCE: 9

Ile Tyr Leu Val Phe Asp Phe Cys Glu His Asp Leu Ala Gly Leu Leu
1               5                   10                  15

Ser Asn Val Leu
            20

<210> SEQ ID NO 10
<211> LENGTH: 20
<212> TYPE: PRT
<213> ORGANISM: Artificial Sequence
<220> FEATURE:
<223> OTHER INFORMATION: CDK10 Aligned Sequence Fragment

<400> SEQUENCE: 10

Ile Phe Leu Val Met Gly Tyr Cys Glu Gln Asp Leu Ala Ser Leu Leu
1               5                   10                  15

Glu Asn Met Pro
            20

<210> SEQ ID NO 11
<211> LENGTH: 20
<212> TYPE: PRT
<213> ORGANISM: Artificial Sequence
<220> FEATURE:
<223> OTHER INFORMATION: CDK11A Aligned Sequence Fragment

<400> SEQUENCE: 11

Ile Tyr Ile Val Met Asn Tyr Val Glu His Asp Leu Lys Ser Leu Met
1               5                   10                  15

Glu Thr Met Lys
            20

<210> SEQ ID NO 12
<211> LENGTH: 20
<212> TYPE: PRT
<213> ORGANISM: Artificial Sequence
<220> FEATURE:
<223> OTHER INFORMATION: CDK11B Aligned Sequence Fragment

<400> SEQUENCE: 12

Ile Tyr Ile Val Met Asn Tyr Val Glu His Asp Leu Lys Ser Leu Met
1               5                   10                  15

Glu Thr Met Lys
            20

<210> SEQ ID NO 13
<211> LENGTH: 20
<212> TYPE: PRT
<213> ORGANISM: Artificial Sequence
<220> FEATURE:
<223> OTHER INFORMATION: CDK12 Aligned Sequence Fragment

<400> SEQUENCE: 13

Phe Tyr Leu Val Phe Glu Tyr Met Asp His Asp Leu Met Gly Leu Leu
1               5                   10                  15

Glu Ser Gly Leu
            20
```

-continued

```
<210> SEQ ID NO 14
<211> LENGTH: 20
<212> TYPE: PRT
<213> ORGANISM: Artificial Sequence
<220> FEATURE:
<223> OTHER INFORMATION: CDK13 Aligned Sequence Fragment

<400> SEQUENCE: 14

Phe Tyr Leu Val Phe Glu Tyr Met Asp His Asp Leu Met Gly Leu Leu
1               5                   10                  15

Glu Ser Gly Leu
            20

<210> SEQ ID NO 15
<211> LENGTH: 20
<212> TYPE: PRT
<213> ORGANISM: Artificial Sequence
<220> FEATURE:
<223> OTHER INFORMATION: CDK14 Aligned Sequence Fragment

<400> SEQUENCE: 15

Leu Thr Leu Val Phe Glu Tyr Val His Thr Asp Leu Cys Gln Tyr Met
1               5                   10                  15

Asp Lys His Pro
            20

<210> SEQ ID NO 16
<211> LENGTH: 20
<212> TYPE: PRT
<213> ORGANISM: Artificial Sequence
<220> FEATURE:
<223> OTHER INFORMATION: CDK15 Aligned Sequence Fragment

<400> SEQUENCE: 16

Leu Thr Phe Val Phe Glu Tyr Met His Thr Asp Leu Ala Gln Tyr Met
1               5                   10                  15

Ser Gln His Pro
            20

<210> SEQ ID NO 17
<211> LENGTH: 20
<212> TYPE: PRT
<213> ORGANISM: Artificial Sequence
<220> FEATURE:
<223> OTHER INFORMATION: CDK16 Aligned Sequence Fragment

<400> SEQUENCE: 17

Leu Thr Leu Val Phe Glu Tyr Leu Asp Lys Asp Leu Lys Gln Tyr Leu
1               5                   10                  15

Asp Asp Cys Gly
            20

<210> SEQ ID NO 18
<211> LENGTH: 20
<212> TYPE: PRT
<213> ORGANISM: Artificial Sequence
<220> FEATURE:
<223> OTHER INFORMATION: CDK17 Aligned Sequence Fragment

<400> SEQUENCE: 18

Leu Thr Leu Val Phe Glu Tyr Leu Asp Lys Asp Leu Lys Gln Tyr Met
1               5                   10                  15

Asp Asp Cys Gly
            20
```

```
<210> SEQ ID NO 19
<211> LENGTH: 20
<212> TYPE: PRT
<213> ORGANISM: Artificial Sequence
<220> FEATURE:
<223> OTHER INFORMATION: CDK18 Aligned Sequence Fragment

<400> SEQUENCE: 19

Leu Thr Leu Val Phe Glu Tyr Leu Asp Ser Asp Leu Lys Gln Tyr Leu
1               5                   10                  15

Asp His Cys Gly
            20

<210> SEQ ID NO 20
<211> LENGTH: 26
<212> TYPE: PRT
<213> ORGANISM: Artificial Sequence
<220> FEATURE:
<223> OTHER INFORMATION: CDK19 Aligned Sequence Fragment

<400> SEQUENCE: 20

Val Trp Leu Leu Phe Asp Tyr Ala Glu His Asp Leu Trp His Ile Ile
1               5                   10                  15

Lys Phe His Arg Ala Ser Lys Ala Asn Lys
            20                  25

<210> SEQ ID NO 21
<211> LENGTH: 20
<212> TYPE: PRT
<213> ORGANISM: Artificial Sequence
<220> FEATURE:
<223> OTHER INFORMATION: CDK20 Aligned Sequence Fragment

<400> SEQUENCE: 21

Phe Val Leu Ala Phe Glu Phe Met Leu Ser Asp Leu Ala Glu Val Val
1               5                   10                  15

Arg His Ala Gln
            20
```

CORTISTATIN ANALOGUES, SYNTHESES, AND USES THEREOF

RELATED APPLICATIONS

This application is Continuation of International Application No. PCT/US2016/031279, filed in the United States Patent and Trademark Office, Receiving Office on May 6, 2016, which related to and claims the benefit of provisional U.S. Application No. 62/158,936, filed May 8, 2015, provisional U.S. Application No. 62/158,982, filed May 8, 2015, provisional U.S. Application No. 62/187,656, filed Jul. 1, 2015, and provisional U.S. Application No. 62/187,669, filed Jul. 1, 2015. The entirety of these provisional applications are hereby incorporated by reference for all purposes.

INCORPORATION BY REFERENCE

The contents of the text file named "15020-011US1 sequence listing ST25.txt" which was created on Jan. 16, 2018, and is 6.72 KB in size, are hereby incorporated by reference in their entirety.

BACKGROUND

The cortistatins are a group of anti-angiogenic steroidal alkaloids first isolated in 2006 from the marine sponge *Corticium simplex*. See, e.g., Aoki, et al., *JACS* (2006) 128: 3148-9. From the date of isolation to the present, these natural products have been the subject of much study, especially in the development of total syntheses and of new unnatural biologically active analogs. See, e.g., Aoki et al., *Bioorganic & Medicinal Chemistry* (2007) 15: 6758-62. Mousseau et al., *Cell Host & Microbe* (2012) 12: 97-108; Chen et al., *Organic & Biomolecular Chemistry* (2010) 8: 2900; Hardin et al., *European Journal of Organic Chemistry* (2010) 19: 3553. Thus, there is an active interest in the development of new cortistatin analogs and methods of their preparation.

U.S. Pat. No. 9,127,019 titled "Cortistatin Analogs and Synthesis Thereof" filed by Flyer, et. al., and assigned to the President and Fellows of Harvard College describes analogs of Cortistatins A, J, K, and L having the general Formula I and salts thereof, and the synthesis thereof, wherein $R_1$, $R_2$, $R_3$, $R_4$, n, and m are as described therein.

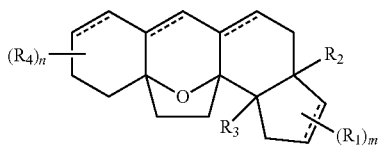

(I)

The '019 patent discloses that such compounds are anti-angiogenic and can be used to treat proliferative diseases.

WO 2015/100420 titled "Cortistatin Analogs and Syntheses and Uses Thereof" filed by Shair, et al., and also assigned to the President and Fellows of Harvard College describes further analogs of Cortistatin and methods and compositions that include the described cortistatin analogs to treat proliferative disorders such as cancer, and in particular, a hematopoietic cancer such as leukemia, multiple myeloma (MM), acute myelocytic leukemia (AML), a myeloproliferative neoplasm, acute lymphoblastic leukemia (ALL), chronic myeolcytic leukemia (CIVIL) and primary myelofibrosis (PMF). More generally, the '420 application describes a method to treat a condition associated with CDK8 and/or CDK19 kinase activity, that includes administering an effective amount of a disclosed compound or its pharmaceutically acceptable salt, quaternary amine, or N-oxide. CDK8 and its regulatory subunit cyclin C are components of the RNA polymerase II haloenyme complex, which phosphorylates the carboxy-terminal of the largest subunit of RNA polymerase II. CDK8 regulates transcription by targeting the CDK7/cyclin H subunits of the general transcription factor TFIIH.

Other synthetic and biological descriptions of Cortistatin A and analogs of Cortistatin A have been described in: Chiu et al., Chemistry (2015), 21: 14287-14291, titled "Formal Total Synthesis of (+)-Cortistatins A and J"; Valente et al., Current HIV Research (2015), 13: 64-79, titled "Didehydro-Cortistatin A Inhibits HIV-1 Tat Mediated Neuroinflammation and Prevents Potentiation of Cocaine Reward in Tat Transgenic Mice"; Motomasa et al., Chemical & Pharma. Bulletin (2013), 61: 1024-1029 titled "Synthetic Studies of Cortistatin A Analog from the CD-ring Fragment of Vitamin D2"; Valente et al., Cell Host & Microbe (2012), 12: 97-108 titled "An Analog of the Natural Steroidal Alkaloid Cortistatin A Potently Suppress Tat-dependent HIV Transcription"; Motomasa et al., ACS Med. Chem. Lett. (2012), 3: 673-677 titled "Creation of Readily Accessible and Orally Active Analog of Cortistatin A"; Danishefsky et al., Tetrahedron (2011) 67: 10249-10260 titled "Synthetic Studies Toward (+)-Cortistatin A"; Motomasa et al., Heterocycles (2011), 83: 1535-1552, titled "Synthetic Study of Carbocyclic Core of Cortistatin A, an Anti-angiogenic Steroidal Alkaloid from Marine Sponge"; Motomasa et al., Org. Lett. (2011), 13: 3514-3517, titled "Stereoselective Synthesis of Core Structure of Cortistatin A"; Baran et al., JACS (2011), 133: 8014-8027, titled "Scalable Synthesis of Cortistatin A and Related Structures"; Hirama et al., JOC (2011), 76: 2408-2425, titled "Total Synthesis of Cortistatins A and J"; Zhai et al., Org. Lett. (2010), 22: 5135-5137, titled "Concise Synthesis of the Oxapentacyclic Core of Cortistatin A"; Stoltz et al., Org. Biomol. Chem. (2010), 13: 2915-2917, titled "Efforts Toward Rapid Construction of the Cortistatin A Carbocyclic Core via Enyne-ene Metathesis"; Sarpong et al., Tetrahedron (2010), 66: 4696-4700, titled "Formal Total Synthesis of (±)-Cortistatin A"; Nicolaou et al., Angewandte Chemie (2009), 48: 8952-8957, titled "Cortistatin A is a High-Affinity Ligand of Protein Kinases ROCK, CDK8, and CDK11".

U.S. Patent Application Publication US2013/0217014 and PCT Application WO2013/122609 titled "Methods of Using CDK8 Antagonists" filed by Firestein, et al., and assigned to Genentech, describes the use of CDK8 antagonists against various cancers.

Despite the progress to date, it would be advantageous to provide new compounds that can be used to treat disorders in a host, including a human.

SUMMARY OF THE INVENTION

In one embodiment, new cortistatin analogs are provided of Formula (A1'), (A2'), (A1"), and (A2"):

(A1')
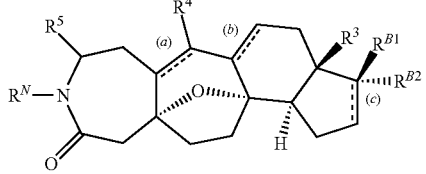

(A2')
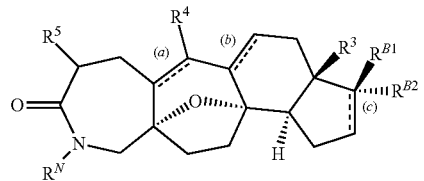

(A1")
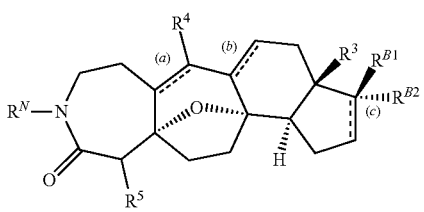

(A2")
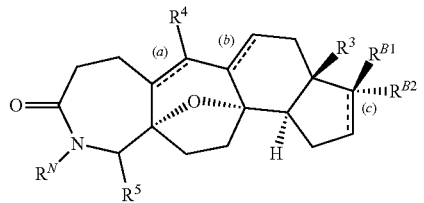

and pharmaceutically acceptable salts thereof, wherein $R^3$, $R^4$, $R^5$, $R^{B1}$, $R^{B2}$, and ≡ are as defined herein. Compounds of Formula (A2') and (A2") have been found to exhibit anti-cancer activity similar to that of cortistatin A.

Further provided are compounds of Formula (C1'), (C2'), (C1'), and (C2'):

(C1')
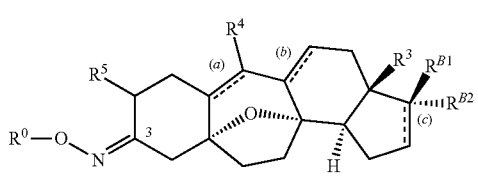

(C2')
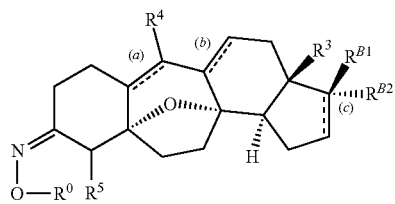

(C1")
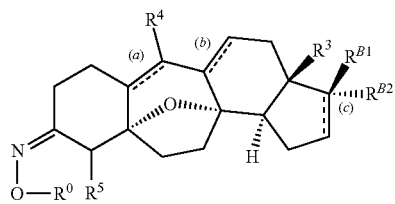

(C2")
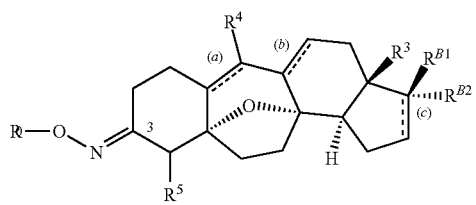

and pharmaceutically acceptable salts thereof, wherein $R^O$, $R^3$, $R^4$, $R^5$, $R^{B1}$, $R^{B2}$, and ≡ are as defined herein. Such compounds are useful in the synthesis of compounds of Formula (A1'), (A2'), (A1"), and (A2"), and are further contemplated to possess anti-cancer activity.

Further provided are compounds of Formula (D1'), (D2'), (D1"), and (D2"):

(D1')
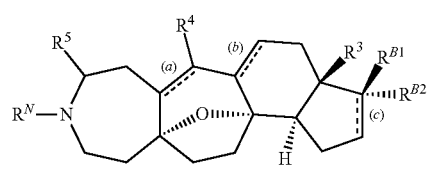

(D2')
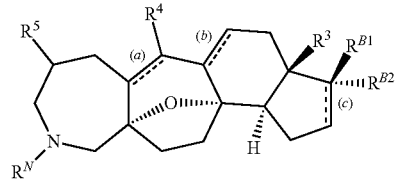

(D1")
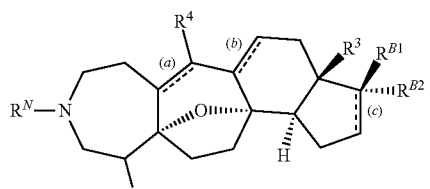

(D2")
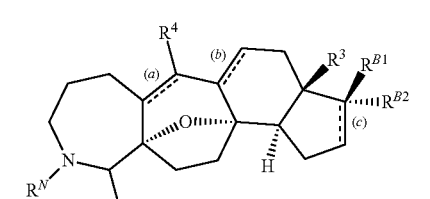

and pharmaceutically acceptable salts thereof, wherein $R^3$, $R^4$, $R^5$, $R^{B1}$, $R^{B2}$, and ≡ are as defined herein. Such compounds are also further contemplated to possess anti-cancer activity.

Further provided are compounds of Formula (E1'), (E2'), (E1"), and (E2"):

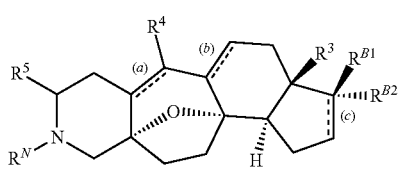

(E1')

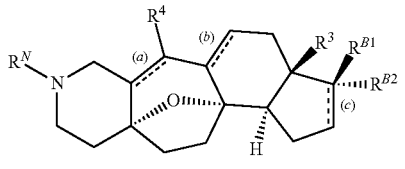

(E2')

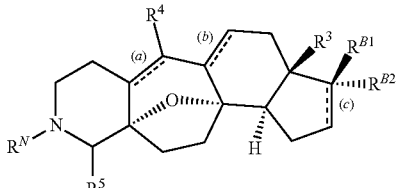

(E1'')

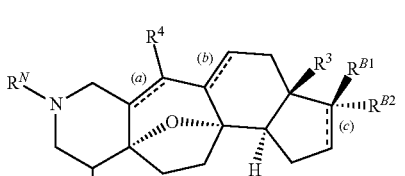

(E2'')

and pharmaceutically acceptable salts thereof, wherein $R^3$, $R^4$, $R^5$, $R^{B1}$, $R^{B2}$, and ═ are as defined herein. Such compounds are also further contemplated to possess anticancer activity.

The cortistatin analogs of Formula (A1'), (A2'), (A1''), or (A2''), wherein $R^N$ is hydrogen, may be synthesized via the Beckmann rearrangement of an oxime of Formula (C') or (C''), wherein $R^O$ may be either a hydrogen or non-hydrogen group, as depicted in Scheme 2A and 2B. Optional substitution of the lactam amino moiety, to provide a compound of Formula (A1'), (A2'), (A1''), or (A2''), wherein $R^N$ is a non-hydrogen group, is further contemplated herein. Reduction of a compound of Formula (A1'), (A2'), (A1''), or (A2''), respectively provides a compound of Formula (D1'), (D2'), (D1''), or (D2'').

The oxime of Formula (C') or (C'') is prepared from a ketone of Formula (B') or (B''), wherein $R^5$ is a hydrogen or non-hydrogen group, as defined herein. For example, compounds of Formula (B') or (B''), wherein $R^5$ is a non-hydrogen group, may be formed via trapping of the Compound of Formula (B0) as the enolate (e.g., via treatment with base and a $P_1$-LG group, wherein $P_1$ is silyl and LG is a leaving group), followed by subsequent oxidation or amination of the double bond, or reaction of the double bond with an electrophilic carbon $C(R^A)_3$-LG, wherein LG is a leaving group, or reaction with a halogenating agent, to provide a substituted ketone product, wherein $R^5$ is a halogen, $-OR^A$, $-OC(=O)R^A$, $-OC(=O)OR^A$, $-OC(=O)N(R^A)_2$, $-OS(=O)_2R^A$, $-N_3$, $-N(R^A)_2$, $-NR^AC(=O)R^A$, $-NR^AC(=O)OR^A$, $-NR^AC(=O)N(R^A)_2$, $-NR^AS(=O)_2R^A$, or $-C(R^A)_3$. See, e.g., Scheme 1.

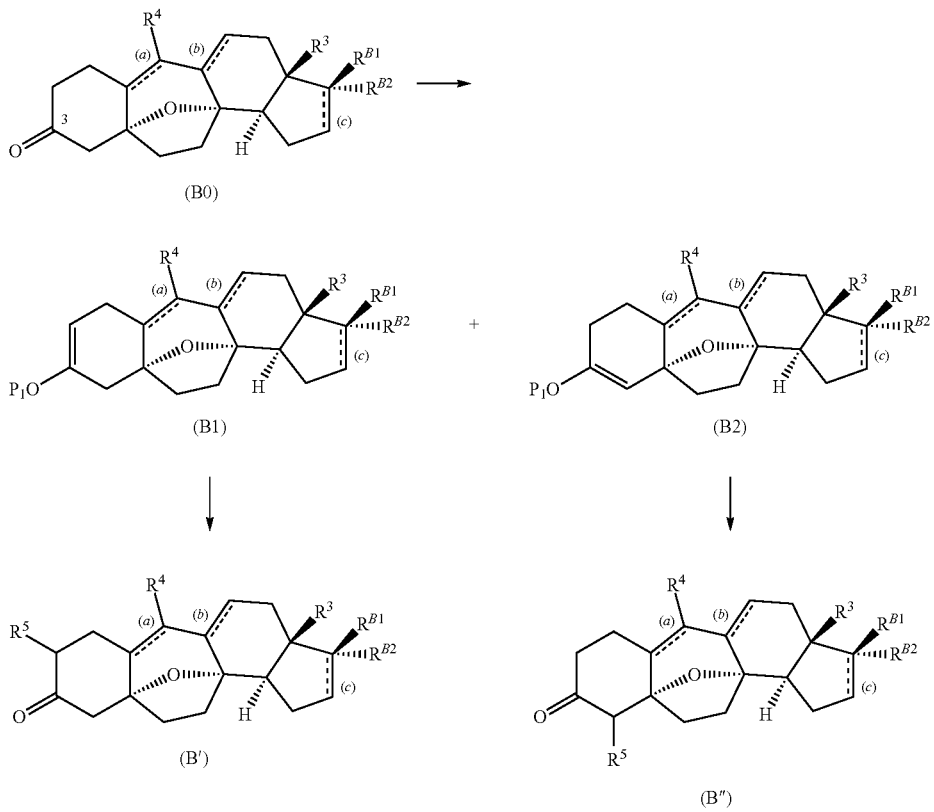

Scheme 1.

It is generally understood that the compound of Formula (C') or (C") may comprise a single oxime C3 isomer, or a mixture of both oxime C3 isomers, i.e., of Formula (C1') and (C2') or (C1") and (C2"). It is also generally understood that the Beckmann rearrangement proceeds by a trans [1,2]-shift, resulting in production of lactone (A1') or (A1") from oxime (C1') or (C1"), and production of lactone (A2') or (A2") from oxime (C2') or (C2"). Thus, in any given reaction, production of one or both lactams of Formula (A1') and (A1"), or (A2') and (A2"), is contemplated.

Scheme 2A.

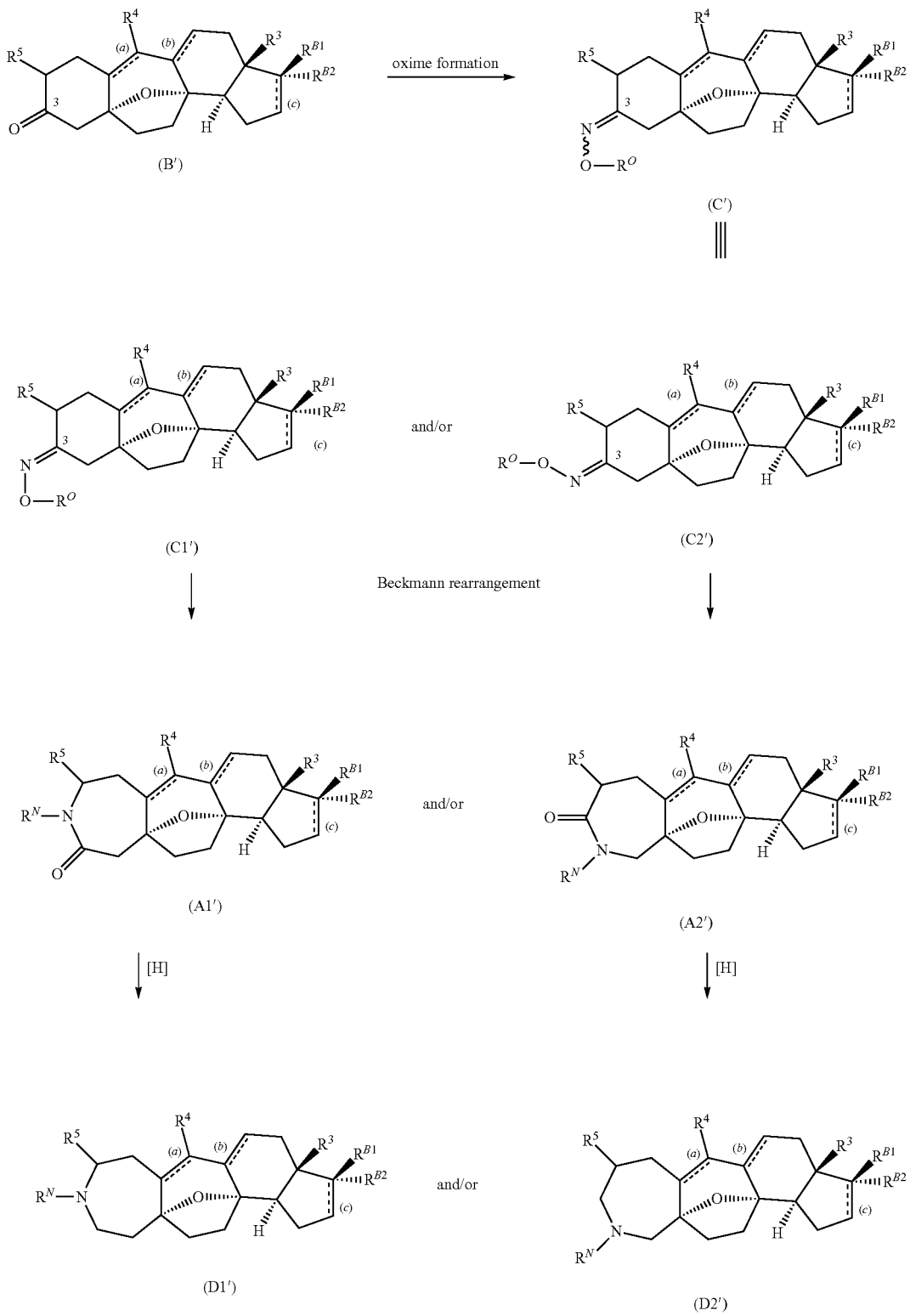

Scheme 2B.

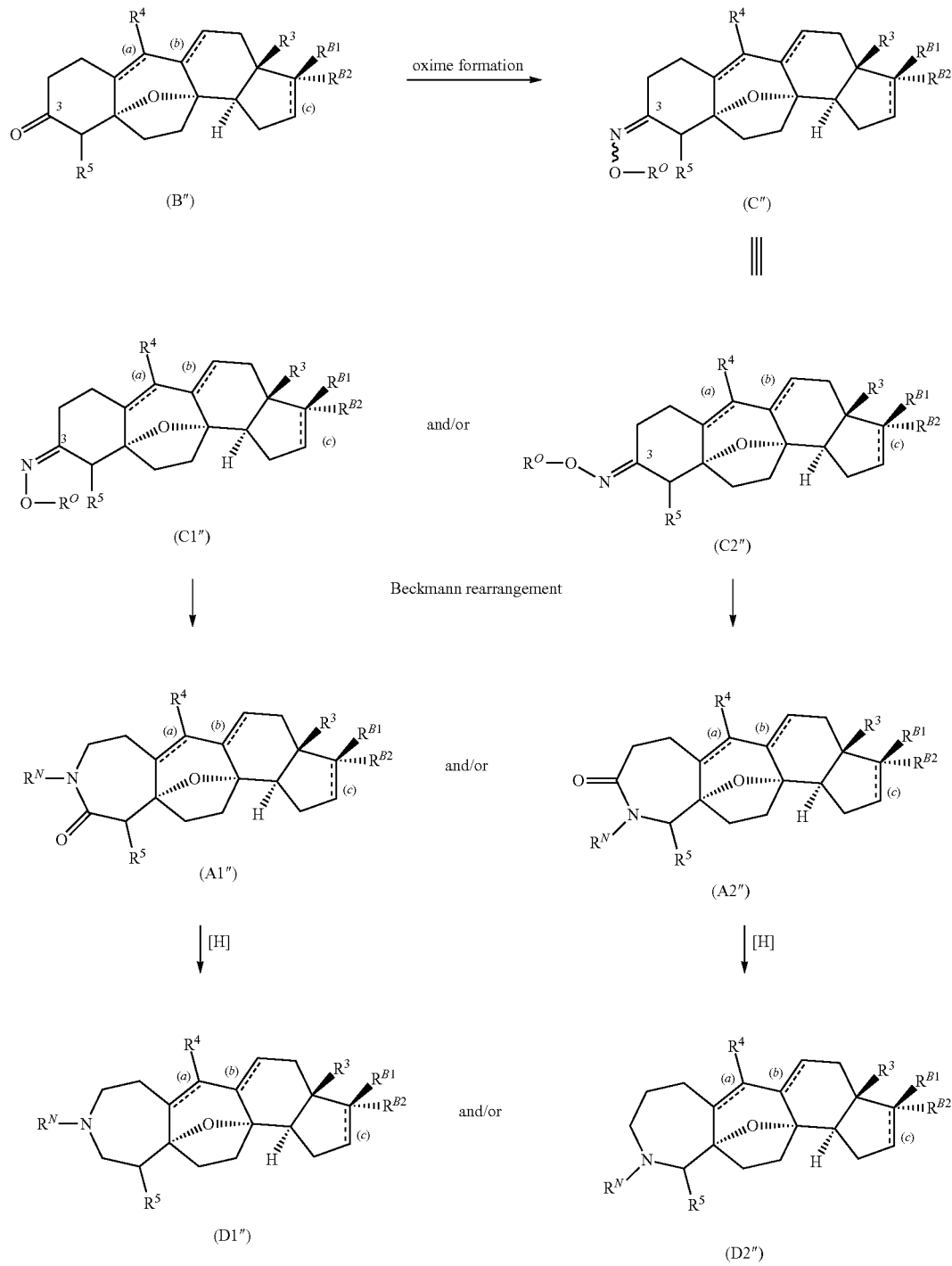

The oxime of Formula (C') or (C'') may be generated from the corresponding ketone of Formula (B') or (B''), as depicted in Scheme 3A and 3B. In one aspect, the oxime of Formula (C') or (C''), wherein $R^O$ is hydrogen, may be generated directly from the ketone upon treatment with hydroxylamine $NH_2OH$, and may under suitable rearrangement conditions, e.g., acidic conditions, directly provide a compound of Formula (A1') or (A1''), and/or (A2') or (A2'').

Alternatively, the oxime of Formula (C') or (C''), wherein $R^O$ is a non-hydrogen group, may be generated from the ketone in a one-step process, e.g., upon treatment with a substituted hydroxyl amine $NH_2OR^O$, wherein $R^O$ is a non-hydrogen group, or may be generated via a two-step process, e.g., first by treatment with hydroxyl amine, $NH_2OH$, followed by treatment with a compound of formula $R^O$-LG, wherein $R^O$ is a non-hydrogen group and LG is a leaving group.

Scheme 3A.

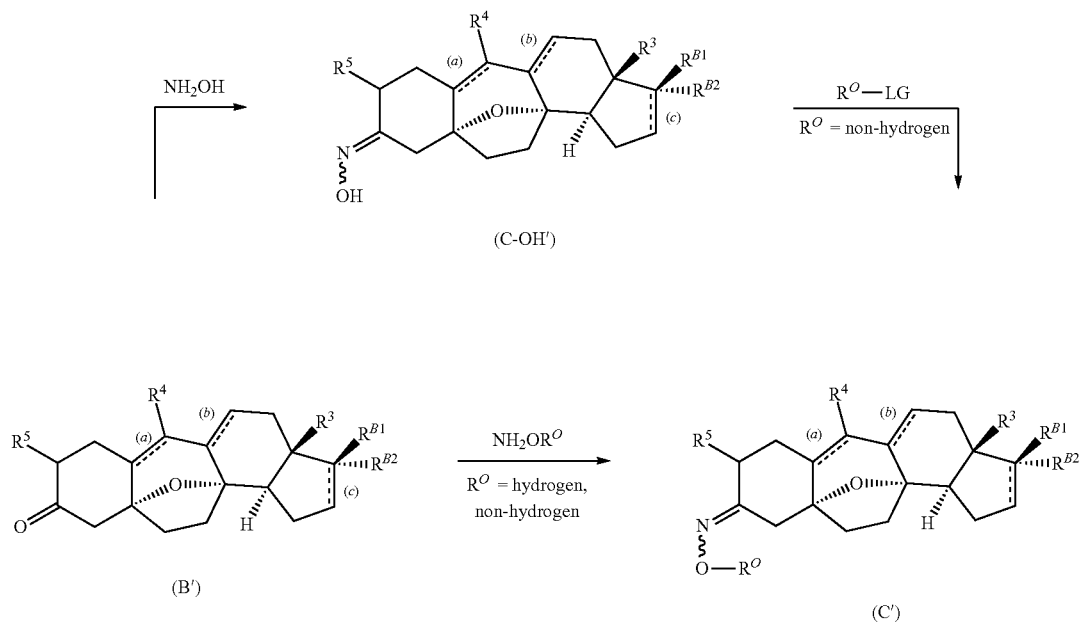

Scheme 3B.

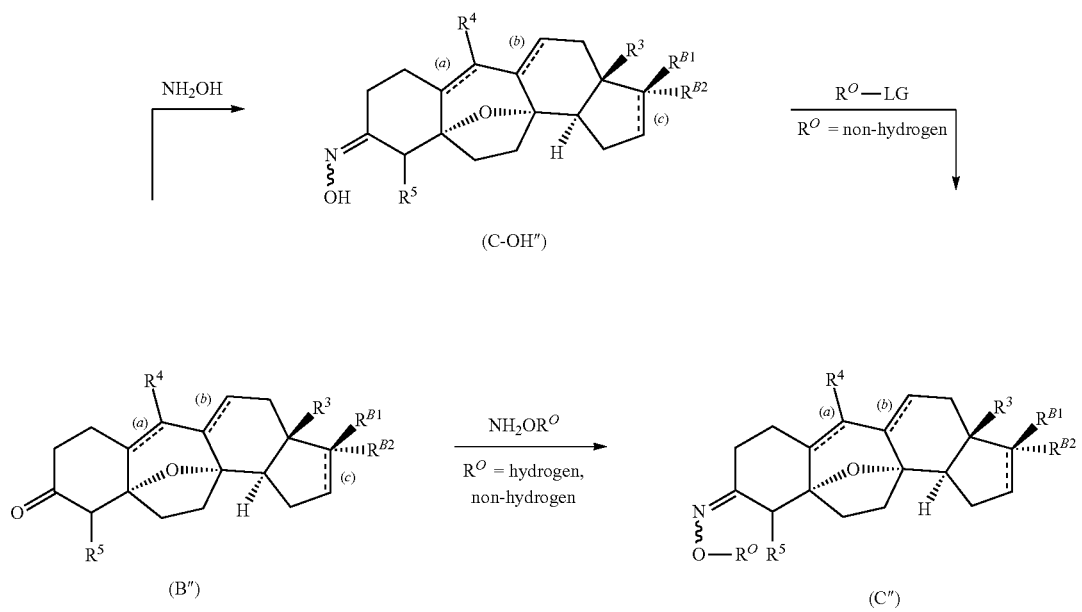

The synthesis of the ketone starting material of Formula (B') or (B") is further described herein, and is more fully described in PCT Application No. PCT/US2014/072365, incorporated herein by reference.

The compound of Formula (E1') or (E1") may be synthesized via hydrolysis of the lactam to the carboxylic acid, followed by decarboxylative halogenation, wherein X is chlorine, bromine, or iodine, and subsequent cyclization. See, e.g., Scheme 4A or 4B.

Scheme 4A.
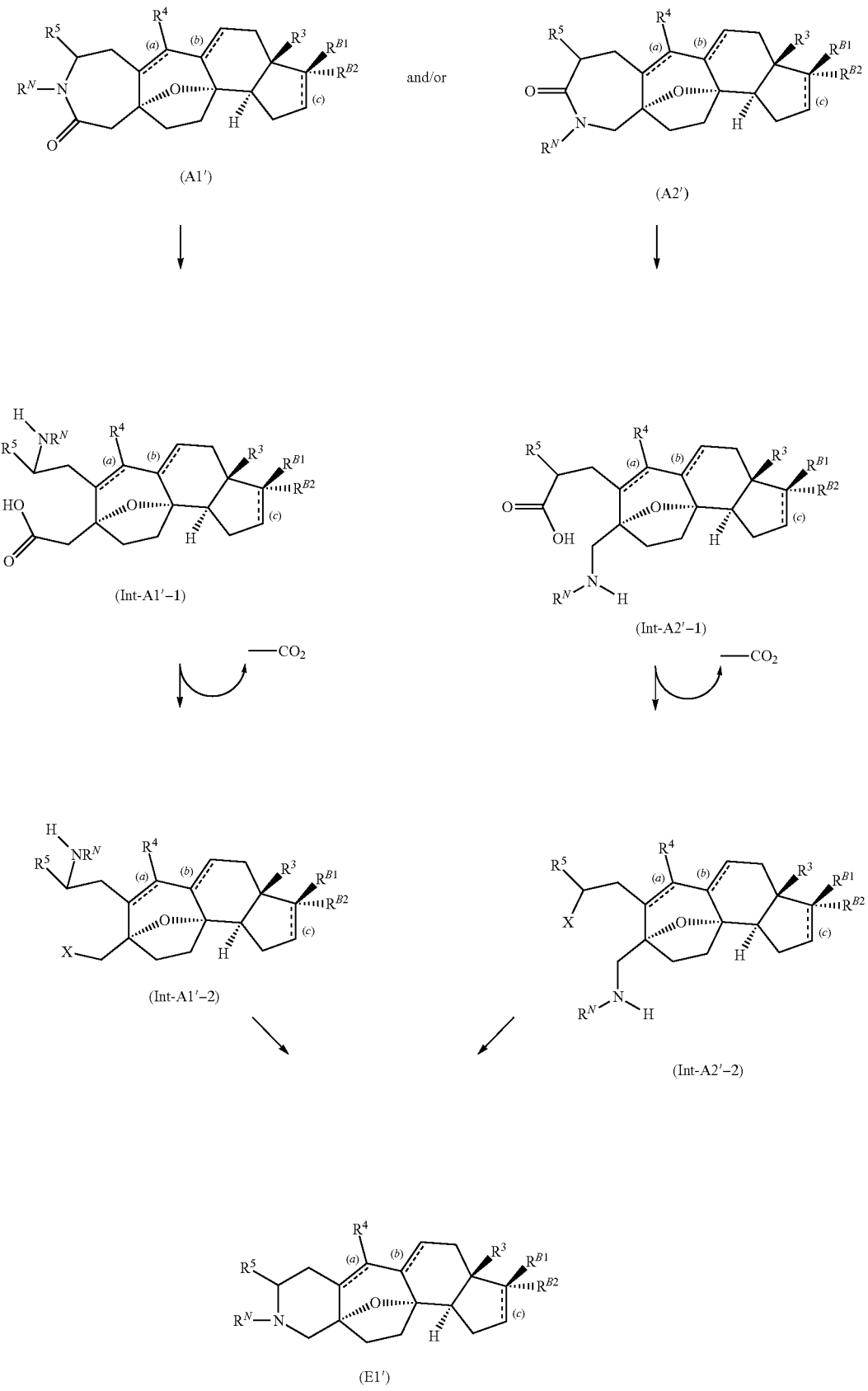

Scheme 4B.

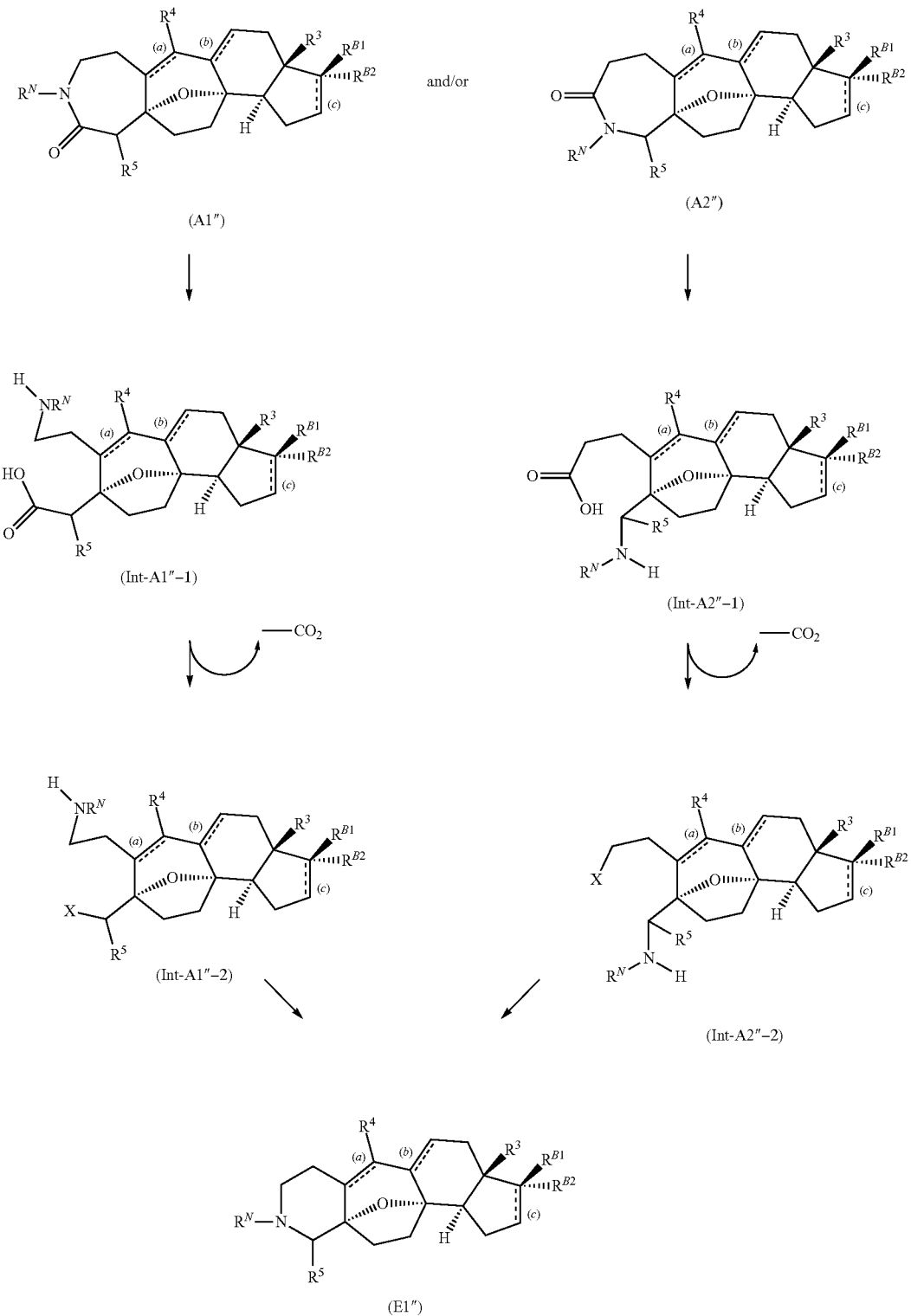

The compound of Formula (E2') or (E2") may be synthesized via enol trapping of the ketone of Formula (B*') or (B*"), wherein $R^O$ is a non-hydrogen group as defined herein, oxidative cleavage of the alkenyl moiety, formation of an acyl azide followed by the Curtius rearrangement to provide the amino moiety, which is subsequently cyclized to provide a lactam, reduced to the piperadinyl product wherein $R^N$ is hydrogen, which may be optionally protected by a non-hydrogen group $R^N$. See, e.g., Scheme 5A or 5B.

Scheme 5A.
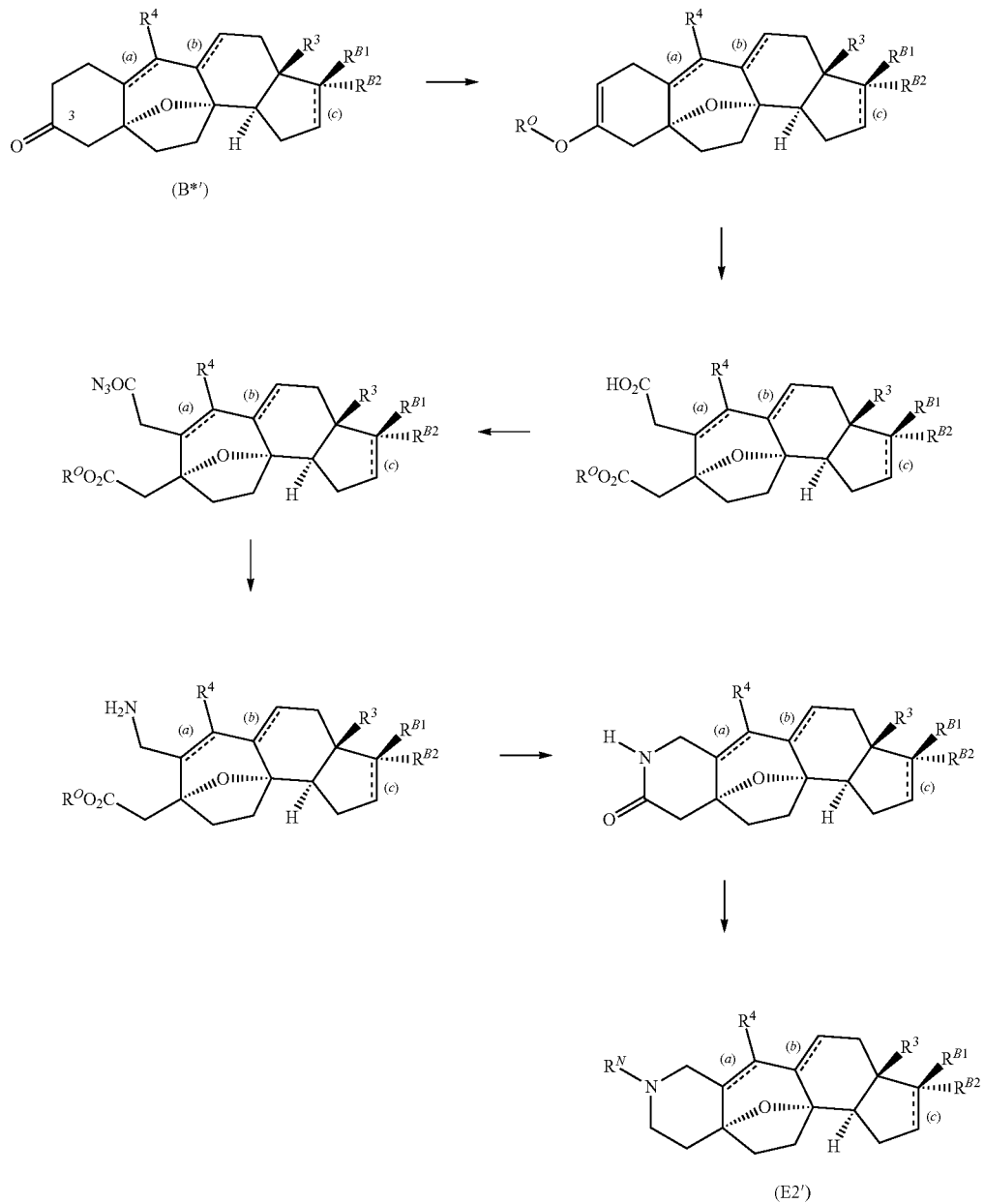
Scheme 5B.
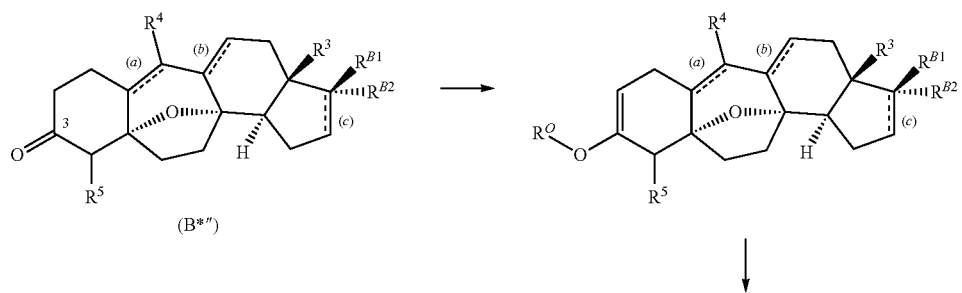

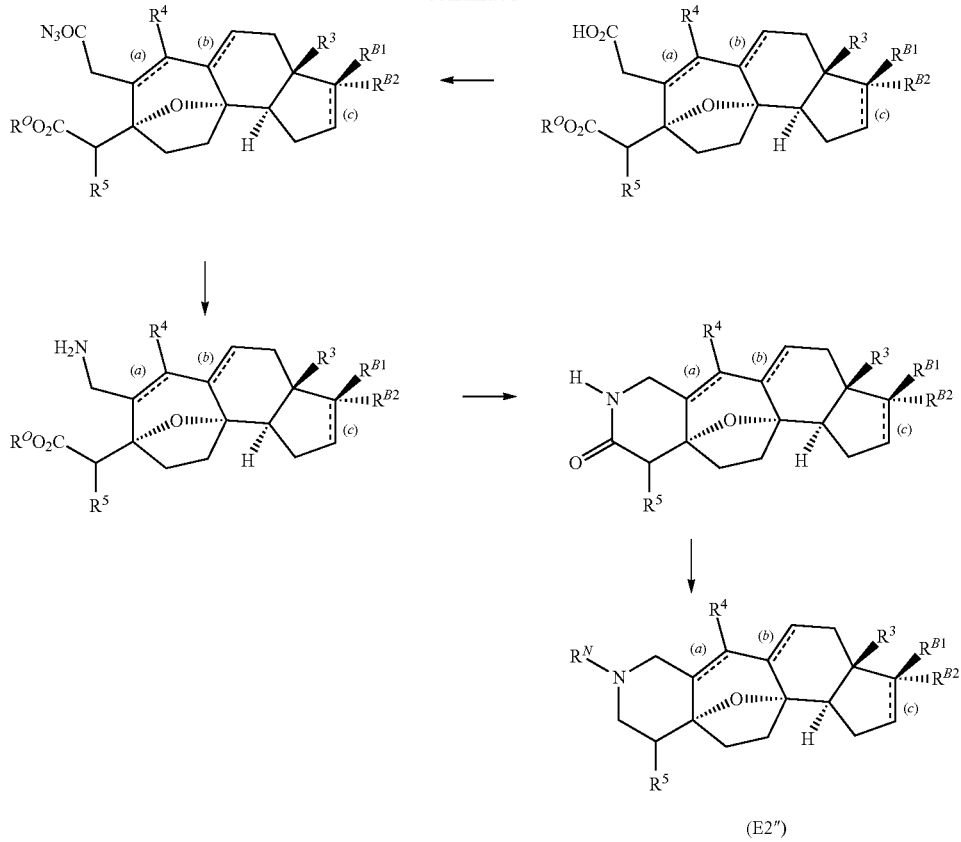

(E2″)

Thus, in one aspect, provided is a method of preparing a compound of Formula (A1″) or (A1″), and/or (A2′) or (A2″), or a pharmaceutically acceptable salt thereof, the method comprising converting an oxime of Formula (C′) or (C″), or a pharmaceutically acceptable salt thereof, to a compound of Formula (A1″) or (A1″), and/or (A2′) or (A2″), or a pharmaceutically acceptable salt thereof.

In another aspect, provided is a method of preparing a compound of Formula (D1′) or (D1″), or a pharmaceutically acceptable salt thereof, the method comprising reducing a compound of Formula (A1′) or (A1″), or a pharmaceutically acceptable salt thereof.

In another aspect, provided is a method of preparing a compound of Formula (D2′) or (D2″), or a pharmaceutically acceptable salt thereof, the method comprising reducing a compound of Formula (A2′) or (A2″), or a pharmaceutically acceptable salt thereof.

In another aspect, provided is a method of preparing a compound of Formula (E1′) or (E1″), or a pharmaceutically acceptable salt thereof, the method comprising hydrolysis of the lactam compound of Formula (A1′) or (A2′), or (A1″) or (A2″), to the ring opened carboxylic acid, followed by decarboxylative halogenation, wherein X is chlorine, bromine, or iodine, and subsequent cyclization.

In another aspect, provided is a method of preparing a compound of Formula (E2′) or (E2″), or a pharmaceutically acceptable salt thereof, the method comprising enol trapping of the ketone of Formula (B*′) or (B*″), wherein $R^O$ is a non-hydrogen group as defined herein, oxidative cleavage of the alkenyl moiety, formation of an acyl azide followed by the Curtius rearrangement to provide an amino compound, and subsequent cyclization and reduction, followed by optional protection.

In another aspect, provided are pharmaceutical compositions comprising an effective treatment amount of a compound of Formula (A1′), (A2′), (C′), (C1′), (C2′), (D1′), (D2′), (E1′), (E2′), (A1″), (A2″), (C″), (C1″), (C2″), (D1″), (D2″), (E1″), (E2″), (G1′), or (G1″), or a pharmaceutically acceptable salt thereof, and a pharmaceutically acceptable excipient.

In another aspect, further provided are methods of using compounds of Formula (A1′), (A2′), (C′), (C1′), (C2′), (D1′), (D2′), (E1′), (E2′), (A1″), (A2″), (C″), (C1″), (C2″), (D1″), (D2″), (E1″), (E2″), (G1′), or (G1″), and pharmaceutically acceptable salts thereof.

For example, in one aspect, provided is a method of treating a condition associated with angiogenesis comprising administering to a subject in need thereof an effective amount of a compound of Formula (A1′), (A2′), (C′), (C1′), (C2′), (D1′), (D2′), (E1′), (E2′), (A1″), (A2″), (C″), (C1″), (C2″), (D1″), (D2″), (E1″), (E2″), (G1′), or (G1″), or a pharmaceutically acceptable salt thereof, or a pharmaceutical composition thereof. In certain embodiments, the condition is a diabetic condition, an inflammatory condition, macular degeneration, obesity, atherosclerosis, or a proliferative disorder.

In yet another aspect, provided is a method of treating a condition associated with CDK8 and/or CDK19 kinase activity, comprising administering to a subject in need thereof an effective amount of a compound of Formula (A1′), (A2′), (C′), (C1′), (C2′), (D1′), (D2′), (E1′), (E2′), (A1″), (A2″), (C″), (C1″), (C2″), (D1″), (D2″), (E1″), (E2″), (G1′), or (G1″), or a pharmaceutically acceptable salt thereof. In certain embodiments, the condition is a proliferative disorder. In certain embodiments, the proliferative disorder is cancer. In certain embodiments, the cancer is a hematopoietic cancer. In certain embodiments, the hematopoietic cancer is lymphoma. In certain embodiments, the hematopoietic cancer is leukemia. In certain embodiments, the hematopoietic cancer is acute myeloid leukemia (AML), myelodysplastic syndrome (MDS), acute lymphoblastic leukemia (ALL), chronic myelogenous leukemia (CML), chronic myelomonocytic leukemia (CMML), or multiple myeloma. In certain embodiments, the acute lymphoblastic leukemia is T-cell acute lymphoblastic leukemia or B-cell acute lymphoblastic leukemia. In certain embodiments, the cancer is breast cancer, ovarian cancer, endometriod carcinoma, or squamous cell cancer. In certain embodiments, the proliferative disorder is a myeloproliferative neoplasm. In certain embodiments, the myeloproliferative neoplasm is primary myelofibrosis (PMF). In certain embodiments, the cancer is a solid tumor.

In yet another aspect, provided is a method of inhibiting CDK8 and/or CDK19 kinase activity in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, provided is a method of modulating the β-catenin pathway in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, provided is a method of modulating STAT1 activity in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, provided is a method of modulating the TGFβ/BMP pathway in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, provided is a method of modulating HIF-1-A (HIF-1-alpha) activity in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, a method is provided for increasing BIM expression to induce apoptosis in a cell comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, provided is a method of treating a disorder which is mediated by the mediator complex, comprising administering to a subject in need thereof an effective amount of a cortistatin, such as any of the compounds described herein or described in a reference cited in the Background of the Invention. In certain embodiments, the condition is a proliferative disorder. In certain embodiments, the proliferative disorder is cancer. In certain embodiments, the cancer is a hematopoietic cancer. In certain embodiments, the hematopoietic cancer is lymphoma. In certain embodiments, the hematopoietic cancer is leukemia. In certain embodiments, the hematopoietic cancer is acute myeloid leukemia (AML), myelodysplastic syndrome (MDS), acute lymphoblastic leukemia (ALL), chronic myelogenous leukemia (CML), chronic myelomonocytic leukemia (CMML), or multiple myeloma. In certain embodiments, the acute lymphoblastic leukemia is T-cell acute lymphoblastic leukemia or B-cell acute lymphoblastic leukemia. In certain embodiments, the cancer is breast cancer, ovarian cancer, endometriod carcinoma, or squamous cell cancer. In certain embodiments, the proliferative disorder is a myeloproliferative neoplasm. In certain embodiments, the myeloproliferative neoplasm is primary myelofibrosis (PMF). In certain embodiments, the cancer is a solid tumor.

In one embodiment, a method is provided for treating a disorder which is mediated by the mediator complex, comprising administering a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

In yet another aspect, a method of modulating the activity of the mediator complex in a cell is provided comprising contacting an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, or a pharmaceutical composition thereof, with the cell.

In yet another aspect, method of treating a host with an infection comprising administering to a subject in need thereof an effective amount of a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In certain embodiments, the viral infection causes cancer. In certain embodiments, the viral infection is a retroviral infection. In certain embodiments, the viral infection is a human immunodeficiency virus (HIV) infection. In certain embodiments, the virus is an oncovirus, i.e., a virus which is associated with oncogenesis and/or causes cancer. In certain embodiments, treatment of the viral infection is associated with inhibition of CDK8 and/or CDK19 kinase activity.

Intermediate compounds (Int-A1'-1), (Int-A1'-2), (Int-A2'-1), (Int-A2'-1), (Int-A1"-1), (Int-A1"-2), (Int-A2"-1), and (Int-A2"-1) are also contemplated active and useful for the aforementioned methods of use.

In any of the above recited methods, the method is an in vitro method or an in vivo method.

The details of one or more embodiments of the invention are set forth in the accompanying Figures. Other features, objects, and advantages of the invention will be apparent from the Detailed Description, the Examples, and from the Claims.

BRIEF DESCRIPTION OF THE DRAWINGS

FIG. 11A is an immunoblot showing differential inhibition of IFN-γ-stimulated STAT1 S727 phosphorylation by CA upon expression of FLAG-CDK8 or FLAG-CDK8 W105M in MOLM-14 cells.

FIG. 11B is an immunoblot showing differential inhibition of IFN-γ-stimulated STAT1 S727 phosphorylation by CA upon expression of FLAG-CDK19 or FLAG-CDK19 W105M in MOLM-14 cells FIG. 12 is a GSEA plot showing significant positive enrichment of MOLM-14 SE-associated genes (SE genes) upon 3 h CA treatment vs DMSO controls.

FIG. 13 is a scatterplot of false discovery rate (FDR-q) versus normalized enrichment score (NES) for gene sets evaluated by GSEA (n=3,867). Gene sets include CD14+ master TFs, MOLM-14 SE genes, MOLM-13 I-BET151 downregulated, and C2 of MSigDB.

FIG. 14 is a cumulative distribution plot of RNA pol II travelling ratio.

FIG. 15 is a bar graph showing the effect of 100 nM CA and 500 nM I-BET151 on mRNA copy number/cell (relative to vehicle) of selected SE genes after 3 h treatment alone or after treatment with I-BET151 for 3 h followed by CA for an additional 3 h (mean±s.e.m., n=3).

FIGS. 37A-37G are immunoblots showing that CA inhibits CDK8-dependent IFN-γ-stimulated STAT1 S727 phosphorylation equally well in cells sensitive or insensitive to the antiproliferative activity of CA including SET-2 (FIG. 37A), SKNO-1 (FIG. 37B), MEG-01 (FIG. 37C), TF-1 (FIG. 37D), K562 (FIG. 37E), HEL (FIG. 37F), and HCT116 (FIG. 37G).

FIGS. 38A-38D are bar graphs showing DNA content and Annexin V staining of in the indicated cell lines upon treatment with CA (mean±s.e.m., n=3) including MOLM-14 (FIG. 38A), SKNO1 (FIG. 38B), MV4;11 (FIG. 38C), and SET-2 (FIG. 38D).

FIGS. 48A-48B are line graphs showing differential sensitivity of MV4;11 (FIG. 48A) and SKNO-1 (FIG. 48B) cells to CA upon expression of FLAG-CDK8, FLAG-CDK19, FLAG-CDK8 W105M and FLAG-CDK19 W105M, legend as in FIGS. 49A-51B (mean±s.e.m., n=3).

FIGS. 49A-51B are line graphs showing that expression of FLAG-CDK8 W105M or FLAG-CDK19 W105M in MOLM-14 (FIGS. 49A and 49B), MV4;11 (FIGS. 50A and 50B), and SKNO-1 (FIGS. 51A and 51B) cells does not confer resistance to antiproliferative agents, paclitaxel and doxorubicin (mean±s.e.m., n=3).

FIG. 52 illustrates a sequence alignment of human CDKs. The sequence alignment was performed on segments of CDK1-20 (SEQ. ID NO. 1-21) using Clustal Omega. The following sequence fragments were aligned:

CDK1
(SEQ. ID NO. 1)
LYLIFEFLSMDLKKYLDSIP

CDK2
(SEQ. ID NO. 2)
LYLVFEFLHQDLKKFMDASA

CDK3
(SEQ. ID NO. 3)
LYLVFEFLSQDLKKYMDSTP

CDK4
(SEQ. ID NO. 4)
VTLVFEHVDQDLRTYLDKAP

CDK5
(SEQ. ID NO. 5)
LTLVFEFCDQDLKKYFDSCN

CDK6
(SEQ. ID NO. 6)
LTLVFEHVDQDLTTYLDKVP

CDK7
(SEQ. ID NO. 7)
ISLVFDFMETDLEVIIKDNS

CDK8
(SEQ. ID NO. 8)
VWLLFDYAEHDLWHIIKFHRASKANK

CDK9
(SEQ. ID NO. 9)
IYLVFDFCEHDLAGLLSNVL

CDK10
(SEQ. ID NO. 10)
IFLVMGYCEQDLASLLENMP

CDK11A
(SEQ. ID NO. 11)
IYIVMNYVEHDLKSLMETMK

CDK11B
(SEQ. ID NO. 12)
IYIVMNYVEHDLKSLMETMK

CDK12
(SEQ. ID NO. 13)
FYLVFEYMDHDLMGLLESGL

CDK13
(SEQ. ID NO. 14)
FYLVFEYMDHDLMGLLESGL

CDK14
(SEQ. ID NO. 15)
LTLVFEYVHTDLCQYMDKHP

CDK15
(SEQ. ID NO. 16)
LTFVFEYMHTDLAQYMSQHP

-continued

```
CDK16
                                          (SEQ. ID NO. 17)
LTLVFEYLDKDLKQYLDDCG

CDK17
                                          (SEQ. ID NO. 18)
LTLVFEYLDKDLKQYMDDCG

CDK18
                                          (SEQ. ID NO. 19)
LTLVFEYLDSDLKQYLDHCG

CDK19
                                          (SEQ. ID NO. 20)
VWLLFDYAEHDLWHIIKFHRASKANK

CDK20
                                          (SEQ. ID NO. 21)
FVLAFEFMLSDLAEVVRHAQ
```

The unique Trp105 residue in CDK8 and CDK19 is highlighted, and is absent from other CDKs. UniProt Knowledgebase entries: CDK1, P06493; CDK2, P24941; CDK3, Q00526; CDK4, P11802; CDK5, Q00535; CDK6, Q00534; CDK7, P50613; CDK8, P49336; CDK9, P50750; CDK10, Q15131; CDK11A, Q9UQ88; CDK11B, P21127; CDK12, Q9NYV4; CDK13, Q14004; CDK14, O94921; CDK15, Q96Q40; CDK16, Q00536; CDK17, Q00537; CDK18, Q07002; CDK19, Q9BWU1; CDK20, Q8IZL9.

FIGS. 53A-53D are GSEA plots showing positive enrichment of SE-associated genes (SE genes) BRD4/K27ac (FIG. 53A), CDK8/K27ac (FIG. 53B), MED1 (FIG. 53C), H3K27ac (FIG. 53D), defined by the ChIP-seq signal for indicated factors, with 3 h CA treatment in MOLM-14 cells (differential expression vs. DMSO controls).

Figure 53A:
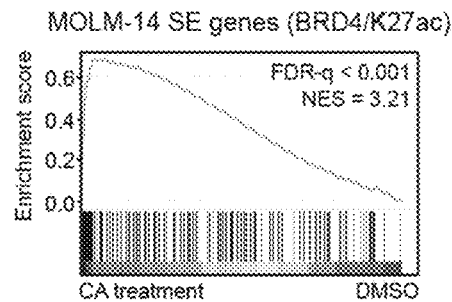
Figure 53B:
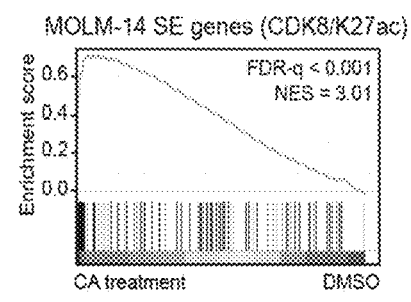
Figure 53C:
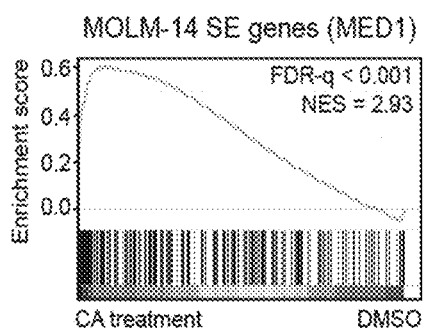
Figure 53D:
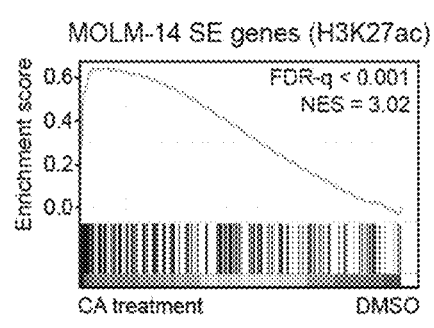
Figure 53E:
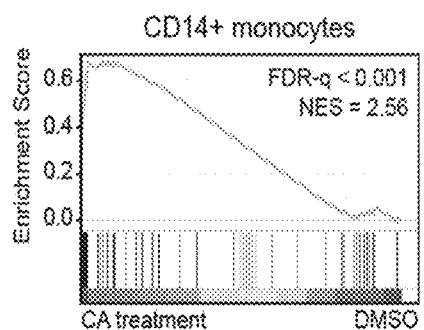

FIG. 53E is a GSEA plot showing positive enrichment of CD14+ master TFs upon 3 h CA treatment (MOLM-14 differential expression).

FIGS. 54-55 are line graphs showing RNA pol II ChIP-seq metagene profile plots of unchanged genes, SE-associated genes, CA upregulated genes with vehicle treatment and CA upregulated genes with 6 h CA treatment.

FIGS. 56A-56B are cumulative distribution plots of RNA pol II traveling ratio (TR) after treatment with CA (25 nM, 6 h) or vehicle across genes ≥1.2-fold downregulated by CA after 3 h (1.16-fold, p=0.31, KS test) (FIG. 56A) and across all genes (FIG. 56B) (1.21-fold, p<2.2e-16, KS test).

FIGS. 57A-57B are bar graphs showing that CA does not significantly change the total amount of RNA (FIG. 57A) or mRNA (FIG. 57B) in MOLM-14 or MV4;11 cells (mean±s.e.m., n=3) after treatment with CA (25 nM, 3 h).

Figure 58:
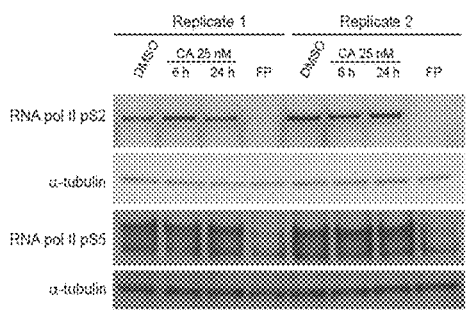

FIG. 58 is an immunoblot showing that global levels of RNA pol II pS2 or RNA pol II pS5 do not change after treatment with CA. Flavopiridol (FP) was used at 300 nM as a positive control.

Figure 59:
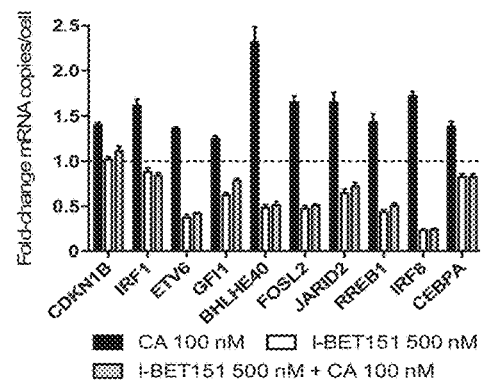
Figure 60A:
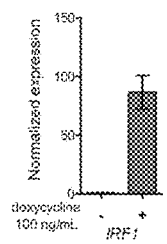
Figure 60B:
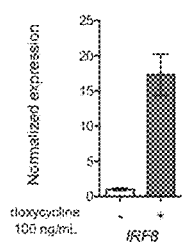
Figure 60C:
Figure 60D:
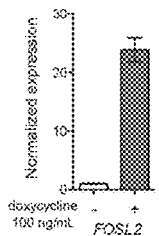
Figure 60E:
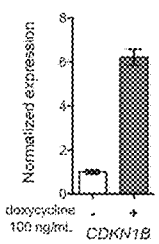

FIG. 59 is a bar graph showing fold-change in mRNA copies/cell of selected SE-associated genes upon 3 h treatment with 100 nM CA, 500 nM I-BET151 or 3 h I-BET151 treatment followed by addition of CA for 3 h (mean±s.e.m., n=3).

FIGS. 60A-60E are bar graphs showing mRNA expression levels of indicated SE-associated genes IRF1 (FIG. 60A), IRF8 (FIG. 60B), ETV6 (FIG. 60C), FOSL2 (FIG. 60D), or CDKN1B (FIG. 60E) either 1 day (FLAG-IRF1, FLAG-IRF8) or 3 days (FLAG-CDKN1B, FLAG-FOSL2, FLAG-ETV6) after induction with doxycycline.

Figure 61:
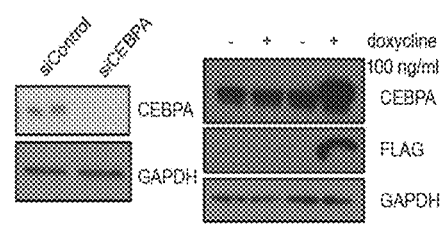

FIG. 61 is an immunoblot showing protein levels of CEBPA 4 days after siRNA electroporation or 1 day after doxycycline-induced expression.

Figure 62:
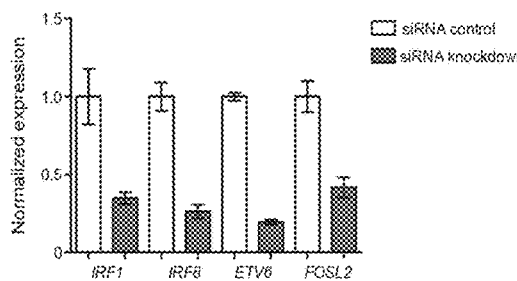

FIG. 62 is a bar graph showing mRNA expression levels of indicated SE-associated genes 2 days after siRNA electroporation (mean±s.e.m., n=3).

Figure 63A:
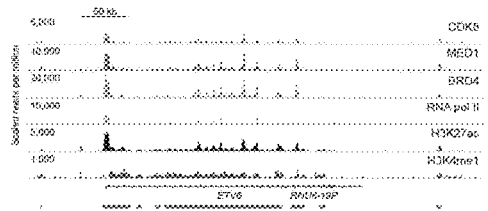
Figure 63B:
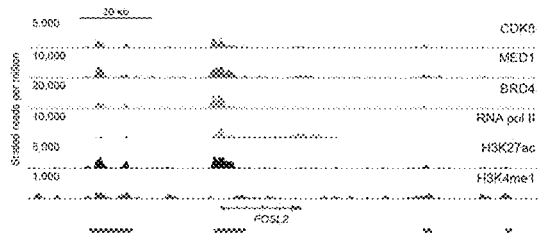

FIGS. 63A-63B are ChIP-seq binding profiles at the FOSL2 (FIG. 63B) and ETV6 (FIG. 63A) loci.

Figure 64:
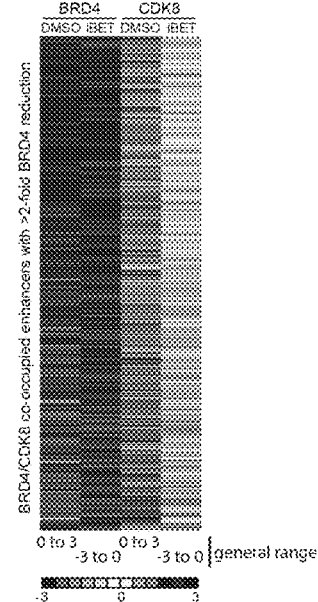

FIG. 64 are heatmaps showing BRD4 and CDK8 ChIP-seq on regions depleted of BRD4 >2-fold upon I-BET151 treatment for 6 h before and after drug treatment.

Figure 65:
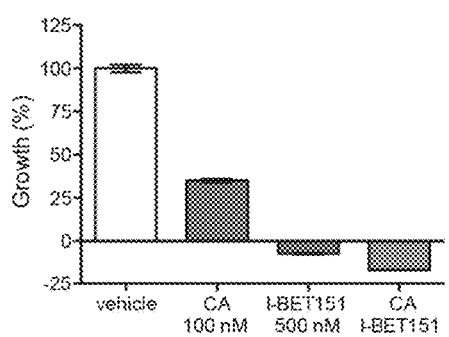

FIG. 65 is a bar graph showing the effect of 3-day treatment with CA, I-BET151 or the combination of CA and I-BET151 on proliferation (Growth (%)) of MOLM-14 cells (mean±s.e.m., n=6).

Figure 66:
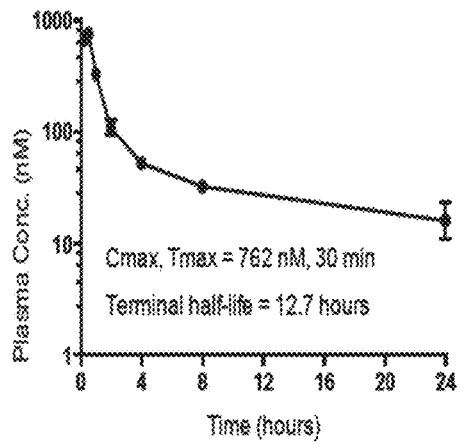

FIG. 66 is a line graph showing plasma concentration (nM) of CA following single IP administration of 1 mg kg CA to male CD-1 mice (mean±s.e.m., n=3).

Figure 67:
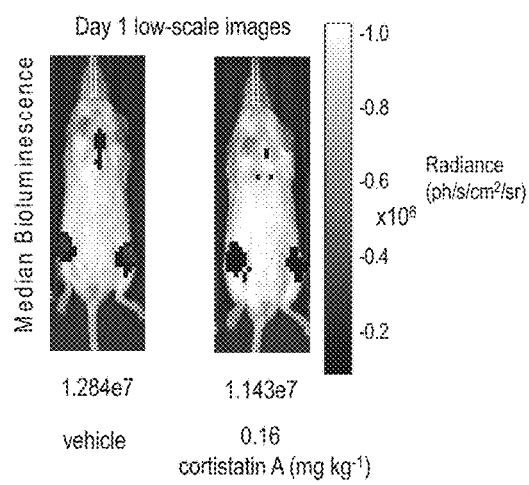

FIG. 67 shows bioluminescence images with the median bioluminescence for each treatment group on treatment day 1, showing engraftment of MV4;11 leukemia cells.

Figure 68A:
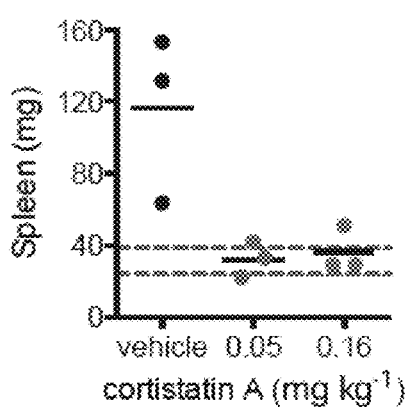
Figure 68B:
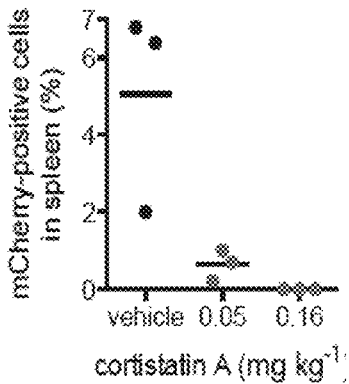
Figure 68C:
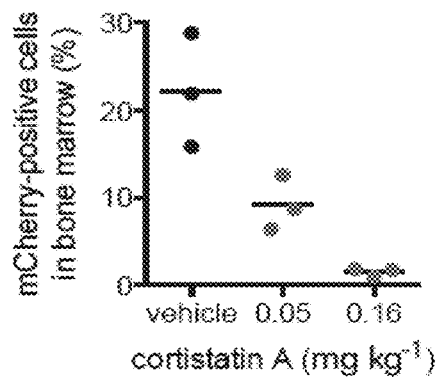

FIGS. 68A-68C are dot plots showing spleen (mg) weight (FIG. 68A) or mCherry-positive cells in spleen (%) (FIGS. 68B and 68C) after treatment of vehicle or CA (mg/kg). Specifically, 30 days after treatment initiation, the mouse with the highest, lowest, and median day 29 bioluminescence for each treatment group was sacrificed and the spleen weight (p<0.05) and percentage of MV4;11 cells (mCherry-positive) in the spleen (p<0.05) and femur bone marrow (p<0.01) was determined. Dotted lines mark the range within 1 s.d. of the mean for healthy 8-week old female NOD-SCID mice, p-values determined by one-way ANOVA.

Figure 69:
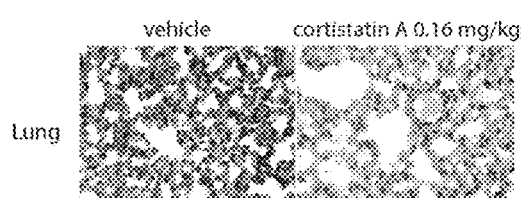
Figure 72:
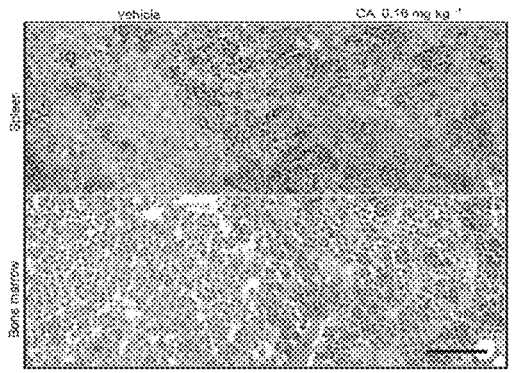

FIGS. 69 and 72 show hematoxylin and eosin staining of day 30 lung, spleen, and bone marrow samples of the median mice in FIGS. 68A-68C. Hypercellular alveoli, evidence of leukemia infiltration, are only observable with vehicle treatment. Spleen sample from the vehicle-treated mouse reveals a large population of cells with a round nucleus and relatively abundant cytoplasm. Similarly, all cells in the vehicle-treated bone marrow have round to oval nuclei and abundant cytoplasm, while normal erythroid or myeloid cells are not observed, suggesting that the spleen and the bone marrow have been dominated by the leukemia cells. In contrast, the pulp from the CA-treated mouse spleen shows a heterogeneous population of mature red blood cells, nucleated red blood cells, immature myeloid cells and megakaryocytes. The bone marrow from a CA-treated mouse also exhibits a mixture of erythroid precursors, myeloid precursors, and megakaryocytes. Scale bars, 250 μm.

Figure 70:
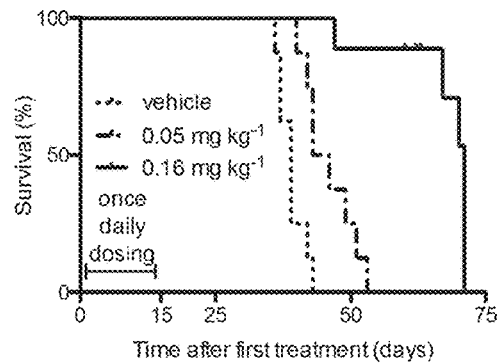

FIG. 70 is a line graph showing survival (%) vs. time after first treatment (days) using a Kaplan-Meier survival analysis (n=8, p<0.0001, log-rank test).

Figure 29:
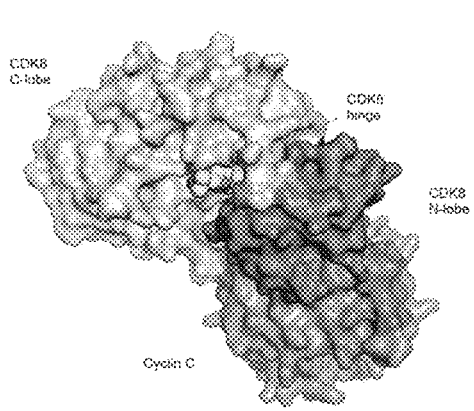
FIG. 29 is a 2.4 Å crystal structure of the human CA/CDK8/CCNC ternary complex shown as a Corey-Pauling-Koltun (CPK) model.
Figure 71:
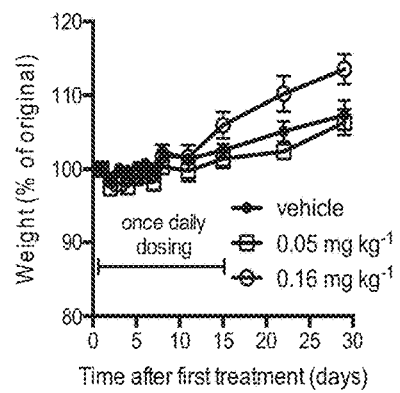

FIG. 71 is a line graph showing mean body weight±s.e.m., n=11, of mice in FIG. 29.

Figure 73:
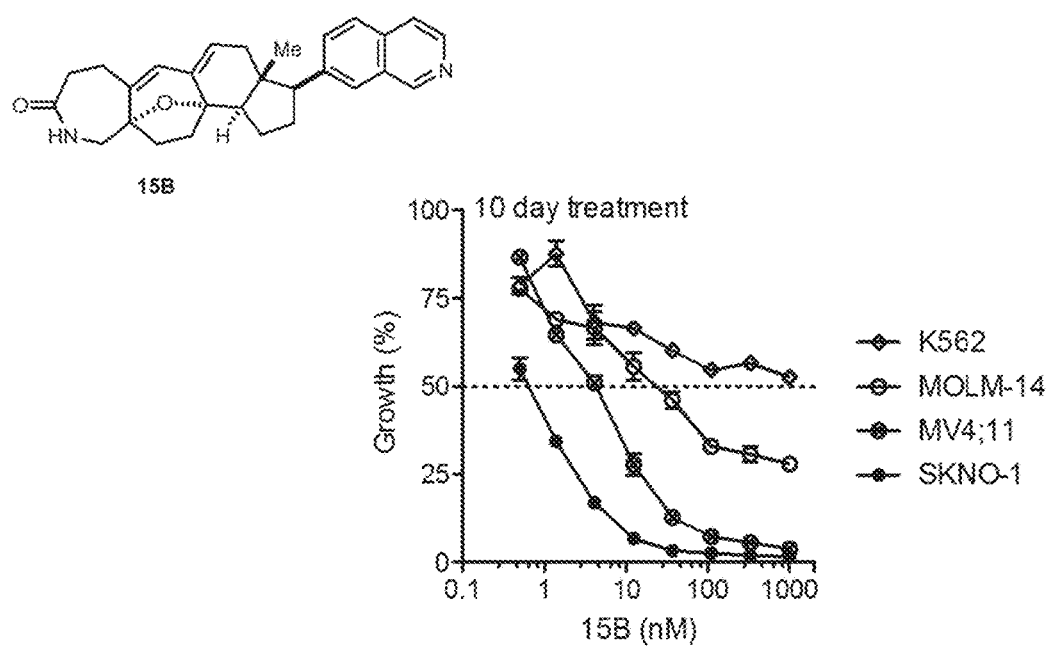

FIG. 73 is a line graph showing growth inhibition using lactam (15B) in human leukemia cell lines SKNO-1, MV4; 11, MOLM-14 and K562. Cells were treated with 15B for 10 days with passaging on days 3 and 7 (mean±s.e.m., n=3).

Figure 74:
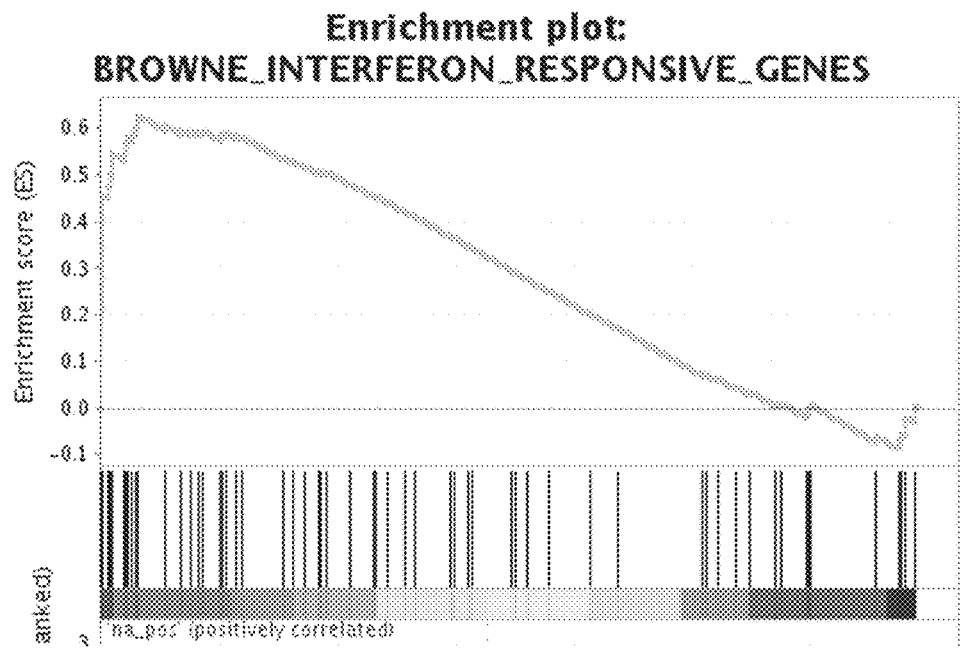
Figure 75:
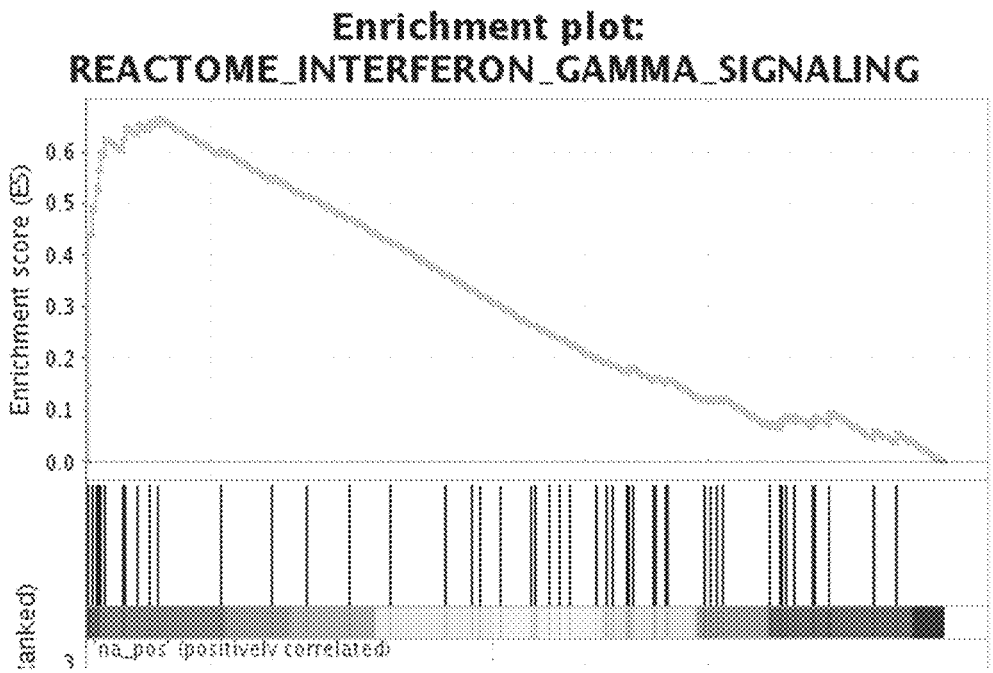

FIGS. 74 and 75 are mountain plots generated by Gene Set Enrichment Analysis (GSEA) from the Broad Molecular Signatures C2 database demonstrating that 24-hour CA treatment increases expression of genes in MOLM1-14 AML cells that are identified as interferon responsive genes (FIG. 74, Normalized Enrichment Score 2.2, False Discovery Rate q=0.005) and interferon gamma signaling genes (FIG. 75, Normalized Enrichment Score=2.26, False Discovery Rate q=0.002).

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. Also contemplated are stereoisomers featuring either a Z or E configuration, or mixture thereof, about a double bond. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGrawHill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures. The mixture may contain two enantiomers, two diastereomers, or a mixture of diastereomers and enantiomers.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. In some embodiments, a compound described herein is prepared by asymmetric synthesis with an enzyme. Enantiomers and diastereomers may be separated by means of fractional crystallization or chromatography (e.g., HPLC with a chiral column). Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In some embodiments, the carbon to which $R^{B1}$ or $R^{B2}$ is attached is in the (5) configuration. In some embodiments, the carbon to which $R^{B1}$ or $R^{B2}$ is attached is in the (R) configuration. In some embodiments, the carbon to which $R^{B1}$ or $R^{B2}$ is attached is in the same configuration as a naturally occurring cortistatin (e.g., cortistatin A, cortistatin B). In some embodiments, the carbon to which $R^{B1}$ or $R^{B2}$ is attached is in the opposite configuration as a naturally occurring cortistatin (e.g., cortistatin A, cortistatin B). In some embodiments, the carbon to which $Y^1$ or $Y^2$ is attached is in the (5) configuration. In some embodiments, the carbon to which $Y^1$ or $Y^2$ is attached is in the (R) configuration. In some embodiments, the carbon to which $Y^1$ or $Y^2$ is attached is in the same configuration as a naturally occurring cortistatin (e.g., cortistatin A, cortistatin B). In some embodiments, the carbon to which $Y^1$ or $Y^2$ is attached is in the opposite configuration as a naturally occurring cortistatin (e.g., cortistatin A, cortistatin B). In some embodiments, the carbon to which $R^3$ is attached is in the (5) configuration. In some embodiments, the carbon to which $R^3$ is attached is in the (R) configuration. In some embodiments, the carbon to which $R^3$ is attached is in the same configuration as a naturally occurring cortistatin (e.g., cortistatin A, cortistatin B). In some embodiments, the carbon to which $R^3$ is attached is in the opposite configuration as a naturally occurring cortistatin (e.g., cortistatin A, cortistatin B). In some embodiments, the carbon to which $R^5$ is attached is in the (5) configuration. In some embodiments, the carbon to which $R^5$ is attached is in the (R) configuration. In some embodiments, the carbon to which $R^5$ is attached is in the same configuration as a naturally occurring cortistatin (e.g., cortistatin A, cortistatin B). In some embodiments, the carbon to which $R^5$ is attached is in the opposite configuration as a naturally occurring cortistatin (e.g., cortistatin A, cortistatin B).

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include $CF_3$, $CF_2CF_3$, $CF_2CF_2CF_3$, $CCl_3$, $CFCl_2$, $CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carboncarbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carboncarbon triple bonds can be internal (such as in 2-butynyl) or terminal (such as in 1-butynyl). Examples of C$_2$-4 alkynyl groups include, without limitation, ethynyl (C$_2$), 1-propynyl (C$_3$), 2-propynyl (C$_3$), 1 butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non aromatic cyclic hydrocarbon group having from 3 to 14 ring carbon atoms ("C$_{3-14}$ carbocyclyl") and zero heteroatoms in the nonaromatic ring system. In some embodiments, a carbocyclyl group has 3 to 10 ring carbon atoms ("C$_{3-10}$ carbocyclyl"). In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_4$-6 carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carboncarbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_4$-6 cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3 to 14 membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8 membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_6$-14 aryl. In certain embodiments, the aryl group is a substituted $C_6$-14 aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6 membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7 membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —NR$^{bb}$P(=O)(OR$^{cc}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR, —SOR, —C(=S)N(R$^{cc}$)$_2$, —C(=O)SR$^{cc}$, —C(=S)SR$^{cc}$ —P(=O)(R$^{aa}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)

NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl), —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, an exemplary substituent is selected from the group consisting of halogen, —CN, —NO$_2$, —N$_3$, —SO$_2$H, —SO$_3$H, —OH, —OR$^{aa}$, —N($R^{bb}$)$_2$, —SH, —SR$^{aa}$, —SSR$^{cc}$, —C(=O)R$^{aa}$, —CO$_2$H, —CHO, —CO$_2$R$^{aa}$, —OC(=O)R$^{aa}$, —OCO$_2$R$^{aa}$, —C(=O)N($R^{bb}$)$_2$, —OC(=O)N($R^{bb}$)$_2$, —NR$^{bb}$C(=O)R$^{aa}$, —NR$^{bb}$CO$_2$R$^{aa}$, —NR$^{bb}$C(=O)N($R^{bb}$)$_2$, —C(=O)NR$^{bb}$ SO$_2$R$^{aa}$, —NR$^{bb}$SO$_2$R$^{aa}$, —SO$_2$N($R^{bb}$)$_2$, —SO$_2$R$^{aa}$, —S(=O)R$^{aa}$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene- 1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, a "leaving group" is an art-understood term referring to a molecular fragment that departs with a pair of electrons in heterolytic bond cleavage, wherein the molecular fragment is an anion or neutral molecule. See, for example, Smith, *March Advanced Organic Chemistry* 6th ed. (501-502). Exemplary leaving groups include, but are not limited to, halo (e.g., chloro, bromo, iodo) and —OSO$_2$R$^{aa}$, wherein R$^{aa}$ as defined herein. The group —OSO$_2$R$^{aa}$ encompasses leaving groups such as tosyl, mesyl, and besyl, wherein R$^{aa}$ is optionally substituted alkyl (e.g., —CH$_3$) or optionally substituted aryl (e.g., phenyl, tolyl).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON($R^{bb}$)$_2$, —OC(=O)SR$^{aa}$, —OC(=O)R$^{aa}$, —OCO$_2$R$^{aa}$, —OC(=O)N($R^{bb}$)$_2$, —OC(=NR$^{bb}$)R$^{aa}$, —OC(=NR$^{bb}$)OR$^{aa}$, —OC(=NR$^{bb}$)N($R^{bb}$)$_2$, —OS(=O)R$^{aa}$, —OSO$_2$R$^{a}$, —OSi($R^{aa}$)$_3$, —OP($R^{cc}$)$_2$, —OP(=O)($R^{aa}$)$_2$, and —OP(=O)(OR$^{cc}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino or a disubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)R$^{aa}$, —NHCO$_2$R$^{aa}$, —NHC(=O)N($R^{bb}$)$_2$, —NHC(=NR$^{bb}$)N($R^{bb}$)$_2$, —NHSO$_2$R$^{aa}$, and —NHP(=O)(OR$^{cc}$)$_2$, wherein R$^{aa}$, R$^{bb}$ and R$^{cc}$ are as defined herein, and wherein R$^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —NR$^{bb}$ C(=O)R$^{aa}$, —NR$^{bb}$CO$_2$R$^{aa}$, —NR$^{bb}$C(=O)N($R^{bb}$)$_2$, —NR$^{bb}$C(=NR$^{bb}$)N($R^{bb}$)$_2$, —NR$^{bb}$SO$_2$R$^{aa}$, and —NR$^{bb}$P(=O)(OR$^{cc}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "sulfonyl" refers to a group selected from —SO$_2$N($R^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is $sp^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N($R^{bb}$)$_2$, —C(=O)NR$^{bb}$SO$_2$R, —C(=S)N($R^{bb}$)$_2$), and imines (—C(=NR$^{bb}$)R$^{aa}$, —C(=NR$^{bb}$)OR$^{aa}$), —C(=NR$^{bb}$)N($R^{bb}$)$_2$), wherein R$^{aa}$ and R$^{bb}$ are as defined herein.

As used herein, the term "silyl" refers to the group —Si($R^{aa}$)$_3$, wherein R$^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N($R^{cc}$)$_2$, —CN, —C(=O)R$^{aa}$, —C(=O)N($R^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N($R^{cc}$)$_2$, —SO$_2$N($R^{cc}$)$_2$, —SO$_2$R$^{cc}$, —SO$_2$OR, —SOR$^{aa}$, —C(=S)N($R^{cc}$)$_2$, —C(=O)SR$^{cc}$, —C(=S)SR$^{cc}$, —P(=O)($R^{aa}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzi soxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), J3-trimethyl silylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p- nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(=O)(R^{aa})_2$, and $—P(=O)(OR^{cc})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(=O)(R^{aa})_2$, and $—P(=O)(OR^{cc})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject", or "host" or "patient" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards, slows, or inhibits the progression of the disease, disorder or condition ("therapeutic treatment"), and also contemplates an action that occurs before a subject begins to suffer from the specified disease, disorder or condition ("prophylactic treatment").

"Disease," "disorder" and "condition" are used interchangeably herein, and refers to all conditions contemplated useful for treatment, including, but not limited to, treatment of cancer and infections.

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces, inhibits, or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "modulating" refers to the ability of a compound to increase or inhibit a particular biological process (e.g., kinase activity, overexpression), e.g., for example in a cell (e.g., in vitro such as a cell in a cell culture, or in vivo such as a cell in a subject) relative to vehicle.

As used herein "inhibition", "inhibiting", "inhibit" and "inhibitor", and the like, refer to the ability of a compound to reduce, slow, halt or prevent activity of a particular biological process (e.g., kinase activity, overexpression, infection), e.g., for example in a cell (e.g., in vitro such as a cell in a cell culture, or in vivo such as a cell in a subject) relative to vehicle.

As used herein "increasing" or "increase", and the like, refer to the ability of a compound to stimulate activity of a particular biological process (e.g., kinase activity), e.g., for example in a cell (e.g., in vitro such as a cell in a cell culture, or in vivo such as a cell in a subject) relative to vehicle.

DETAILED DESCRIPTION OF THE INVENTION

As generally described herein, new cortistatin analogs are provided. In one embodiment, the described compounds may be synthesized, in part, by the Beckmann rearrangement of an oxime of Formula (C') or (C") to provide lactam compounds of Formula (A1') or (A1"), and/or (A2') or (A2") wherein $R^N$ is hydrogen or (upon optional substitution) a non-hydrogen group. See, e.g., Scheme 2A and 2B, supra. The oxime of Formula (C') or (C") may be generated via condensation of a hydroxylamine with a ketone of Formula (B') or (B"). See, e.g., Scheme 3A and 3B, supra. The synthesis of the ketone starting material of Formula (B') or (B") is described herein (see., e.g., Scheme 1, supra), and is also more fully described in PCT Application No. PCT/US2014/072365, incorporated herein by reference. Compounds of Formula (E1') or (E1") may be generated from compounds of Formula (A1') or (A1"), and/or (A2') or (A2"). See, e.g., Scheme 4A and 4B, supra. Compounds of Formula (E2') or (E2") may be generated from compounds of Formula (B*') or (B*"). See, e.g., Scheme 5A and 5B, supra.

Compounds of Formula (A1'), (A1"). (A2'), (A2"), (B'), (B"), (C'), (C"), wherein oxime of Formula (C') or (C") encompasses isomers (C1'), (C1"), (C2') and (C2"), (D1'), (D1″) (D2′), (D2″), (E1′), (E1″), (E2′), (E2″), (G1′), and (G1″) and pharmaceutically acceptable salts thereof, are thus contemplated herein:
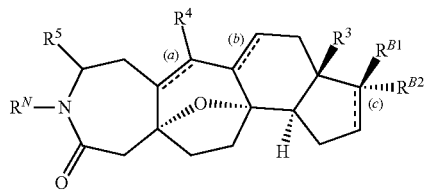
(A1′)
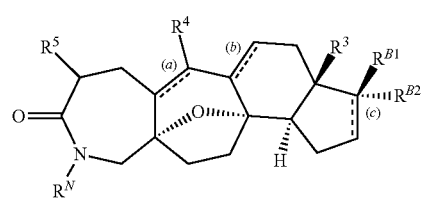
(A2′)
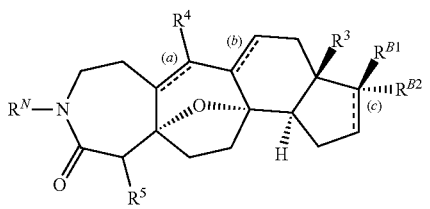
(A1″)
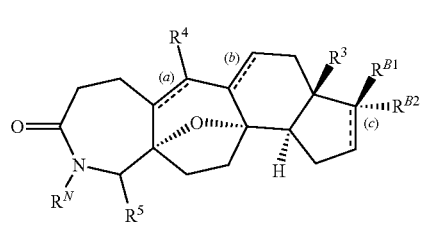
(A2″)
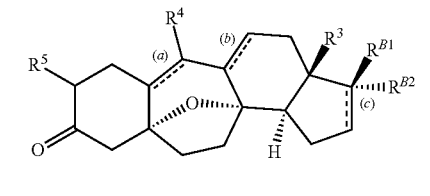
(B′)
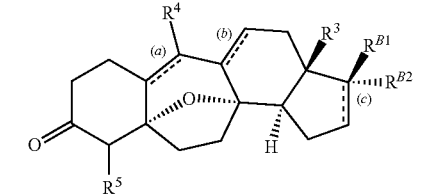
(B″)
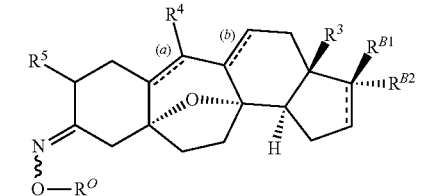
(C′)
-continued
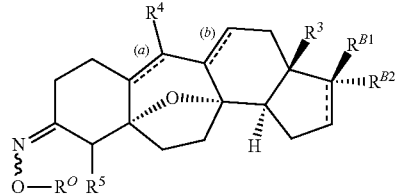
(C″)
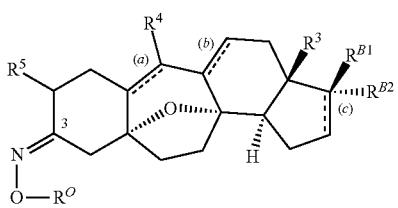
(C1′)
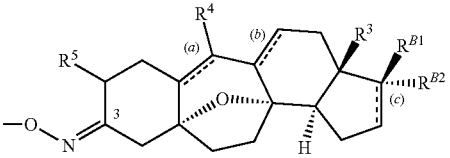
(C2′)
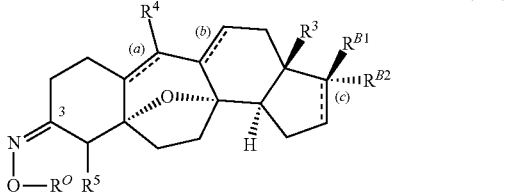
(C1″)
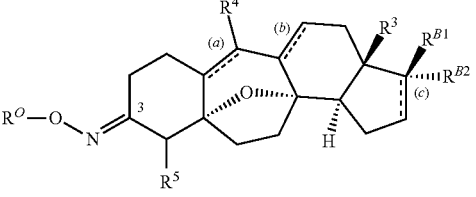
(C2″)
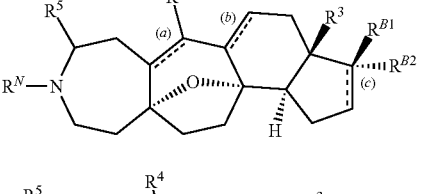
(D1′)
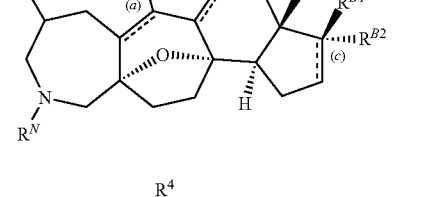
(D2′)
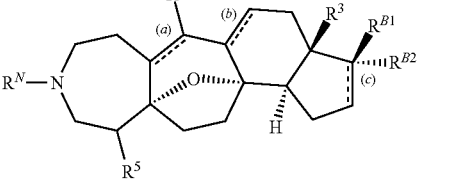
(D1″)

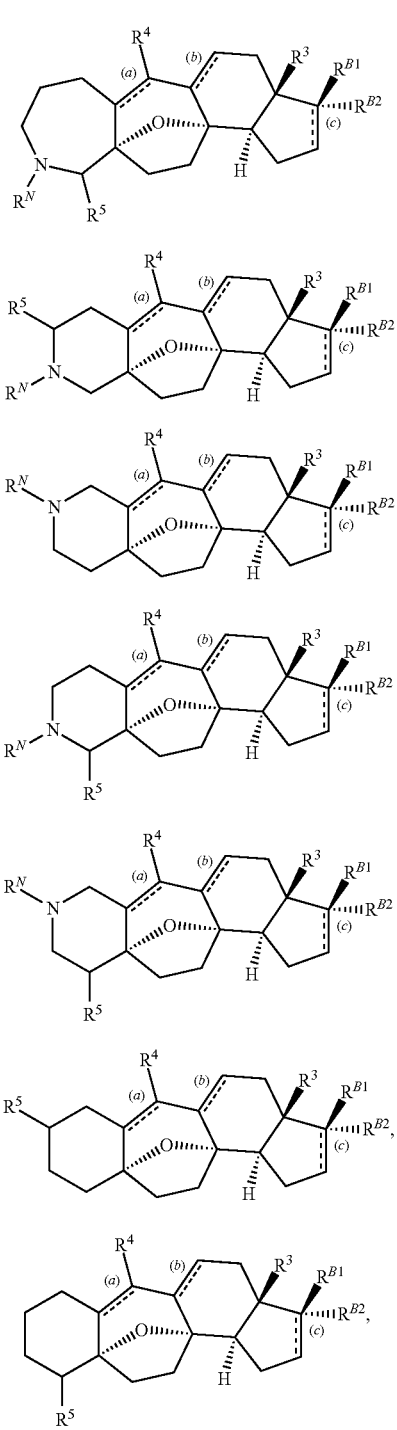

or a pharmaceutically acceptable salt thereof;
wherein:
R$^N$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —C(=O)R$^A$, —C(=O)OR$^A$, C(=O)N(R$^A$)$_2$, —S(=O)$_2$R$^A$, or a nitrogen protecting group;

R$^O$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)N(R$^A$)$_2$, —S(=O)$_2$R$^A$, —Si(R$^A$)$_3$, —P(=O)(R$^A$)$_2$, —P(=O)(OR$^A$)$_2$, —P(=O)(NR$^A$)$_2$, —P(=O)$_2$R$^A$, —P(=O)$_2$(OR$^A$), —P(=O)$_2$N(R$^A$)$_2$, or an oxygen protecting group;

R$^3$ is hydrogen or optionally substituted alkyl;

R$^4$ is hydrogen, halogen, optionally substituted alkyl, or —Si(R$^A$)$_3$;

R$^5$ is hydrogen, halogen, optionally substituted alkyl, —OR$^A$, —OC(=O)R$^A$, —OC(=O)OR$^A$, —OC(=O)N(R$^A$)$_2$, —OS(=O)$_2$R$^A$, —N$_3$, —N(R$^A$)$_2$, —NR$^A$C(=O)R$^A$, —NR$^A$C(=O)OR$^A$, —NR$^A$C(=O)N(R$^A$)$_2$, —NR$^A$S(=O)$_2$R$^A$, or —C(R$^A$)$_3$;

each instance of ≡, designated as (a), (b), and (c), represents a single or double bond, provided that when ≡ designated as (c) represents a double bond, then one of R$^{B1}$ and R$^{B2}$ is absent, and provided that when ≡ designated as (c) represents a single bond, then both R$^{B1}$ and R$^{B2}$ are present;

each instance of R$^{B1}$ and R$^{B2}$ is, independently, hydrogen, -L$_1$-R$^{B3}$, or —X$^A$R$^A$ wherein X$^A$ is —O—, —S—, or —N(R$^A$)—; or R$^{B1}$ and R$^{B2}$ are joined to form an oxo group, provided that at least one of R$^{B1}$ and R$^{B2}$ is not hydrogen;

L$_1$ is a bond, —CH(CH$_3$)(CH$_2$)$_2$—, —CH(CH$_3$)—CH=CH—, —C(=O)—, —C(=O)O—, —C(=O)S—, —C(=O)N(R$^L$)—, or —N(R$^L$)—(C(R$^{LL}$)$_2$)$_p$—, wherein R$^L$ is hydrogen, optionally substituted alkyl, or a nitrogen protecting group, each instance of R$^{LL}$ is independently hydrogen, halogen, or optionally substituted alkyl, and p is 0, 1, or 2;

R$^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when L$_1$ is a bond, then R$^{B3}$ is not hydrogen; and each instance of R$^A$ is independently hydrogen, halogen (e.g., when attached to a phosphorus atom), optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen, optionally when attached to N the two R$^A$ groups may be joined to form an optionally substituted heterocyclyl or optionally substituted heteroaryl ring, and optionally when R$^{B1}$ and R$^{B2}$ are each —X$^A$R$^A$ then two R$^A$ groups may be joined to form an optionally substituted heterocyclyl ring.

It is generally understood that any atom encompassed by any of the formula described herein may be replaced with an isotope of that atom, e.g., for example, a hydrogen atom ($^1$H) may be replaced with a deuterium ($^2$H, D) or tritium ($^3$H, T) atom, a carbon atom ($^{12}$C) may be replaced with its $^{14}$C isotope, and a fluorine atom ($^{18}$F) may be replaced by its $^{19}$F isotope.

In one embodiment, the present invention includes compounds of Formulas (A1'), (A2'), (C'), (C1'), (C2'), (D1'), (D2'), (E1'), (E2'), (A1''), (A2''), (C''), (C1''), (C2''), (D1''), (D2''), (E1''), (E2''), (G1'), or (G1'') and additional active compounds described herein, and the use of these compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. A typical isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group when at least one of the variables within the R group is hydrogen (e.g., $^2H$ or D) or alkyl (e.g., CHD, $CD_2$, $CD_3$). For example, when any of R groups are, or contain for example through substitution, methyl, ethyl, or another alkyl group, the alkyl residue can be deuterated, e.g., $CD_3$, $CH_2CD_3$ or $CD_2CD_3$. In certain other embodiments, when any of the above mentioned R groups are hydrogen, the hydrogen may be isotopically enriched as deuterium (i.e., $^2H$).

In some embodiments, $R^{B1}$ is deuterium. In some embodiments, $R^{B1}$ comprises an isotopically enriched atom (e.g., $^2H$, $^3H$, $^{13}C$, $^{14}C$, $^{18}F$). In some embodiments, $R^{B2}$ is deuterium. In some embodiments, $R^{B2}$ comprises an isotopically enriched atom (e.g., $^2H$, $^3H$, $^{13}C$, $^{14}C$, $^8F$). In some embodiments, $R^3$ is deuterium. In some embodiments, $R^3$ comprises an isotopically enriched atom (e.g., $^2H$, $^3H$, $^{13}C$, $^{14}C$, $^{18}F$). In some embodiments, $R^4$ is deuterium. In some embodiments, $R^4$ comprises an isotopically enriched atom (e.g., $^2H$, $^3H$, $^{13}C$, $^{14}C$, $^{18}F$). In some embodiments, $R^5$ is deuterium. In some embodiments, $R^5$ comprises an isotopically enriched atom (e.g., $^2H$, $^3H$, $^{13}C$, $^{14}C$, $^{18}F$). In some embodiments, $R^N$ is deuterium. In some embodiments, $R^N$ comprises an isotopically enriched atom (e.g., $^2H$, $^3H$, $^{13}C$, $^{14}C$, $^{18}F$). In some embodiments, $R^O$ is deuterium. In some embodiments, $R^O$ comprises an isotopically enriched atom (e.g., $^2H$, $^3H$, $^{13}C$, $^{14}C$, $^{18}F$). In some embodiments, $R^1$ or $R^2$ is deuterium. In some embodiments, $R^1$ or $R^2$ comprises an isotopically enriched atom (e.g., $^2H$, $^3H$, $^{13}C$, $^{14}C$, $^{18}F$). In some embodiments, a hydrogen on ring A (see below) is substituted with deuterium. In some embodiments, a hydrogen on ring B is substituted with deuterium. In some embodiments, a hydrogen on ring C is substituted with deuterium. In some embodiments, a hydrogen on ring D is substituted with deuterium.

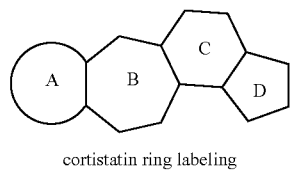

cortistatin ring labeling

In some embodiments, $R^5$ or another position of ring A is deuterated by trapping of an enolate with a deuterium source, such as $D_2O$ or a deuterated acid. In some embodiments, a position of ring B, C, or D is deuterated by reduction of double bond (a), (b), or (c) respectively with a deuterium source (e.g., D2, HD, a deuterated borohydride). In some embodiments, a position of ring D is deuterated by trapping of an enolate (e.g., for a compound of Formula (XXI)) with a deuterium source, such as $D_2O$ or a deuterated acid.

Group $R^N$

As generally defined herein, $R^N$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —C(=O) $R^A$, —C(=O)$OR^A$, —C(=O)N($R^A$)$_2$, —S(=O)$_2R^A$, or a nitrogen protecting group.

In certain embodiments, $R^N$ is hydrogen. It is generally understood herein that compounds of Formula (A1'), (A2'), (A1"), or (A2"), wherein $R^N$ is hydrogen, may be prepared upon rearrangement of an oxime of Formula (C') or (C") as depicted in Scheme 2A and 2B, supra.

In certain embodiments, $R^N$ is a non-hydrogen group, e.g., an optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —C(=O)$R^A$, —C(=O)$OR^A$, —C(=O)N($R^A$)$_2$, —S(=O)$_2R^A$, or a nitrogen protecting group. The free amino moiety of the lactam may be reacted with a compound of formula $R^N$-LG, wherein $R^N$ is a non-hydrogen group and LG is a leaving group, to provide compounds of Formula (A1'), (A2'), (A1"), or (A2"), wherein $R^N$ is a non-hydrogen group. See, e.g., Scheme 6A and 6B. Exemplary leaving groups (LG) include halo (e.g., chloro, bromo, iodo) and —$OSO_2R^{aa}$, wherein $R^{aa}$ as defined herein. The group —$OSO_2R^{aa}$ encompasses leaving groups such as tosyl, mesyl, and besyl, wherein $R^{aa}$ is optionally substituted alkyl (e.g., —$CH_3$) or optionally substituted aryl (e.g., phenyl, tolyl). Similar substitution is contemplated for protection of the amino moiety of Formula (D1'), (D2'), (E1'), (E2'), (D1"), (D2"), (E1"), and (E2").

Scheme 6A.

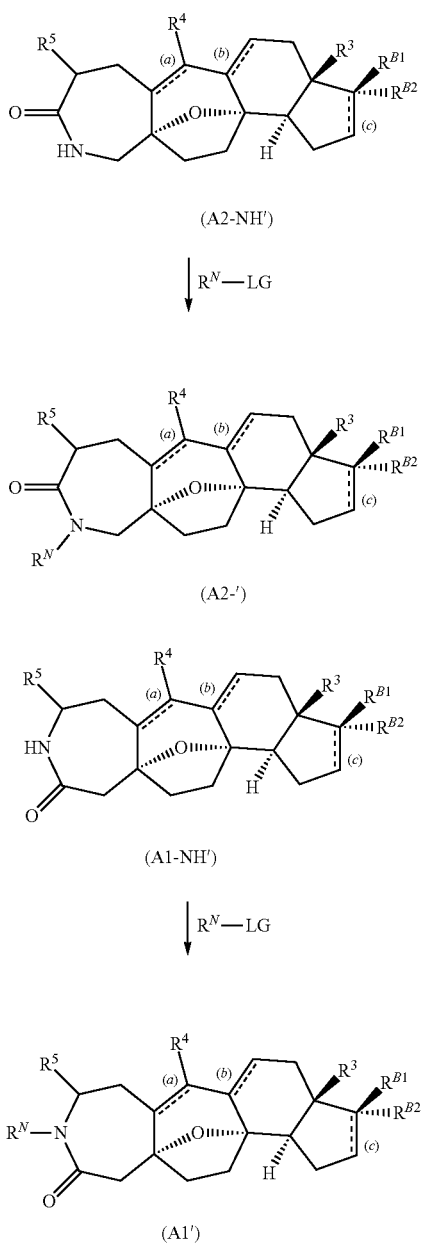

Scheme 6B.

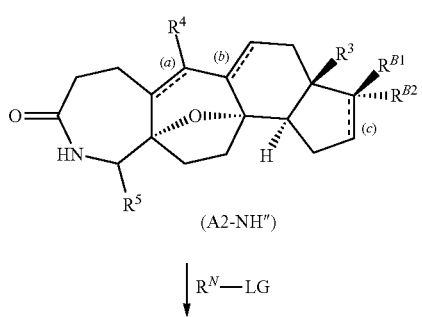

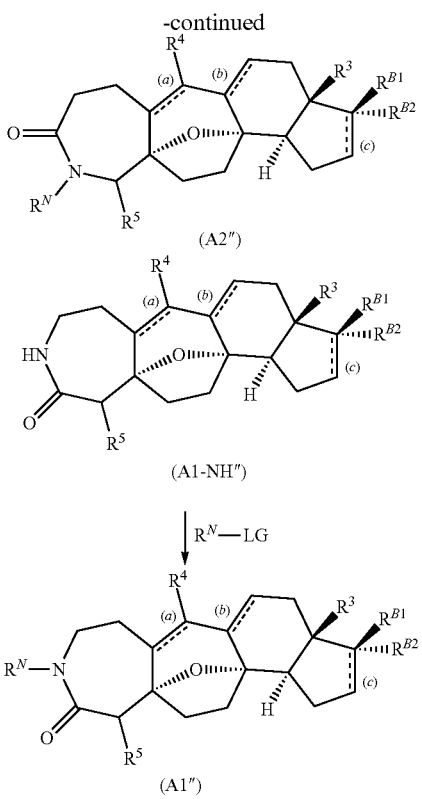

In certain embodiments, $R^N$ is optionally substituted alkyl, e.g., optionally substituted $C_{1-6}$alkyl. In certain embodiments, $R^N$ is optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl.

In certain embodiments, $R^N$ is optionally substituted alkenyl, e.g., optionally substituted $C_{2-6}$alkenyl. In certain embodiments, $R^N$ is optionally substituted $C_2$alkenyl, optionally substituted $C_3$alkenyl, optionally substituted $C_4$alkenyl, optionally substituted $C_5$alkenyl, or optionally substituted $C_6$alkenyl.

In certain embodiments, $R^N$ is optionally substituted alkynyl, e.g., optionally substituted $C_{2-6}$alkynyl. In certain embodiments, $R^N$ is optionally substituted $C_2$alkynyl, optionally substituted $C_3$alkynyl, optionally substituted $C_4$alkynyl, optionally substituted $C_5$alkynyl, or optionally substituted $C_6$alkynyl.

In certain embodiments, $R^N$ is optionally substituted carbocyclyl, e.g., optionally substituted $C_{3-6}$carbocyclyl. In certain embodiments, $R^N$ is optionally substituted C3 carbocyclyl, optionally substituted $C_4$ carbocyclyl, optionally substituted C5 carbocyclyl, or optionally substituted C6 carbocyclyl.

In certain embodiments, $R^N$ is optionally substituted heterocyclyl, e.g., optionally substituted 3-6 membered heterocyclyl. In certain embodiments, $R^N$ is optionally substituted 3-membered heterocyclyl, optionally substituted 4-membered heterocyclyl, optionally substituted 5-membered heterocyclyl, or optionally substituted 6-membered heterocyclyl In certain embodiments, $R^N$ is optionally substituted aryl, e.g., optionally substituted phenyl.

In certain embodiments, $R^N$ is optionally substituted heteroaryl, e.g., optionally substituted 5-6 membered heteroaryl.

In certain embodiments, $R^N$ is —C(=O)$R^4$, —C(=O)O$R^4$, or —C(=O)N($R^4$)$_2$. In certain embodiments, $R^4$ is optionally substituted alkyl, e.g., —CH$_3$.

In certain embodiments, $R^N$ is —S(=O)$_2R^4$. In certain embodiments, $R^4$ is optionally substituted phenyl.

In certain embodiments, $R^N$ is a nitrogen protecting group.

Group $R^O$

As generally defined herein, $R^O$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^4$, —C(=O)O$R^4$, —C(=O)N($R^4$)$_2$, —S(=O)$_2R^4$, —Si($R^4$)$_3$, —P(=O)($R^4$)$_2$, —P(=O)(O$R^4$)$_2$, —P(=O)(N$R^4$)$_2$, —P(=O)$_2R^4$, —P(=O)$_2$(O$R^4$), —P(=O)$_2$N($R^4$)$_2$, or an oxygen protecting group.

In certain embodiments, $R^O$ is hydrogen.

Alternatively, in certain embodiments, $R^O$ is a non-hydrogen group, i.e., optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^4$, —C(=O)O$R^4$, —C(=O)N($R^4$)$_2$, —S(=O)$_2R^4$, —Si($R^4$)$_3$, —P(=O)($R^4$)$_2$, —P(=O)(O$R^4$)$_2$, —P(=O)(N$R^4$)$_2$, —P(=O)$_2R^4$, —P(=O)$_2$(O$R^4$), —P(=O)$_2$N($R^4$)$_2$, or an oxygen protecting group.

In certain embodiments, $R^O$ is optionally substituted alkyl, e.g., optionally substituted $C_{1-6}$alkyl. In certain embodiments, $R^O$ is optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl.

In certain embodiments, $R^O$ is optionally substituted alkenyl, e.g., optionally substituted $C_{2-6}$alkenyl. In certain embodiments, $R^O$ is optionally substituted $C_2$alkenyl, optionally substituted $C_3$alkenyl, optionally substituted $C_4$alkenyl, optionally substituted $C_5$alkenyl, or optionally substituted $C_6$alkenyl.

In certain embodiments, $R^O$ is optionally substituted alkynyl, e.g., optionally substituted $C_{2-6}$alkynyl. In certain embodiments, $R^O$ is optionally substituted $C_2$alkynyl, optionally substituted $C_3$alkynyl, optionally substituted $C_4$alkynyl, optionally substituted $C_5$alkynyl, or optionally substituted $C_6$alkynyl.

In certain embodiments, $R^O$ is optionally substituted carbocyclyl, e.g., optionally substituted $C_{3-6}$carbocyclyl. In certain embodiments, $R^O$ is optionally substituted $C_3$ carbocyclyl, optionally substituted $C_4$ carbocyclyl, optionally substituted $C_5$ carbocyclyl, or optionally substituted $C_6$ carbocyclyl.

In certain embodiments, $R^O$ is optionally substituted heterocyclyl, e.g., optionally substituted 3-6 membered heterocyclyl. In certain embodiments, $R^O$ is optionally substituted 3-membered heterocyclyl, optionally substituted 4-membered heterocyclyl, optionally substituted 5-membered heterocyclyl, or optionally substituted 6-membered heterocyclyl In certain embodiments, $R^O$ is optionally substituted aryl, e.g., optionally substituted phenyl.

In certain embodiments, $R^O$ is optionally substituted heteroaryl, e.g., optionally substituted 5-6 membered heteroaryl.

In certain embodiments, $R^O$ is —C(=O)$R^4$, —C(=O)O$R^4$, or —C(=O)N($R^4$)$_2$. In certain embodiments, $R^4$ is optionally substituted alkyl, e.g., —CH$_3$.

In certain embodiments, $R^O$ is —S(=O)$_2R^4$. In certain embodiments, $R^4$ is optionally substituted alkyl (e.g., —CH$_3$, —CF$_3$) or optionally substituted phenyl.

In certain embodiments, $R^O$ is —Si($R^4$)$_3$. In certain embodiments, $R^4$ is optionally substituted alkyl (e.g., —CH$_3$, —CH(CH$_3$)$_3$) or optionally substituted phenyl.

In certain embodiments, $R^O$ is —P(=O)($R^4$)$_2$, —P(=O)(O$R^4$)$_2$, —P(=O)(N$R^4$)$_2$, —P(=O)$_2R^4$, —P(=O)$_2$(O$R^4$), or —P(=O)$_2$N($R^4$)$_2$.

In certain embodiments, $R^O$ is an oxygen protecting group.

Group $R^3$, $R^4$, $R^5$, and Bonds (a), (b), and (c) of Formula ═

As generally defined herein, $R^3$ is hydrogen or optionally substituted alkyl.

In certain embodiments, $R^3$ is hydrogen. In certain embodiments, $R^3$ is optionally substituted alkyl, e.g., methyl (—CH$_3$).

As generally defined herein, $R^4$ is hydrogen, halogen, optionally substituted alkyl, or —Si($R^4$)$_3$. In certain embodiments, $R^4$ is hydrogen. In certain embodiments, $R^4$ is optionally substituted alkyl, e.g., methyl. In certain embodiments, $R^4$ is —Si($R^4$)$_3$, e.g., wherein each instance of $R^4$ is independently optionally substituted alkyl or optionally substituted phenyl.

As generally defined herein, $R^5$ is hydrogen, halogen, optionally substituted alkyl, —O$R^4$, —OC(=O)$R^4$, —OC(=O)O$R^4$, —OC(=O)N($R^4$)$_2$, —OS(=O)$_2R^4$, —N$_3$, —N($R^4$)$_2$, —N$R^4$C(=O)$R^4$, —N$R^4$C(=O)O$R^4$, —N$R^4$C(=O)N($R^4$)$_2$, —N$R^4$S(=O)$_2R^4$, or —C($R^4$)$_3$. In certain embodiments, $R^5$ is hydrogen. In certain embodiments, $R^5$ is a non-hydrogen group. In certain embodiments, $R^5$ is halogen (e.g., bromo, iodo, chloro). In certain embodiments, $R^5$ is optionally substituted alkyl (e.g., —CH$_3$). In certain embodiments, $R^5$ is —O$R^4$ (e.g., —OH, —OCH$_3$).

In certain embodiments, $R^5$ is hydrogen, halogen, optionally substituted alkyl, or —O$R^4$.

In certain embodiments, $R^5$ is —O$R^4$, —OC(=O)$R^4$, —OC(=O)O$R^4$, —OC(=O)N($R^4$)$_2$, —OS(=O)$_2R^4$.

In certain embodiments, $R^5$ is —N$_3$, —N($R^4$)$_2$, —N$R^4$C(=O)$R^4$, —N$R^4$C(=O)O$R^4$, —N$R^4$C(=O)N($R^4$)$_2$, or —N$R^4$S(=O)$_2R^4$.

In certain embodiments, $R^5$ is —C($R^4$)$_3$.

In certain embodiments, the group $R^5$ is in the alpha (down) configuration. In certain embodiments, the group $R^5$ is in the beta (up) configuration.

As generally defined herein, each instance of ═, designated as (a), (b), and (c), represents a single or double bond, provided that when ═ designated as (c) represents a double bond, then one of $R^{B1}$ and $R^{B2}$ is absent, and provided that when ═ designated as (c) represents a single bond, then both $R^{B1}$ and $R^{B2}$ are present.

In certain embodiments, the bond ═ designated as (a) is a single bond. In certain embodiments, the bond ═ designated as (a) is a double bond.

In certain embodiments, the bond ═ designated as (b) is a single bond. In certain embodiments, the bond ═ designated as (b) is a double bond.

In certain embodiments, the bond ═ designated as (c) is a single bond. In certain embodiments, the bond ═ designated as (c) is a double bond, and $R^{B2}$ is absent.

In certain embodiments, the bond ═ designated as (a) is double bond, and the bond ═ designated as (b) is a double bond. In this instance, in certain embodiments, the bond ═ designated as (c) is a double bond, and $R^{B2}$ is absent. However, in this instance, in other embodiments, the bond ═ designated as (c) is a single bond.

For example, in certain embodiments of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), and (G1"), wherein $R^3$ is methyl, $R^4$ is hydrogen, (a) and (b) are double bonds, and the bond designated (c) is a single bond, provided are compounds of formula:
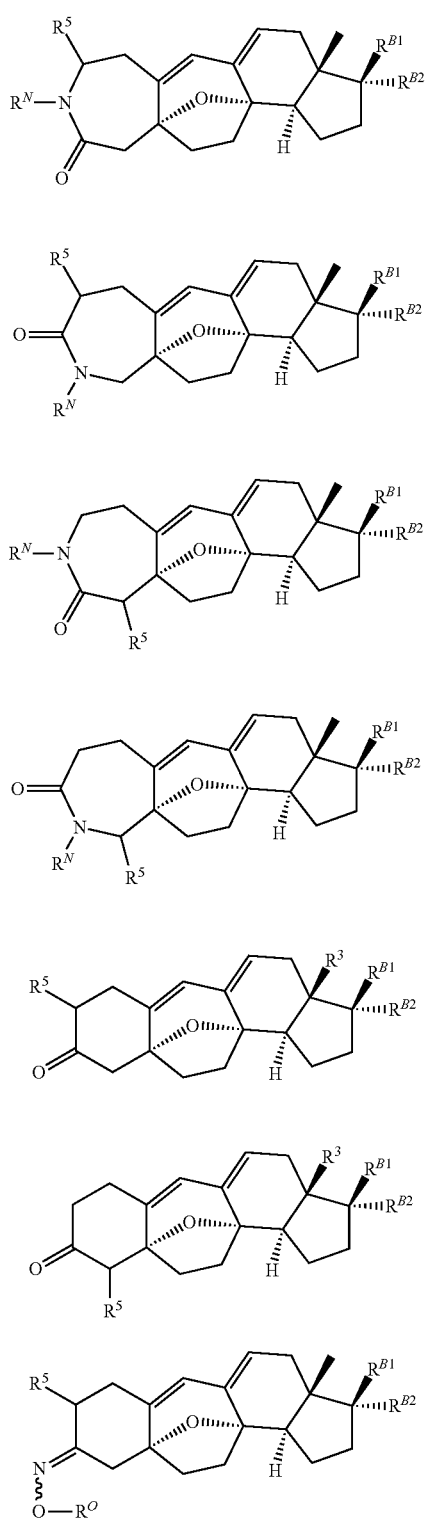
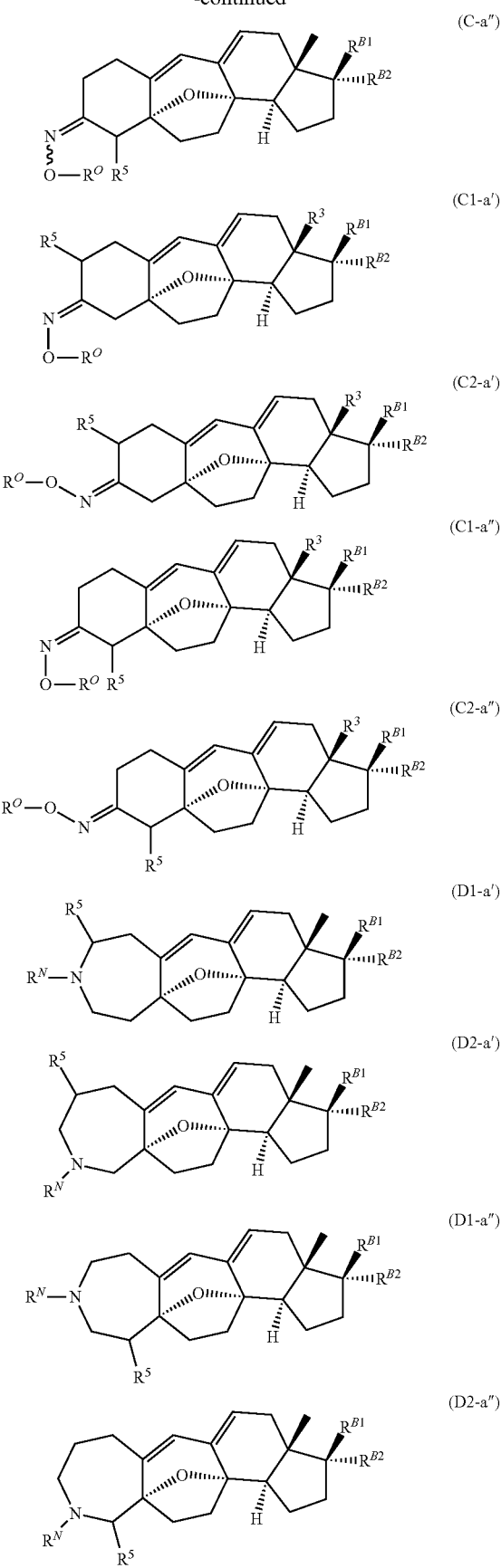

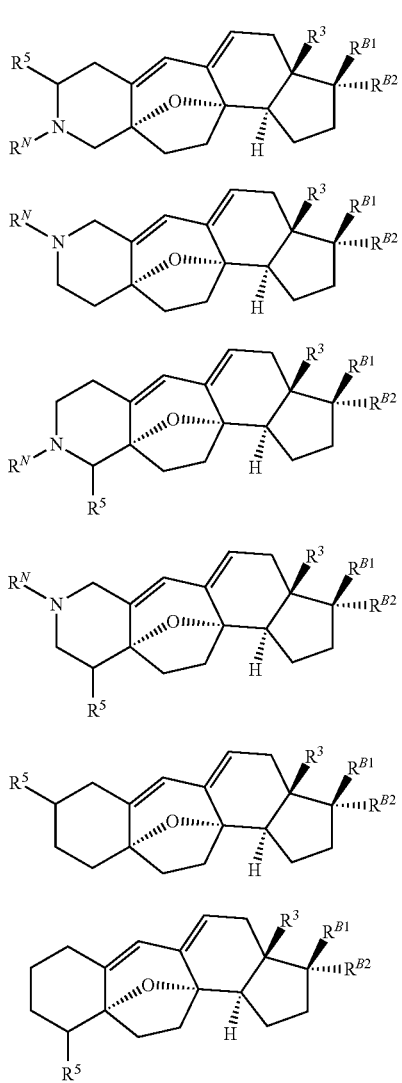

(E1-a')
(E2-a')
(E1-a'')
(E2-a'')
(G1-a')
(G1-a'')

or a pharmaceutically acceptable salt thereof.

Groups $R^{B1}$ and $R^{B2}$

As generally defined herein, each instance of $R^{B1}$ and $R^{B2}$ is, independently, hydrogen, -$L_1$-$R^{B3}$, or —$X^A R^A$ wherein $X^A$ is —O—, —S—, or —N($R^A$)—; or $R^{B1}$ and $R^{B2}$ are joined to form an oxo group, provided that at least one of $R^{B1}$ and $R^{B2}$ is not hydrogen;

$L_1$ is a bond, —CH(CH$_3$)(CH$_2$)$_2$—, —CH(CH$_3$)— CH=CH—, —C(=O)—, —C(=O)O—, —C(=O)S—, —C(=O)N($R^L$)—, or —N($R^L$)—(C($R^{LL}$)$_2$)$_p$—, wherein $R^L$ is hydrogen, optionally substituted alkyl, or a nitrogen protecting group, each instance of $R^{LL}$ is independently hydrogen, halogen, or optionally substituted alkyl, and p is 0, 1, or 2;

$R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when $L_1$ is a bond, then $R^{B3}$ is not hydrogen; and each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen, optionally when attached to N the two $R^A$ groups may be joined to form an optionally substituted heterocyclyl or optionally substituted heteroaryl ring, and optionally when $R^{B1}$ and $R^{B2}$ are each —$X^A R^A$ then two $R^A$ groups may be joined to form an optionally substituted heterocyclyl ring.

In certain embodiments, at least one instance of $R^{B1}$ and $R^{B2}$ is —$X^A R^A$. In this instance, in certain embodiments, the other of $R^{B1}$ and $R^{B2}$ is hydrogen or —$X^A R^A$ (e.g., —O$R^A$). For example, in certain embodiments, when ═ designated as (c) represents a single bond, then $R^{B1}$ is —$X^A R^A$ (e.g., —O$R^A$) and $R^{B2}$ is hydrogen or —$X^A R^A$ (e.g., —O$R^A$). In other embodiments, when ═ designated as (c) represents a single bond, then $R^{B2}$ is —$X^A R^A$ (e.g., —O$R^A$) and $R^{B1}$ is hydrogen or —$X^A R^A$ (e.g., —O$R^A$). Alternatively, in certain embodiments, when ═ designated as (c) represents a double bond, then $R^{B1}$ is —$X^A R^A$ (e.g., —O$R^A$ wherein $R^A$ is not hydrogen) and $R^{B2}$ is absent.

In certain embodiments, $R^{B1}$ and $R^{B2}$ are joined to form an oxo group (=O).

Furthermore, in certain embodiments, at least one instance of $R^{B1}$ and $R^{B2}$ is -$L_1$-$R^{B3}$. In this instance, in certain embodiments, the other of $R^{B1}$ and $R^{B2}$ is hydrogen or —$X^A R^A$ (e.g., —O$R^A$). For example, in certain embodiments, when ═ designated as (c) represents a single bond, then $R^{B1}$ is -$L_1$-$R^{B3}$ and $R^{B2}$ is hydrogen or —$X^A R^A$ (e.g., —O$R^A$). In other embodiments, when ═ designated as (c) represents a single bond, then $R^{B2}$ is -$L_1$-$R^{B3}$ and $R^{B1}$ is hydrogen or —$X^A R^A$ (e.g., —O$R^A$). Alternatively, in certain embodiments, when ═ designated as (c) represents a double bond, then $R^{B1}$ is -$L_1$-$R^{B3}$ and $R^{B2}$ is absent.

For example, in certain embodiments of Formula (A1'), (A2'), (C'), (C1'), (C2'), (D1'), (D2'), (E1'), (E2'), (A1''), (A2''), (C''), (C1''), (C2''), (D1''), (D2''), (E1''), (E2''), (G1'), and (G1''), wherein $R^{B1}$ is -$L_1$-$R^{B3}$, provided are compounds of Formula:

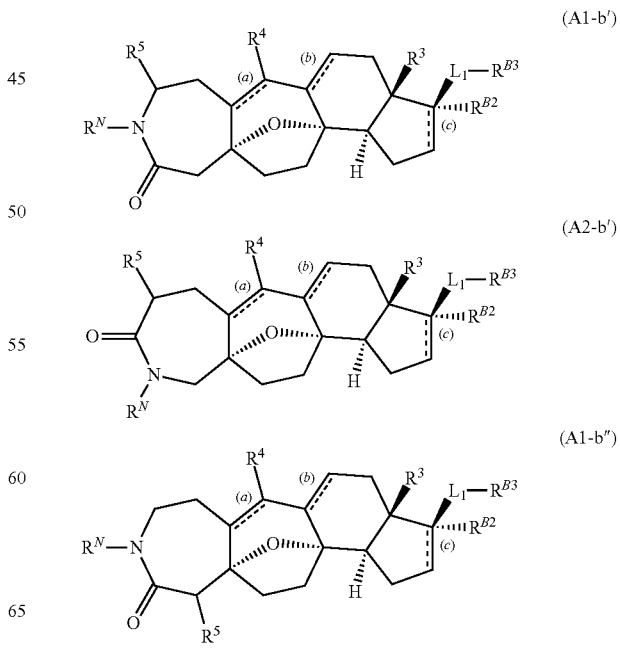

(A1-b')
(A2-b')
(A1-b'')

(A2-b″)
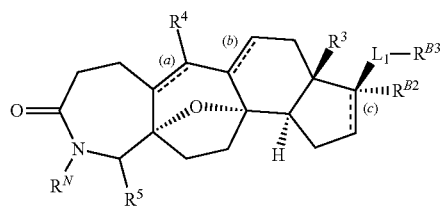
(B-b′)
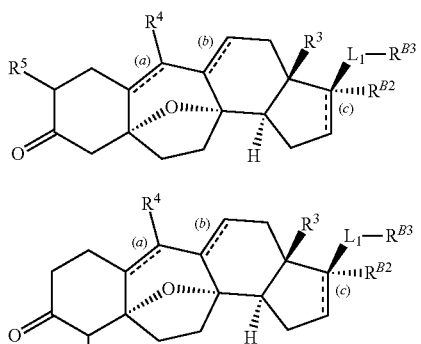
(B-b″)
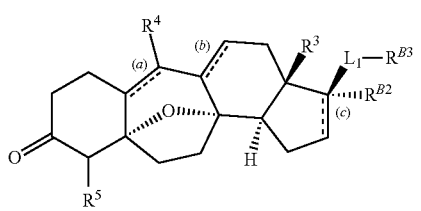
(C-b′)
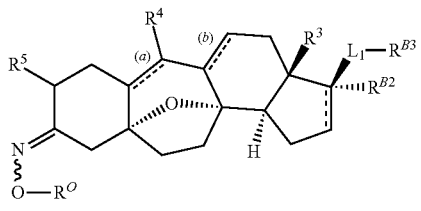
(C-b″)
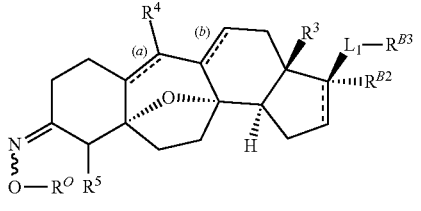
(C1-b′)
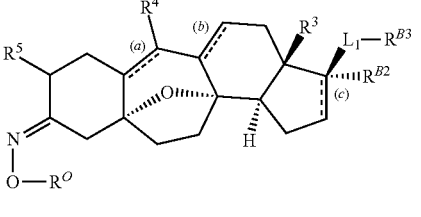
(C2-b′)
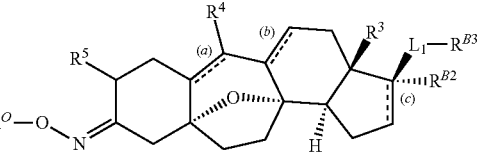
(C1-b″)
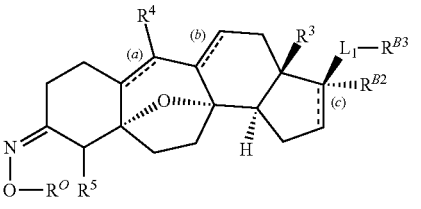
(C2-b″)
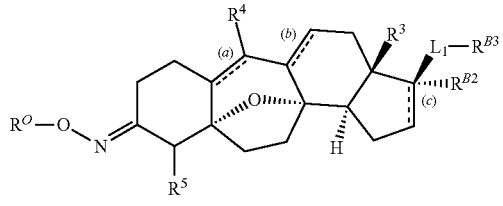
(D1-b′)
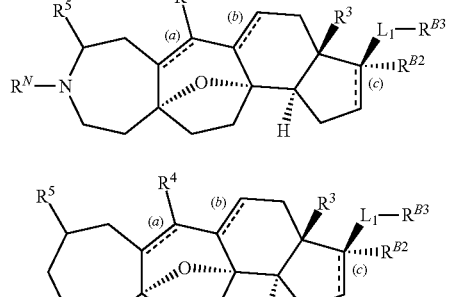
(D2-b′)
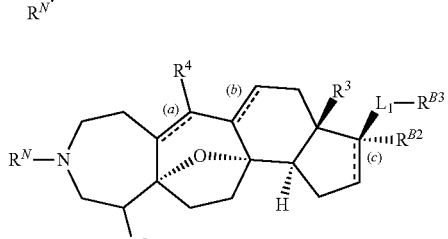
(D1-b″)
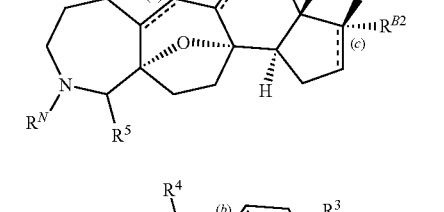
(D2-b″)
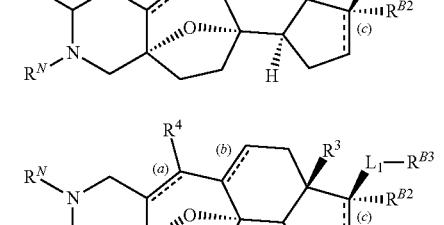
(E1-b′)
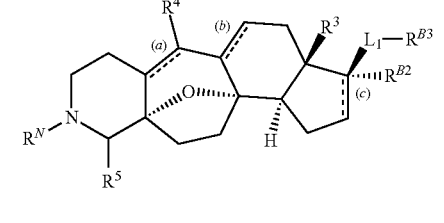
(E2-b′)
(E1-b″)

-continued

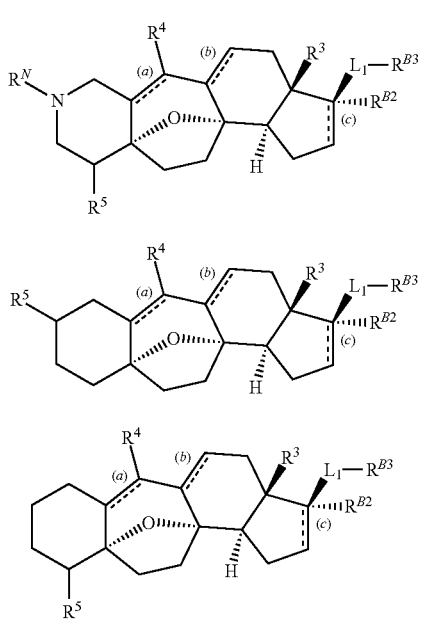

(E2-b″)

(G1-b′)

(G1-b″)

or a pharmaceutically acceptable salt thereof.

In certain embodiments, $L_1$ is a bond, and $R^{B3}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $L_1$ is a bond.

In certain embodiments, $L_1$ is —CH(CH$_3$)(CH$_2$)$_2$— or —CH(CH$_3$)—CH═CH—.

In certain embodiments, $L_1$ is —C(═O)—, —C(═O)O—, or —C(═O)S—.

In certain embodiments, $L_1$ is —C(═O)N(R$^L$)—, or —N(R$^L$)—(C(R$^{LL}$)$_2$)$_p$—, wherein $R^L$ is hydrogen, optionally substituted alkyl, or a nitrogen protecting group, each instance of $R^{LL}$ is independently hydrogen, halogen, or optionally substituted alkyl, and $R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $L_1$ is —C(═O)—. In certain embodiments, $L_1$ is —C(═O)O—. In certain embodiments, $L_1$ is —C(═O)S—. In certain embodiments, $L_1$ is —C(═O)N(R$^L$)—. In certain embodiments, $L_1$ is —N(R$^L$)—C(R$^{LL}$)$_2$-. In certain embodiments, $R^L$ is hydrogen or optionally substituted alkyl, e.g., methyl. In certain embodiments, each instance of $R^{LL}$ is independently hydrogen, optionally substituted alkyl, e.g., methyl, or fluoro. In certain embodiments, p is 0. In certain embodiments, p is 1. In certain embodiments, p is 2.

In certain embodiments, when $L_1$ is —CH(CH$_3$)(CH$_2$)$_2$—, —CH(CH$_3$)—CH═CH—, —C(═O)—, —C(═O)O—, —C(═O)S—, —C(═O)N(R$^L$)—, or —N(R$^L$)—(C(R$^{LL}$)$_2$)$_p$—, and $R^{B3}$ is hydrogen, provided is a group of formula —CH(CH$_3$)(CH$_2$)CH$_3$, —CH(CH$_3$)—CH═CH$_2$, —C(═O)H, —C(═O)OH, —C(═O)SH, —C(═O)N(R$^L$)H, or —N(R$^L$)H.

However, in certain embodiments when $L_1$ is a bond, —CH(CH$_3$)(CH$_2$)$_2$—, —CH(CH$_3$)—CH═CH—, —C(═O)—, —C(═O)O—, —C(═O)S—, —C(═O)N(R$^L$)—, or —N(R$^L$)—(C(R$^{LL}$)$_2$)$_p$—, $R^{B3}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^{B3}$ is an acyclic group, e.g., $R^{B3}$ is an optionally substituted alkyl, optionally substituted alkenyl, or optionally substituted alkynyl. In certain embodiments, $R^{B3}$ is optionally substituted alkyl, e.g., optionally substituted C$_{1-6}$alkyl. In certain embodiments, $R^{B3}$ is optionally substituted alkenyl, e.g., optionally substituted C$_{2-6}$alkenyl. In certain embodiments, $R^{B3}$ is optionally substituted alkynyl, e.g., optionally substituted C$_{2-6}$alkynyl.

However, in certain embodiments, $R^{B3}$ is a cyclic group, e.g., $R^{B3}$ is optionally substituted carbocyclyl, optionally substituted heterocyclyl, optionally substituted aryl, or optionally substituted heteroaryl. In certain embodiments, $R^{B3}$ is a nonaromatic cyclic group, e.g., in certain embodiments, $R^{B3}$ is optionally substituted carbocyclyl or optionally substituted heterocyclyl. In certain embodiments, $R^{B3}$ is an aromatic cyclic group, e.g., in certain embodiments, $R^{B3}$ is optionally substituted aryl or optionally substituted heteroaryl.

In certain embodiments, $R^{B3}$ is optionally substituted carbocyclyl, e.g., optionally substituted C$_{3-6}$carbocyclyl. In certain embodiments $R^{B3}$ is optionally substituted C$_3$ carbocyclyl, optionally substituted C$_4$ carbocyclyl, optionally substituted C$_5$ carbocyclyl, or optionally substituted C$_6$ carbocyclyl. In certain embodiments, $R^{B3}$ is optionally substituted cyclopenyl (C$_5$) or optionally substituted cyclohexyl (C$_6$).

In certain embodiments, $R^{B3}$ is optionally substituted carbocyclyl fused to an optionally substituted aryl or optionally substituted heteroaryl ring, wherein the point of attachment is on the carbocyclyl ring. In certain embodiments, $R^{B3}$ is optionally substituted carbocyclyl, e.g., optionally substituted C$_{3-6}$carbocyclyl, fused to an optionally substituted aryl or optionally substituted heteroaryl ring. In certain embodiments $R^{B3}$ is optionally substituted C$_3$ carbocyclyl, optionally substituted C$_4$ carbocyclyl, optionally substituted C$_5$ carbocyclyl, or optionally substituted C$_6$ carbocyclyl, fused to an optionally substituted aryl or optionally substituted heteroaryl ring. In certain embodiments, $R^{B3}$ is optionally substituted cyclopenyl (C$_5$) or optionally substituted cyclohexyl (C$_6$) fused to an optionally substituted aryl or optionally substituted heteroaryl ring. In certain embodiments, the fused aryl ring is an optionally substituted phenyl ring. In certain embodiments, the fused heteroaryl ring is an optionally substituted 6-membered heteroaryl ring, e.g., an optionally substituted pyridinyl ring.

In certain embodiments, $R^{B3}$ is optionally substituted heterocyclyl, e.g., optionally substituted 3-6 membered heterocyclyl. In certain embodiments $R^{B3}$ is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen.

In certain embodiments, $R^{B3}$ is optionally substituted heterocyclyl fused to an optionally substituted aryl or optionally substituted heteroaryl ring, wherein the point of attachment is on the heterocyclyl ring. In certain embodiments, $R^{B3}$ is optionally substituted heterocyclyl, e.g., optionally substituted 3-6 membered heterocyclyl, fused to an optionally substituted aryl or optionally substituted heteroaryl ring. In certain embodiments $R^{B3}$ is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen, fused to an optionally substituted aryl or optionally substituted heteroaryl ring. In certain embodiments, the fused aryl ring is a fused optionally substituted phenyl ring. In certain embodiments, the fused heteroaryl ring is a 6-membered heteroaryl ring, e.g., an optionally substituted pyridinyl ring. In certain embodiments, the point of attachment of $R^{B3}$ is via a nitrogen atom. In certain embodiments, $R^{B3}$ is an optionally substituted 1,2,3,4-tetrahydro-2,7-naphthyridinyl ring, a 3,4-dihydropyrido[4,3-d]pyrimidinyl ring, a 3,4-dihydropyrido[4,3-d]pyrimidin-2-one ring, or a 3,4-dihydro-2H-pyrido[3,4-e][1,3]oxazin-2-one ring, wherein the point of attachment is on the non-aromatic heterocyclyl ring.

In certain embodiments, $R^{B3}$ is optionally substituted aryl, e.g., optionally substituted $C_{6-14}$aryl. In certain embodiments, $R^{B3}$ is optionally substituted phenyl. In certain embodiments, $R^{B3}$ is optionally substituted naphthyl. In certain embodiments, $R^{B3}$ is optionally substituted phenyl fused to an optionally substituted heterocyclyl ring; such as an optionally substituted phenyl tetrahydroisoquinolinyl. It is understood in reference to optionally substituted aryl ring systems comprising a fused heterocyclyl ring that the point of attachment to the parent molecule is on the aryl (e.g., phenyl) ring.

In certain embodiments, $R^{B3}$ is optionally substituted heteroaryl, e.g., optionally substituted 5-14 membered heteroaryl. In certain embodiments, $R^{B3}$ is an optionally substituted 5-membered heteroaryl or an optionally substituted 6-membered heteroaryl. In certain embodiments, $R^{B3}$ is an optionally substituted bicyclic heteroaryl, e.g., an optionally substituted 5,6-bicyclic heteroaryl, or optionally substituted 6,6-bicyclic heteroaryl. In certain embodiments, $R^{B3}$ is an optionally substituted 5,6-bicyclic heteroaryl or optionally substituted 6,6-bicyclic heteroaryl ring system selected from the group consisting of optionally substituted naphthyridinyl, optionally substituted pteridinyl, optionally substituted quinolinyl, optionally substituted isoquinolinyl, optionally substituted cinnolinyl, optionally substituted quinoxalinyl, optionally substituted phthalazinyl, and optionally substituted quinazolinyl. In certain embodiments, the point of attachment of $R^{B3}$ is via a nitrogen atom.

In certain embodiments, wherein $R^{B3}$ is an optionally substituted heterocyclyl, -$L_1$-$R^{B3}$ is selected from the group consisting of:

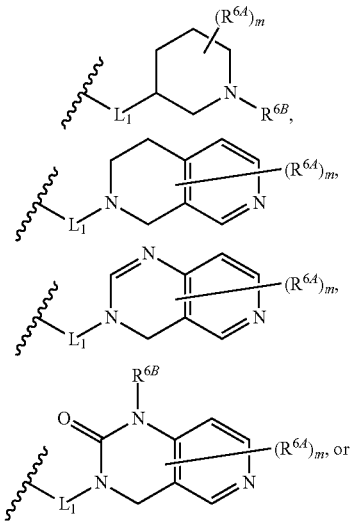

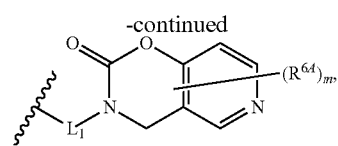

wherein:
each instance of $R^{64}$ is independently halogen, —$NO_2$, —CN, —$OR^{6C}$, —$SR^{6C}$, —$N(R^{6C})_2$, —$C(\!=\!O)R^{6C}$, —$C(\!=\!O)OR^{6C}$, —$C(\!=\!O)N(R^{6C})_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{6B}$ is independently hydrogen, optionally substituted alkyl, or a nitrogen protecting group when attached to nitrogen;

wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and m is 0 or an integer between 1 and 4, inclusive,
provided $L^1$ is not —$N(R^L)$—$(C(R^{LL})_2)_p$— wherein p is 0.

In certain embodiments, wherein $R^{B3}$ is an optionally substituted aryl or optionally substituted heteroaryl, -$L_1$-$R^{B3}$ is selected from the group consisting of:

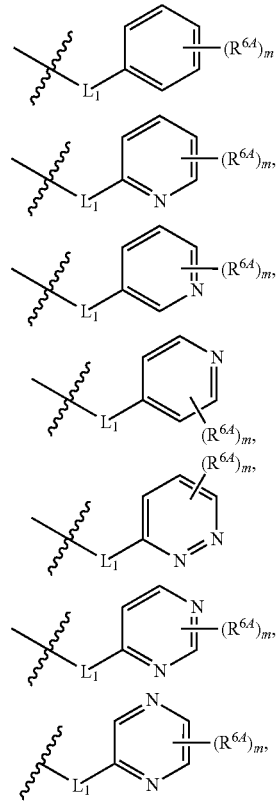

-continued

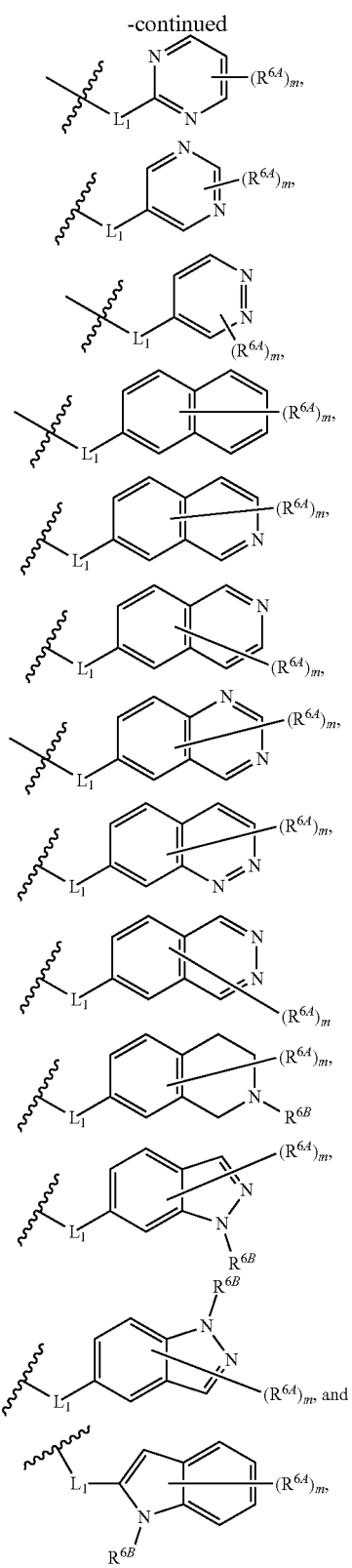

wherein:

each instance of $R^{6A}$ is independently halogen, —$NO_2$, —CN, $OR^6$, $SR^6$, $N(R^6)_2$, —C(=O)$R^{6C}$, —C(=O)$OR^{6C}$, —C(=O)N($R^{6C}$)$_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{6B}$ is independently hydrogen, optionally substituted alkyl, or a nitrogen protecting group when attached to nitrogen;

wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and m is 0 or an integer between 1 and 4, inclusive.

In certain embodiments, m is 0. In certain embodiments, m is 1, 2, 3, or 4. In certain embodiments, wherein m is 1, 2, 3, or 4, at least one $R^{6A}$ is halogen (e.g., fluoro), —$OR^{6C}$, —$SR^6C$, or —N($R^{6C}$)$_2$.

In certain embodiments, $L_1$ is a bond or —C(=O)N($R^L$)—, wherein $R^L$ is hydrogen or an optionally substituted alkyl (e.g., methyl), and $R^{B3}$ is optionally substituted aryl or optionally substituted heteroaryl, as described herein.

For example, in certain embodiments of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), and (G1"), wherein the group -$L_1$-$R^{B3}$ is a group of formula:

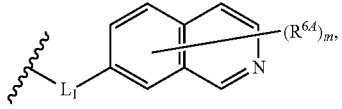

wherein $L_1$ is a bond, provided are compounds of Formula:

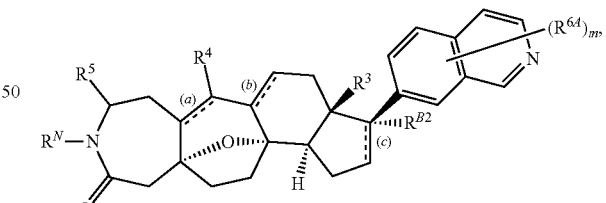

(A1-c')

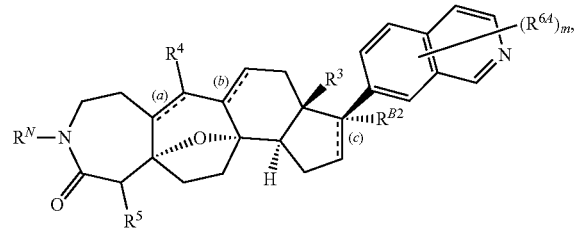

(A1-c")

-continued (A2-c')

(A2-c'')

(B-c')

(B-c'')

(C-c')

(C-c'')

-continued (C1-c')

(C1-c'')

(C2-c')

(C2-c'')

(D1-c')

(D1-c'')

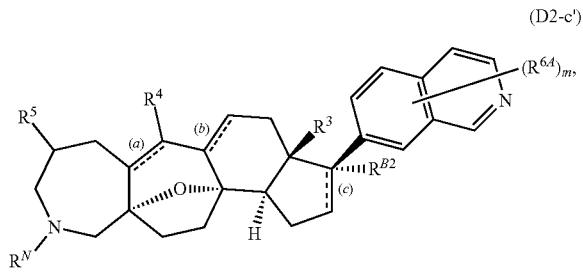 (D2-c')

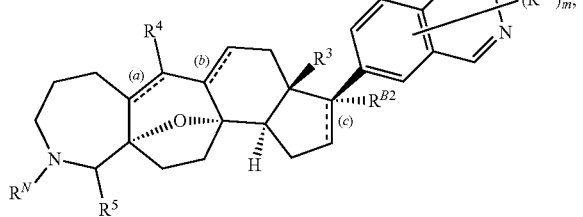 (D2-c")

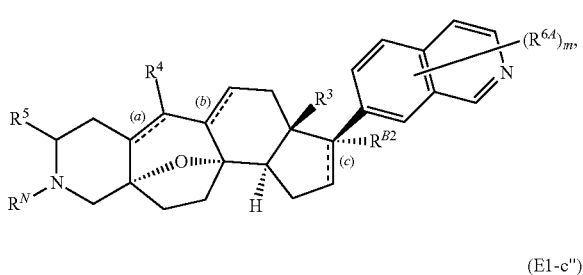 (E1-c')

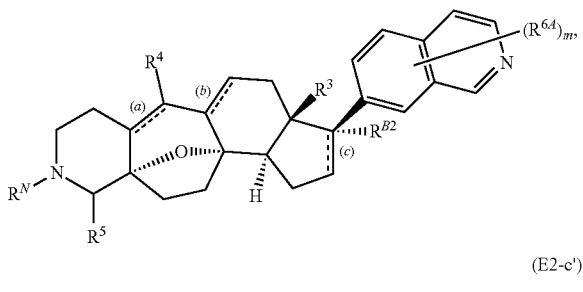 (E1-c")

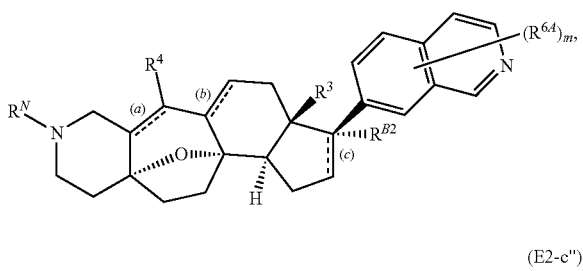 (E2-c')

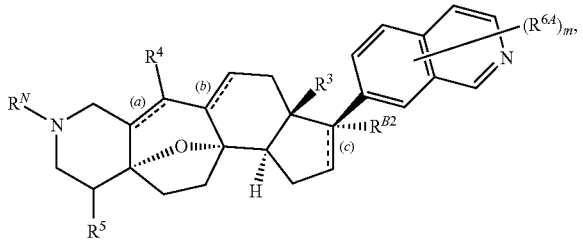 (E2-c")

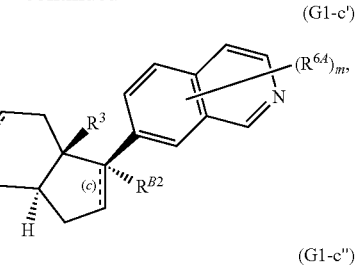 (G1-c')

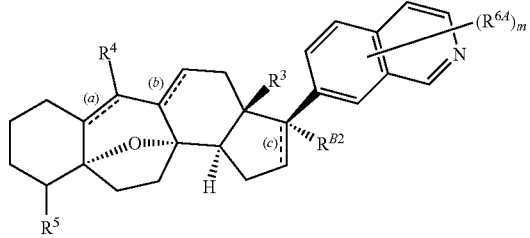 (G1-c")

and pharmaceutically acceptable salts thereof.

Exemplary Compounds

Various combinations of certain embodiments are further contemplated herein.

For example, in certain embodiments of Formula (A1-c'), (A2-c'), (B-c'), (C-c'), (C1-c'), (C2-c'), (D1-c'), (D2-c'), (E1-c'), (E2-c'), (G1-c') (A1-c"), (A2-c"), (B-c"), (C-c"), (C1-c"), (C2-c"), (D1-c"), (D2-c"), (E1-c"), (E2-c"), and (G1-c") wherein the bond ══ designated as (c) is a single bond, and $R^{B2}$ is hydrogen, provided is a compound of Formula:

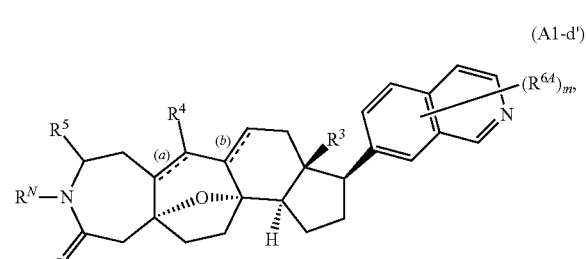 (A1-d')

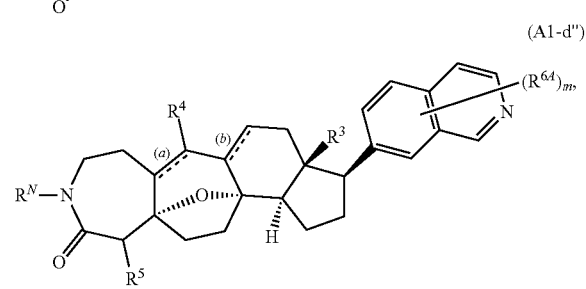 (A1-d")

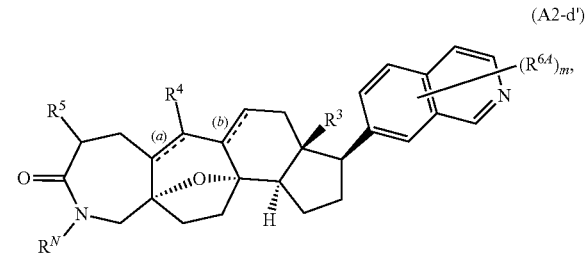 (A2-d')

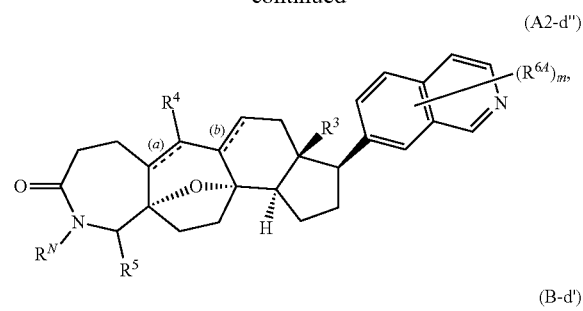
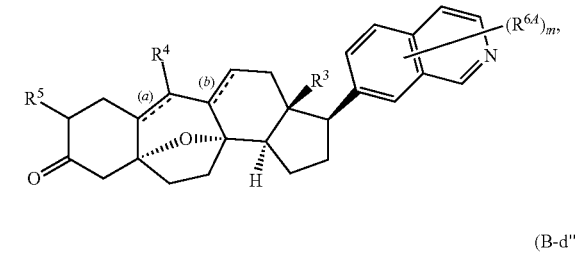
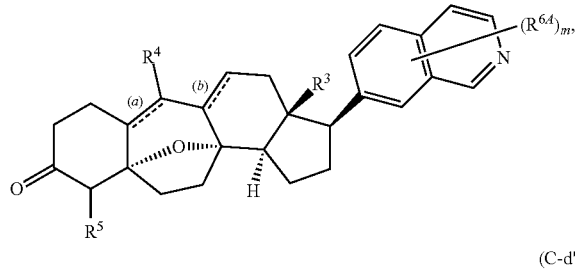
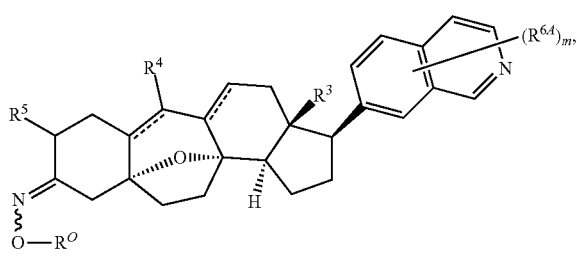
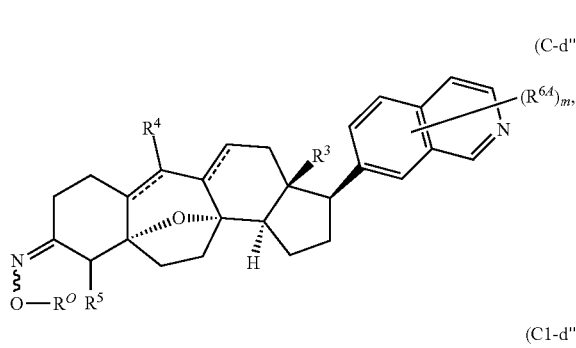
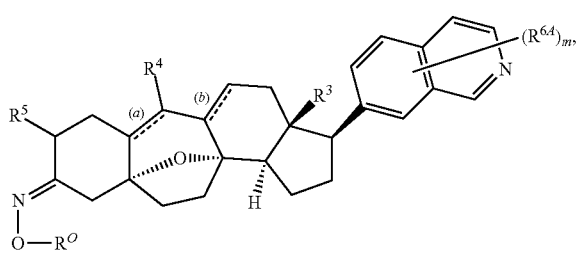

(D2-d") 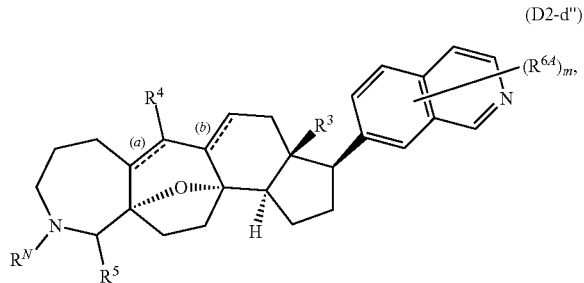

(E1-d') 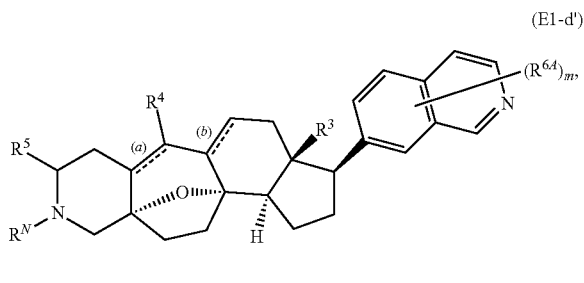

(E1-d") 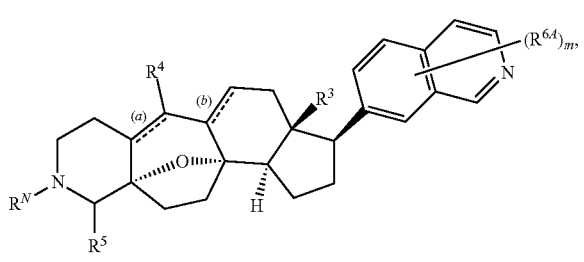

(E2-d') 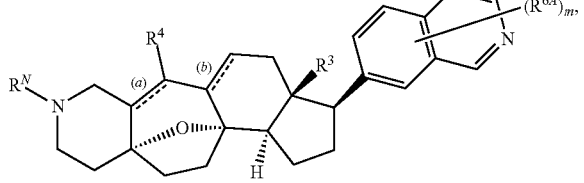

(E2-d") 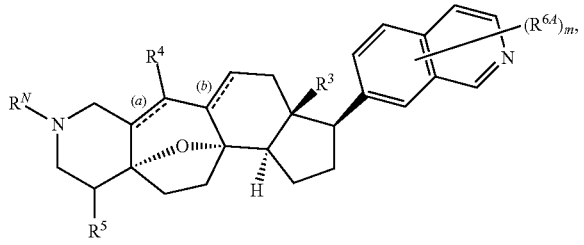

(G1-d') 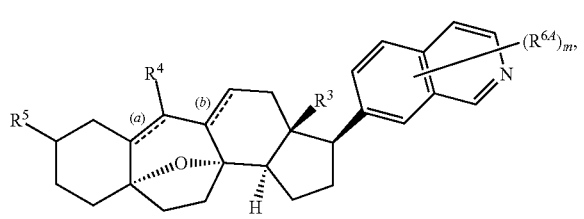

(G1-d") 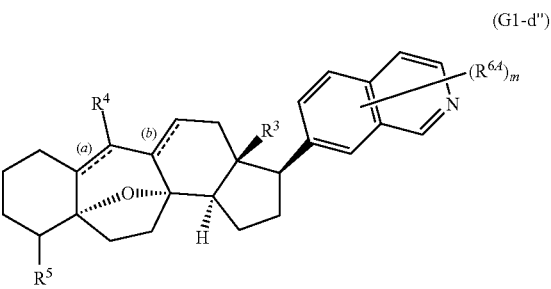

or a pharmaceutically acceptable salt thereof. In certain embodiments, $R^3$ is methyl. In certain embodiments, $R^4$ is hydrogen. In certain embodiments, $R^5$ is hydrogen. In certain embodiments, $R^5$ is a non-hydrogen group. In certain embodiments the bonds ⇌ designated as (a) and (b) are double bonds. In certain embodiments, m is 0 or 1.

In certain embodiments of Formula (A1-d'), (A2-d'), (B-d'), (C-d'), (C1-d'), (C2-d'), (D1-d'), (D2-d'), (E1-d'), (E2-d'), (G1-d'), (A1-d"), (A2-d"), (B-d"), (C-d"), (C1-d"), (C2-d"), (D1-d"), (D2-d"), (E1-d"), (E2-d"), and (G1-d") wherein $R^3$ is methyl, $R^4$ and $R^5$ are hydrogen, and the bonds ⇌ designated as (a) and (b) are double bonds, provided is a compound of Formula:

(A1-e)
(A2-e)
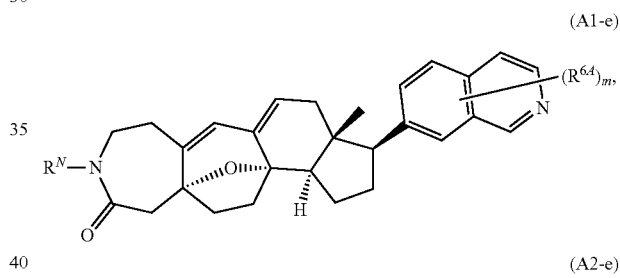

(B-e)
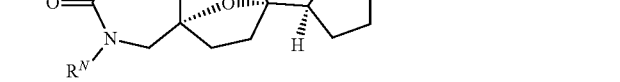

(C-e)
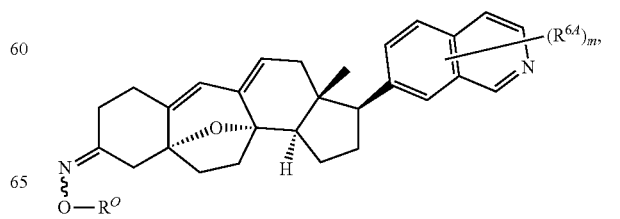

-continued (C1-e)
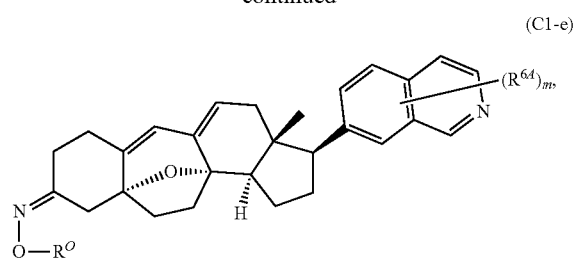

(C2-e)
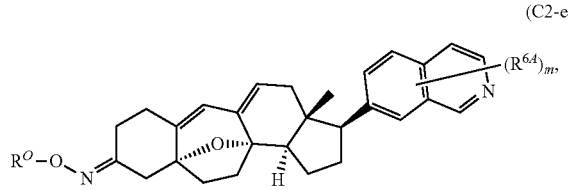

(D1-e)
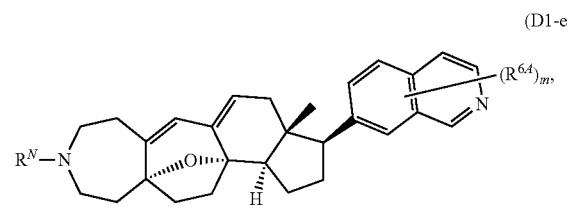

(D2-e)
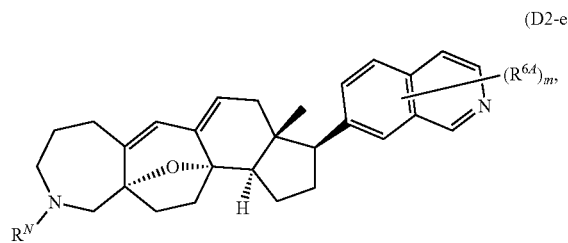

(E1-e)
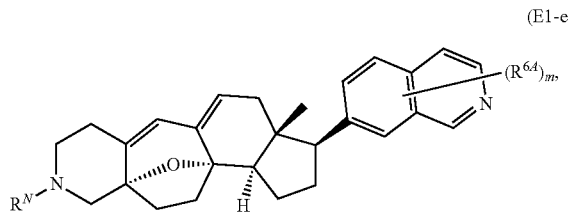

(E2-e)
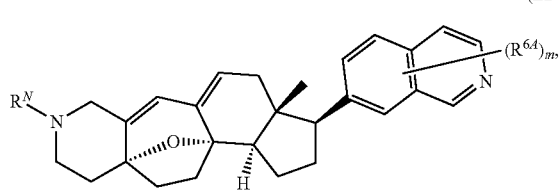

(G1-e)
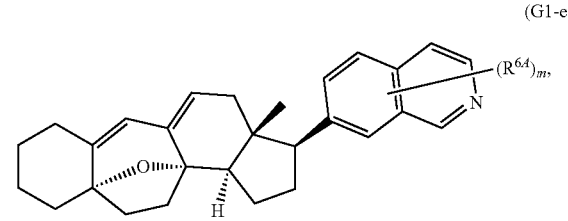

or a pharmaceutically acceptable salt thereof. In certain embodiments, m is 0 or 1.

Exemplary compounds of Formula (A1') or (A1") include, but are not limited to:

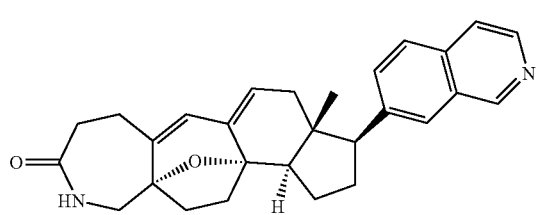 [SMILES: C[C@]12CC=C3C=C4CCC(=O)NC[C@]45CC[C@]3(O5)[C@@H]1CC[C@@H]2c1ccc2ccncc2c1]

and pharmaceutically acceptable salts thereof.

Exemplary compounds of Formula (A2') or (A2") include, but are not limited to:

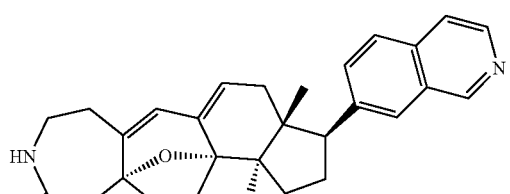

and pharmaceutically acceptable salts thereof.

Exemplary compounds of Formula (B') or (B") include, but are not limited to:

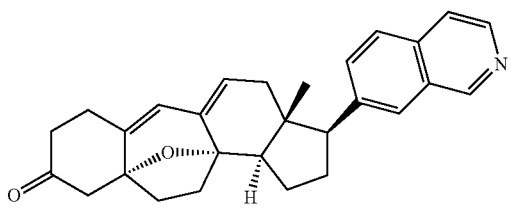 [SMILES: C[C@]12CC=C3C=C4CCC(=O)C[C@]45CC[C@]3(O5)[C@@H]1CC[C@@H]2c1ccc2ccncc2c1]

and pharmaceutically acceptable salts thereof.

Exemplary compounds of Formula (C') or (C") include, but are not limited to:

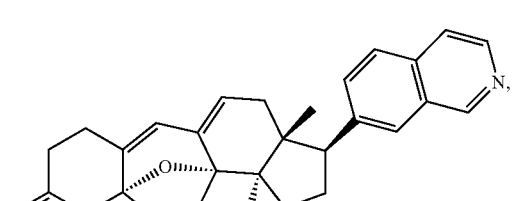

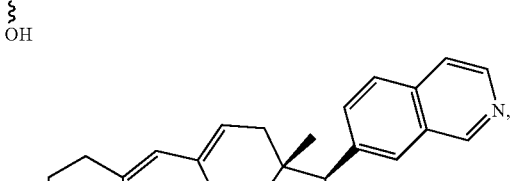

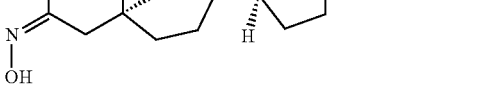

-continued

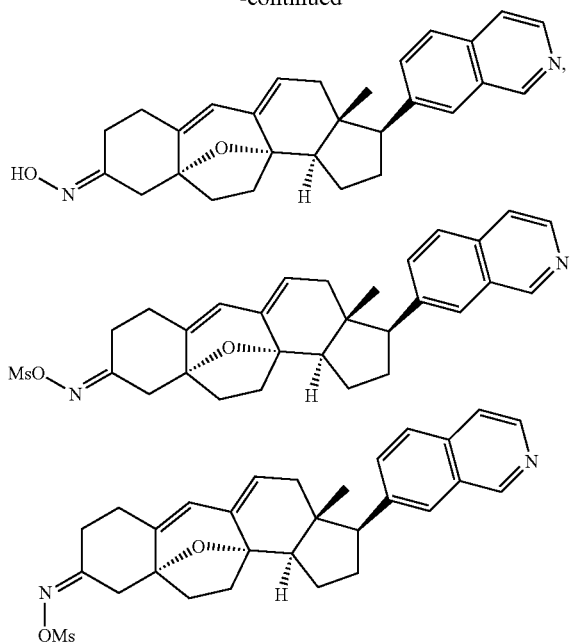

and pharmaceutically acceptable salts thereof, wherein Ms is —S(O₂)CH₃.

Exemplary compounds of Formula (D1') or (D1") include, but are not limited to:

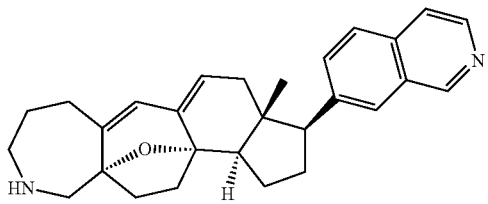 [SMILES: C[C@]12CC=C3C=C4CCCNC[C@]45CC[C@]3(O5)[C@@H]1CC[C@@H]2c1ccc2ccncc2c1]

and pharmaceutically acceptable salts thereof.

Exemplary compounds of Formula (D2') or (D2") include, but are not limited to:

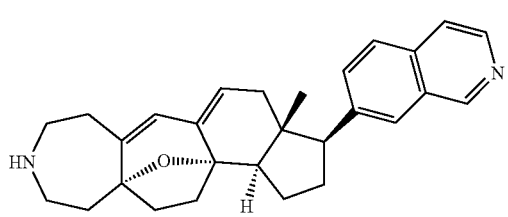 [SMILES: C[C@]12CC=C3C=C4CCNCC[C@]45CC[C@]3(O5)[C@@H]1CC[C@@H]2c1ccc2ccncc2c1]

and pharmaceutically acceptable salts thereof.

Exemplary compounds of Formula (E1') or (E1") include, but are not limited to:

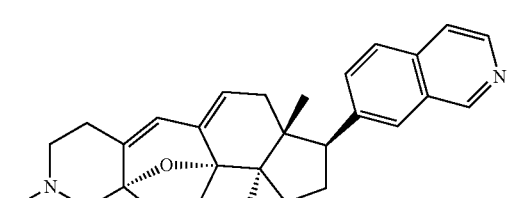

and pharmaceutically acceptable salts thereof.

Exemplary compounds of Formula (E2') or (E2") include, but are not limited to:

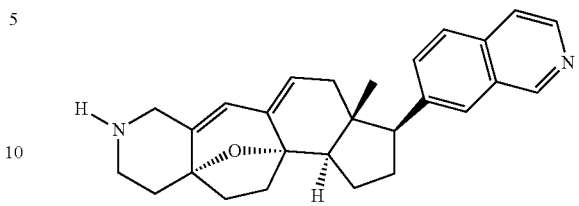

and pharmaceutically acceptable salts thereof.

Pharmaceutical Compositions

In certain embodiments, the present invention provides pharmaceutical compositions comprising a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, and a pharmaceutically acceptable excipient. In certain embodiments, the compound is present in an effective amount, e.g., a therapeutically effective amount or a prophylactically effective amount.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient. In some embodiments, the composition comprises between 0.1% and 1%, between 1% and 10%, between 10% and 20%, between 20% and 30%, between 30% and 40%, between 40% and 50%, between 50% and 60%, between 60% and 70%, between 70% and 80%, between 80% and 90%, or between 90% and 100% (w/w) of active ingredient. In the absence of a statement to the contrary, the composition comprises between 0.1 and 100% (w/w) of active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredient(s), the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, polymer conjugates (e.g., IT-101/CLRX101), and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow the absorption of the active ingredient from subcutaneous or intramuscular injection. This can be accomplished by the use of a liquid suspension of crystalline or amorphous material with poor water solubility. The rate of absorption of the active ingredient then depends upon its rate of dissolution which, in turn, may depend upon crystal size and crystalline form. Alternatively, delayed absorption of a parenterally administered form is accomplished by dissolving or suspending the active ingredient in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient(s) can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT Publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT Publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. In some embodiments, the formulation suitable for nasal administration comprises between 0.1% and 1%, between 1% and 10%, between 10% and 20%, between 20% and 30%, between 30% and 40%, between 40% and 50%, between 50% and 60%, between 60% and 70%, between 70% and 80%, between 80% and 90%, or between 90% and 100% (w/w) of active ingredient. In the absence of a statement to the contrary, the formulation suitable for nasal administration comprises between 0.1 and 100% (w/w) of active ingredient. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or atomized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment

Figure 1:
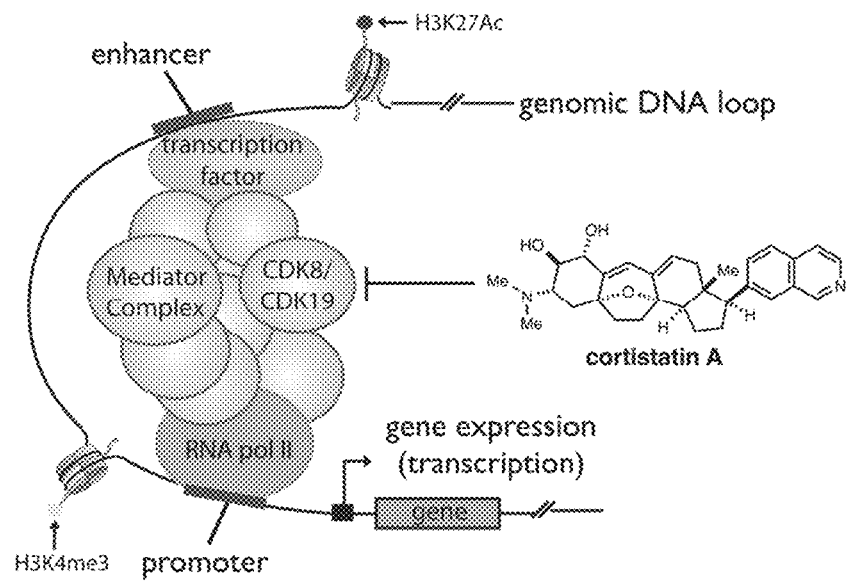
FIG. 1 is an illustration showing that CDK8 and CDK19 associate with the Mediator Complex and regulate transcription.

CDK8 and CDK19, referred to as "Mediator kinases", assemble in multi-protein complexes that reversibly bind the Mediator complex (FIG. 1). The Mediator complex links enhancer-bound transcription factors to promoter-bound RNA pol II holoenzyme and it influences chromatin architecture to regulate transcription and gene expression through still poorly understood mechanisms. Recent comprehensive genome-wide sequencing of samples from 200 AML patients revealed that, remarkably, nearly all mutations in presumably cancer-driving proteins are associated with regulating gene expression. See, e.g., Aerts, et al., *Nature* (2013) 499:35-36; The Cancer Genome Atlas Research Network, 2013. Genomic and Epigenomic Landscapes of Adult De Novo Acute Myeloid Leukemia. *N. Engl. J. Med.* 368, 2059-2074. Therefore, specific inhibition of Mediator kinases might be a new means to disrupt the ability of some AML mutations to deregulate gene expression programs that drive AML cell growth. Specific small molecule inhibition of CDK8/CDK19 may also prove beneficial for treating other cancers that rely on deregulated gene expression. CDK8/cyclin C was further observed to be more highly expressed in neurons and astrocytes of Alzheimer's disease (AD) patients, and thus specific small molecule inhibition of CDK8 may also prove beneficial for treating degenerative disorders, such as AD. See, e.g., Hessel et al., *Neurobiology of Aging* (2003) 24:427-435, wherein Cortistatin A has been reported to bind to CDK8 and CDK19. See, e.g., Cee et al., *Angew Chem Int Ed* (2009) 48:8952 and US 20120071477. Furthermore, as FIG. 15B demonstrates, cortistatin A inhibits CDK8 kinase activity, in part due to this binding. CDK8 and CDK19 have very similar sequences and catalytic domains suggesting that inhibiting CDK8 will likely also inhibit CDK19. See, e.g., Ries et al., *Semin. Cell Dev. Biol.* (2011) 22:735-740. Blast alignment of CDK8 vs. CDK19 also indicate that the amino acids are 70% identical and 82% similar.

Thus, in one aspect, provided is a method of inhibiting CDK8 and/or CDK19 kinase activity in a cell comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method. In another aspect, provided is a method of treating a condition associated with CDK8 and/or CDK19 kinase activity, comprising administering to a subject in need thereof a compound Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

In certain embodiments, the condition associated with CDK8 and/or CDK19 kinase activity is a proliferative disorder, e.g., cancer. CDK8 kinase activity has been linked to colon cancer. See, e.g., Firestein, et al., *Nature* (2008) 455:547-551.

In certain embodiments, the condition associated with CDK8 and/or CDK19 kinase activity is a diabetic condition, e.g., diabetes.

In certain embodiments, the condition associated with CDK8 and/or CDK19 kinase activity is a degenerative disorder, e.g., Alzheimer's disease (AD).

CDK8 has been linked to regulation of a number of signaling pathways and transcriptional programs that have been implicated in maintaining and driving diseases such as cancer. These pathways and programs include Wnt/beta-catenin pathway, Notch pathway, TGF-beta/BMP signaling, JAK-STAT pathway, p53 pathway, and hypoxia response. Aberrant Wnt/beta-catenin signaling is associated with leukemias and many other cancers. For instance, the most common mutations in colon cancer are ones that lead to activation of Wnt/beta-catenin signaling, expression of Wnt-target genes, and tumorigenesis. Given its central role in tumorigenesis, there is much interest in identifying safe, effective inhibitors of Wnt/beta-catenin signaling. See, e.g., Wang, et al., *Science* (2010) 327:1650-1653. Polakis, *EMBO J.* (2012) 31: 2737-2746.

In yet another aspect, provided is a method of treating a disorder which is mediated by the mediator complex, comprising administering to a subject in need thereof an effective amount of a cortistatin, such as any of the compounds described herein or described in a reference cited in the Background of the Invention. In certain embodiments, the condition is a proliferative disorder. In certain embodiments, the proliferative disorder is cancer. In certain embodiments, the cancer is a hematopoietic cancer. In certain embodiments, the hematopoietic cancer is lymphoma. In certain embodiments, the hematopoietic cancer is leukemia. In certain embodiments, the hematopoietic cancer is acute myeloid leukemia (AML), myelodysplastic syndrome (MDS), acute lymphoblastic leukemia (ALL), chronic myelogenous leukemia (CML), chronic myelomonocytic leukemia (CMML), or multiple myeloma. In certain embodiments, the acute lymphoblastic leukemia is T-cell acute lymphoblastic leukemia or B-cell acute lymphoblastic leukemia. In certain embodiments, the cancer is breast cancer, ovarian cancer, endometriod carcinoma, or squamous cell cancer. In certain embodiments, the proliferative disorder is a myeloproliferative neoplasm. In certain embodiments, the myeloproliferative neoplasm is primary myelofibrosis (PMF). In certain embodiments, the cancer is a solid tumor. In one embodiment, a method is provided for treating a disorder which is mediated by the mediator complex, comprising administering a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

Thus, in another aspect, provided is a method of treating a β-catenin pathway-associated condition comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In another aspect, provided is a method of modulating the β-catenin pathway (e.g., by inhibiting the expression of beta-catenin target genes) in a cell comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method.

The inventors have previously found cortistatin A inhibits beta-catenin activated transcription in a reporter gene assay and expression of putative Wnt/beta-catenin target genes in AML cells. See, e.g., PCT/US2014/072365, incorporated herein by reference. Numerous studies have linked beta-catenin pathway activation to tumor initiation, maintenance, and growth. Wnt/beta-catenin pathway alterations have been observed in breast cancer, colorectal cancer, hepatocellular carcinoma, medulloblastoma, pancreatic cancer, lymphoma/leukemia, lung cancer, kidney cancer, and Wilms' tumor. See, e.g., Saito-Diaz, et al., *Growth Factors* (2013) 31:1-31. In addition to cancer, other diseases with overactivation of the Wnt/beta-catenin pathway include high bone mass diseases and hypertrophic obesity. Furthermore, variants of the Wnt-beta catenin pathway transcription factor TCF7L2 have been associated with diabetes. See, e.g., MacDonald et al., *Developmental Cell* (2009) 17, 9-26.

In another aspect, provided is a method of treating a JAK-STAT pathway-associated condition comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In another aspect, provided is a method of modulating the STAT1 activity in a cell (e.g., by inhibiting phosphorylation of STAT1 S727 in the JAK-STAT pathway, leading to up- or down-regulation of specific STAT1-associated genes) comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method.

The inventors have previously found cortistatin A also inhibits interferon-gamma-stimulated STAT1 phosphorylation. See, e.g., PCT/US2014/072365, incorporated herein by reference. Inhibition of STAT1 phosphorylation may thus be a therapeutic strategy to treat aberrant inflammation, including in atherosclerosis, to treat cancers, including MPNs and leukemias, and to treat diabetes, through prevention of STAT1-mediated beta-cell apoptosis. IFN-gamma is expressed at high levels in atherosclerotic lesions leading to increased inflammation through STAT1 activation and IFN-gamma activates STAT1 to induce beta-cell apoptosis. See, e.g., Gysemans et al., *Biochem. Soc. Trans* (2008) 36:328. Phosphorylation of STAT1 by CDK8 has also been shown to restrain NK activation and tumor survellience. Therefore, inhibition of CDK8 kinase activity may beneficially enable an NK-mediated tumor cell killing in addition to directly inhibiting the proliferation of tumor cells. See, e.g., Putz et al., *Cell Reports* (2013) 4:437-444.

It has been reported that nuclear CDKs, such as CDK8, drive SMAD transcriptional activation and turnover in BMP and TGF-beta. See, e.g., Alarcon et al., *Cell* (2009) 139: 757-769. Thus, in yet another aspect, provided is a method of treating a TGF-beta/BMP pathway-associated condition comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In another aspect, provided is a method of modulating the TGF-beta/BMP pathway (e.g., by inhibiting CDK8/CDK19 phosphorylation SMAD proteins in the TGF-beta/BMP pathway leading to up- or down-regulation of specific SMAD protein-associated genes) in a cell comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method.

TGF-beta and BMP pathways are critical for tissue homeostasis, modulation of TGF-beta and BMP pathway activity may be a treatment strategy for conditions including but not limited to muscle dystrophy, immune response to transplants, cancer, fibrosis, and Marfan syndrome. See, e.g., Ceco, *FEBS J.* (2013) 280:4198-4209; Akhurst and Hata, *Nat Rev Drug Discov* (2012) 11:790-811.

Hypoxia is a condition in which the body or region of the body is deprived of adequate oxygen supply, and may result from altitude sickness, ischemia, stroke, heart attack, anemia, cancer, and carbon monoxide poisoning. CDK8 has been linked to regulation of hypoxic response, playing a role in induction of HIF-1-A (HIF-1-alpha) target genes. These genes are involved in angiogenesis, glycolysis, metabolic adaption, and cell survival, processes critical to tumor maintenance and growth. See, e.g., Galbraith, et al., *Cell* 153:1327-1339.

Thus, in one aspect, provided is a method of treating a condition associated with hypoxia comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt, quaternary amine, or N-oxide thereof. In another aspect, provided is a method of reducing hypoxia injury comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In yet another aspect, provided is a method of modulating HIF-1-A (HIF-1-alpha) activity (e.g., by inhibiting the expression HIF-1-alpha associated genes) in a cell comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method.

In another aspect, provided is a method of increasing BIM expression (e.g., BCLC2L11 expression) to induce apoptosis in a cell comprising contacting a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof, with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is downregulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., *Nat. Med.* (2012) 18:521-528.

Furthermore, the cortistatins as a class of compounds have been found to have anti-antiogenic activity. See, e.g., Aoki, et al., *JACS* (2006) 128: 3148-9. Angiogenesis is the process of generating new capillary blood vessels from the pre-existing vasculature. After birth, angiogenesis contributes to organ growth, but in adulthood it is strictly regulated and occurs only during wound healing and in the female reproductive cycle. See, e.g., Klagsbrun et al., Molecular angiogenesis. *Chemistry & Biology* 1999, 6 (8), R217-R224. Under normal physiological conditions, angiogenesis is tightly controlled by a series of pro-angiogenic and anti-angiogenic factors, which allow vascular growth for controlled periods of time. See, e.g., Ferrara, Vascular Endothelial Growth Factor as a Target for Anticancer Therapy. *The Oncologist* 2004, 9:2-10. Persistent, unregulated angiogenesis has been implicated in a wide range of diseases, including rheumatoid arthritis, macular degeneration, atherosclerosis, obesity, benign neoplasms, and cancers. See, e.g., Moulton et al., Angiogenesis inhibitors endostatin or TNP-470 reduce intimal neovascularization and plaque growth in apolipoprotein E-deficient mice. *Circulation* 1999, 99, (13), 1726-1732; and Hanahan et al., The hallmarks of cancer. *Cell* 2000, 100, (1), 57-70. That these pathological states are unified by their status as "angiogenesis-dependent diseases" but are otherwise unrelated has led Folkman to propose the concept of angiogenesis as an "organizing principle" in biology, by which many types of seemingly dissimilar phenomena may be connected. See Folkman, Opinion-Angiogenesis: an organizing principle for drug discovery? *Nature Reviews Drug Discovery* 2007, 6(4):273-286.

Thus, in yet another aspect, provided is a method of treating a condition associated with angiogenesis, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

In certain embodiments, the condition associated with angiogenesis is a diabetic condition or associated complication. In certain embodiments, provided is a method of treating a diabetic condition or associated complication comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

As used herein, a "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type 2 diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes.

All forms of diabetes increase the risk of long-term complications (referred to herein as the "associated complication" of the diabetic condition). These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

As will be appreciated by those of ordinary skill in this art, in treating a diabetic condition or complication, an effective amount of a compound administered may, for example, reduce, prevent, or delay the onset, of any one of the following symptoms: reduce fasting plasma glucose level [typical diabetic level is ≥7.0 mmol/l (126 mg/dl); typical prediabetic range is 6.1 to 6.9 mmol/1]; reduce plasma glucose [typical diabetic level is ≥11.1 mmol/l (200 mg/dL) two hours after a 75 g oral glucose load as in a glucose tolerance test]; reduce symptoms of hyperglycemia and casual plasma glucose [typical diabetic level is ≥11.1 mmol/l (200 mg/dl)]; reduce levels of glycated hemoglobin (Hb A1C) [typical diabetic level is ≥6.5%]. Subjects with fasting glucose levels from 110 to 125 mg/dl (6.1 to 6.9 mmol/1) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

In certain embodiments, the associated complication is diabetic retinopathy. For example, in certain embodiments, provided is a method of treating diabetic retinopathy comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

In certain embodiments, the condition associated with angiogenesis is macular degeneration. In certain embodiments, provided is a method of treating macular degeneration comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, provided is a method of treating obesity comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. Evidence suggests that adipose tissue expansion is dependent on vasculature development. Therefore, inhibition of angiogenesis may be therapeutic strategy for restricting the expansion of adipose tissue to prevent and treat obesity. See, e.g., Christiaens and Lijnen, *Molecular and Cellular Endocrinology* (2010) 318: 2-9.

In certain embodiments, the condition associated with angiogenesis is atherosclerosis. In certain embodiments, provided is a method of treating atherosclerosis comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. Evidence suggests that new angiogenesis occurs in atherosclerotic lesions, contributing to their growth and rupture. Therefore, inhibition of angiogenesis may be a therapeutic strategy for restricting the expansion, growth, and ultimate rupture of atherosclerotic plaques to prevent and treat atherosclerosis. See, e.g., Ho-Tin-Noé et al., *Trends Cariovasc. Med.* (2011) 21:183-187.

In certain embodiments, the condition associated with angiogenesis is a proliferative disorder. In certain embodiments, provided is a method of treating a proliferative disorder comprising administering to a subject in need thereof a compound of Formula (A1'), (A2'), (C'), (C1'), (C2'), (A1"), (A2"), (C"), (C1"), or (C2"), or a pharmaceutically acceptable salt thereof.

Exemplary proliferative disorders include, but are not limited to, tumors (e.g., solid tumors), benign neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., endometriod carcinoma, e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myeloid leukemia (AML) (e.g., B-cell AML, T-cell AML), chronic myelogenous leukemia (CML) (e.g., B-cell CML, T-cell CML), chronic myelomonocytic leukemia (CMML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the cancer is associated with CDK8 and/or CDK19 kinase activity.

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML). The inventors have previously found that cortistatin A and cortistatin A analogs inhibit proliferation of AML cell lines in vitro and cortistatin A inhibits AML progression in vivo. See, e.g., PCT/US2014/072365, incorporated herein by reference.

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

Human host proteins, including transcriptional cyclin-dependent kinases (CDKs), have been demonstrated to contribute to the replication of several viruses, including herpes simplex virus (HSV), human immunodeficiency virus (HIV) and human cytomegalovirus (HCMV). See, e.g., Schang et al., J. Virol. (2002) 76:7874-7882. In fact, in fish, it has been demonstrated that walleye dermal sarcoma virus (WDSV) encodes a retroviral cyclin that binds to CDK8 to enhance its kinase activity and thereby modulate viral interferon resistance. See, e.g., Brewster et al., J. Virol. (2015) 89:5450-5461. In agreement with a role of CDK8 activity in interferon response, which is also important in cancer cell survival, treatment with cortistatin A increases expression of genes in MOLM-14 AML cells that have been identified as interferon gamma signaling genes and interferon responsive genes (FIG. 74 and FIG. 75). See, e.g., Browne et al., J. Virol. (2001) 75:12319-12330. HIV has been shown to block interferon induction in multiple cell types. See, e.g., Harman et. al., J Virol. (2015) Apr. 8. pii: JVI.00889-15. [Epub ahead of print]. Collectively, these findings suggest that inhibition of CDK8 and/or CDK19 activity may inhibit viral activity, as well as bacterial, fungal and protozoa activity.

Thus, in yet another aspect, provided is a method of treating an infection comprising administering to a subject in need thereof a compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1"), or a pharmaceutically acceptable salt thereof. In certain embodiments, the infection is a bacterial infection. In certain embodiments, the infection is a fungal infection. In certain embodiments, the infection is a protozoal infection. In certain embodiments, the infection is a viral infection. In certain embodiments, the viral infection is a retroviral infection, and the virus is a retrovirus, i.e., of the family Retroviridae. In certain embodiments, the viral infection is a retroviral infection, and the virus is of the family Retroviridae and subfamily Orthoretrovirinae, Alpharetrovirus, Betaretrovirus, Deltaretrovirus, Epsilonretrovirus, Gammaretrovirus, or Lentivirus. In certain embodiments, the viral infection is a retroviral infection, and the virus is of the family Retroviridae and subfamily Lentivirus. Exemplary virus of the subfamily Lentivirus includes human immunodeficiency virus (HIV), simian immunodeficiency virus (SIV), feline immunodeficiency virus (FIV), equine infectious anemia virus (EIAV), and Visna virus are all examples of lentiviruses. In certain embodiments, the viral infection is a human immunodeficiency virus (HIV) infection. Other viral infections contemplated are infections with the herpes simplex virus (HSV), human immunodeficiency virus (HIV) or human cytomegalovirus (HCMV). In certain embodiments, the virus is an oncovirus, i.e., a virus which is associated with oncogenesis and/or causes cancer. In certain embodiments, treatment of the viral infection is associated with inhibition of CDK8 and/or CDK19 kinase activity.

Compounds of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), and (G1"), and pharmaceutically acceptable salts thereof, may be formulated in dosage unit form for ease of administration and uniformity of dosage. It will be understood, however, that the total daily usage of the compositions comprising a compound as described herein will be decided by the attending physician within the scope of sound medical judgment. The specific therapeutically effective dose level for any particular subject or organism will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 0.1 mg to about 10 mg, or about 0.1 mg to about 15 mg, of a compound per unit dosage form. In certain embodiments, an effective amount of an active agent for administration to a 70 kg adult human comprises about 1 mg, about 5 mg, about 10 mg, about 15 mg, about 20 mg, about 25 mg, about 30 mg, about 40 mg, about 50 mg, about 60 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, about 850 mg, about 900 mg, about 950 mg, or about 1000 mg.

In certain embodiments, the compound may be administered orally or parenterally to an adult human at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 0.01 mg/kg to about 1 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the compound or composition with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically active agent is an anti-cancer agent, e.g., radiation therapy and/or one or more anti-cancer agents.

Exemplary anti-cancer agents include, but are not limited to, interferons, cytokines (e.g., tumor necrosis factor, interferon α, interferon γ), vaccines, hematopoietic growth factors, monoclonal antibody therapy (e.g., CTLA-4 monoclonal antibody therapy), immunostimulants and/or immunodulatory agents (e.g., IL-1, 2, 4, 6, or 12; e.g., anti-PD1 immunotherapy (e.g., lambrolizumab), anti-PD-L1 immunotherapy), immune cell growth factors (e.g., GM-CSF), antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)), JAK1/2 inhibitors (e.g., Ruxolitinib, Tofacitinib, Baricitinib, CYT387, GLPG0634, GSK2586184, Lestaurtinib, Pacritinib, and TG101348), CDK8/19 inhibitors, BLC2 inhibitors (e.g., ABT-199), Pembrolizumiab, Ipilimumiab, Nivoluxiab, MEDI4736, Tremelimumab., MPDL3280A, an IDO1 inhibitor, INCB024360, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin, satraplatin, picoplatin, Nedaplatin, Triplatin, Lipoplatin), vinca alkaloids (e.g. vincristine, vinblastine, vindesine, and vinorelbine), taxoids (e.g. paclitaxel or a paclitaxel equivalent such as nanoparticle albumin-bound paclitaxel, docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), thalidomide, lenalidomide, tyrosine kinase inhibitors (e.g., axitinib (AG013736), bosutinib (SKI-606), cediranib (RECENTIN$^T$, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the compound of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), or (G1") is administered in combination with an anti-cancer agent selected from the group consisting of a monoclonal antibody therapy (e.g., CTLA-4 monoclonal antibody therapy), anti-PD1 immunotherapy (e.g., lambrolizumab), anti-PD-L1 immunotherapy, JAK1/2 inhibitors (e.g., Ruxolitinib, Tofacitinib, Baricitinib, CYT387, GLPG0634, GSK2586184, Lestaurtinib, Pacritinib, and TG101348), CDK8/19 inhibitors, BCL2 inhibitor such as ABT-199, Pembrolizumab, Ipilimumab, Nivolumab, MEDI4736, Tremelimumab, MPDL3280A, an IDO1 inhibitor, and INCB024360.

Intermediate compounds (Int-A1'-1), (Int-A1'-2), (Int-A2'-1), (Int-A2'-1), (Int-A1"-1), (Int-A1"-2), (Int-A2"-1), and (Int-A2"-1) are also contemplated active and useful for the aforementioned methods of use.

Methods of Preparation

Still further provided are methods of preparing compounds of Formula (A1'), (A2'), (C'), (C1'), (C2'), (D1'), (D2'), (E1'), (E2'), (A1"), (A2"), (C"), (C1"), (C2"), (D1"), (D2"), (E1"), (E2"), (G1'), and (G1"). An exemplary synthesis of compounds contemplated herein is provided in Schemes 7 to 18.

The synthesis initially is contemplated using a compound of Formula (I) as starting material. Oxidation (e.g., DDQ, MnO$_2$) of estrone (wherein R$^3$ is —CH$_3$) or norestrone (wherein R$^3$ is H) (I) provides the compound of Formula (III). See, e.g., Stephan et al., *Steroid,* 1995, 60, 809-811. The compound of Formula (III) is protected as an acetal or ketal (e.g., via reaction with HX$^4$R$^4$, or HX$^4$R$^4$—R$^4$X$^4$H, wherein the two R$^4$ groups are joined, wherein R$^{B1}$ and R$^{B2}$ are each independently —X$^4$R$^4$) to give a mixture (e.g., 1:1 mixture) of (IV)-A and (IV)-B. Exemplary conditions contemplated for protection include PTSA and ethylene glycol, PTSA and CH(OMe)$_3$, PTSA and CH(OEt)$_3$, PTSA and 2,2-dimethyl-1,3-propandiol). The protected compounds are then alkylated (e.g., methylated) using an alkylating agent (e.g., Me$_2$SO$_4$ and K$_2$CO$_3$, EtN(i-Pr)$_2$ and TMS-diazomethane) to afford (V)-A and (V)-B, wherein E is optionally substituted alkyl. See Scheme 7.

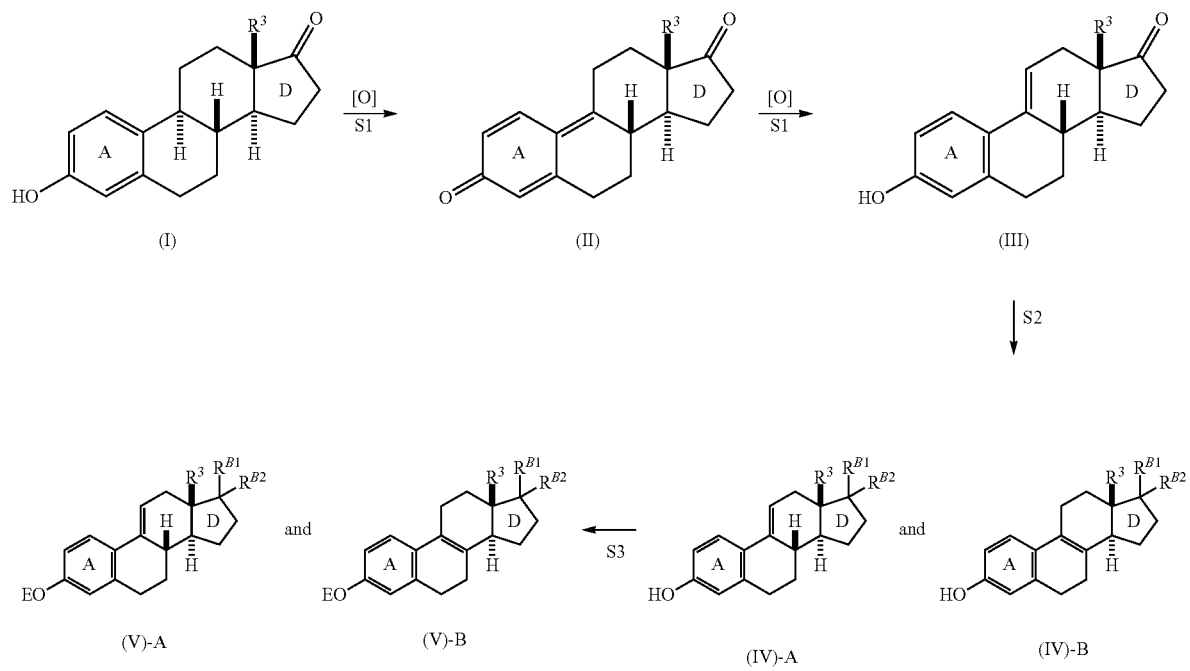

Scheme 8(i)-(iii) provides other exemplary routes to provide a compound of Formula (IV-B), e.g., wherein R$^3$ is —CH$_3$. For example, the compound of Formula (V)-B is achieved as racemic mixtures from 6-methoxy-1-tetralone in four steps as described in Scheme 8(i). For the Grignard reaction, see, e.g., Saraber et al., *Tetrahedron,* 2006, 62, 1726-1742. For hydrogenation, see, e.g., Sugahara et al., *Tetrahedron Lett,* 1996, 37, 7403-7406. Scheme 8(ii) shows method to obtain enantiopure Torgov's intermediate by chiral resolution. See, e.g., Bucourt et al., *J. Bull. Soc. Chim. Fr.* (1967) 561-563. Scheme 8(iii) provides another method of preparing enantiopure Torgov's intermediate aided by enzymatic reduction. See, e.g., Gibian et al., *Tetrahedron Lett.* (1966) 7:2321-2330.

Scheme 8.

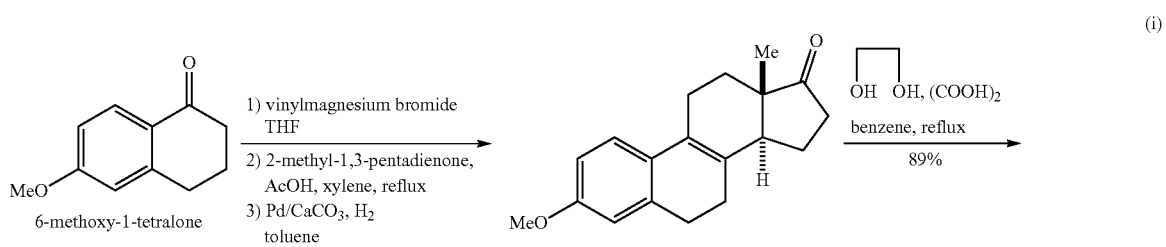

-continued
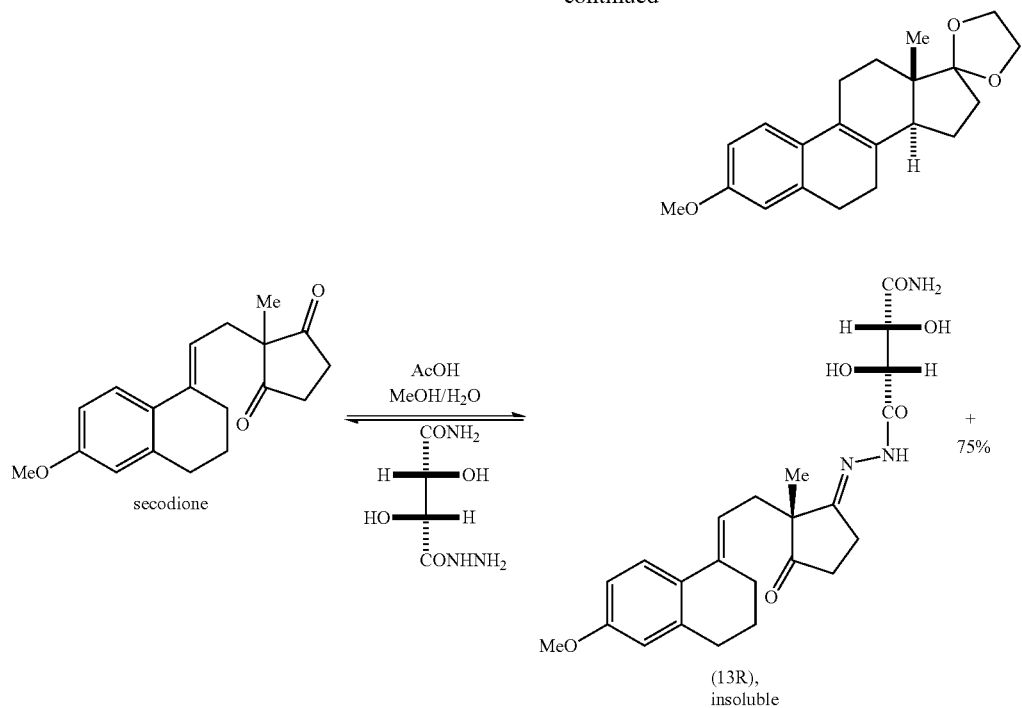
(ii)
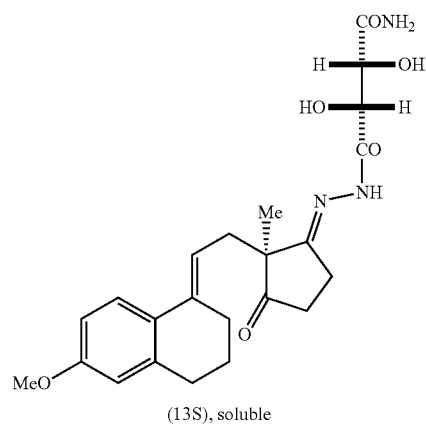
(iii)
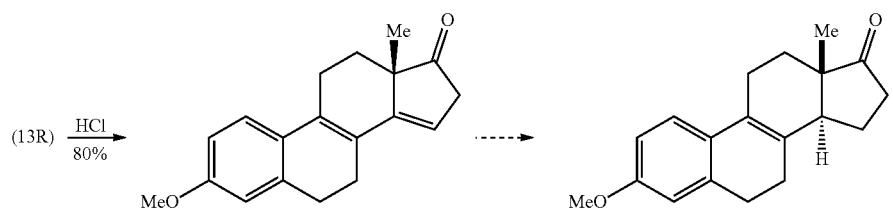
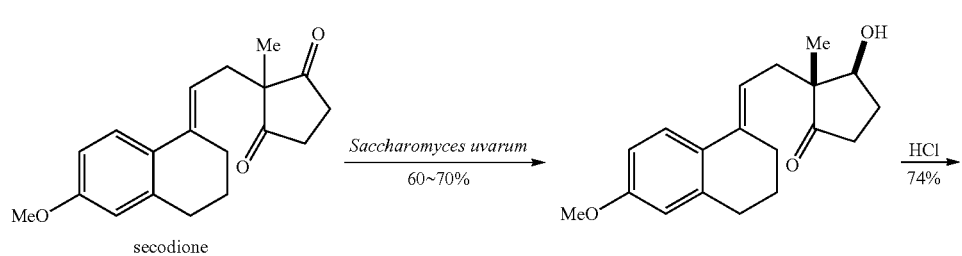

107
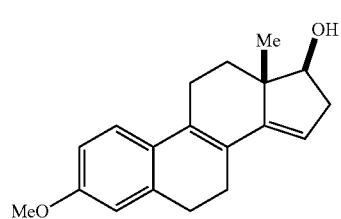
108
-continued
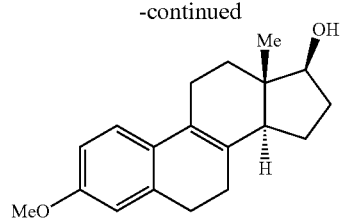
With compounds of Formula (IV-A) and (IV-B) in hand, epoxidation/epoxide opening/epoxidation reactions are conducted (e.g., MMPP, mCPBA) in one-pot to provide the compound of Formula (IX-A) and (IX-B), which are under equilibrium with (IX-A) as a major compound. See Schemes 9A and 9B.
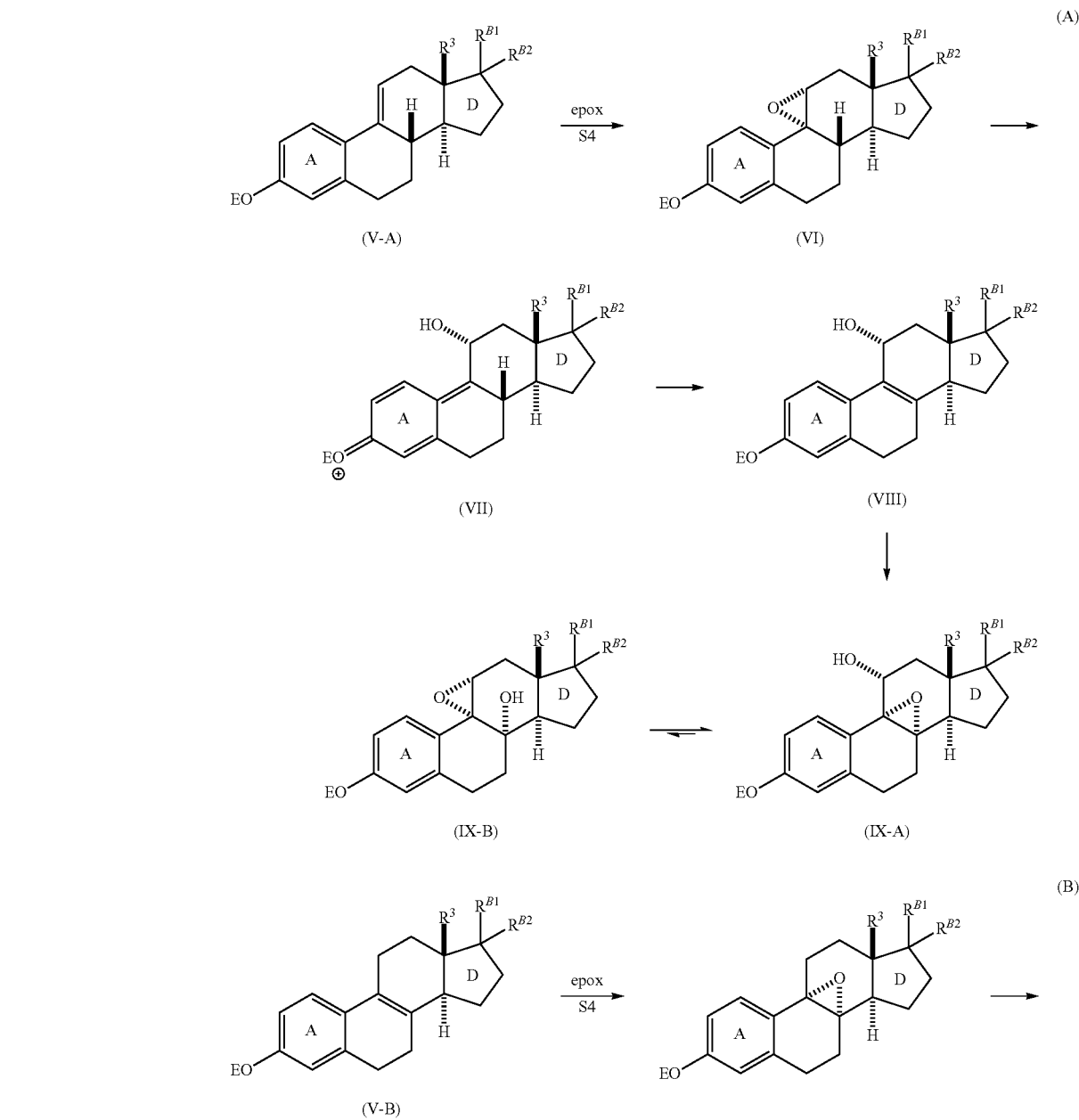

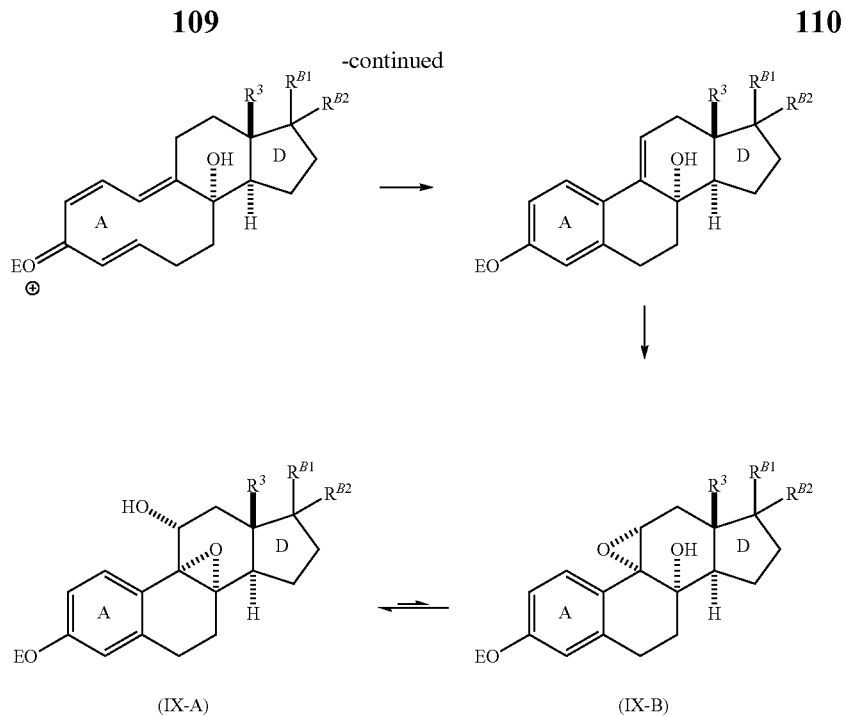

The compound of Formula (IX-A) and (IX-B) are exposed to Birch reduction condition (e.g., Li/NH₃ and t-BuOH, Na/NH₃ and t-BuOH) to give dearomatized compound (X). C3 of A-ring is then protected as an acetal or ketal (e.g., via reaction with HX$^A$R$^A$, or HX$^A$R$^A$—R$^A$X$^A$H, wherein the two R$^A$ groups are joined, and wherein R$^{B1}$ and R$^{B2}$ are each independently —X$^A$R$^A$) to afford the compound (XI). Exemplary protection conditions include PTSA and ethylene glycol, PTSA and CH(OMe)₃, PTSA and CH(OEt)₃, and PTSA and 2,2-dimethyl-1,3-propandiol. See Scheme 10.

Scheme 10.

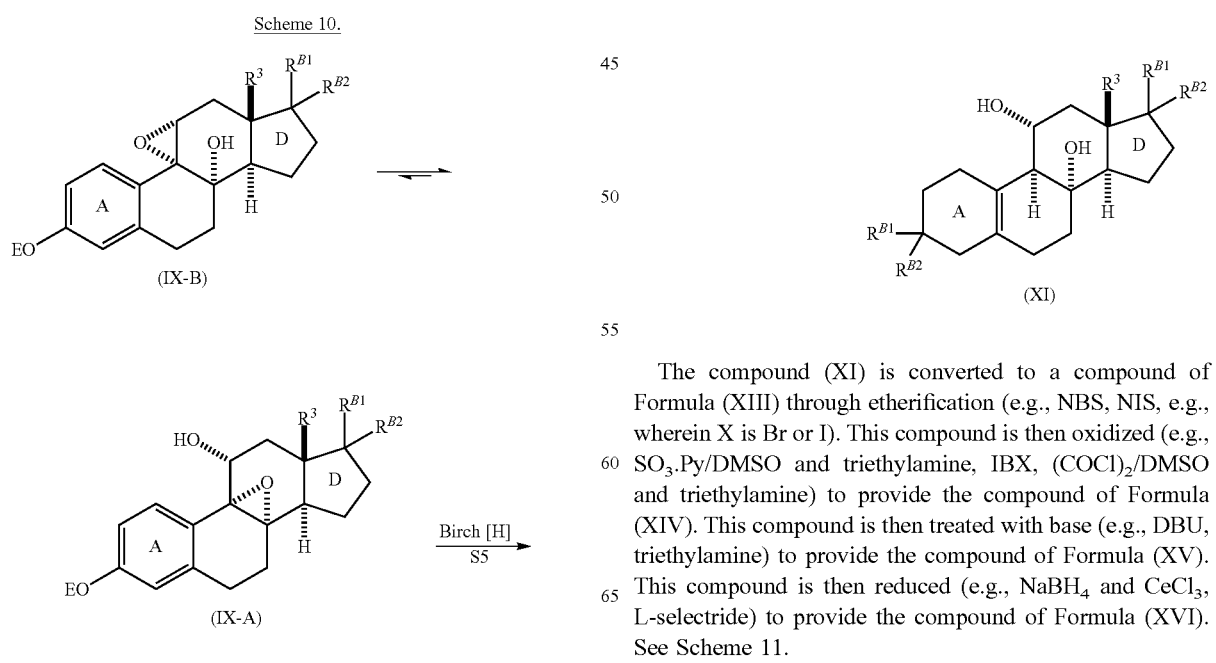

The compound (XI) is converted to a compound of Formula (XIII) through etherification (e.g., NBS, NIS, e.g., wherein X is Br or I). This compound is then oxidized (e.g., SO₃.Py/DMSO and triethylamine, IBX, (COCl)₂/DMSO and triethylamine) to provide the compound of Formula (XIV). This compound is then treated with base (e.g., DBU, triethylamine) to provide the compound of Formula (XV). This compound is then reduced (e.g., NaBH₄ and CeCl₃, L-selectride) to provide the compound of Formula (XVI). See Scheme 11.

Scheme 11.

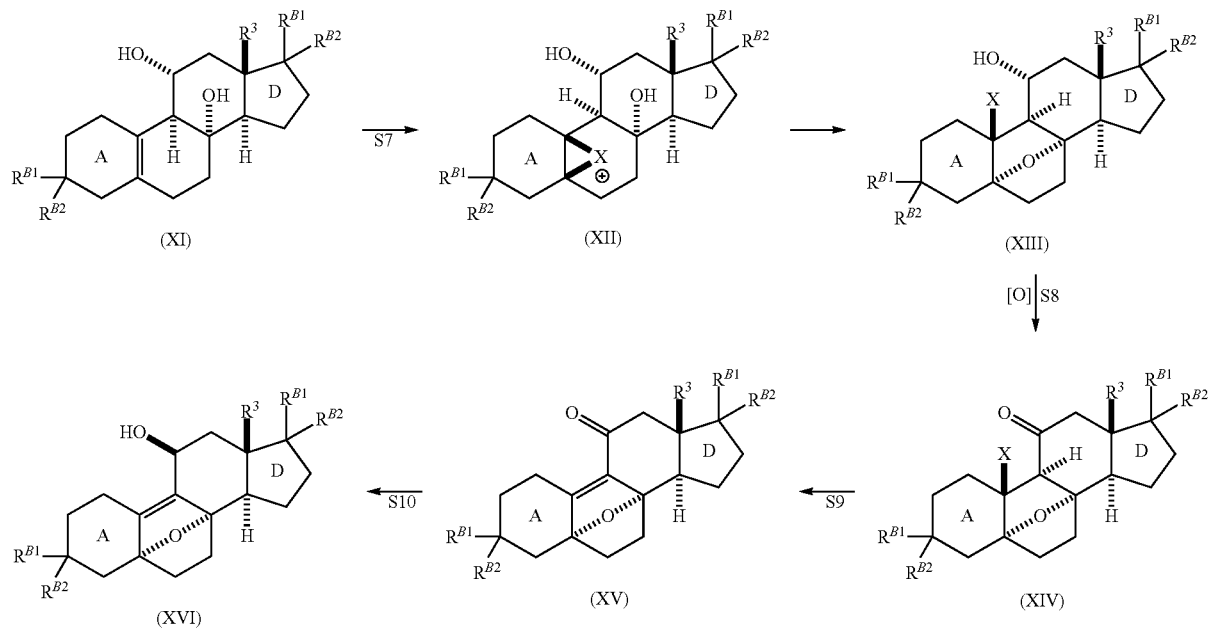

The compound of Formula (XVI) is then treated with cyclopropanation reagents (e.g., ZnEt$_2$ and ClCH$_2$I, ZnEt$_2$ and CH$_2$I$_2$, Zn—Cu and CH$_2$I$_2$) to provide a compound of Formula (XVII). The alcohol of the cyclopropanated product is activated, wherein LG$^1$ is a sulfonyl (e.g., the alcohol is treated with Tf$_2$O, MsCl, to provide an activated alcohol wherein LG$^1$ is Tf or Ms) and treated with base (e.g., 2,6-di-t-butyl-4-methylpyridine, 2,6-lutidine, triethylamine) to provide the compound of Formula (XX). See, e.g., Magnus et al., *Org. Lett.* 2009, 11, 3938-3941. See Scheme 12.

Protecting group on D-ring of the compound of Formula (XX) is then deprotected under acidic conditions (e.g., PTSA and acetone/water, TFA/water) to provide the ketone intermediate of Formula (XXI). This product is treated with a compound of Formula R$^{B1}$-M (e.g., R$^{B1}$—CeCl$_2$, R$^{B1}$—Mg) which is prepared from R$^{B1}$—X (e.g., R$^{B1}$—Br, R$^{B1}$—I) to provide a compound of Formula (XXII), wherein R$^{B1}$ is a non-hydrogen group as defined herein. The compound of Formula (XXII) is activated (e.g., TFAA and pyridine, PhNCS and KH) to provide a compound of Formula (XXIII). Reduction of the compound of Formula (XXIII)

(e.g., AIBN and Bu$_3$SnH) provides the compound of Formula (XXIV). For steps S14, S15 and S16, see, e.g., Flyer et al., *Nature. Chem.* 2010, 2, 886-892, and Yamashita et al., *J. Org. Chem.* 2011, 76, 2408-2425. See Scheme 13A.

Compound (XXIV) may also be prepared from (XX) through conversion to an activated alcohol, wherein LG$^2$ is a sulfonyl (e.g., the alcohol is treated with Tf$_2$O, MsCl, to provide an activated alcohol wherein LG$^2$ is Tf or Ms; by triflation, e.g., KHMDS and PhNTf$_2$, LiHMDS and PhNTf$_2$, Tf$_2$O and 2,6-di-t-butyl-4-methylpyridine) followed by palladium-catalyzed cross coupling with R$^{B1}$-M, wherein M is a substituted boron (e.g., such as —B(R')$_2$, wherein each R' is —OR" or alkyl wherein the alkyl and R" is alkyl or may be joined to form a ring) to provide the compound of Formula (XXVI). Exemplary palladium-catalyzed cross coupling conditions include, but are not limited to, R$^{B1}$—B(pin), R$^{B1}$-(9-BBN—H), R$^{B1}$-OBBD, or R$^{B1}$—B(cat), and Pd(PPh$_3$)$_4$ and Na$_2$CO$_3$, or Pd(dppf)Cl$_2$ and K$_3$PO$_4$) (pin=pinacol; cat=catechol; OBBD=9-oxa-10-brabicyclo[3.3.2]decane; 9-BBN—H=9-broabicyclo[3.3.1]nonane). See, e.g., Nicolaou et al., *J. Am. Chem. Soc.* 2009, 131, 10587-10597. Hydrogenation of C16-C17 double bond (e.g., Pd/C and H$_2$, Raney Ni and H$_2$) gives the compound of Formula (XXIV). See Scheme 13B.

Any one of the compounds of Formula (XXVI) or (XXIV) may then be deprotected (e.g., PTSA and acetone/water, TFA/water, HCl) and the resulting ketone may be trapped as the enolate, followed by subsequent oxidation or amination of the double bond, or reaction of the double bond with an electrophilic carbon C(R$^A$)$_3$-LG, wherein LG is a leaving group, to provide a substituted ketone product, wherein R$^5$ is —OR$^A$, —OC(=O)R$^A$, —OC(=O)OR$^A$, —OC(=O)N(R$^A$)$_2$, —OS(=O)$_2$R$^A$, —N$_3$, —N(R$^A$)$_2$, —NR$^A$C(=O)R$^A$, —NR$^A$C(=O)OR$^A$, —NR$^A$C(=O)N(R$^A$)$_2$, —NR$^A$S(=O)$_2$R$^A$, or —C(R$^A$)$_3$. See Schemes 14A (i) and (ii) and 14B (i) and (ii). Exemplary conditions contemplated for enolate trapping include a combination of a base (e.g., lithium diisopropyl amide (LDA)) and a trapping reagent P$_1$-LG, wherein P$_1$ is silyl and LG is a leaving group (e.g., such as trimethylsilyl chloride).

Exemplary oxidative conditions, e.g., to install a —OR$^A$, —OC(=O)R$^A$, —OC(=O)OR$^A$, —OC(=O)N(R$^A$)$_2$, or —OS(=O)$_2$R$^A$ group at the R$^5$ position include treating the trapped enolate with an oxidant, such as meta-chloroperoxybenzoic acid (MCPBA), MoOOPh, or DMSO, to pro-

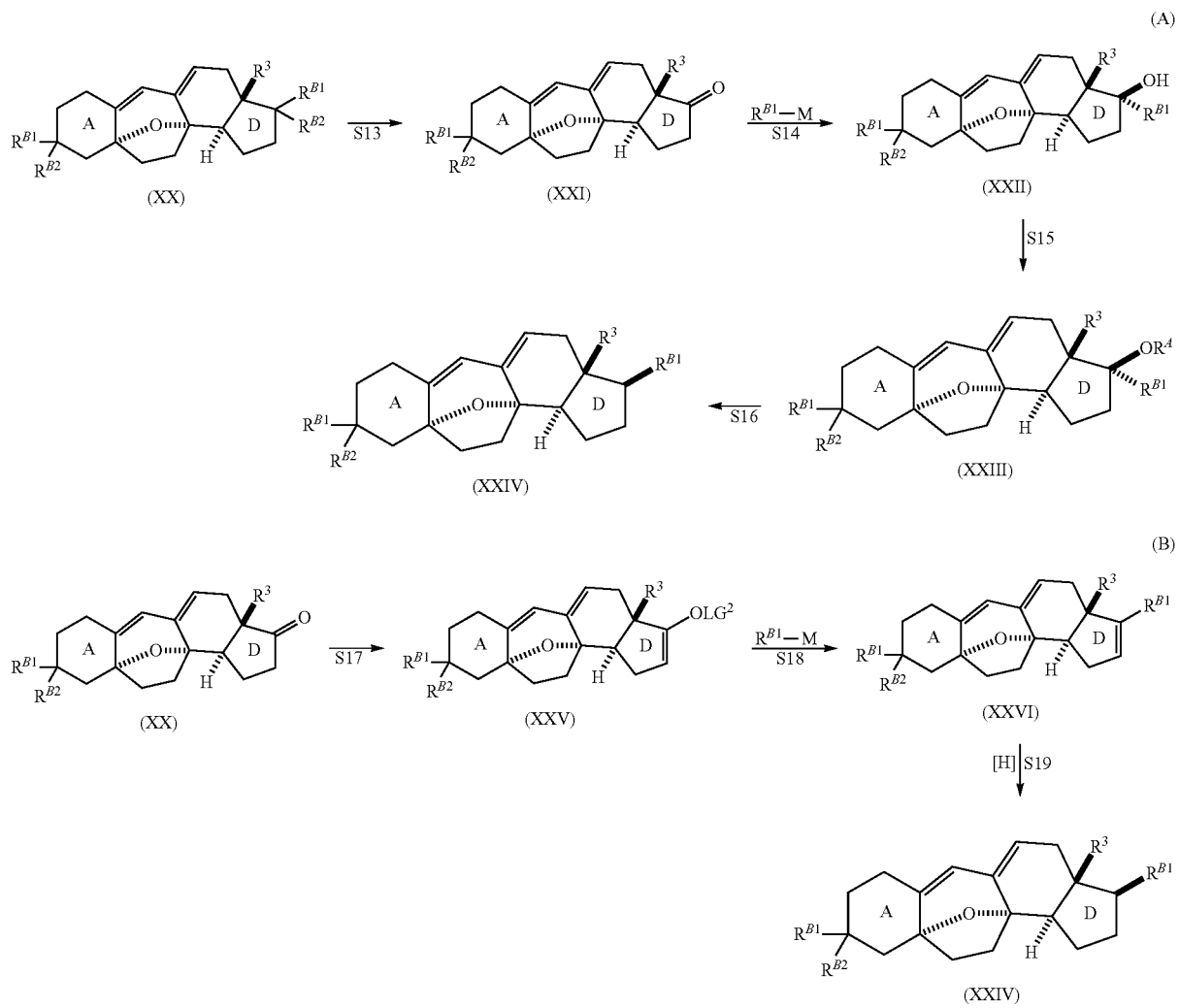

Scheme 13.

vide substituted ketone wherein $R^5$ is —OH, followed by optional protection, e.g., via treatment of the compound wherein $R^5$ is —OH with a compound of formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound wherein $R^5$ is —O$R^A$ (wherein $R^A$ is a non-hydrogen group), —OC(=O)$R^A$, —OC(=O)O$R^A$, —OC(=O)N($R^A$)$_2$, or —OS(=O)$_2R^A$.

Exemplary aminating conditions, e.g., to install an —$N_3$, —N($R^A$)$_2$, —N$R^A$C(=O)$R^A$, —N$R^A$C(=O)O$R^A$, —N$R^A$C(=O)N($R^A$)$_2$, or —N$R^A$S(=O)$_2R^A$ group at the $R^5$ position include treating the trapped enolate with a compound $N_3$-LG wherein LG is a leaving group (e.g., such as trisylazide) to provide substituted ketone wherein $R^5$ is —$N_3$. The substituted ketone wherein $R^5$ is —$N_3$ may be treated with a reducing agent (e.g., such as $PPh_3$) to provide a compound wherein $R^5$ is —$NH_2$, followed by optional protection, e.g., via treatment of the compound wherein $R^5$ is —$NH_2$ with a compound of formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound wherein $R^5$ is —N($R^A$)$_2$ (wherein at least one of $R^A$ is a non-hydrogen group), —N$R^A$C(=O)$R^A$, —N$R^A$C(=O)O$R^A$, —N$R^A$C(=O)N($R^A$)$_2$, or —N$R^A$S(=O)$_2R^A$.

Scheme 14A.

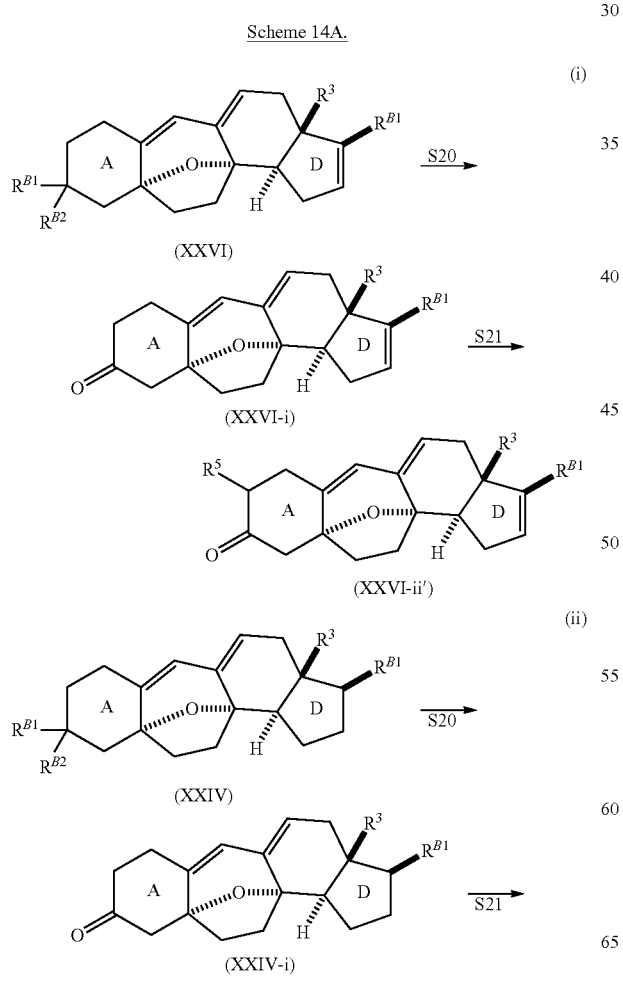

Scheme 14B.

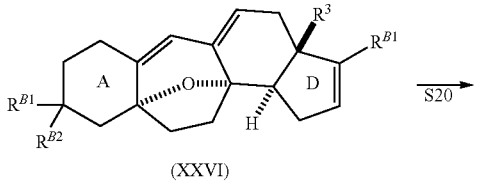

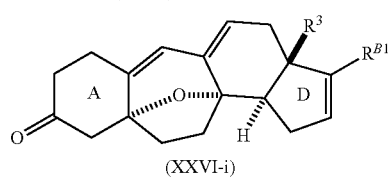

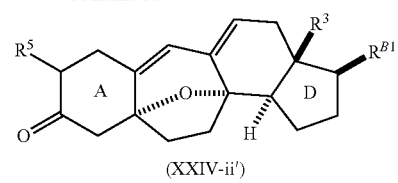

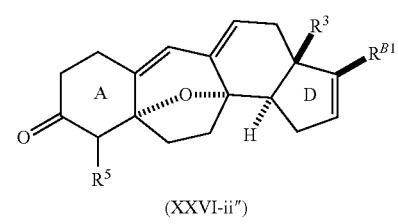

The compound of Formula (XXV) can be converted to the compound of Formula (XXV-i) through palladium-catalyzed carbonylative amination with CO and HN($R^L$)$R^{B3}$ (e.g., Pd(PPh$_3$)$_4$ and triethylamine, Pd(dppf)Cl$_2$ and triethylamine). Conditions for the following steps to get to the compound of Formula (XXV-i), (XXV-iii), (XXV-iv'), (XXV-v'), (XXV-iv"), and (XXV-v") are the same as described previously. See Scheme 15A and 15B.

Scheme 15A.
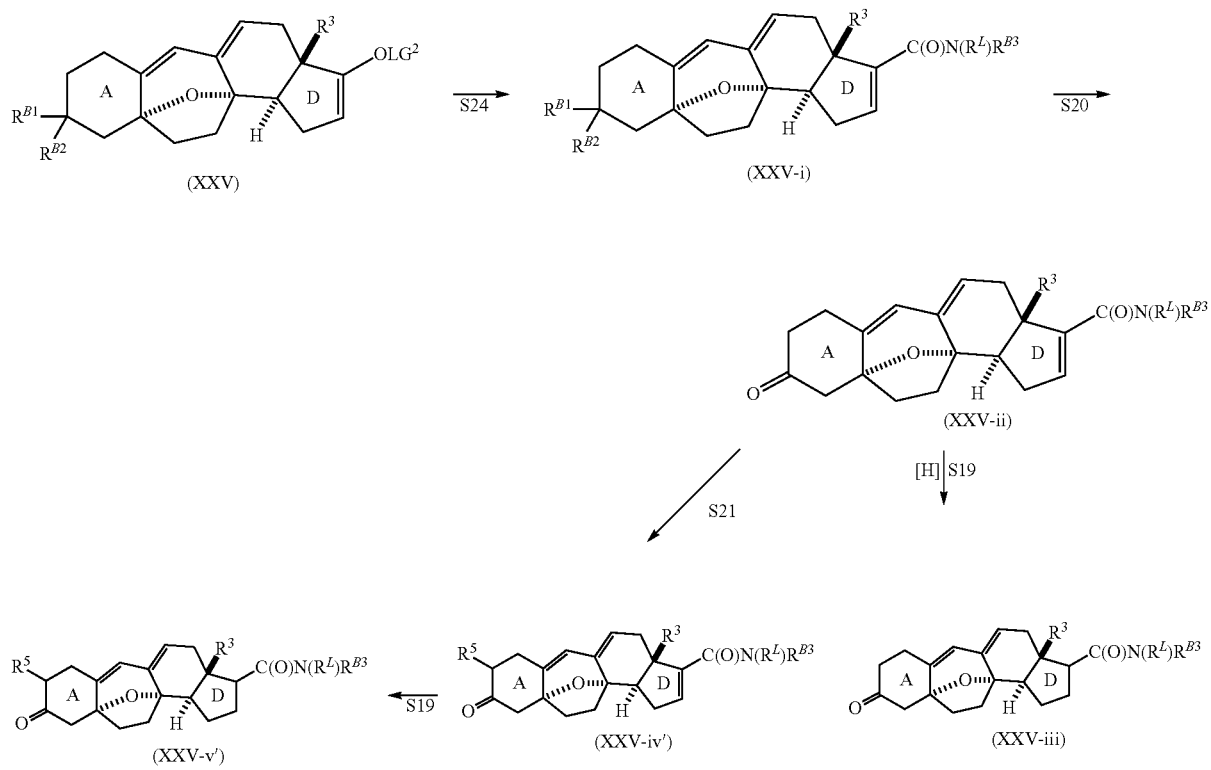
Scheme 15B.
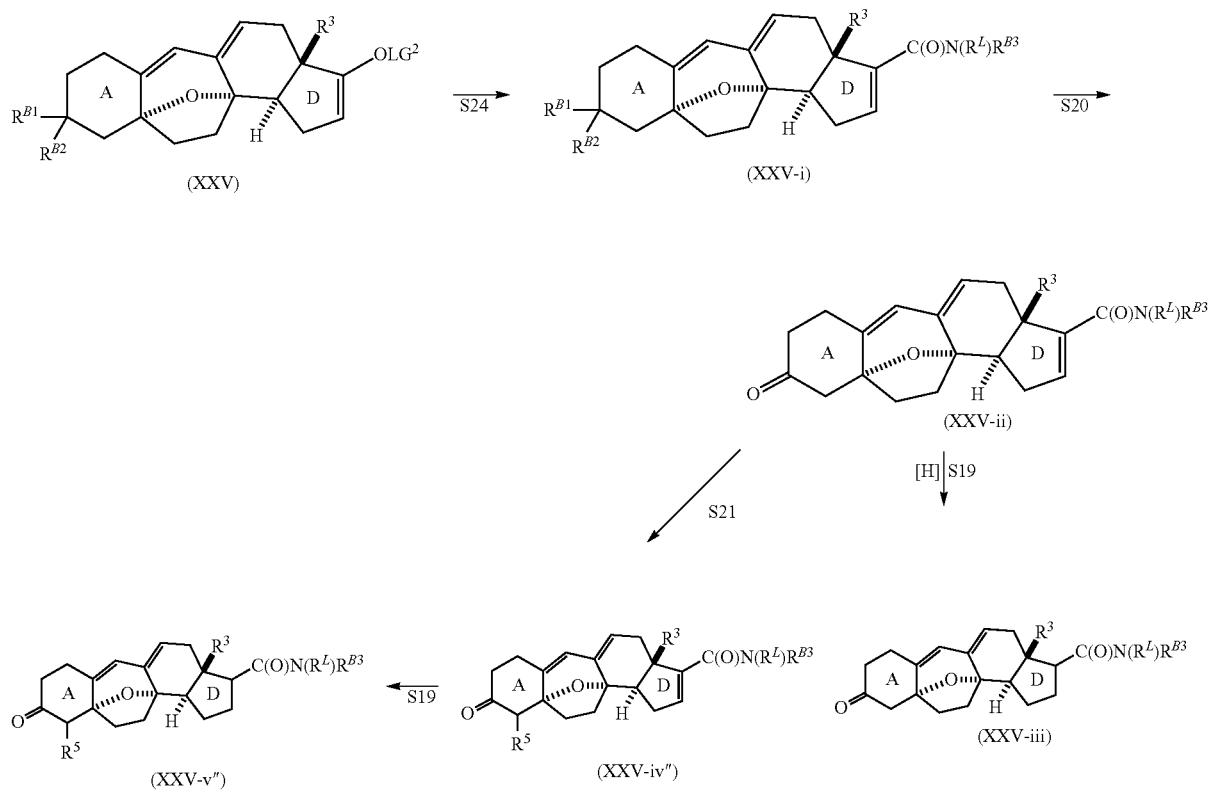

The monoketone compound (XXI) can be reductively aminated with HNR$^{B4}$R$^{B5}$ (e.g., 1,2,3,4-tetrahydro-[2,7] naphthyridine) under conditions previously described to provide the compound of Formula (XXVII). Compound (XXVII) can be converted to the corresponding ketones, imines, and lactones as described previously. See Scheme 16A and 16B.

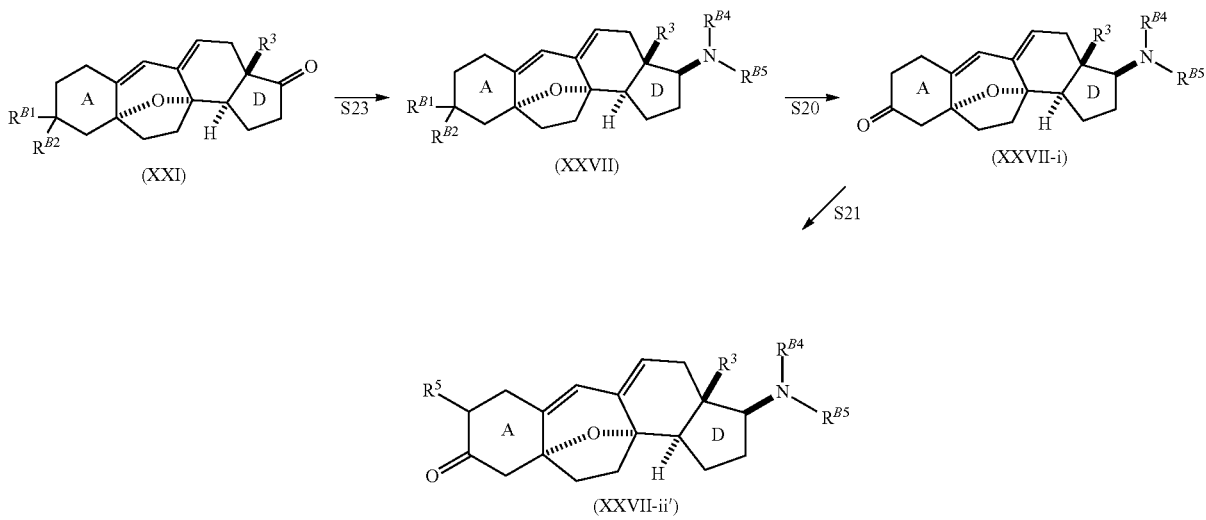

Scheme 16A.

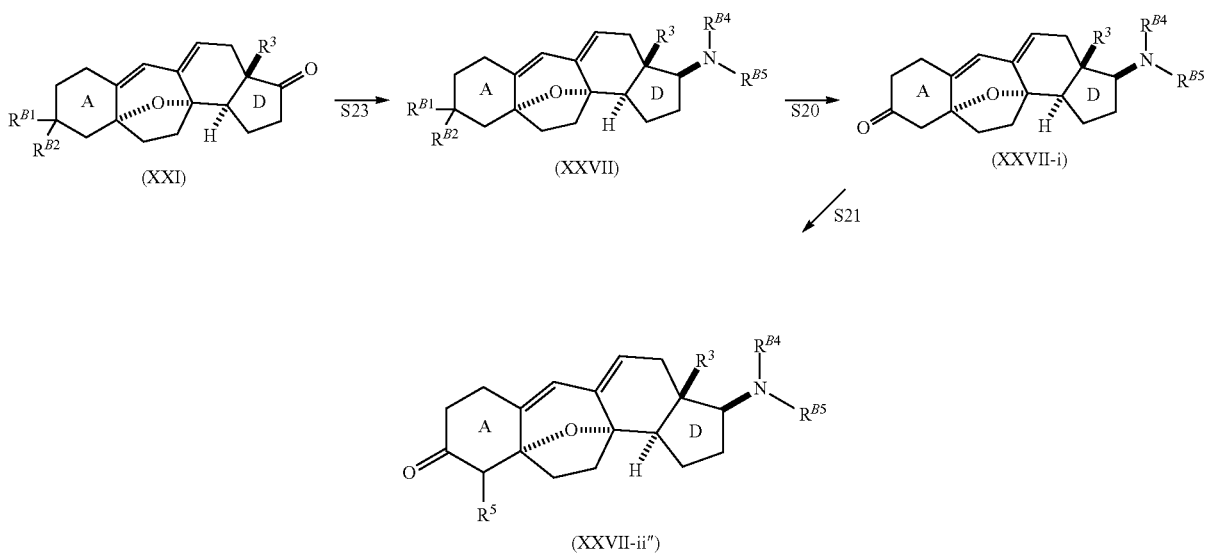

Scheme 16B.

The ketone may then be further synthetically manipulated to provide compounds as described herein. Taking the ketone of formula (XXIV-i) as an example, the ketone may be converted to the free oxime (see, e.g., Scheme 17) or a substituted oxime wherein R$^O$ is a non-hydrogen group (see, e.g., Scheme 18), and then converted via the Beckmann rearrangement to provide the desired lactam products. For example, the free oxime may be generated from the ketone upon treatment with hydroxylamine NH$_2$OH, and may, under suitable rearrangement conditions (e.g. acidic conditions, e.g., H$_2$SO$_4$, HCl, AcOH) directly provide the lactam products. see, e.g., Scheme 17.

Scheme 17.

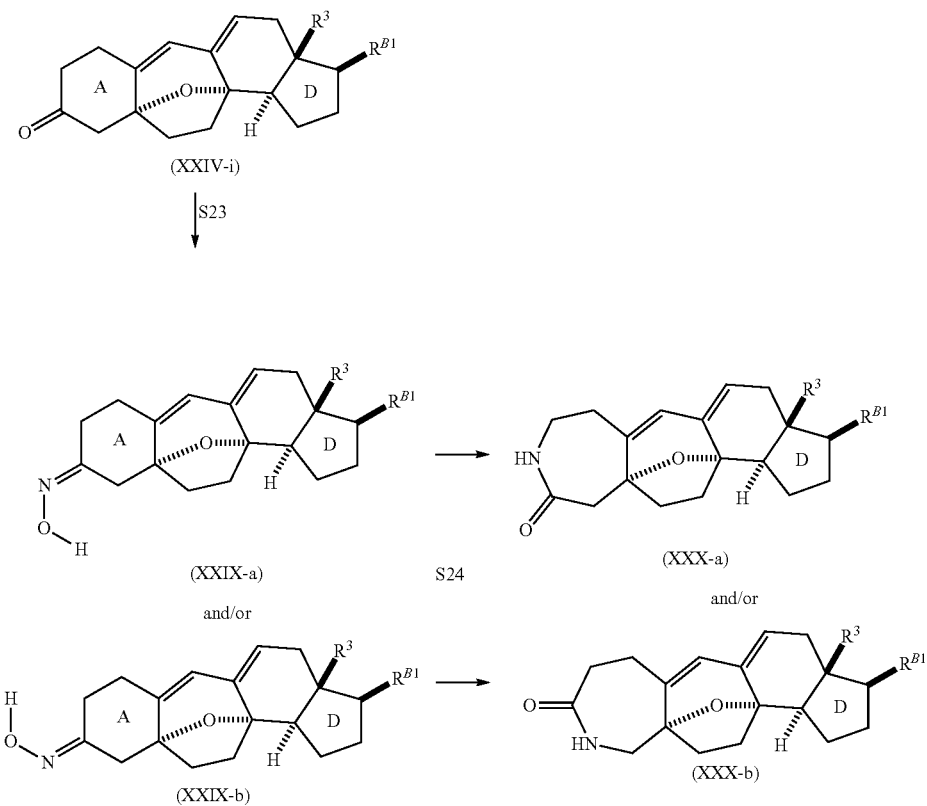

Alternatively, the substituted oxime, wherein $R^O$ is a non-hydrogen group, may be generated from the ketone in a one-step process (S26), e.g., upon treatment with a substituted hydroxyl amine $NH_2OR$, wherein $R^O$ is a non-hydrogen group, or may be generated via a two-step process (S23) and (S27), e.g., first by treatment with hydroxyl amine, $NH_2OH$, followed by treatment with a compound of formula $R^O$-LG, wherein $R^O$ is a non-hydrogen group and LG is a leaving group. See, e.g., Scheme 17. Exemplary leaving groups (LG) include halo (e.g., chloro, bromo, iodo) and —$OSO_2R^{aa}$, wherein $R^{aa}$ as defined herein. The group —$OSO_2R^{aa}$ encompasses leaving groups such as tosyl, mesyl, and besyl, wherein $R^{aa}$ is optionally substituted alkyl (e.g., —$CH_3$) or optionally substituted aryl (e.g., phenyl, tolyl). Exemplary compounds of formula $R^O$-LG include LG-C(=O)$R^A$, LG-C(=O)O$R^A$, LG-C(=O)N($R^A$)$_2$, LG-S(=O)$_2R^A$, LG-Si($R^A$)$_3$, LG-P(=O)($R^A$)$_2$, LG-P(=O)(O$R^A$)$_2$, LG-P(=O)(N$R^A$)$_2$, LG-P(=O)$_2R^A$, LG-P(=O)$_2$(O$R^A$), or LG-P(=O)$_2$N($R^A$)$_2$, wherein LG is as defined herein. Specifically contemplated compounds of formula LG-S(=O)$_2R^A$ include Cl—S(=O)$_2$CH$_3$ (MsCl), Cl—S(=O)$_2$C$_6$H$_4$-($_p$CH$_3$) (TsCl), and Cl—S(=O)$_2$C$_6$H$_5$ (BsCl). The substituted oxime may, under suitable rearrangement conditions (e.g. acidic conditions, e.g., $H_2SO_4$, HCl, AcOH) directly provide the lactam products.

Scheme 18.

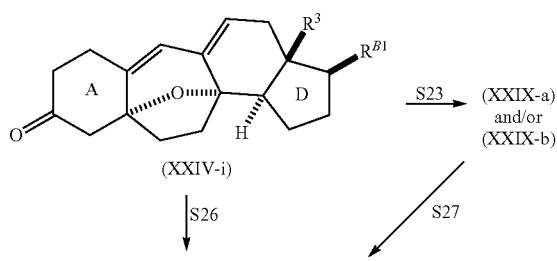

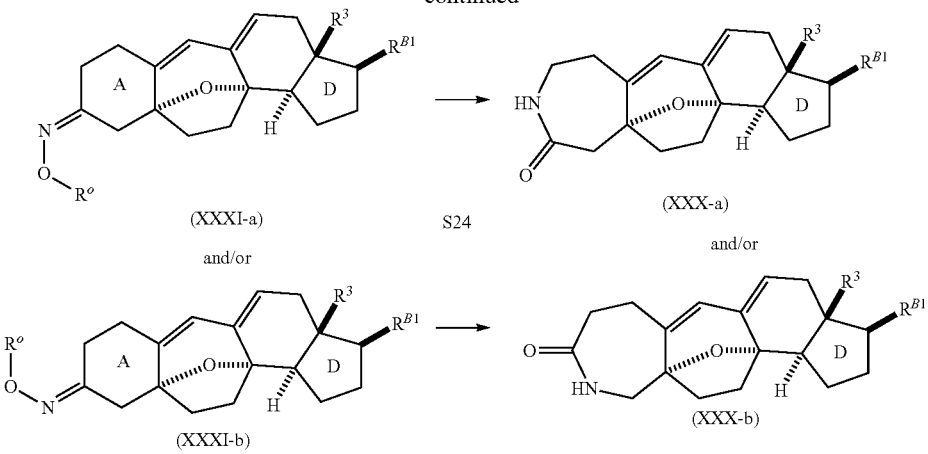

Alternatively, the ketone may be reduced (as depicted in step S30) under Wolff-Kishner reductive conditions to provide compounds of Formula (G1') and (G1"). See Scheme 19. Exemplary Wolff-Kishner conditions are described in Furrow, M. E.; Myers, A. G. (2004). "Practical Procedures for the Preparation of N-tert-Butyldimethylsilylhydrazones and Their Use in Modified Wolff-Kishner Reductions and in the Synthesis of Vinyl Halides andgem-Dihalides". *Journal of the American Chemical Society* 126 (17): 5436-5445, incorporated herein by reference.

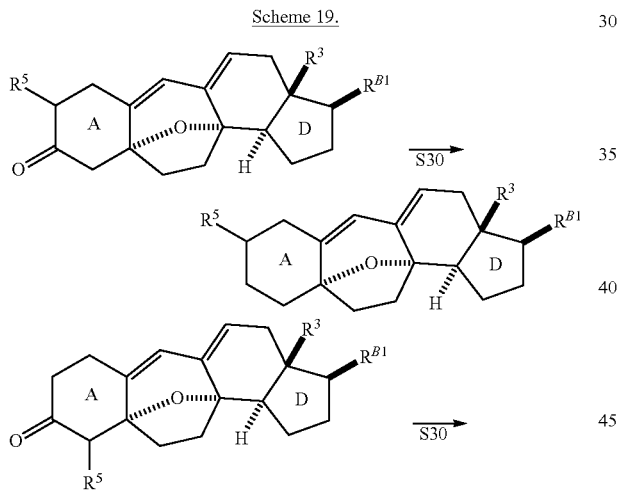

As understood herein, the oxime produced via the above described reactions may comprise a single oxime C3 isomeric product, or a mixture of both oxime C3 isomeric products. It is also generally understood that the Beckmann rearrangement proceeds by a trans [1,2]-shift; thus, in any given reaction, production of a mixture of lactam products, and wherein one lactam is the major product, is contemplated.

The lactam products may then be reduced to the azepine product using a variety of conditions, e.g., for example, use of hydrides (e.g., lithium aluminum hydride), the Clemmenson reduction (e.g, Zn(Hg)/HCl), and the Wolff-Kishner reduction (e.g., hydrazine and base (e.g., KOH), with heat). See, e.g., Scheme 20.

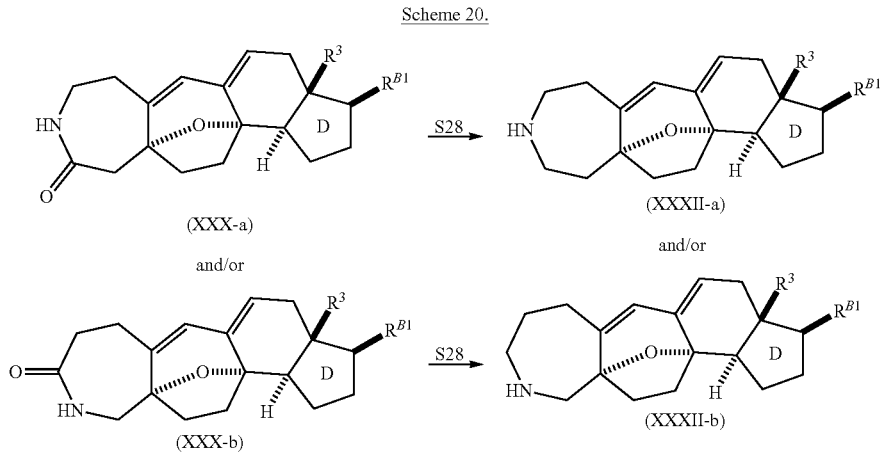

Various other compounds, such as the piperadine products, e.g., of Formula (E1'), (E2'), (E1"), (E2"), (G1'), and (G1") may be synthesized as described herein.

As used herein, a "major product" or "major component" refers to the product of the reaction or component of a mixture (e.g., the oxime, lactam, azepine or piperadine product or mixture) that is in excess (e.g., produced or provided in excess) of the other corresponding product or component, i.e., greater than 50% of the sum of the two products produced from the reaction, e.g., greater than 60%, 70%, 80%, 90%, or 95% of the sum of the two products or components.

Thus, in one aspect, provided is a method of preparing a compound of Formula (A1-NH'), (A2-NH'), (A1-NH"), or (A2-NH"):

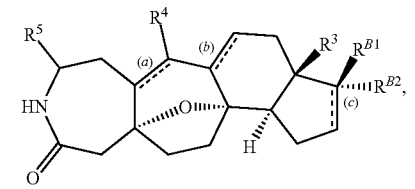
(A1-NH')

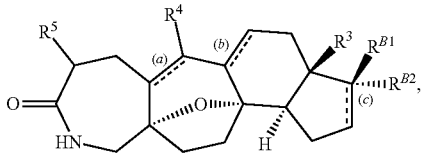
(A2-NH')

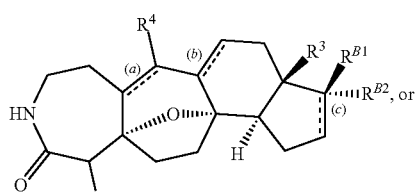
(A1-NH")

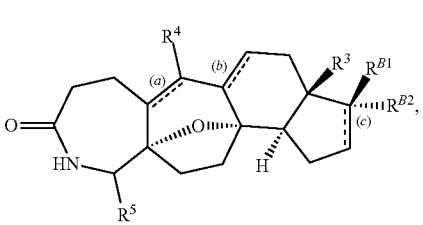
(A2-NH")

or a pharmaceutically acceptable salt thereof;
the method comprising converting a compound of Formula (C—OH'), (C'), (C—OH"), or (C"), wherein $R^O$ is a non-hydrogen group:

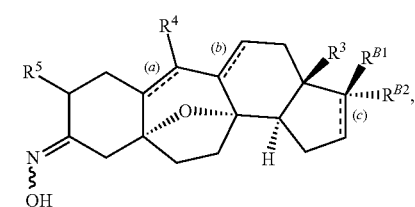
(C-OH')

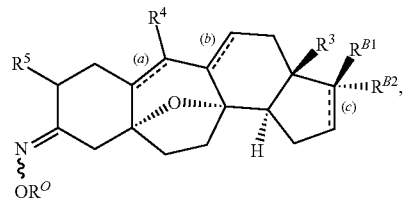
(C')

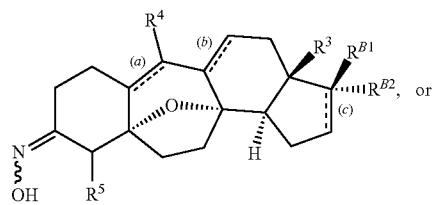
(C-OH")

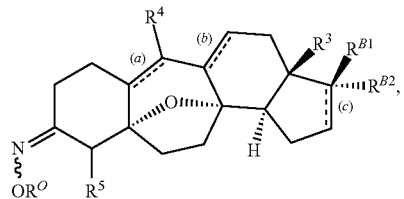
(C")

or a pharmaceutically acceptable salt thereof, to provide a compound of Formula (A1-NH') or (A2-NH'), and/or (A1-NH") or (A2-NH"), or pharmaceutically acceptable salt thereof.

In certain embodiments, the compound of Formula (C—OH') or (C—OH") comprises a mixture of oximes, wherein the oxime of Formula (C1-OH') or (C1-OH") is the major component:

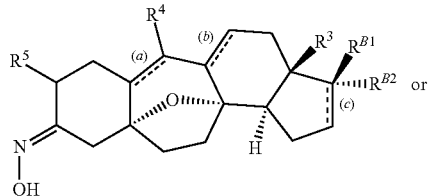
(C1-OH')

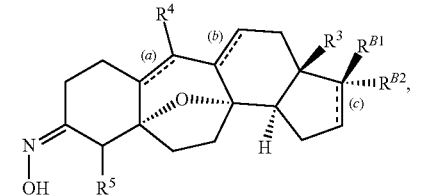
(C1-OH")

or a pharmaceutically acceptable salt thereof.

In certain embodiments, wherein the compound of Formula (C—OH') or (C—OH") comprises a mixture of oximes, and wherein the compound of Formula (C1-OH') or (C1-OH") is the major component, the compound of Formula (A1-NH') or (A1-NH") is produced as the major product.

In certain embodiments, the compound of Formula (C—OH') or (C—OH") comprises a mixture of oximes, wherein the compound of Formula (C2-OH') or (C2-OH") is the major component:

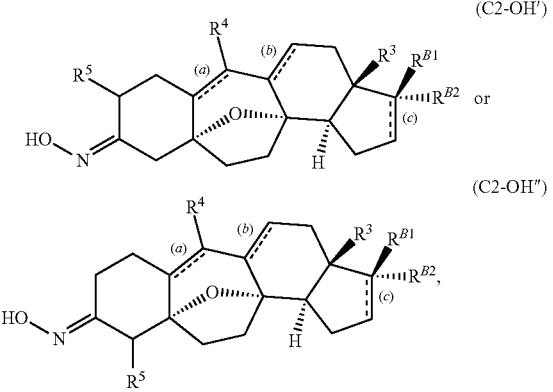

(C2-OH')

(C2-OH")

or a pharmaceutically acceptable salt thereof.

In certain embodiments, wherein the compound of Formula (C—OH') or (C—OH") comprises a mixture of oximes, and wherein the compound of Formula (C2-OH') or (C2-OH") is the major component, the compound of Formula (A2-NH') or (A2-NH") is produced as the major product.

In certain embodiments, the compound of Formula (C—OH') or (C—OH") is prepared by treating a compound of Formula (B') or (B"):

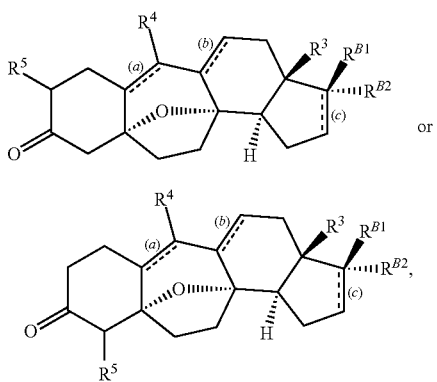

(B')

or (B")

or a pharmaceutically acceptable salt thereof, with a compound of formula $NH_2OH$.

In certain embodiments, the compound of Formula (C') or (C"), wherein $R^O$ is a non-hydrogen group, is prepared by treating a compound of Formula (B') or (B"):

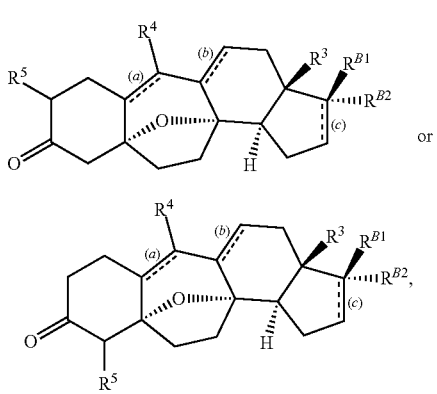

(B')

or (B")

or a pharmaceutically acceptable salt thereof, with $NH_2OR^O$ or $NH_2OH$ followed by treatment with $R^O$-LG.

In one aspect, provided is a method of preparing a compound of Formula (B') or (B"), or a pharmaceutically acceptable salt, quaternary amine salt, or N-oxide thereof, wherein $R^5$ is $—OR^A$, $—OC(\!\!=\!\!O)R^A$, $—OC(\!\!=\!\!O)OR^A$, $—OC(\!\!=\!\!O)N(R^A)_2$, or $—OS(\!\!=\!\!O)_2R^A$ comprising treating a compound of formula (B1):

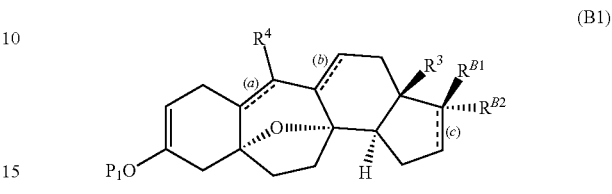

(B1)

or a pharmaceutically acceptable salt, quaternary amine salt, or N-oxide thereof; wherein $P_1$ is silyl, under oxidative conditions.

In certain embodiments, the compound resulting from treatment of the compound of Formula (B1) under oxidative conditions is a compound wherein $R^5$ is —OH. In certain embodiments, the compound of Formula (B') or (B") wherein $R^5$ is —OH is optionally treated with a compound of formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound of Formula (B') or (B") wherein $R^5$ is —O$R^A$ (wherein $R^A$ is a non-hydrogen group), —OC(=O)$R^A$, —OC(=O)O$R^A$, —OC(=O)N($R^A$)$_2$, or —OS(=O)$_2R^A$.

In another aspect, provided is a method of preparing a compound of Formula (B') or (B"), or a pharmaceutically acceptable salt, quaternary amine salt, or N-oxide thereof, wherein $R^5$ is $—N_3$, $—N(R^A)_2$, $—NR^AC(\!\!=\!\!O)R^A$, $—NR^AC(\!\!=\!\!O)OR^A$, $—NR^AC(\!\!=\!\!O)N(R^A)_2$, or $—NR^AS(\!\!=\!\!O)_2R^A$, comprising treating a compound of formula (B1):

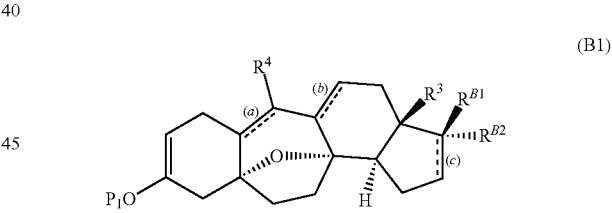

(B1)

or a pharmaceutically acceptable salt, quaternary amine salt, or N-oxide thereof; wherein $P_1$ is silyl, under aminating conditions.

In certain embodiments, the compound resulting from treatment of the compound of Formula (B1) under aminating conditions is a compound wherein $R^5$ is $—N_3$. In certain embodiments, the compound of Formula (B') or (B") wherein $R^5$ is $—N_3$ is reduced to a compound of Formula (B') or (B") wherein $R^5$ is $—NH_2$. In certain embodiments, the compound of Formula (B') or (B") wherein $R^5$ is $—NH_2$ is treated with a compound of Formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound of Formula (B') or (B") wherein $R^5$ is $—N(R^A)_2$ (wherein at least one of $R^A$ is a non-hydrogen group), $—NR^AC(\!\!=\!\!O)R^A$, $—NR^AC(\!\!=\!\!O)OR^A$, $—NR^AC(\!\!=\!\!O)N(R^A)_2$, or $—NR^AS(\!\!=\!\!O)_2R^A$.

In still yet another aspect, provided is a method of preparing a compound of Formula (B') or (B"), or a pharmaceutically acceptable salt, quaternary amine salt, or N-oxide thereof, wherein $R^5$ is —C($R^A$)$_3$, comprising treating a compound of formula (B1):

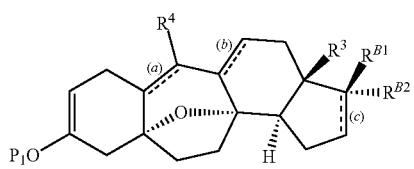
(B1)

or a pharmaceutically acceptable salt, quaternary amine salt, or N-oxide thereof; wherein $P_1$ is silyl, with a compound of formula C($R^A$)$_3$-LG, wherein LG is a leaving group.

In still yet another aspect, provided is a method of preparing a compound of Formula (B1):

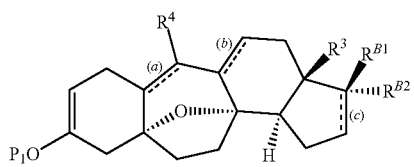
(B1)

or a pharmaceutically acceptable salt, quaternary amine salt, or N-oxide thereof; the method comprising contacting a compound of Formula (B0):

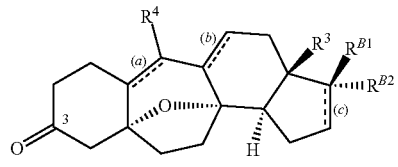
(B0)

with a base and a compound of formula $P_1$-LG, wherein LG is a leaving group.

In certain embodiments, the method further comprises protecting the free lactam moiety. For example, in certain embodiments, the method further comprises treating a compound of Formula (A1-NH'), (A2-NH'), (A1-NH"), or (A2-NH") with a compound of formula $R^N$-LG, wherein $R^N$ is a non-hydrogen group and LG is a leaving group, to provide compounds of Formula (A1'), (A2'), (A1"), or (A2"):

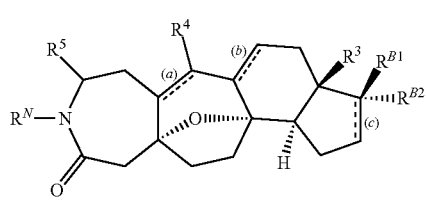
(A1')

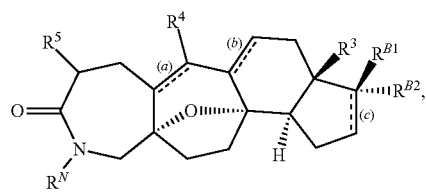
(A2')

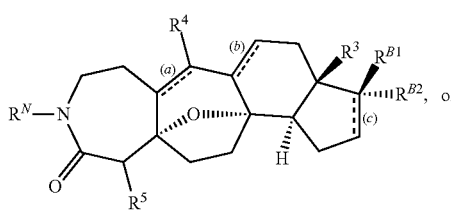
(A1")

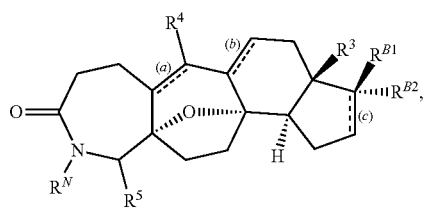
(A2")

or a pharmaceutically acceptable salt thereof, wherein $R^N$ is a non-hydrogen group.

In another aspect, provided is a method of preparing a compound of Formula (D1') or (D1"):

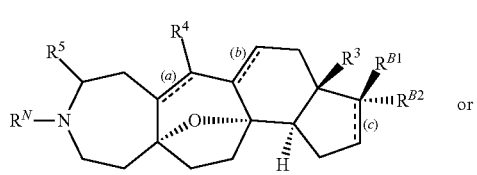
(D1')

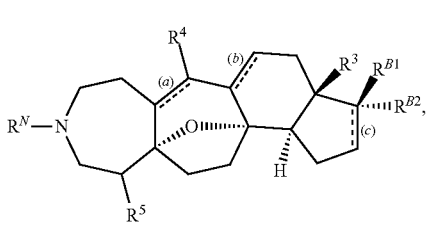
(D1")

or pharmaceutically acceptable salt thereof, the method comprising the step of reducing a compound of Formula (A1') or (A1"):

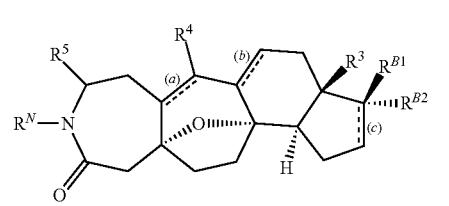
(A1')

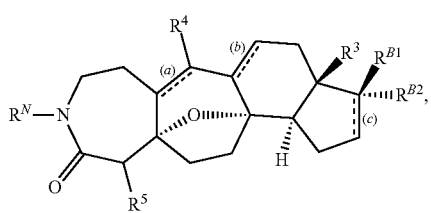
(A1″)

or pharmaceutically acceptable salt thereof, to provide the compound of Formula (D1') or (D1″), or pharmaceutically acceptable salt thereof.

In yet another aspect, provided is a method of preparing a compound of Formula (D2') or (D2″):

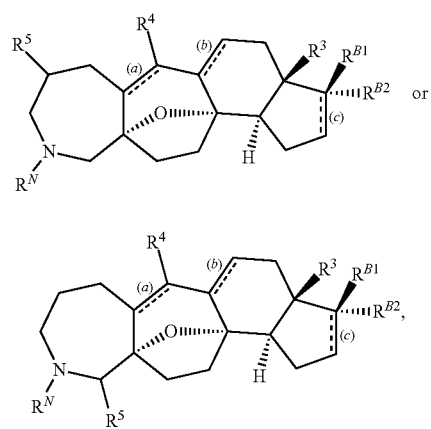
(D2')
(D2″)

or pharmaceutically acceptable salt thereof, the method comprising the step of reducing a compound of Formula (A2') or (A2″):

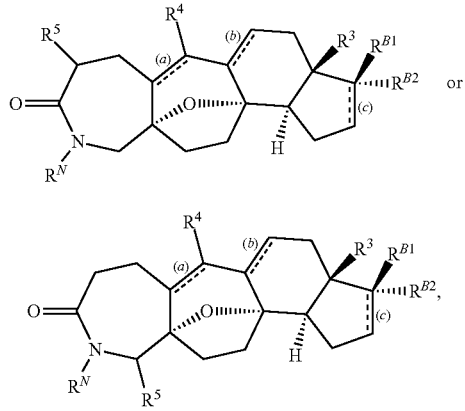
(A2')
(A2″)

or pharmaceutically acceptable salt thereof, to provide the compound of Formula (D2') or (D2″), or pharmaceutically acceptable salt thereof.

In certain embodiments, the reducing step comprises reducing with lithium aluminum hydride (LAH).

In another aspect, provided is a method of preparing a compound of Formula (E1') or (E1″):

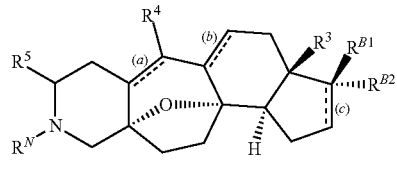
(E1')

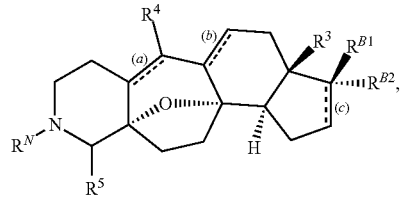
(E1″)

or a pharmaceutically acceptable salt thereof:

the method comprising:

hydrolyzing of the lactam compound of Formula (A1'), (A2'), (A1″), or (A2″):

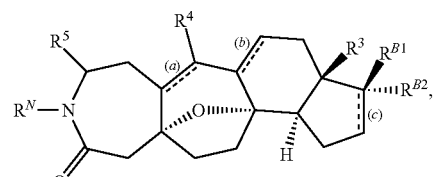
(A1')

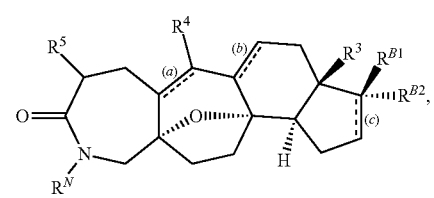
(A2')

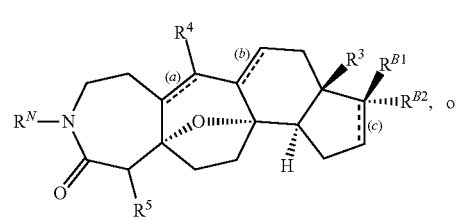
(A1″)

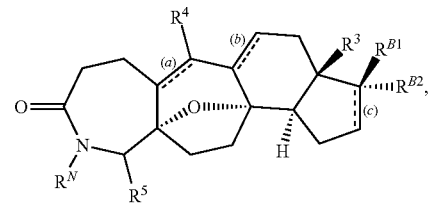
(A2″)

to the ring opened carboxylic acid of formula:

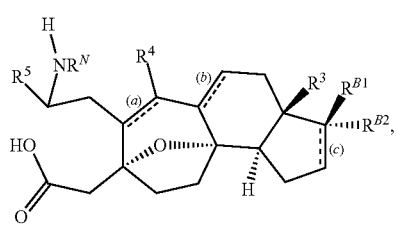
(Int-A1'-1)

-continued

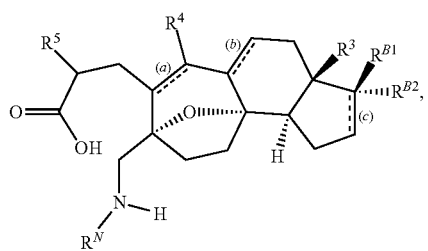
(Int-A2'-1)

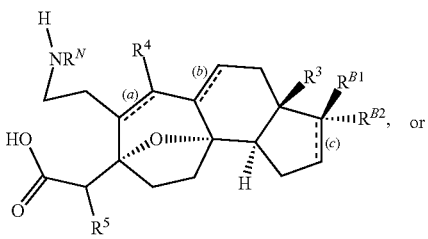
(Int-A1''-1)

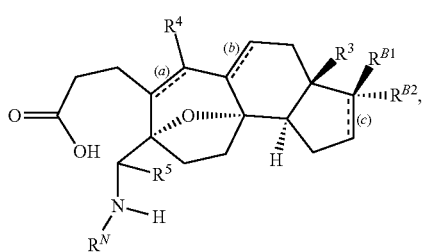
(Int-A2''-1)

decarboxylatively halogenating the ring opened carboxylic acid to provide a halogenated compound of formula:

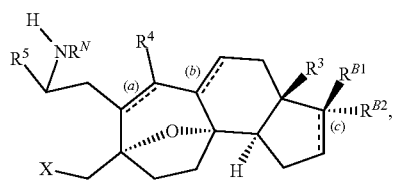
(Int-A1'-2)

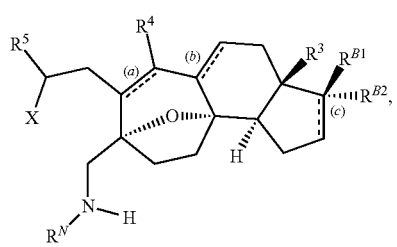
(Int-A2'-2)

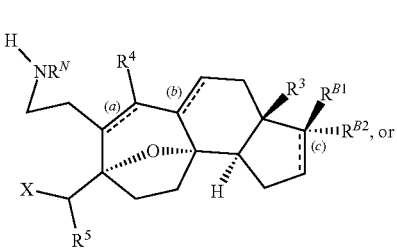
(Int-A1''-2)

-continued

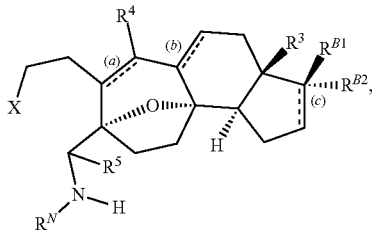
(Int-A2''-2)

wherein X is chlorine, bromine, or iodine, and cyclizing the halogenated compound to provide the compound of Formula (E1') or (E1'').

In another aspect, provided is a method of preparing a compound of Formula (E2') or (E2''):

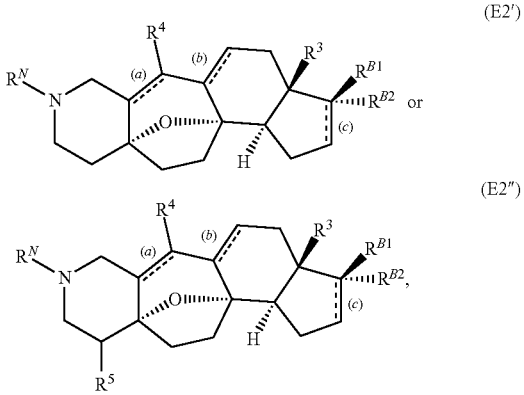
(E2')

(E2'')

or a pharmaceutically acceptable salt thereof:
the method comprising enol trapping of the ketone of Formula (B*') or (B*''):

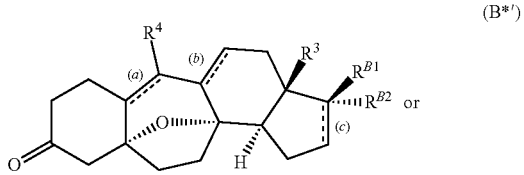
(B*')

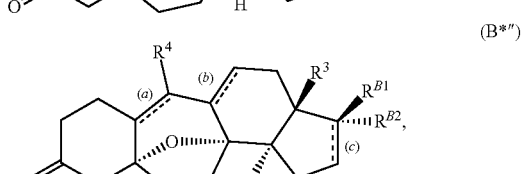
(B*'')

or pharmaceutically acceptable salt thereof, with a compound of formula $R^O$-LG,
  wherein:
    LG is a leaving group, and
    $R^O$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^A$, —C(=O)O$R^A$, —C(=O)N(R^A)_2, —S(=O)_2R^A, —Si(R^A)_3, —P(=O)(R^A)_2, —P(=O)(OR^A)_2, —P(=O)(NR^A)_2, —P(=O)_2R^A, —P(=O)_2(OR^A), —P(=O)_2N(R^A)_2, or an oxygen protecting group, to provide a compound of formula:

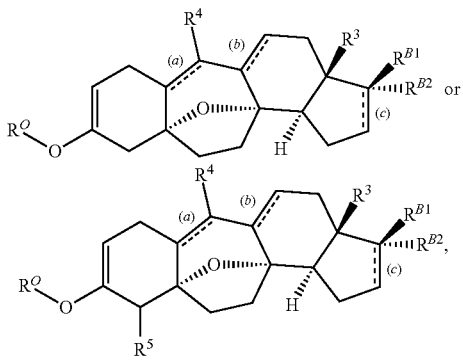

or pharmaceutically acceptable salt thereof;

oxidatively cleaving the alkenyl moiety (e.g., with OsO_4; Pb(OAc)_4)) to provide a compound of formula:

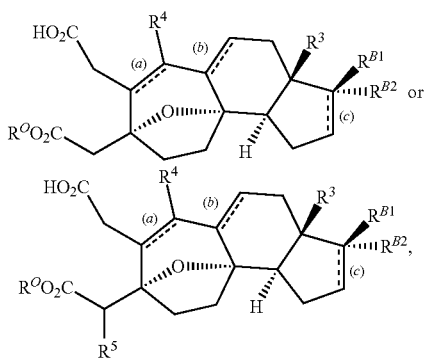

or pharmaceutically acceptable salt thereof;

forming an acyl azide (e.g., with SOCl_2, TMSN_3) to provide a compound of formula:

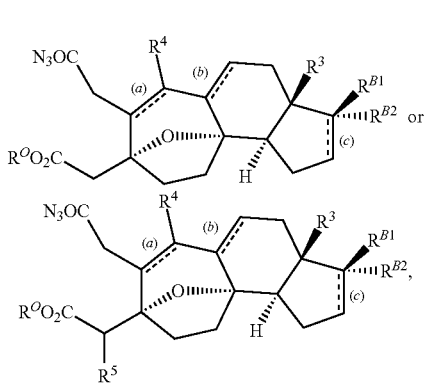

or pharmaceutically acceptable salt thereof;

reacting the he acyl azide under Curtius rearrangement conditions (e.g., heating) to provide the amino compound of formula:

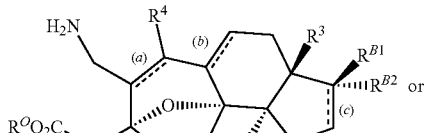

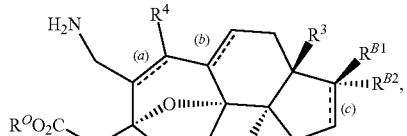

or pharmaceutically acceptable salt thereof;

cyclizing the amino compound (e.g., in situ, with heat) to provide a lactam compound of formula:

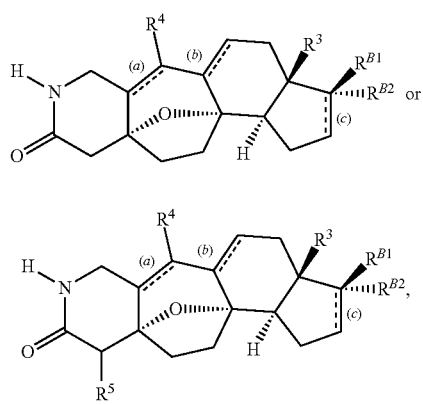

or pharmaceutically acceptable salt thereof, and reducing the lactam compound (e.g., with lithium aluminum hydride) to provide a compound of Formula (E2') or (E2"):

(E2')

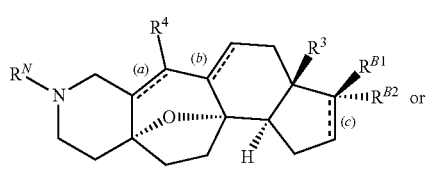

(E2")

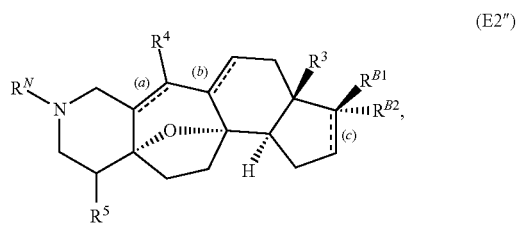

or pharmaceutically acceptable salt thereof, wherein $R^N$ is hydrogen, optionally followed by amino protection wherein $R^N$ is a non-hydrogen group as defined herein.

In another aspect, provided is method of preparing a compound of Formula (G1'):

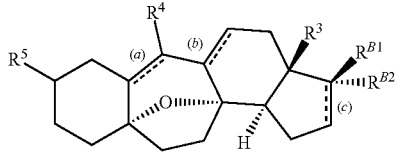

(G1')

or a pharmaceutically acceptable salt, quaternary amine salt, or N-oxide thereof; the method comprising reducing a compound of Formula (B'):

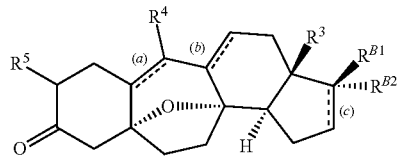

(B')

or a pharmaceutically acceptable salt, quaternary amine salt, or N-oxide thereof.

In another aspect, provided is method of preparing a compound of Formula (G1"):

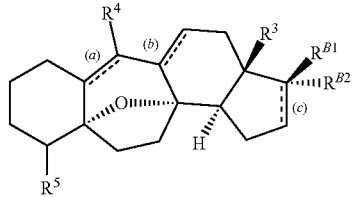

(G1")

or a pharmaceutically acceptable salt, quaternary amine salt, or N-oxide thereof, the method comprising reducing a compound of Formula (B"):

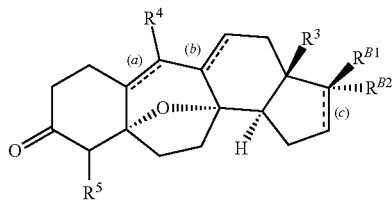

(B")

or a pharmaceutically acceptable salt, quaternary amine salt, or N-oxide thereof.

Exemplary Synthetic Methods

Materials and Instrumentation

All reactions were performed in flame-dried glassware under a positive pressure of argon unless otherwise noted. Flash column chromatography was performed as described by Still et al., *J. Org. Chem.* 1978, 43, 2923-2925 employing silica gel 60 (40-63 µm, Whatman).

Commercial reagents and solvents were used as received with the following exceptions: tetrahydrofuran (THF), dichloromethane ($CH_2Cl_2$) were degassed with argon and passed through a solvent purification system (designed by J. C. Meyer of Glass Contour) utilizing alumina columns as described by Pangborn et al., *Organometallics* 1996, 15, 1518-1520. Pyridine and triethylamine were distilled over calcium hydride before use. The celite used was Celite® 545, purchased from J. T. Baker. The molarities of n-butyllithium solutions were determined by titration using 1,10-phenanthroline as an indicator (average of three determinations).

$^1H$ NMR spectra were recorded with a Varian INOVA-600 or Varian INOVA-500 spectrometer. Proton chemical shifts are reported in parts per million (δ scale) and are calibrated using residual undeuterated solvent as an internal reference ($CDCl_3$: δ 7.26 ($CHCl_3$), $C_6D_6$: δ 7.15 ($C_6D_5H$)). Data for $^1H$ NMR spectra are reported as follows: chemical shift (δ ppm) (multiplicity, coupling constant (Hz), integration). Multiplicities are reported as follows: s=singlet, d=doublet, t=triplet, q=quartet, m=multiplet, br=broad, app=apparent, or combinations thereof. $^{13}C$ NMR spectra were recorded with a Varian INOVA-500 spectrometer. High-resolution mass spectra (HRMS) were obtained from the Harvard University Mass Spectrometry Laboratory where electrospray ionization (ESI) mass spectroscopy (MS) experiments were performed on an Agilent 6210 TOF LC/MS instrument.

Example 1

Synthesis of Ketone Starting Material

Scheme 1-1.
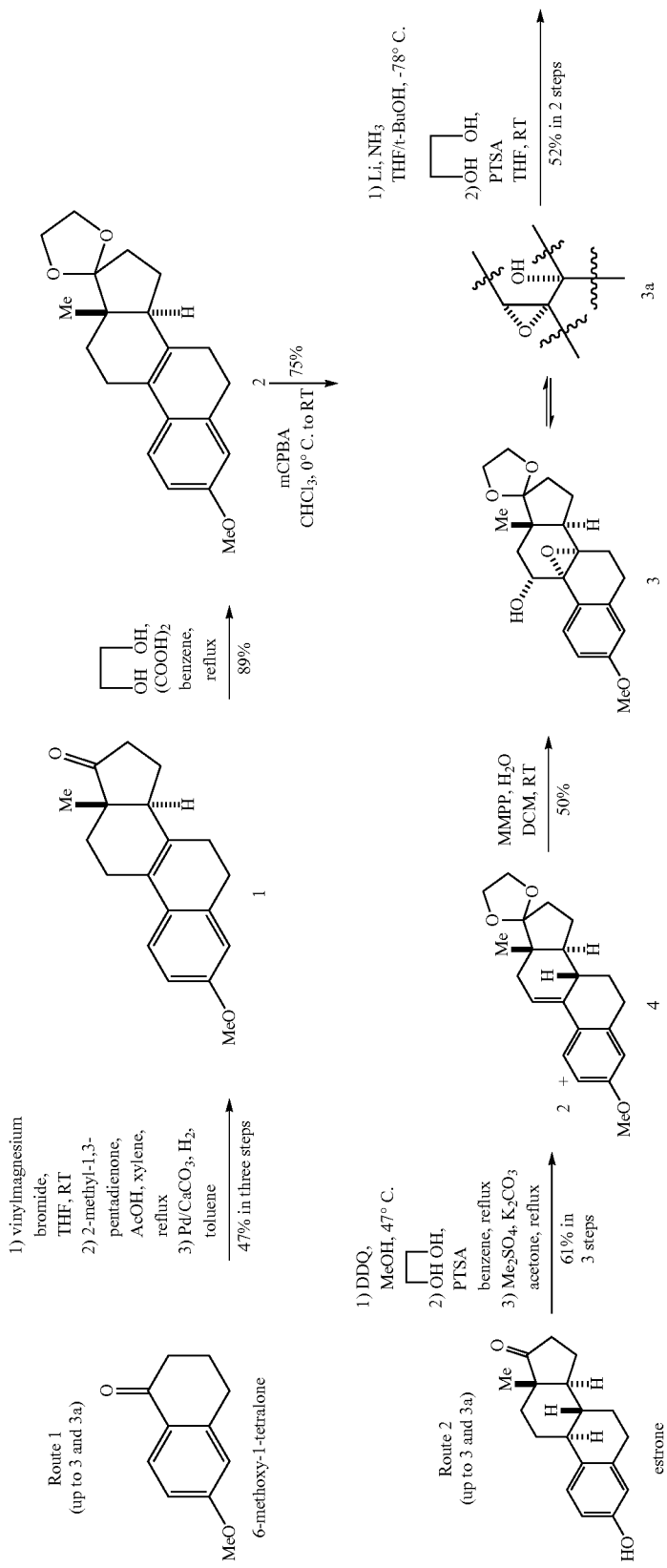

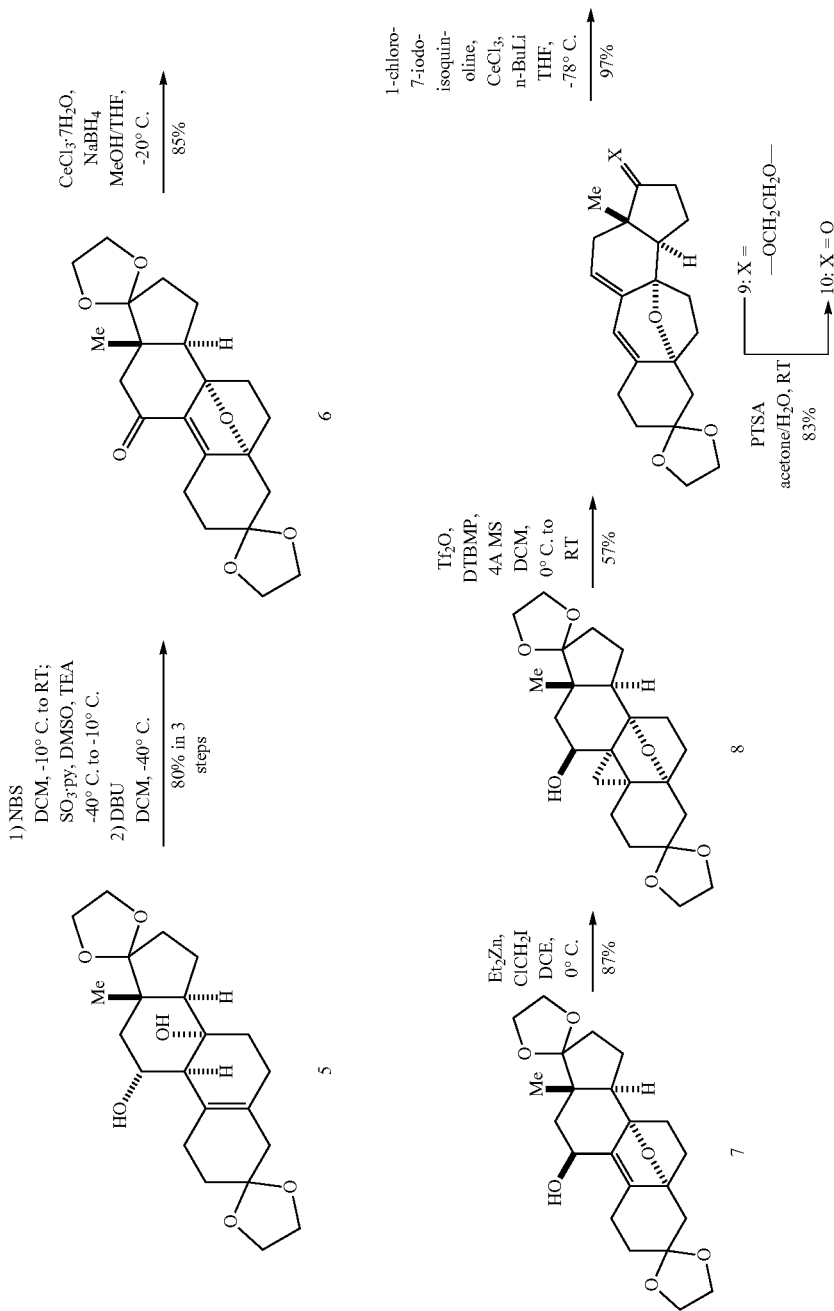

-continued
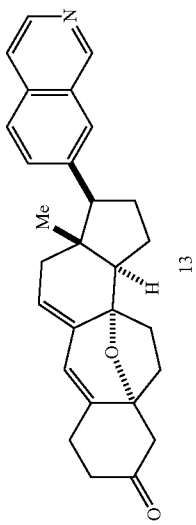
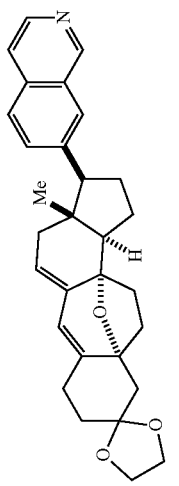
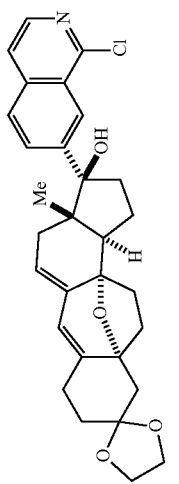

Route 1: Synthesis of 8,9-unsaturated methoxyetheneketone from 6-methoxy-1-tetralone (Compound 1)

The Grignard reaction was done with 20.0 g (113 mmol, 1.00 equiv) of 6-methoxy-1-tetralone and the product was used without purification by flash chromatography. See, e.g., Saraber et al., *Tetrahedron* 2006, 62, 1726-1742. To a solution of Grignard reaction product and 2-methyl-1,3-pentadienone (12.8 g, 114 mmol, 1.01 equiv) in xylene (140 mL) was added AcOH (64.6 mL, 1.13 mol, 10.0 equiv) and the reaction mixture was warmed to reflux. After 2 h, the reaction was allowed to cool to room temperature and the concentrated under reduced pressure. The mixture of 1:1 of toluene and ethyl ether was added to dissolve the solid residue and the mixture was filtered. The filtrate was washed sequentially with saturated $NaHCO_3$ solution (200 mL) and brine, dried over $MgSO_4$, and concentrated under reduced pressure. The residue was purified by flash chromatography (silica gel, eluent: 20:1:1 Hexanes:EtOAc:DCM) to afford the Torgov's diene. Spectral data was consistent with those previously reported. See, e.g., Soorukram, D.; Knochel, P. *Org. Lett.* 2007, 9, 1021-1023. The Torgov's diene was converted to 8,9-unsaturated methoxyetheneketone compound 1 (15.0 g, 47% over 3 steps) based on the literature known procedure. See, e.g., Sugahara et al., *Tetrahedron Lett.* 1996, 37, 7403-7406.

Route 1: Synthesis of 8,9-unsaturated methoxyetheneketal (Compound 2)

To a solution of compound 1 (15.0 g, 53.1 mmol, 1.0 equiv) in benzene (215 mL) and ethylene glycol (72 mL) was added oxalic acid (2.30 g, 12.1 mmol, 0.22 equiv). The reaction mixture was allowed to warm to reflux and water was trapped by Dean-Stark apparatus. After 16 h, the reaction was cool to room temperature and saturated $NaHCO_3$ solution (150 mL) was added. The organic and aqueous layers were separated and the aqueous phase was extracted with ethyl acetate (2×200 mL). The combined organic phases were washed with brine (150 mL) and dried over $Na_2SO_4$. The solvent was evaporated under reduced pressure and the residue was purified by flash chromatography (silica gel, eluent: 15:1 Hexanes:EtOAc) to provide 8,9-unsaturated methoxyetheneketal compound 2 (15.5 g, 89%). $^1$H NMR (500 MHz, $CDCl_3$) Shift=7.13 (d, J=8.3 Hz, 1 H), 6.73-6.67 (m, 2 H), 4.05-3.85 (m, 4 H), 3.79 (s, 3 H), 2.82-2.65 (m, 2 H), 2.52-2.45 (m, 2 H), 2.23-2.17 (m, 2 H), 2.14 (ddd, J=2.2, 11.6, 14.0 Hz, 1H), 1.99-1.82 (m, 4 H), 1.64 (td, J=4.2, 12.2 Hz, 1 H), 1.49 (dq, J=6.8, 11.6 Hz, 1 H), 0.86 (s, 3H). HRMS (ESI) (m/z) calc'd for $C_{21}H_{27}O_3$ [M+H]$^+$: 327.1955, found 327.1947.

Route 1: Synthesis of Epoxy Alcohols 3 and 3a

A solution of 8,9-unsaturated ethyleneketal 2 (1.63 g, 5.00 mmol, 1.0 equiv) in $CHCl_3$ (50 mL) was cooled to 0° C. and mCPBA (77% max, 2.46 g, 11.0 mmol, 2.2 equiv) was added. The reaction mixture was stirred for 10 min at 0° C. and warmed to room temperature. After additional 50 min, 10% $Na_2S_2O_3$ solution (40 mL) and saturated $NaHCO_3$ solution (40 mL) were sequentially added. The organic and aqueous layers were separated and the aqueous phase was extracted with dichloromethane (3×50 mL). The combined organic phases were washed with brine (50 mL), dried over $Na_2SO_4$, and concentrated under reduced pressure. The residue was purified by flash chromatography (silica gel, eluent: 3:1→1:1 Hexanes:EtOAc) to afford epoxy alcohol 3 and 3a (1.40 g, 75%). 3 and 3a were under equilibration in any solvent, with a major of 3. H NMR was analyzed for epoxy alcohol 3. Where indicted, cortistatin analogs (12, 13, 14A, 14B, 15B, 16B, and 17B) were applied to the biological experiments as racemic mixtures constructed from 6-methoxy-1-tetralone.

$^1$H NMR (500 MHz, $CDCl_3$) Shift=7.77 (d, J=8.3 Hz, 1 H), 6.76 (dd, J=2.0, 8.3 Hz, 1 H), 6.63 (d, J=2.0 Hz, 1 H), 4.78 (dd, J=7.8, 9.8 Hz, 1 H), 3.95-3.87 (m, 4 H), 3.78 (s, 3 H), 2.84 (dt, J=5.9, 14.4 Hz, 1 H), 2.49 (dd, J=4.4, 15.1 Hz, 1 H), 2.36-2.29 (m, 1 H), 2.26 (dd, J=5.9, 14.2 Hz, 2 H), 2.06 (t, J=11.7 Hz, 1 H), 1.97 (dd, J=7.3, 12.2 Hz, 1 H), 1.94-1.88 (m, 2 H), 1.75 (dt, J=5.4, 14.2 Hz, 1 H), 1.63-1.53 (m, 1 H), 1.46 (t, J=11.0 Hz, 1 H), 0.75 (s, 3 H). HRMS (ESI) (m/z) calc'd for $C_{21}H_{27}O_5$ [M+H]$^+$: 359.1853, found 359.1852.

Route 2: Synthesis of 8,9 and 9,11-unsaturated methoxyetheneketal Compounds 2 and 4

The DDQ oxidation was done with 22.0 g (81.4 mmol, 1.0 equiv) of estrone and the product was used without purification by flash chromatography. See, e.g., Stephan et al., *Steroid.* 1995, 60, 809-811. To a solution of 9,11-unsaturated estrone in benzene (375 mL) was added ethylene glycol (110 mL, 1.99 mol, 24.4 equiv) and PTSA (3.00 g, 16.3 mmol, 0.20 equiv). The reaction mixture was warmed to reflux and water was trapped by Dean-Stark apparatus. After 18 h, the reaction was allowed to cool to room temperature and saturated $NaHCO_3$ solution (300 mL) was applied. The aqueous phase was extracted with ethyl acetate (2×300 mL) and the combined organic phases were washed with brine (200 mL). The organic phase was dried ($Na_2SO_4$) and the solvent was evaporated under reduced pressure. The product was used in the next step without further purification.

The ethyleneketal (mixture of the 8,9 and 9,11-unsaturated regioisomers) was dissolved in acetone (420 mL) and $K_2CO_3$ (22.5 g, 163 mmol, 2.00 equiv) was added. This was followed by the addition of $Me_2SO_4$ (9.30 mL, 97.6 mmol, 1.20 equiv) and the reaction mixture was warmed to reflux. After 18 h, the reaction was allowed to cool to room temperature and the acetone was evaporated. 2M NaOH solution was added (300 mL) and the aqueous phase was extracted with ethyl acetate (2×300 mL). The combined organic phases were dried ($Na_2SO_4$) and the solvent was evaporated under reduced pressure. The residue was purified by flash chromatography (silica gel, eluent: 15:1 Hexanes:EtOAc) to afford mixture of 8,9 and 9,11-unsaturated methoxyetheneketal compounds 2 and 4 (16.3 g, 61% in three steps, ~4:5 mixture of 8,9-unsaturated:9,11-unsaturated regioisomers).

For 9,11-unsaturated isomer, only distinguishable peaks were assigned: $^1$H NMR (500 MHz, $CDCl_3$) Shift=7.53 (d, J=8.8 Hz, 1 H), 6.60 (d, J=2.0 Hz, 1 H), 6.13 (td, J=2.6, 5.0 Hz, 1 H), 3.79 (s, 3 H), 2.59 (td, J=3.2, 17.6 Hz, 1 H), 2.09-2.00 (m, 3 H), 1.45-1.33 (m, 2H), 0.90 (s, 3 H). HRMS (ESI) (m/z) calc'd for $C_{21}H_{27}O_3$ [M+H]$^+$: 327.1955, found 327.1951.

Route 2: Epoxy Alcohol Compounds 3 and 3a

To a solution of mixture of 8,9 and 9,11-unsaturated ethyleneketal compounds 2 and 4 (15.7 g, 48.1 mmol, 1.00 equiv) in dichloromethane (700 mL) was added magnesium monoperoxyphthalate hexahydrate (68.4 g, 111 mmol, 2.30 equiv) and water (4.8 mL). The reaction mixture was stirred for 20 h at room temperature and then quenched with the mixture of 10% aqueous Na₂S₂O₃ (300 mL) and saturated NaHCO₃ solution (300 mL). The organic and aqueous layers were separated and the aqueous phase was extracted with dichloromethane (2×500 mL). The combined organic phases were washed with brine (300 mL) and dried (Na₂SO₄). The solvent was evaporated under reduced pressure and the residue was purified by flash chromatography (silica gel, eluent: 3:1→2:1 Hexanes:EtOAc) to provide epoxy alcohol 3 and 3a (8.60 g, 50%). Spectral data was consistent with epoxy alcohol 3 and 3a constructed from 8,9-unsaturated methoxyethyleneketal 2.

Synthesis of Diol Compound 5

Ammonia gas was condensed (240 mL) and to the liquid ammonia was added Li (3.90 g, 565 mmol, 25.0 equiv) at −78° C. After stirring for 30 min, epoxy alcohol 3 and 3a (8.10 g, 22.6 mmol, 1.0 equiv) in THF (110 mL) was cannulated and stirred additional 1.5 h at that temperature. To the reaction mixture was added the mixture of t-BuOH (32 mL) and THF (16 mL) at −78° C. and stirred additional 20 min at that temperature. The mixture of t-BuOH (92 mL) and THF (38 mL) was added followed by benzene (50 mL) and water (50 mL) at −78° C., and the flask was opened to gently evaporate liquid ammonia by removing the cooling bath. Water (200 mL) was added and the aqueous phase was extracted with ethyl acetate (2×250 mL). The combined organic phases were washed with brine (150 mL), dried (Na₂SO₄), and concentrated under reduced pressure. The product was used in the next step without further purification.

To a solution of Birch reduction product in THF (300 mL) and ethylene glycol (75 mL) was added PTSA (430 mg, 2.26 mmol, 0.10 equiv). The reaction mixture was stirred for 30 min at room temperature and saturated NaHCO₃ solution (200 mL) was added. The organic and aqueous layers were separated and the aqueous phase was extracted with ethyl acetate (4×250 mL). The combined organic phases washed with brine (200 mL) and dried (Na₂SO₄). The solvent was evaporated under reduced pressure and the residue was purified by flash chromatography (silica gel, eluent: 4:1 Hexanes:EtOAc→100% EtOAc→10:1 EtOAc:MeOH) to provide diol 5 (4.60 g, 52%).

¹H NMR (500 MHz, C₆D₆) Shift=3.67-3.42 (m, 9 H), 3.25-3.14 (m, 1 H), 2.40 (dd, J=5.9, 13.2 Hz, 1 H), 2.31 (br. s, 2 H), 2.23-2.09 (m, 2 H), 2.03 (t, J=10.7 Hz, 1 H), 1.97-1.90 (m, 2 H), 1.89 (dd, J=8.3, 14.2 Hz, 1 H), 1.85-1.75 (m, 4 H), 1.66-1.50 (m, 4 H), 1.00 (s, 3 H). HRMS (ESI) (m/z) calc'd for C₂₂H₃₂NaO₆ [M+Na]⁺: 415.2091, found 415.2076.

Scheme 1-3. Optimized Route 2

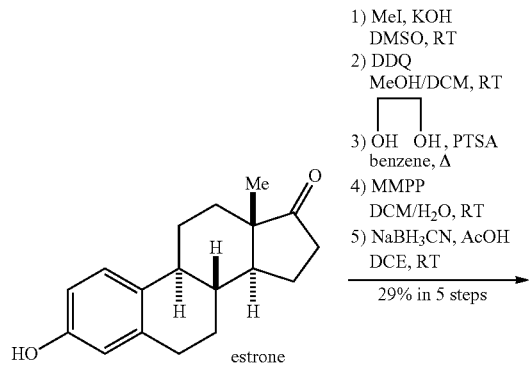

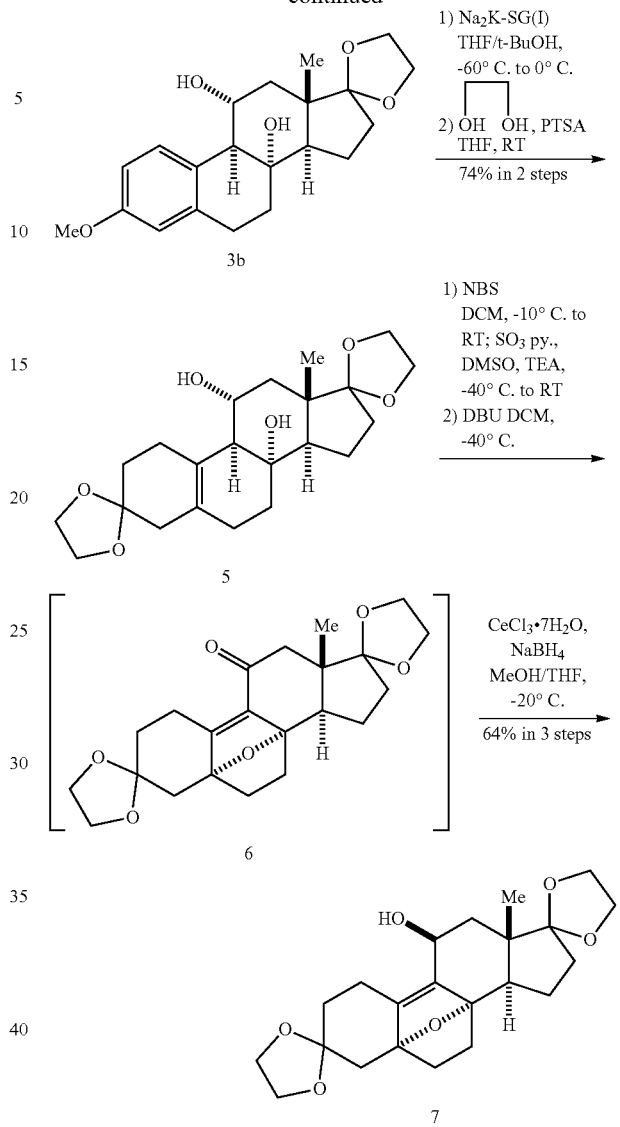

Ketal Compound 3b

To a solution of estrone (195 g, 721 mmol, 1.00 equiv) in DMSO (2.8 L) was added KOH pellet (85% technical grade, 162 g, 2.45 mol, 3.40 equiv) and CH₃I (89.8 mL, 1.44 mol, 2.00 equiv). The reaction mixture was stirred for 3.5 hours at room temperature and distilled water (2 L) was slowly added at 0° C. The aqueous layer was extracted with dichloromethane (3×1.5 L) and the combined organic layer was washed with brine (1.5 L). The organic layer was concentrated under nitrogen flow to give white crystalline, which was washed with cold methanol. The 180 g of crude mixture was used in the next step without further purification.

To a solution of the crude mixture (100 g, 352 mmol, 1.00 equiv) in methanol (750 mL) and dichloromethane (750 mL) was added NaHCO₃ (93.8 g, 1.05 mmol, 3.00 equiv). DDQ (120 g, 527 mmol, 1.50 equiv) was added in four portions with 5 min interval and the reaction mixture was stirred for 2 hours and then quenched with the 10% aqueous Na₂S₂O₃ (500 mL). The reaction flask was stirred for additional 30 min and filtered through celite, washed with chloroform. The 2 M NaOH solution (500 mL) was added and the organic and aqueous layers were separated and the aqueous phase was extracted with chloroform (3×700 mL). The combined organic phases were washed with brine (700 mL) and dried ($Na_2SO_4$). The solvent was evaporated under reduced pressure and the 89 g of crude mixture was used in the next step without further purification. The DDQ oxidation step was conducted in two batches.

To a solution of the crude mixture (151 g, 480 mmol, 1.00 equiv) in benzene (2 L) was added ethylene glycol (268 mL, 4.80 mol, 10 equiv) and PTSA (27.4 g, 144 mmol, 0.30 equiv). The reaction mixture was warmed to reflux and water was trapped by Dean-Stark apparatus. After 36 hours, the reaction was allowed to cool to room temperature and saturated $NaHCO_3$ solution (1 L) was applied. The aqueous phase was extracted with ethyl acetate (3×500 mL) and the combined organic phases were washed with brine (1 L). The organic phase was dried ($Na_2SO_4$) and the solvent was evaporated under reduced pressure. The 170 g of crude product was used in the next step without further purification.

To a solution of crude mixture (480 mmol, 1.00 equiv) in dichloromethane (2.5 L) was added magnesium monoperoxyphthalate hexahydrate (~80% technical grade, 683 g, 1.10 mol, 2.30 equiv) and water (50 mL). The reaction mixture was stirred for 16 hours at room temperature and then filtered through celite pad. To the filtrate was added saturated $NaHCO_3$ solution (1.5 L) and the organic and aqueous layers were separated and the aqueous phase was extracted with dichloromethane (3×1.4 L). The combined organic phases were washed with brine (1.4 L) and dried ($Na_2SO_4$). The solvent was evaporated under reduced pressure and the crude mixture was used in the next step without further purification.

To a solution of crude mixture (480 mmol, 1.00 equiv) in 1,2-dichloroethane (2 L) was added $NaBH_3CN$ (60.3 g, 960 mmol, 2.00 equiv) and AcOH (55 mL, 960 mmol, 2.00 equiv) sequentially at room temperature. After 2.5 hours, saturated $NaHCO_3$ solution (1.4 L) was added and the organic and aqueous layers were separated. The aqueous phase was extracted with dichloromethane (3×1.4 L). The combined organic phases were washed with brine (1.5 L), dried over $Na_2SO_4$, and concentrated under reduced pressure. The residue was purified by flash chromatography (silica gel, eluent: 2:1 Hexanes:EtOAc→1:1→1:2→1:3→100% EtOAc) to provide compound 3b (75 g, 29% in 5 steps).

$^1H$ NMR (500 MHz, $CDCl_3$) Shift=7.21 (d, J=8.8 Hz, 1 H), 6.75 (dd, J=2.4, 8.3 Hz, 1 H), 6.72 (d, J=2.4 Hz, 1 H), 3.98-3.82 (m, 4 H), 3.79 (s, 3 H), 3.80-3.76 (m, 1 H), 3.54 (dt, J=4.4, 10.5 Hz, 1 H), 3.03-2.91 (m, 1 H), 2.81 (td, J=4.4, 18.1 Hz, 1 H), 2.33 (d, J=9.8 Hz, 1 H), 2.23 (dd, J=6.8, 13.2 Hz, 1 H), 2.09-1.98 (m, 1 H), 1.90 (ddd, J=5.9, 9.8, 14.6 Hz, 1 H), 1.85 (dd, J=4.6, 9.5 Hz, 2 H), 1.82-1.77 (m, 1 H), 1.77-1.70 (m, 1 H), 1.65 (dq, J=6.3, 12.7 Hz, 1 H), 1.02 (s, 3 H). HRMS (ESI) (m/z) calc'd for $C_{21}H_{28}O_5$ $[M+H]^+$: 361.2010, found 361.2022.

Diol Compound 5

To a slurry of $Na_2K$-SG(I) (200 g) in THF and t-BuOH (500 mL and 200 mL of each solvent, sequentially added at −60° C.) was cannulated compound 3b (40 g, 111 mmol, 1.00 equiv) in THF (500 mL) at −60° C. and allowed to warm to 0° C. The reaction was followed by MS. After stirring for 7 hours at 0° C. the reaction was quenched by slow addition of MeOH (150 mL) and $H_2O$ (250 mL) and was allowed to warm to room temperature. After decanting the solution to separate out the silica gel, EtOAc (1 L) was added and the organic layer and the aqueous layers were separated. The aqueous phase was extracted with EtOAc (3×500 ml). The combined organic phases were washed with brine (2×1 L), dried over $Na_2SO_4$, and concentrated under reduced pressure. The product was used without further purification. Ketalization condition is the same as was described for compound 3b to give compound 5 (32 g, 74% in 2 steps).

Allylic Alcohol 7

To a solution of diol 7 (7.1 g, 18.1 mmol, 1.00 equiv) in dichloromethane (230 mL) was added NBS (3.54 g, 19.9 mmol, 1.10 equiv) at one portion at −10° C. and the reaction mixture was warmed to room temperature. The reaction was monitored by TLC (about 2 h min for the completion). Once the reaction is done, the reaction mixture was cooled to −40° C. and triethylamine (30.3 mL, 217 mmol, 12.0 equiv) was added. Pre-stirred $SO_3Py$ (28.8 g, 181 mmol, 10.0 equiv) in DMSO (200 mL) for 20 min at room temperature was added to the reaction mixture at −40° C., which was subsequently allowed to warm slowly to room temperature. After 3 hours, saturated $NH_4Cl$ solution (200 mL) was added and the reaction was allowed to warm to room temperature. The organic and aqueous layers were separated and the aqueous phase was extracted with dichloromethane (2×350 mL). The combined organic phases were washed with brine (350 mL), dried over $Na_2SO_4$, and concentrated under reduced pressure. The crude mixture was used without further purification.

The crude mixture was dissolved in dichloromethane (600 mL) and the reaction mixture was cooled to −40° C. followed by the slow addition of DBU (6.76 mL, 45.3 mmol, 2.50 equiv). After 15 min, saturated $NH_4Cl$ solution (200 mL) was added and the reaction was allowed to warm to room temperature. The organic and aqueous layers were separated and the aqueous phase was extracted with dichloromethane (2×200 mL). The combined organic phases were washed with brine (150 mL), dried over $Na_2SO_4$, and concentrated under reduced pressure.

To a solution of crude mixture (6.50 g, 16.7 mmol, 1.00 equiv) in MeOH (250 mL) and THF (30 mL) was added $CeCl_3.7H_2O$ (18.7 g, 50.2 mmol, 3.00 equiv) at room temperature. After stirring 5 min, the reaction was cooled to −20° C. followed by the addition of $NaBH_4$ (1.26 g, 33.4 mmol, 2.00 equiv). After 30 min, saturated $NH_4Cl$ solution (100 mL) and water (100 mL) was added, which was allowed to warm to room temperature. The aqueous phase was extracted with ethyl acetate (3×250 mL) and the combined organic phases were washed with brine (200 mL), dried over $Na_2SO_4$, and concentrated under reduced pressure. The residue was purified by flash chromatography (silica gel, eluent: 20:1 DCM:MeOH) to afford allylic alcohol 7 (4.20 g, 60% in 3 steps).

$^1H$ NMR (500 MHz, $C_6D_6$) Shift=4.39-4.30 (m, 1 H), 3.58-3.36 (m, 8 H), 3.22 (dd, J=3.7, 16.4 Hz, 1 H), 2.94 (dd, J=7.1, 12.5 Hz, 1 H), 2.66 (d, J=13.2 Hz, 1 H), 2.49-2.41 (m, 1 H), 2.39 (dd, J=2.2, 12.9 Hz, 1 H), 2.07-1.99 (m, 1 H), 1.96-1.79 (m, 6 H), 1.73 (br. s, 3 H), 1.66-1.57 (m, 1 H), 1.15-1.07 (m, 1 H), 0.86 (s, 3 H); $^{13}C$ NMR (500 MHz, $C_6D_6$) Shift=140.6, 139.1, 118.7, 109.5, 88.3, 86.2, 67.1, 65.4, 64.6, 64.2, 47.9, 46.5, 41.3, 40.9, 34.7, 34.2, 33.9, 30.0, 20.4, 19.8, 15.6; HRMS (ESI) (m/z) calc'd for $C_{22}H_{30}NaO_6$ $[M+Na]^+$: 413.1935, found 413.1942.

Cyclopropane 8

To a solution of $C_1CH_2I$ (5.74 mL, 78.9 mmol, 4.00 equiv) in 1,2-dichloroethane (400 mL) was added a solution of $Et_2Zn$ in diethyl ether (1M, 39.4 mL, 39.4 mmol, 2.00 equiv) at −10° C. After stirring 5 min, allylic alcohol 7 (7.70 g, 19.7 mmol, 1.00 equiv) in 1,2-dichloroethane (200 mL)

was added to the reaction flask at −10° C. After 30 min, the reaction was quenched by saturated NH$_4$Cl solution (300 mL) and allowed to warm to room temperature. The organic and aqueous layers were separated and the aqueous phase was extracted with dichloromethane (2×350 mL). The combined organic phases were washed with brine (300 mL), dried over Na$_2$SO$_4$, and concentrated under reduced pressure. The residue was purified by flash chromatography (silica gel, eluent: 2:1→1:1 Hexanes:EtOAc) to afford cyclopropane 8 (6.93 g, 87%).

$^1$H NMR (500 MHz, C$_6$D$_6$) Shift=3.92 (dd, J=3.7, 11.0 Hz, 1 H), 3.51-3.40 (m, 8 H), 2.72 (dd, J=7.1, 12.9 Hz, 1 H), 2.39 (dd, J=5.4, 17.6 Hz, 1 H), 2.38 (d, J=12.2 Hz, 1 H), 2.15 (d, J=12.2 Hz, 1 H), 2.12 (dt, J=4.9, 12.2 Hz, 1 H), 2.02 (ddd, J=2.9, 11.2, 14.6 Hz, 1 H), 1.92-1.82 (m, 3H), 1.82-1.73 (m, 2H), 1.69-1.54 (m, 5H), 1.52 (dd, J=6.1, 12.0 Hz, 1 H), 1.49-1.44 (m, 1 H), 0.98 (s, 3 H), 0.86 (d, J=2.4 Hz, 1 H), 0.15 (d, J=2.9 Hz, 1 H); $^{13}$C NMR (500 MHz, C$_6$D$_6$) Shift=118.5, 110.4, 85.4, 84.0, 65.3, 64.9, 64.7, 64.6, 64.1, 48.1, 45.4, 41.5, 40.0, 39.9, 35.4, 34.8, 33.7, 32.7, 29.1, 22.1, 19.3, 16.5, 4.0; HRMS (ESI) (m/z) calc'd for C$_{23}$H$_{32}$NaO$_6$ [M+Na]$^+$: 427.2091, found 427.2088.

Oxabicyclo[3.2.1]octene Skeleton 9

Cyclopropane 8 (6.90 g, 17.1 mmol, 1.00 equiv) and 2,6-di-tert-butyl-4-methylpyridine (12.3 g, 59.7 mmol, 3.50 equiv) were azeotropically dried with benzene and dissolved in dichloromethane (330 mL). 4 Å molecular sieves (8.6 g) were added and the reaction flask was cooled to 0° C. A solution of triflic anhydride in dichloromethane (1 M, 34.1 mL, 34.1 mmol, 2.00 equiv) was added dropwise and the ice bath was removed to warm the reaction flask to room temperature. After 2 hours, the reaction was quenched with triethylamine (55 mL) and the filtered through a pad of celite. Saturated NaHCO$_3$ solution (300 mL) was added and the aqueous phase was extracted with dichloromethane (2×350 mL). The combined organic phases were washed with brine (300 mL), dried over Na$_2$SO$_4$, and concentrated under reduced pressure. The residue was purified by flash chromatography (silica gel, eluent: 9:1→4:1 Benzene:Diethyl ether) to afford oxabicyclo[3.2.1]octene core skeleton 9 (3.76 g, 57%).

$^1$H NMR (500 MHz, CDCl$_3$) Shift=5.73 (s, 1 H), 5.29-5.26 (m, 1 H), 4.04-3.76 (m, 8 H), 2.58-2.50 (m, 1 H), 2.46 (t, J=15.1 Hz, 1 H), 2.31-2.24 (m, 2 H), 2.19 (t, J=11.2 Hz, 1 H), 2.09 (d, J=13.2 Hz, 1 H), 1.99 (dt, J=4.4, 13.2 Hz, 1 H), 1.94 (dd, J=2.4, 13.2 Hz, 1 H), 1.91-1.84 (m, 1 H), 1.83-1.71 (m, 3 H), 1.71-1.53 (m, 5 H), 0.88 (s, 3 H); $^{13}$C NMR (500 MHz, CDCl$_3$) Shift=140.6, 139.9, 119.9, 119.8, 118.5, 108.9, 81.5, 80.0, 65.2, 64.6, 64.5, 64.2, 46.2, 45.9, 42.4, 39.8, 34.0, 33.2, 32.4, 31.1, 28.0, 18.5, 17.0; HRMS (ESI) (m/z) calc'd for C$_{23}$H$_{31}$O$_5$ [M+H]$^+$: 387.2166, found 387.2180.

Monoketone 10

To a solution of oxabicyclo[3.2.1]octene core skeleton 9 (3.24 g, 8.38 mmol, 1.00 equiv) in acetone (400 mL) and water (100 mL) was added PTSA (797 mg, 4.19 mmol, 0.50 equiv) and the reaction mixture was stirred for 3 days. Saturated NaHCO$_3$ solution (210 mL) and ethyl acetate (300 mL) were sequentially added to the reaction. The layers were separated and the aqueous layer was extracted with ethyl acetate (2×200 mL). The organic layers were combined, washed with brine (150 mL), dried over Na$_2$SO$_4$ and concentrated under reduced pressure. The resulting residue was then purified by flash chromatography (silica gel, eluent: 4:1 Hexanes:EtOAc) to afford monoketone 10 (2.50 g, 87%).

$^1$H NMR (500 MHz, CDCl$_3$) Shift=5.73 (s, 1 H), 5.29-5.25 (m, 1 H), 3.98-3.90 (m, 4 H), 2.48 (dd, J=8.8, 19.5 Hz, 1 H), 2.46-2.40 (m, 1 H), 2.36 (dd, J=5.9, 12.7 Hz, 1H), 2.34-2.25 (m, 2 H), 2.24-2.08 (m, 5 H), 2.09 (d, J=13.2 Hz, 1 H), 1.95 (dd, J=2.4, 13.2 Hz, 1 H), 1.90-1.81 (m, 1 H), 1.79-1.70 (m, 2 H), 1.70-1.61 (m, 2 H), 0.89 (s, 3 H); $^{13}$C NMR (500 MHz, CDCl$_3$) Shift=220.9, 141.5, 140.6, 119.7, 118.6, 108.8, 81.1, 80.5, 64.7, 64.3, 47.9, 47.3, 42.5, 39.9, 36.0, 34.0, 33.9, 31.7, 28.1, 18.9, 17.0; HRMS (ESI) (m/z) calc'd for C$_{21}$H$_{27}$O$_4$ [M+H]$^+$: 343.1909, found 343.1919.

1-Chloroisoquinoline Adduct 11

CeCl$_3$ (565 mg, 2.30 mmol, 10.0 equiv) in reaction flask was heated at 140° C. under vacuum for 2 h. The flask was charged with Ar and cooled to 0° C. After 30 min, THF (2.8 mL) was added and stirred at 0° C. for 2 h. The flask was then allowed to warm to room temperature and stirred for additional 16 h.

To a solution of CeCl$_3$/THF complex was added 1-chloro-7-iodoisoquinoline (396 mg, 1.40 mmol, 6.00 equiv) in THF (1.4 mL) followed by stirring for 10 min at room temperature, which was then allowed to cool to −78° C. A solution of n-butyllithium in hexanes (1.6 M, 716 µL, 1.10 mmol, 5.00 equiv) was then added dropwise. The reaction mixture was stirred additional 30 min at the same temperature and monoketone 10 (78.5 mg, 229 µmol) was cannulated in THF (1.4 mL). After additional 30 min, saturated NH$_4$Cl solution (5 mL) was added to the stirred reaction mixture, which was then allowed to warm to room temperature. The mixture was diluted with EtOAc (5 mL) and the layers were separated. The aqueous layer was extracted with EtOAc (3×5 mL) and the organic layers were combined, washed with brine (5 mL), and dried over Na$_2$SO$_4$ and concentrated under reduced pressure. The resulting residue was then purified by flash chromatography (silica gel, eluent: 2:1 Hexanes:EtOAc) to provide 1-chloroisoquinoline adduct 11 (115 mg, 97%).

$^1$H NMR (500 MHz, CDCl$_3$) Shift=8.34 (br. s, 1 H), 8.24 (d, J=5.9 Hz, 1 H), 7.89-7.83 (m, 1 H), 7.76 (d, J=8.3 Hz, 1 H), 7.56 (d, J=5.9 Hz, 1 H), 5.63 (s, 1 H), 5.16-4.99 (m, 1 H), 4.02-3.87 (m, 4 H), 2.62 (ddd, J=4.4, 9.8, 14.2 Hz, 1 H), 2.48-2.38 (m, 2 H), 2.36-2.26 (m, 3 H), 2.26-2.19 (m, 1 H), 2.18-2.08 (m, 2 H), 1.96 (dd, J=2.4, 13.7 Hz, 1 H), 1.88 (dd, J=5.1, 17.8 Hz, 1 H), 1.82-1.70 (m, 2 H), 1.67-1.57 (m, 3 H), 1.49 (d, J=17.6 Hz, 1 H), 1.20-1.08 (m, 3H); HRMS (ESI) (m/z) calc'd for C$_{22}$H$_{26}$NaO$_5$ [M+Na]$^+$: 393.1673, found 393.1657.

Isoquinoline 12

A solution of 1-chloroisowuinoline adduct 11 (115 mg, 227 µmol) in dichloromethane (20 mL) was cooled to 0° C. Pyridine (183 µL, 2.30 mmol, 10.0 equiv) and DMAP (13.9 mg, 114 µmol, 0.50 equiv) were then added sequentially to the solution. After 5 min, trifluoroacetic anhydride (158 µL, 1.14 mmol, 5.00 equiv) was added dropwise and stirred additional 30 min, at which point pH 7 phosphate buffer (15 mL) was added followed by warming the reaction flask to room temperature. The organic and aqueous layers were separated and the aqueous layer was extracted with dichloromethane (2×15 mL). The organic layers were combined, washed with brine (25 mL), dried over Na$_2$SO$_4$, and concentrated under reduced pressure. The resulting residue was then purified by short flash column chromatography (silica gel, eluent: 2:1 Hexanes:EtOAc) to afford trifluoroacetylated product which was quickly used for the next step.

Trifluoroacetylated product (130 mg, 216 mmol) was azeotropically dried with benzene and dissolved in benzene (4.3 mL). AIBN (106 mg, 647 µmol, 3.00 equiv) was added and the reaction flask was degassed by the freeze-pump thaw process (3 cycles). Bu₃SnH (1.16 mL, 4.31 mmol, 20.0 equiv) was added and the reaction mixture was allowed to warm to reflux. After 3 h, the reaction mixture was cooled to room temperature and concentrated under reduced pressure. The resulting residue was then purified by flash column chromatography (silica gel, eluent: 4:1 to 3:1 to 1:1 Hexanes:EtOAc) to provide isoquinoline 12 (67.0 mg, 65% in two steps).

¹H NMR (500 MHz, CDCl₃) Shift=9.21 (s, 1 H), 8.46 (d, J=5.9 Hz, 1 H), 7.77 (s, 1 H), 7.73 (d, J=8.3 Hz, 1 H), 7.61 (d, J=5.9 Hz, 1 H), 7.57 (d, J=8.3 Hz, 1 H), 5.74 (s, 1 H), 5.29-5.23 (m, 1 H), 4.00-3.90 (m, 4 H), 3.11 (t, J=10.0 Hz, 1 H), 2.49 (dd, J=8.3, 11.2 Hz, 1 H), 2.47-2.41 (m, 1 H), 2.38-2.24 (m, 4 H), 2.24-2.14 (m, 2 H), 2.12 (d, J=13.2 Hz, 1H), 2.06-1.95 (m, 2 H), 1.91 (dd, J=5.4, 17.6 Hz, 1 H), 1.83 (dq, J=4.9, 11.7 Hz, 1 H), 1.77 (td, J=2.3, 12.9 Hz, 1 H), 1.72-1.59 (m, 3 H), 0.52 (s, 3 H); ¹³C NMR (500 MHz, CDCl₃) Shift=152.4, 142.6, 141.2, 140.6, 140.2, 134.7, 132.1, 128.7, 126.4, 125.8, 120.2, 119.9, 119.3, 108.9, 81.4, 80.3, 64.7, 64.3, 57.1, 51.8, 44.9, 42.6, 40.1, 39.8, 34.2, 30.9, 28.2, 26.5, 20.7, 15.3; HRMS (ESI) (m/z) calc'd for C₃₀H₃₃NaNO₃ [M+Na]⁺: 478.2353, found 478.2347.

Ketone 13

To a solution of isoquinoline 12 (365 mg, 0.801 mmol, 1.00 equiv) in acetone and water (4:1, 0.025 M) was added PTSA (412 mg, 2.16 mmol, 2.70 equiv) and the reaction mixture was warmed to 55° C. After 14.5 hours, the reaction was cooled to room temperature and saturated NaHCO₃ solution and ethyl acetate were sequentially added to the reaction. The layers were separated and the aqueous layer was extracted with ethyl acetate. The organic layers were combined, washed with brine, dried over Na₂SO₄ and concentrated under reduced pressure. The resulting residue was then purified by flash chromatography (silica gel, eluent: 3:2-1:2 Hexanes:EtOAc) to afford ketone 13 (289 mg, 87%).

¹H NMR (500 MHz, CDCl₃) Shift=9.23 (s, 1 H), 8.48 (d, J=5.9 Hz, 1 H), 7.80 (s, 1 H), 7.78 (d, J=8.3 Hz, 1 H), 7.65 (d, J=5.9 Hz, 1 H), 7.61 (d, J=8.3 Hz, 1 H), 5.91 (s, 1 H), 5.40-5.35 (m, 1 H), 3.15 (t, J=10.0 Hz, 1 H), 2.94 (d, J=15.1 Hz, 1 H), 2.68 (d, J=15.1 Hz, 1 H), 2.67-2.59 (m, 1 H), 2.58-2.41 (m, 4 H), 2.41-2.24 (m, 3 H), 2.24-2.10 (m, 2 H), 2.04 (tt, J=4.6, 13.2 Hz, 1 H), 1.96 (dd, J=5.4, 17.6 Hz, 1 H), 1.86 (dq, J=5.1, 12.1 Hz, 1 H), 1.80-1.67 (m, 2 H), 0.55 (s, 3 H); ¹³C NMR (500 MHz, CDCl₃) Shift=208.9, 152.2, 142.2, 140.3, 140.2, 139.4, 134.9, 132.3, 128.7, 126.5, 126.0, 121.5, 120.9, 120.4, 82.8, 80.4, 57.1, 51.7, 49.2, 44.8, 40.1, 40.0, 39.8, 30.8, 29.8, 28.1, 26.5, 20.7, 15.4; HRMS (ESI) (m/z) calc'd for C₂₈H₃₀NO₂ [M+H]⁺: 412.2271, found 412.2288.

Scheme 1-4. Optimized Route 3

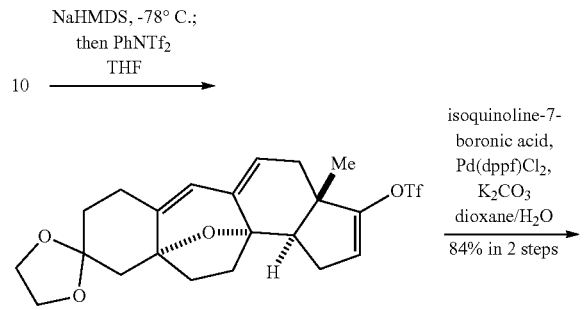

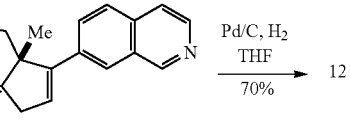

Triflate

To a solution of monoketone 10 (2.50 g, 7.30 mmol, 1.00 equiv) in THF (45 mL) was added NaHMDS (1 M, 8.76 mL, 8.76 mmol, 1.20 equiv) at −78° C., dropwise. After stirring 1.5 hours, PhNTf₂ (3.91 g, 11.0 mmol, 1.50 equiv) in THF (20 mL) was cannulated and the reaction mixture was warmed up to 0° C. After additional 30 min, saturated NH₄Cl solution (50 mL) was added to the stirred reaction mixture and diluted with EtOAc (70 mL). The layers were separated and the aqueous layer was extracted with EtOAc (2×45 mL) and the organic layers were combined, washed with brine (80 mL), dried over Na₂SO₄, and concentrated under reduced pressure. The resulting residue was then purified by flash column chromatography (silica gel, eluent: 8:1→5:1 Hexanes:EtOAc) to provide triflate (3.33 g, yield was calculated after cross-coupling due to the inseparable minor impurity).

¹H NMR (500 MHz, CDCl₃) Shift=5.76 (s, 1H), 5.67 (br. s., 1H), 5.32 (dd, J=2.0, 4.9 Hz, 1 H), 4.02-3.94 (m, 4 H), 2.67 (dd, J=6.8, 10.7 Hz, 1 H), 2.49 (t, J=14.6 Hz, 1 H), 2.45 (ddd, J=3.7, 6.5, 15.2 Hz, 1 H), 2.38-2.28 (m, 4 H), 2.17 (ddd, J=1.5, 10.7, 12.7 Hz, 1 H), 2.12 (d, J=13.2 Hz, 1 H), 2.10 (dd, J=5.9, 17.6 Hz, 1 H), 1.98 (dd, J=2.7, 13.4 Hz, 1 H), 1.88 (ddd, J=7.6, 8.9, 12.8 Hz, 1 H), 1.80 (tdd, J=2.4, 4.8, 12.7 Hz, 1 H), 1.74-1.63 (m, 2 H), 1.03 (s, 3 H); HRMS (ESI) (m/z) calc'd for C₂₂H₂₆O₆F₃S [M+H]⁺: 475.1397, found 475.1411.

C16-C17 Unsaturated Isoquinoline

To a solution of triflate (3.33 mg, 7.02 mmol, 1.00 equiv) and isoquinoline-7-boronic acid (3.64 g, 21.1 mmol, 3.00 equiv) in 1,4-dioxane (300 mL) and H₂O (30 mL) was added K₂CO₃ (2.91 g, 21.1 mmol, 3.00 equiv) and the solution was bubbled through inert Ar for 5 min. Pd(dppf)Cl₂—CH₂Cl₂ (286 mg, 350 μmol, 0.05 equiv) was added and the reaction mixture was stirred at 80° C. for 1 hour. The mixture was allowed to cool to room temperature and saturated NaHCO₃ solution (200 mL) was applied. The mixture was diluted with EtOAc (350 mL) and the layers were separated. The aqueous layer was extracted with EtOAc (2×300 mL) and the combined organic layers were washed with brine (500 mL), dried over Na₂SO₄, and concentrated under reduced pressure. The crude mixture was purified by flash column chromatography (silica gel, eluent: 2:1→1:1→1:2 Hexanes:EtOAc) to provide C16-C17 unsaturated isoquinoline (2.67 mg, 84% over 2 steps).

¹H NMR (500 MHz, CDCl₃) Shift=9.23 (s, 1H), 8.49 (d, J=5.4 Hz, 1 H), 7.94 (s, 1 H), 7.85-7.81 (m, 1 H), 7.80-7.75 (m, 1 H), 7.63 (d, J=5.4 Hz, 1 H), 6.26 (br. s., 1 H), 5.82 (s, 1 H), 5.40 (d, J=3.4 Hz, 1 H), 4.08-3.90 (m, 4 H), 2.76 (dd, J=7.1, 11.0 Hz, 1 H), 2.58 (dt, J=5.4, 17.6 Hz, 1 H), 2.56-2.40 (m, 3 H), 2.40-2.28 (m, 4 H), 2.16 (d, J=13.2 Hz, 1H), 2.02 (dd, J=2.0, 13.2 Hz, 1 H), 1.94 (td, J=8.8, 13.2 Hz, 1 H), 1.81 (td, J=2.0, 12.7 Hz, 1H), 1.76-1.67 (m, 2 H), 1.18 (s, 3H; HRMS (ESI) (m/z) calc'd for C₃₀H₃₂NO₃ [M+H]⁺: 454.2377, found 454.2366.

Isoquinoline 12

To a solution of 17,18-unsaturated isoquinoline (534 mg, 1.17 mmol, 1.00 equiv) in THF (48 mL) was added 10 wt % Pd/C (374 mg, 351 μmol, 0.30 equiv) and H2 balloon was installed. After 3 h, the reaction mixture was filtered through a pad of celite and washed with 0.2 M NH₃ solution in MeOH (50 mL), concentrated under reduced pressure. The residue was purified by flash column chromatography (silica gel, eluent: 40:1→30:1 DCM:MeOH) to provide isoquinoline 12 (452 mg, 84%).

Example 2

Synthesis of Lactams of Formula (A1') (A1") (A2), and (A2") Lactam 15B

To a solution of crude mixture (13.6 μmol, 1.00 equiv) in DCM (350 μL) was added trimethylamine (11.4 μL, 81.6 μmol, 6.00 equiv). At 0° C., methanesulfonic anhydride (4.7 mg, 27.2 μmol, 2.00 equiv) was added. The reaction mixture was stirred 15 min at 0° C. and warmed up to room temperature for additional 15 min stirring. The reaction mixture was quenched with NaHCO₃ (300 μL) and extracted with DCM (3×300 μL), and the combined organic phases were washed with brine (300 μL), dried over Na₂SO₄, and concentrated under reduced pressure. The crude mixture was used in the next step without further purification.

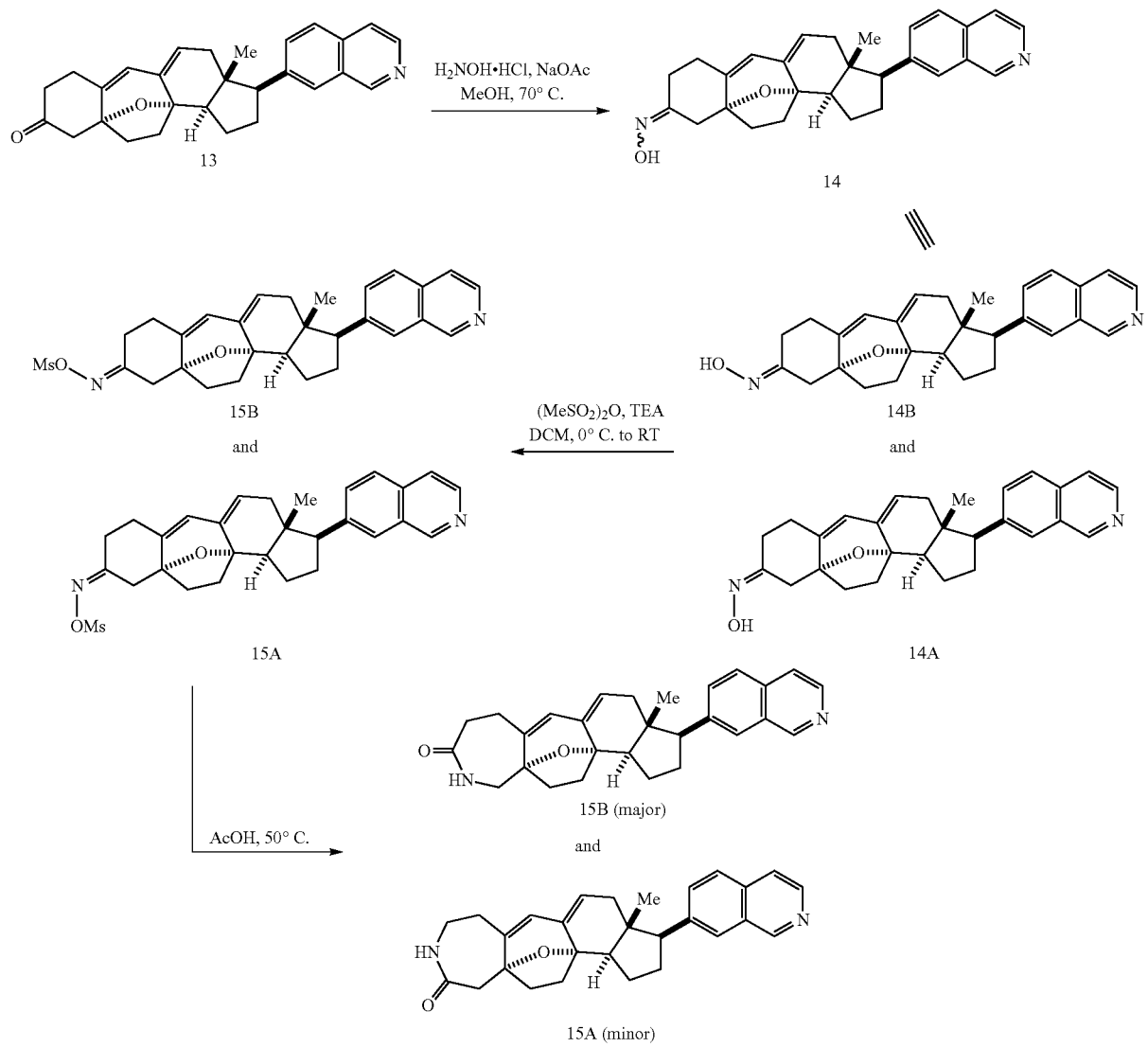

To a solution of ketone 13 (5.5 mg, 13.6 μmol, 1.00 equiv) in MeOH (350 μL) was added H₂NOH.HCl (2.5 mg, 27.2 μmol, 2.00 equiv) and NaOAc (4.9 mg, 27.2 μmol, 2.00 equiv). After stirring 1.5 h at 70° C., the reaction mixture was cooled to room temperature and roughly concentrated. H₂O (300 μL) was added and extracted with ethyl acetate (3×300 μL), and the combined organic phases were washed with brine (300 μL), dried over Na₂SO₄, and concentrated under reduced pressure. The crude mixture was used in the next step without further purification.

The crude mixture was dissolved in AcOH (300 μL) and stirred at 50° C. for 16 h. The reaction mixture was roughly concentrated and NaHCO₃ (300 μL) was applied. It was extracted with ethyl acetate (3×300 μL), and the combined organic phases were washed with brine (300 μL), dried over Na₂SO₄, and concentrated under reduced pressure. The crude mixture was purified by preparative TLC (silica gel, eluent: 5:5:1 EtOAc:DCM:TEA) to afford lactam 15B (1.5 mg, 26% in three steps).

$^{1}$H NMR (500 MHz, CDCl$_3$) Shift=9.22 (s, 1 H), 8.49 (d, J=5.9 Hz, 1 H), 7.79 (s, 1 H), 7.76 (d, J=8.2 Hz, 1 H), 7.63 (d, J=5.3 Hz, 1 H), 7.58 (dd, J=1.5, 8.5 Hz, 1H), 5.87 (s, 1H), 5.78 (t, J=6.5 Hz, 1H), 5.34 (dd, J=2.6, 5.0 Hz, 1H), 3.57 (dd, J=5.6, 15.0 Hz, 1 H), 3.33 (dd, J=7.6, 15.3 Hz, 1 H), 3.15 (dd, J=9.1, 10.9 Hz, 1 H), 2.66 (ddd, J=4.7, 10.0, 14.7 Hz, 1 H), 2.62-2.53 (m, 2 H), 2.52-2.46 (m, 2 H), 2.35 (br. s., 1 H), 2.38-2.30 (m, 1 H), 2.28-2.22 (m, 1 H), 2.22-2.12 (m, 2 H), 2.01 (qt, J=4.1, 9.4 Hz, 1 H), 1.96 (dd, J=5.3, 17.6 Hz, 1 H), 1.90-1.79 (m, J=5.3, 12.3, 12.3 Hz, 1 H), 1.75 (td, J=8.2, 12.3 Hz, 1 H), 1.68 (dt, J=7.3, 10.7 Hz, 1 H), 0.54 (s, 3 H). HRMS (ESI) (m/z) calc'd for C$_{28}$H$_{31}$N$_2$O$_2$ [M+H]$^+$: 427.2380, found 427.2395.

Exemplary Biological Methods

In vitro Data

All media was supplemented with 100 U/mL penicillin and 100 μg/mL streptomycin. Human cancer cell lines were grown in the following media: MV4; 11, K562, MOLM-14 in RPMI-1640, 10% FBS; SKNO-1 in RPMI-1640, 10% FBS, and 10 ng/mL GM-CSF; MV4;11 and K562 were from ATCC. SKNO-1 was from DSMZ.

Cell Growth Assay. All leukemia cells were plated (96-well) in triplicate at 5,000 to 30,000 cells/well with treatments. Viable cell number was estimated after 3, 7, and 10 days by counting viable cells from one vehicle well, generating a cell dilution series, transferring 20 L/well in duplicate to a 384-well plate, and performing a linear regression to CellTiter-Glo (Promega) response (SPECTRAmax M3, Molecular Devices). Cells from all wells were also 4-fold diluted in media and transferred in duplicate for CellTiter-Glo measurement. On days 3 and 7, an equal volume for all wells were split-back with fresh media and compound, such that the resulting cell density for the vehicle well matched the initial seeding density. For days 7 and 10, estimated cell number represents the split-adjusted theoretical cell number.

Compounds for testing were prepared as 100% DMSO stock solutions and stored under argon at −80° C.

TABLE 1

Cell Growth Inhibition Data (also, see FIG. 73).

| | SKNO-1 GI50 day 10 (nM) | MOLM14 GI50 day 10 (nM) | MV4;11 GI50 day 10 (nM) | K562 GI50 day 10 (nM)* |
|---|---|---|---|---|
| Cortistatin A | <0.4 | 5 | 3.5 | >1000 |
| 15B | 0.6 | 17.5 | 3.75 | >1000 |

*lack of activity at inhibiting the proliferation of K562 is evidence that analogs are on-target and match the selective antiproliferative activity of CA.

EXAMPLES

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

Introduction

Super-enhancers (SEs), which are composed of large clusters of enhancers densely loaded with the Mediator complex, transcription factors (TFs), and chromatin regulators, drive high expression of genes implicated in cell identity and disease, such as lineage-controlling TFs and oncogenes (Hnisz, D. et al. Super-enhancers in the control of cell identity and disease. Cell 155, 934-947 (2013) and Whyte, W. A. et al. Master Transcription Factors and Mediator Establish Super-Enhancers at Key Cell Identity Genes. Cell 153, 307-319 (2013)). BRD4 and CDK7 are positive regulators of SE-mediated transcription and their pharmacological inhibition is an approach for treatment of haematological cancers (Loven, J. et al. Selective Inhibition of Tumor Oncogenes by Disruption of Super-Enhancers. Cell 153, 320-334 (2013); Dawson, M. A. et al. Recurrent mutations, including NPM1c, activate a BRD4-dependent core transcriptional program in acute myeloid leukemia. Leukemia 28, 311-320 (2013); and Kwiatkowski, N. et al. Targeting transcription regulation in cancer with a covalent CDK7 inhibitor. Nature 511, 616-620 (2014)). In contrast, negative regulators of SE-associated genes have not been well described, but their inhibition might also impart anticancer activity. Here, Mediator-associated kinases cyclin-dependent kinase 8 (CDK8) and CDK19 are reported to restrain activation of SE-associated genes in acute myeloid leukemia (AML) cells. The small molecule natural product cortistatin A (CA) was determined to selectively inhibit the Mediator kinases from amongst 387 kinases and is a high affinity ligand for CDK8/Cyclin C ($K_d$=195 pM). It was found that CA has antileukemic activity in vitro and in vivo, and that AML sensitivity coincided with upregulation of SE-associated genes. In AML cells, CA upregulated SE-associated genes with tumor suppressor and lineage-controlling functions, including the TFs CEBPA, IRF8, IRF1 and ETV6 (Prange, K. H. M., Singh, A. A. & Martens, J. H. A. The genome-wide molecular signature of transcription factors in leukemia. Exp. Hematol. 42, 637-650 (2014); Fragale, A., Marsili, G. & Battistini A. Genetic and Epigenetic Regulation of Interferon Regulatory Factor Expression: Implications in Human Malignancies. J. Genet. Syndr. Gene Ther. 4: 205 (2013); and de Braekeleer, E. et al. ETV6 fusion genes in hematological malignancies: a review. Leuk. Res. 36, 945-961 (2012)). The BRD4 inhibitor I-BET151 downregulated these SE-associated genes, yet also had antileukemic activity. Individually increasing or decreasing expression of these TFs suppressed AML cell growth, providing evidence that upregulation of SE-associated genes by CA contributes to its anti-cancer activity and that human leukemia cells are sensitive to dosage of SE-associated genes. These results demonstrate that Mediator kinases can negatively regulate SE-associated gene expression.

Figure 2:
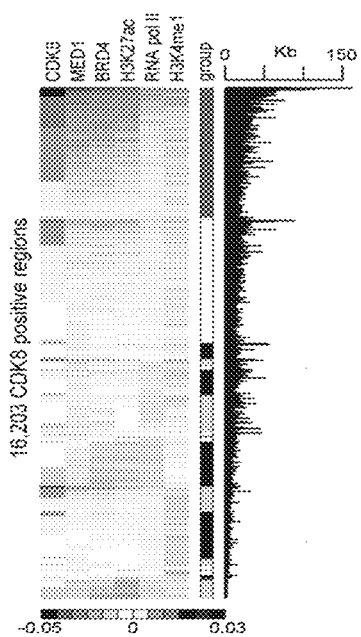
FIG. 2 is a heatmap showing semi-supervised clustering of total ChIP-seq signal of CDK8, MED1, BRD4, H3K27ac, RNA pol II, and H3K4me1 on CDK8 positive regions. Each respective cluster is ordered by CDK8 signal.
Figure 3:
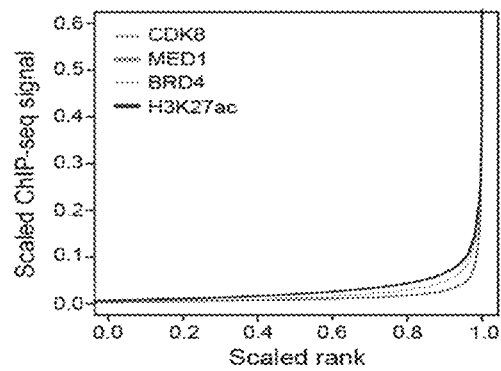
FIG. 3 is a line graph showing the distribution of CDK8, MED1, BRD4, and H3K27ac across putative enhancer regions. Regions to the right of the distribution inflection point are considered Super Enhancers ("SE").
Figure 4:
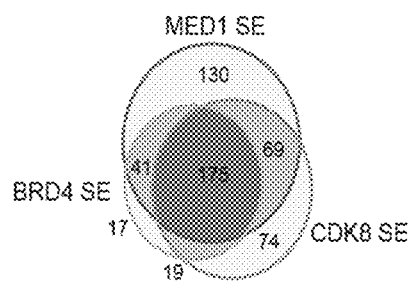
FIG. 4 is a Venn diagram showing overlap between SEs independently identified by ChIP-seq signal for CDK8, MED1 and BRD4 based on the collapsed superset of regions identified by any one factor.
Figure 5:
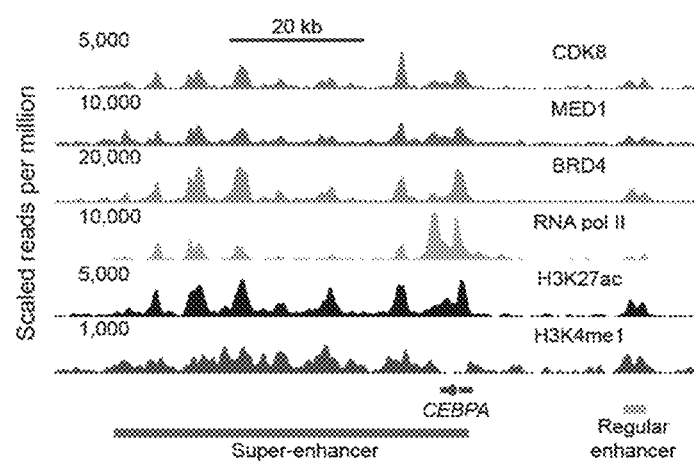
FIG. 5 illustrates ChIP-seq binding profiles at the CEBPA locus.
Figure 25:
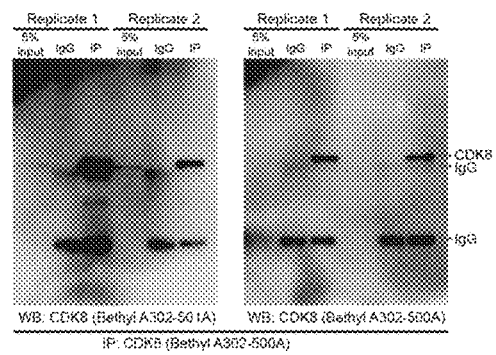
FIG. 25 is an immunoblot showing that the antibody used for CDK8 ChIP-seq (Bethyl A302-500A) was validated by IP-western. Specifically, IP was conducted with Bethyl A302-500A (2 µg) on MOLM-14 whole cell extract and Western blot (WB) was performed on split IP lysate or 5% input with either anti-CDK8 Bethyl A302-501A (left panel), anti-CDK8 Bethyl A302-500A (right panel), or normal rabbit IgG (CST, 2729).
Figure 26:
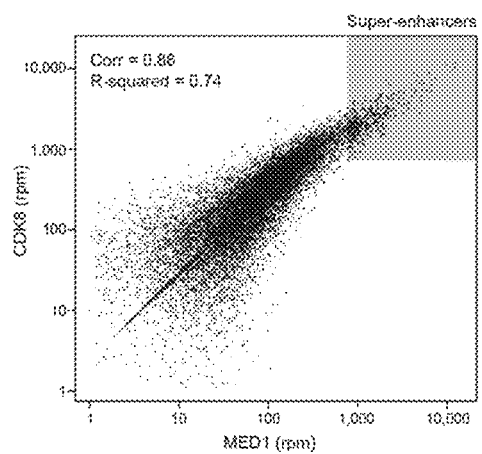
FIG. 26 is a scatterplot showing that MED1 and CDK8 density is highly correlated on active enhancer regions marked by H3K4me1 and H3K27ac (Corr=0.86, $R^2$=0.84) in MOLM-14 cells. The box in the top right corner represents SEs.
Figure 27:
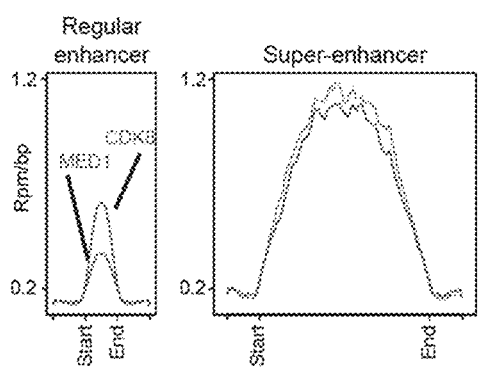
FIG. 27 illustrates ChIP-seq profile plots centered around MED1-defined SE and regular enhancer regions. Flanking regions are 2.5 kb.

CDK8 associates with CCNC (Cyclin C), MED12, and MED13 to form a CDK8 module that can reversibly associate with the 26-subunit Mediator complex (Allen, B. L. & Taatjes, D. J. The Mediator complex: a central integrator of transcription. Nat. Rev. Mol. Cell Biol. 16, 155-166 (2015)). Because SEs are disproportionately loaded with Mediator (Whyte, W. A. et al. Master Transcription Factors and Mediator Establish Super-Enhancers at Key Cell Identity Genes. Cell 153, 307-319 (2013), it was examined whether CDK8, as a Mediator-associated kinase, might regulate SE function. Using chromatin immunoprecipitation coupled with high-throughput sequencing (ChIP-seq), genome-wide occupancy of CDK8, along with known SE-associated factors and histone modifications, in the AML cell line MOLM-14 was investigated. Semi-supervised hierarchical clustering revealed that CDK8 most closely associated with MED1, followed by BRD4 and H3K27ac, and that these factors predominately colocalized at putative enhancer elements marked with H3K4me1 (FIG. 2 and FIGS. 25-26). A fraction of these regions were particularly large and densely loaded with CDK8, MED1 and BRD4, suggesting they may represent SEs. Consistent with this notion, the majority of CDK8, MED1, BRD4 and H3K27ac ChIP-seq signal was disproportionately located on a small number of SEs separately identified by each factor (FIG. 3 and FIG. 27). These SEs significantly overlapped (FIG. 4 and FIG. 5). Genes associated with these SEs were enriched with gene ontology terms pertinent to hematopoiesis, cellular differentiation, and transcription, supporting the notion that SEs regulate cellular identity (Table 2).

TABLE 2

Gene ontology analysis on SE-associated genes in MOLM-14 cells.

| Gene ontology | Enrichment | P value |
|---|---|---|
| Molecular function | | |
| Transcription factor activity | 2.57 | $10^{-8}$ |
| Transcription regulator activity | 2.16 | $10^{-8}$ |
| DNA binding | 1.62 | $10^{-7}$ |
| Biological Process | | |
| Hemopoistic or lymphoid organ development | 4.32 | $10^{-7}$ |
| Immuns system development | 4.07 | $10^{-8}$ |
| Cell activation | 3.91 | $10^{-6}$ |
| Leukocyte activation | 4.15 | $10^{-6}$ |
| Lymphocyte activation | 4.45 | $10^{-5}$ |
| Hemopoissis | 4.01 | $10^{-5}$ |

Figure 7:
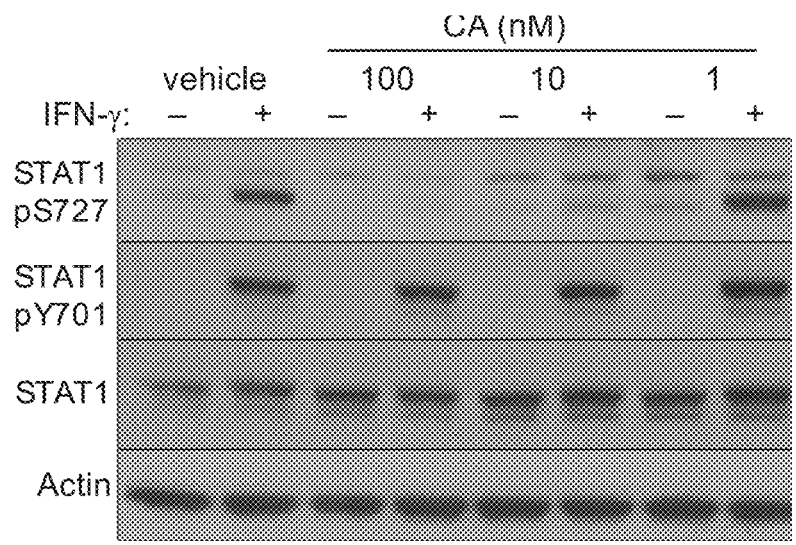
FIG. 7 is an immunoblot showing CA inhibition of CDK8-dependent IFN-γ-stimulated STAT1 S727 phosphorylation in MOLM-14 cells.
Figure 28:
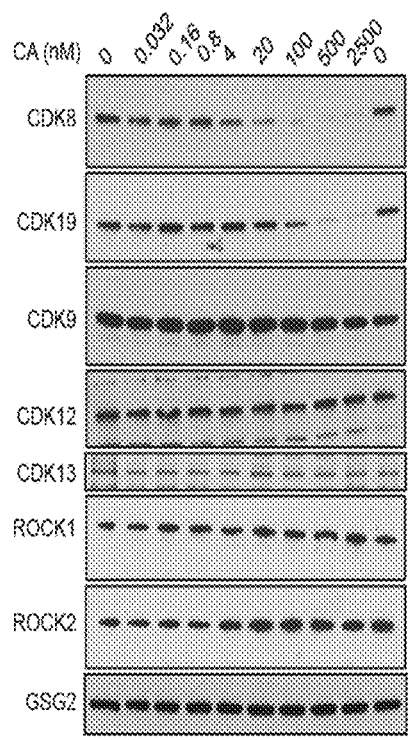
FIG. 28 is an immunoblot showing that CA selectively and dose-dependently inhibits capture of native CDK8 and CDK19 from MOLM-14 lysates.
Figure 30:
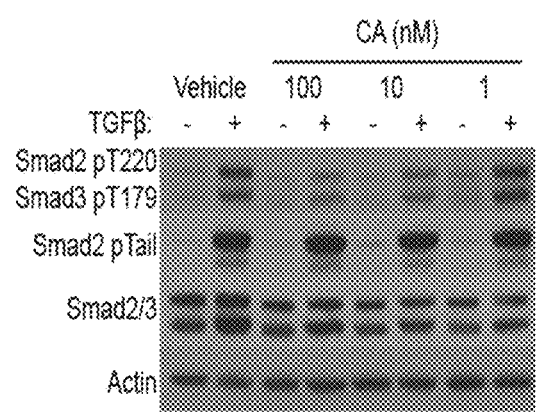
FIG. 30 is an immunoblot showing CA inhibition of TGF-β-stimulated Smad2 T220 and Smad3 T179 phosphorylation in HaCaT cells.

To determine whether pharmacologic inhibition of Mediator kinases, in analogy to BRD4, regulates SE function and inhibits AML proliferation, the marine natural product cortistatin A (CA),

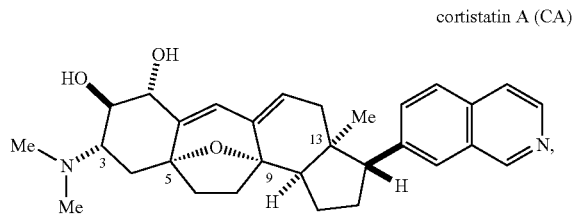 [SMILES: CN(C)[C@H]1C[C@@]23CC[C@@]4(O2)C(=CC[C@@]2(C)[C@@H](c5ccc6ccncc6c5)CC[C@H]24)C=C3[C@@H](O)[C@@H]1O]

cortistatin A (CA)

was characterized as an inhibitor of CDK8 and its highly homologous paralog, CDK19 (77% identical overall and 94% in the catalytic domain). Whereas CA was reported to bind CDK8 and CDK19 as individual proteins in vitro (Cee, V. J., Chen, D. Y.-K., Lee, M. R. & Nicolaou, K. C. Cortistatin A is a high-affinity ligand of protein kinases ROCK, CDK8, and CDK11. Angew. Chem. Int. Ed. Engl. 48, 8952-8957 (2009)), its ability to inhibit their kinase activity was not determined. This is particularly important because CDK8 and CDK19 appear to function in the context of a four-protein module with CCNC, MED12, and MED13 (Daniels, D. L. et al. Mutual Exclusivity of MED12/MED12L, MED13/13L, and CDK8/19 Paralogs Revealed within the CDK-Mediator Kinase Module. J. Proteomics Bioinform. S2:004 (2013)). In fact, CDK8 requires association with CCNC and MED12 for full catalytic activity (Knuesel, M. T., Meyer, K. D., Donner, A. J., Espinosa, J. M. & Taatjes, D. J. The human CDK8 subcomplex is a histone kinase that requires Med12 for activity and can function independently of mediator. Mol. Cell. Biol. 29, 650-661 (2009)). CA was synthesized (Lee, H. M., Nieto-Oberhuber, C. & Shair, M. D. Enantioselective synthesis of (+)-cortistatin A, a potent and selective inhibitor of endothelial cell proliferation. J. Am. Chem. Soc. 130, 16864-16866 (2008) and Flyer, A. N., Si, C. & Myers, A. G. Synthesis of cortistatins A, J, K and L. Nat. Chem. 2, 886-892 (2010)) and it was determined that it potently inhibited the kinase activity of the CDK8 module in vitro. In contrast, CA did not inhibit other transcriptional cyclin-dependent kinases CDK7 (TFIIH) or CDK9 (P-TEFb) in vitro, nor did it bind CDK9, CDK12 or CDK13 at up to 2500 nM in MOLM-14 cell lysate (FIG. 28). CA was reported to bind ROCK1 and ROCK2 in vitro, but CA was observed to not bind either of these kinases in MOLM-14 cell lysate up to 2500 nM (FIG. 28). In cells, CA dose-dependently inhibited phosphorylation of known CDK8 substrates STAT1 S727 (Bancerek J. et al. CDK8 kinase phosphorylates transcription factor STAT1 to selectively regulate the interferon response. Immunity 38, 250-262 (2013)), Smad2 T220 and Smad3 T179 (Alarcón, C. et al. Nuclear CDKs drive Smad transcriptional activation and turnover in BMP and TGF-β pathways, Cell 139, 757-769 (2009)) (FIG. 7 and FIG. 30). No kinase substrates have been reported for CDK19.

Figure 6A:
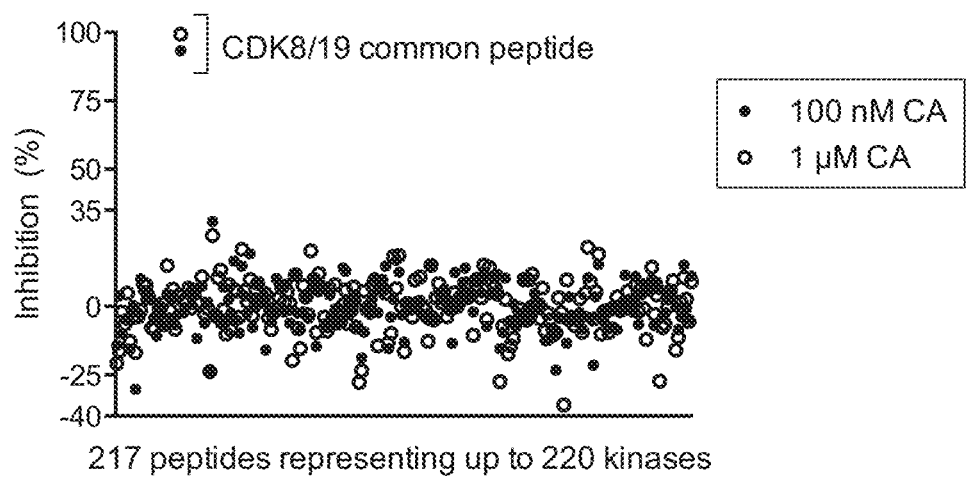
FIG. 6A is a dot plot showing kinome profiling in MOLM-14 lysate showing CA selective inhibition of CDK8/19 in MOLM-14 kinome. Specifically, each dot represents a distinct peptide and values <35% indicate no change (mean, n=2 for each concentration).
Figure 6B:
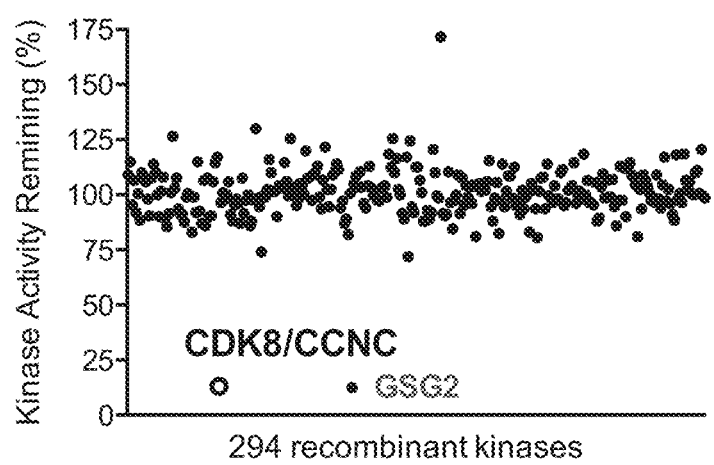
FIG. 6B is a dot plot showing in vitro kinase activity profiling (mean for kinase reaction, n=2 biological replicates, experiment performed once; wildtype-profiler, ProQinase) showing that cortistatin A (600 nM, 100× its $IC_{50}$ for CDK8/CCNC) selectively inhibits CDK8 kinase activity. Cortistatin A (CA) only inhibits CDK8/CCNC and GSG2 in vitro from among the 294 recombinant kinases. Each dot represents a distinct kinase reaction (mean, n=2).
Figure 31:
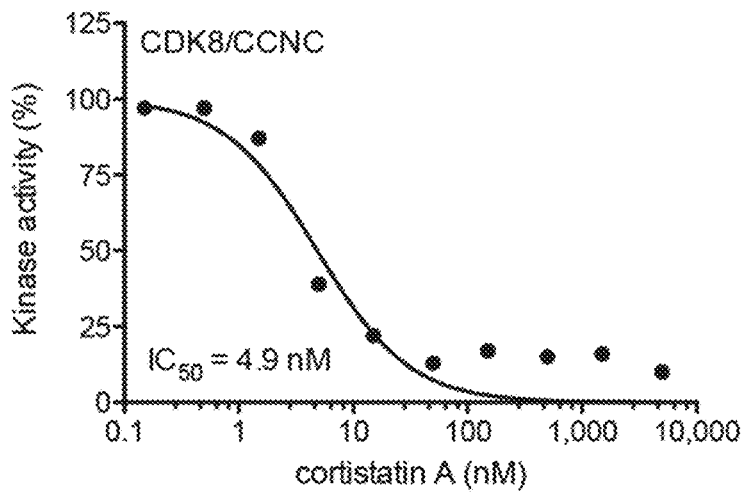
FIG. 31 is a line graph showing CA dose-dependent inhibition of the CDK8/CCNC complex as measured for the recombinant kinome profiling in FIG. 16A (n=1).
Figure 32A:
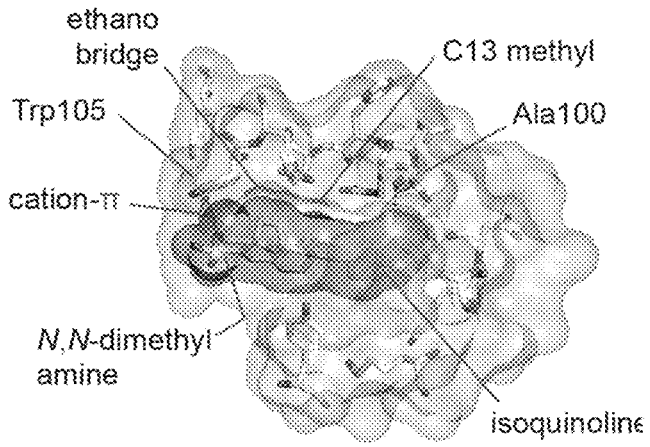
FIG. 32A and FIG. 32B is a portion of the CA-CDK8-CCNC crystal structure showing the CA binding pocket of CDK8 (with and without a semi-transparent surface; CA in dark grey, CDK8 in gray) with certain residues and CA in stick representation. Dotted lines indicate H-bonds. Key residues and binding elements are labelled.
Figure 32B:
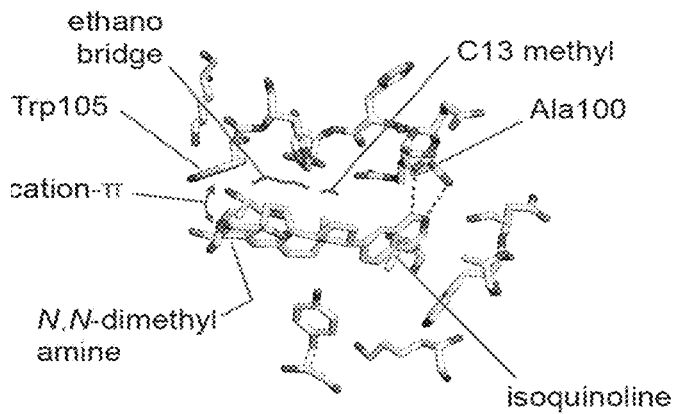
Figure 33:
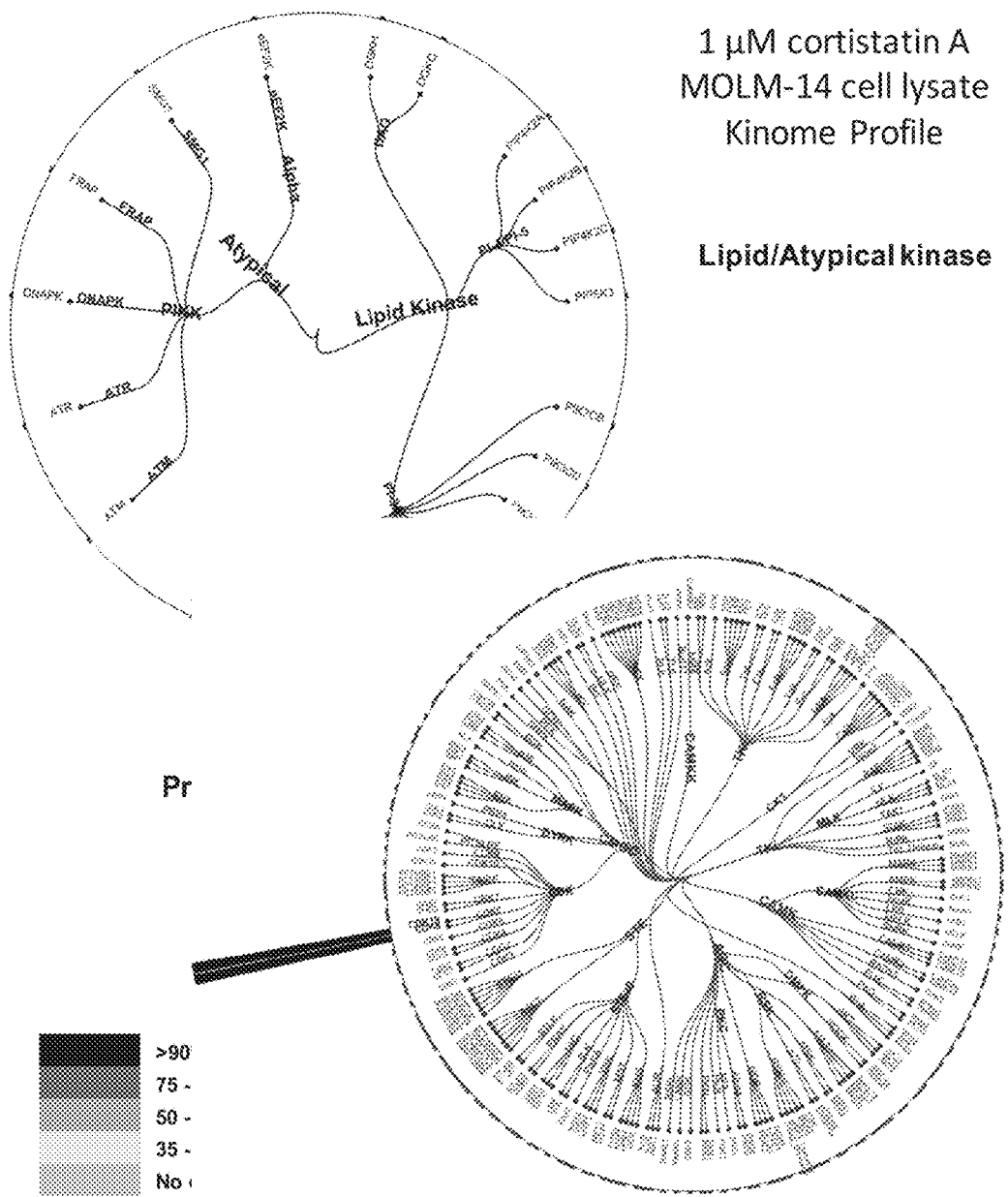
FIG. 33 illustrates a native kinase profiling dendrogram of CA. The Dendrogram is a representation of results shown in FIG. 6A for 1 μM CA.
Figure 34:
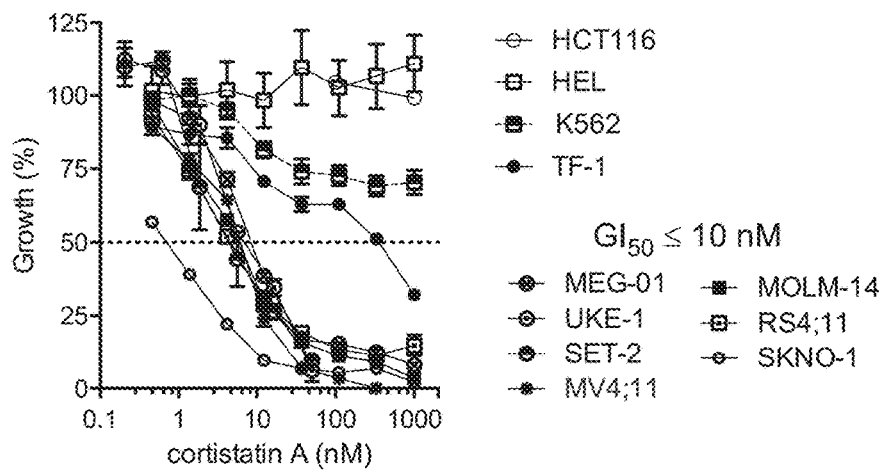
FIG. 34 is a line graph showing Growth (%) vs. CA (nM) concentration for various cell lines (mean±s.e.m., n=3).
Figure 35A:
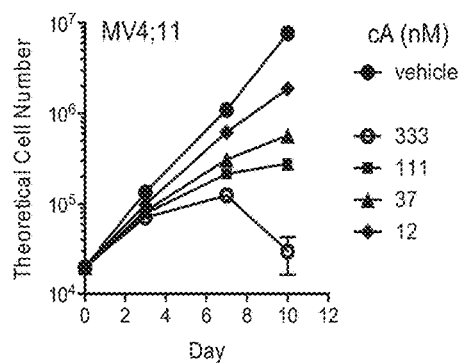
FIGS. 35A-35C are line graphs showing the delayed antiproliferative activity of CA over time for selected sensitive cell lines MV4;11 (FIG. 35A), SET-2 (FIG. 35B), or SKNO-1 (FIG. 35C) (mean±s.e.m., n=3).
Figure 35B:
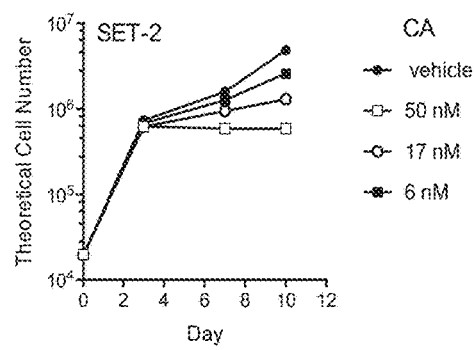
Figure 35C:
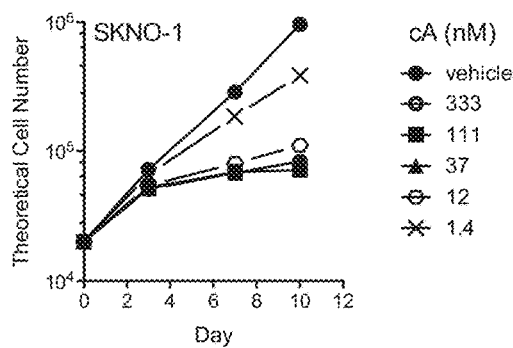
Figure 36A:
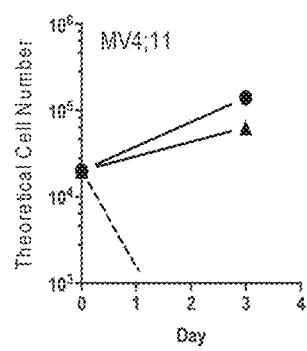
FIGS. 36A-36C are line graphs showing the antiproliferative activity of I-BET151 for the cell lines MV4;11 (FIG. 36A), SET-2 (FIG. 36B), or SKNO-1 (FIG. 36C) for the lowest maximum growth inhibitory concentration and a dose 3-fold lower (mean±s.e.m., n=3).
Figure 36B:
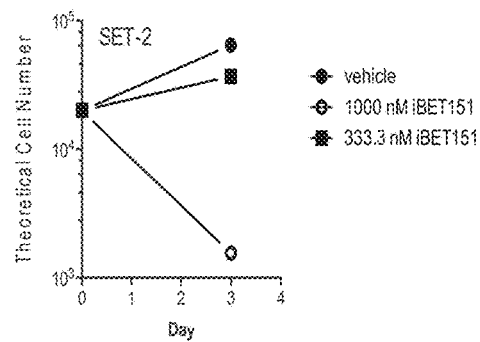
Figure 36C:
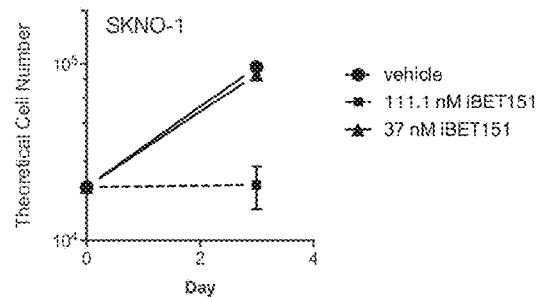
Figure 38C:
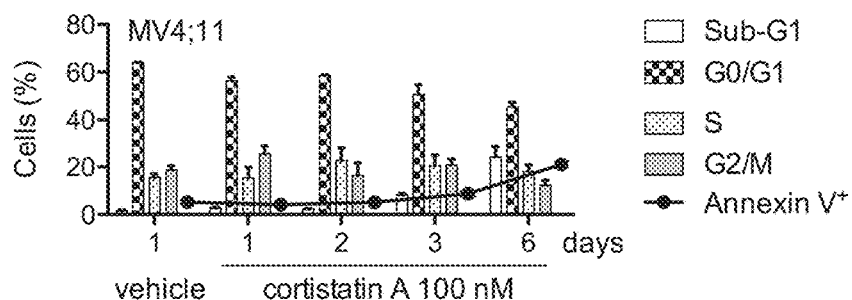
Figure 38D:
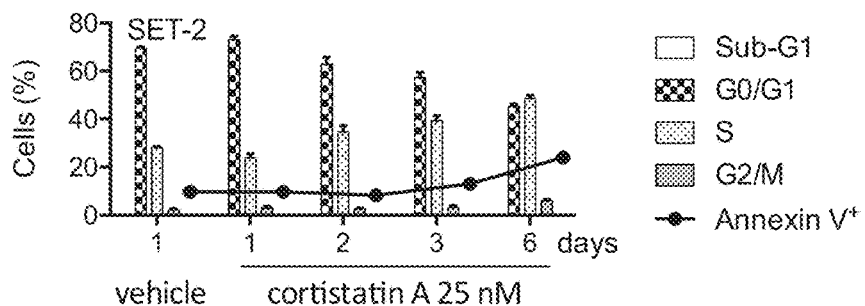
Figure 39:
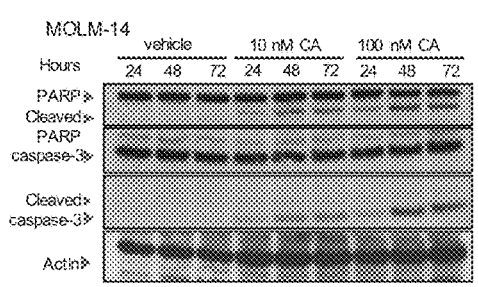
FIGS. 39-42 are immunoblots of CA-dose and time-dependent induction of PARP and caspase-3 cleavage for indicated cell lines including MOLM-14 (FIG. 39), MV5;11 (FIG. 40), SET-2 (FIG. 41), and SKNO-1 (FIG. 42).
Figure 40:
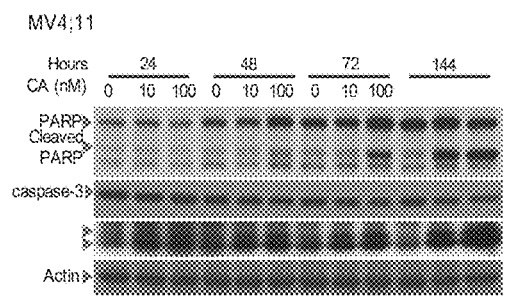
Figure 41:
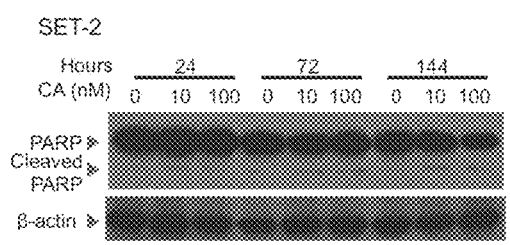
Figure 42:
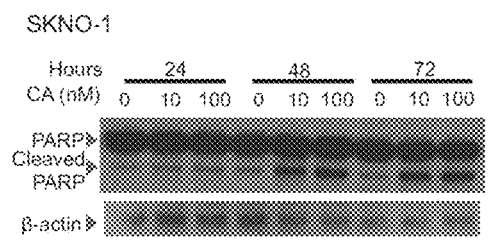
Figure 43:
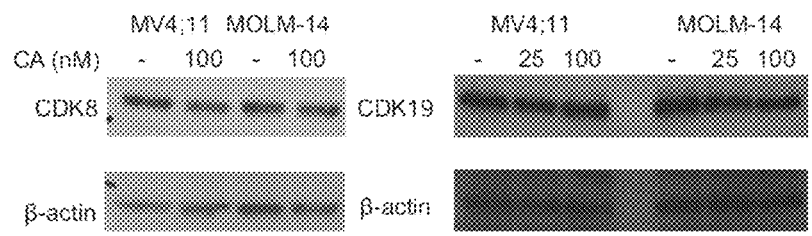
FIG. 43 are immunoblots showing CDK8 and CDK19 levels upon 24 h CA treatment in sensitive cell lines MV4;11 and MOLM-14.
Figure 44A:
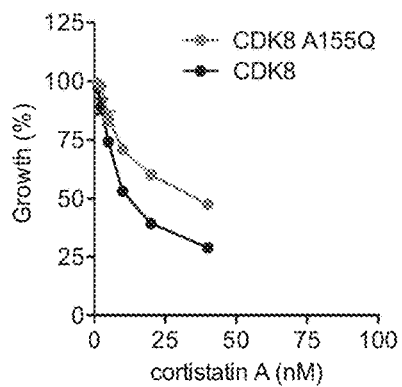
FIGS. 44A-44E are line graphs showing Growth (%) vs. CA (nM) concentration. Point mutations to CDK8 residues lining the CA-binding pocket: Ala155, His106, Asp103, and Trp105 were evaluated. Expression of CDK8 mutants A155Q (FIG. 44A), A155I (FIG. 44B), A155F (FIG. 44C), H106K (FIG. 44D), and D103E (FIG. 44E) in MOLM-14 cells afforded only modest desensitization to CA. Differential sensitivity of MOLM-14 cells to CA upon expression of indicated mutant FLAG-CDK8 proteins (mean±s.e.m., n=3).
Figure 44B:
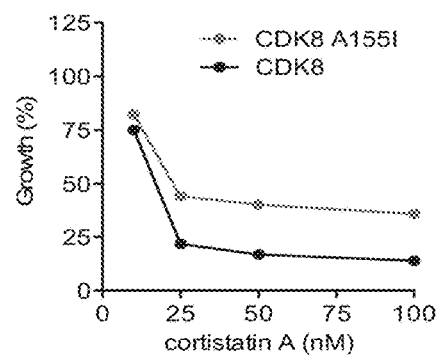
Figure 44C:
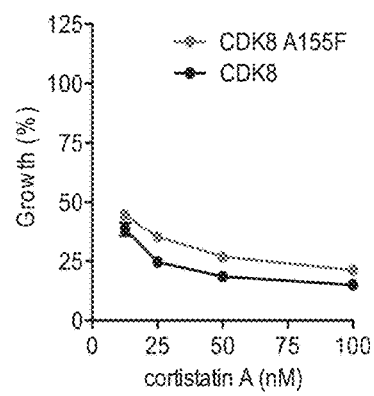
Figure 44D:
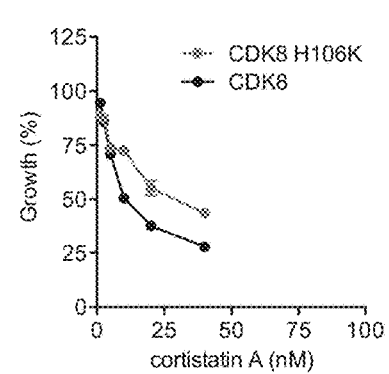
Figure 44E:
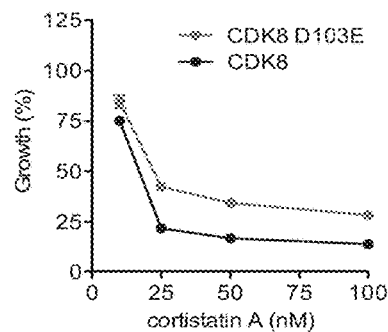
Figure 45:
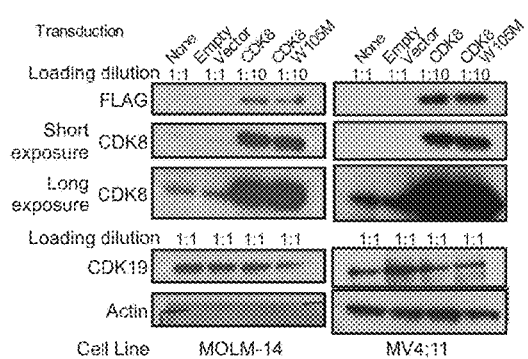
FIGS. 45-47 are immunoblots showing that FLAG-CDK8 or FLAG-CDK19 and FLAG-CDK8 W105M or FLAG-CDK19 W105M are expressed at similar levels in MOLM-14, MV4;11, (FIG. 45 and FIG. 46) and SKNO-1 cells (FIG. 47).
Figure 46:
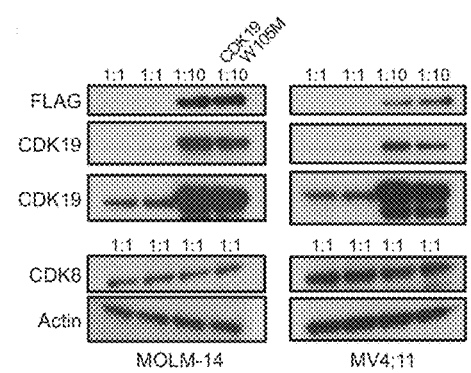
Figure 47:
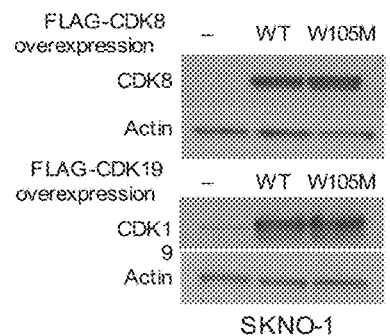

CA selectivity was broadly evaluated using two kinome profiling methods that together tested 387 kinases. A mass spectrometry-based native kinase affinity capture method (KiNativ) (Patricelli, M. P. et al. In Situ Kinase Profiling Reveals Functionally Relevant Properties of Native Kinases. Chem. Biol. 18, 699-710 (2011)) revealed that CA, tested at 100-times its CDK8 $IC_{50}$ in the assay (FIG. 31), only inhibited capture of CDK8/CDK19 from among 220 kinases detected from MOLM-14 cell lysate (FIG. 6A and FIG. 33). Likewise, an in vitro kinase activity panel revealed that CA, again tested at 100-times its CDK8/CCNC $IC_{50}$ (FIG. 31), only strongly inhibited the kinase activity of CDK8/CCNC and GSG2 from among 294 purified recombinant kinases (FIG. 6B). Although CA inhibited GSG2 in vitro, it did not bind GSG2 in MOLM-14 cell lysate at up to 2500 nM (FIG. 28). CA also exhibited high affinity binding, slow binding kinetics and a long residence time in its interaction with CDK8/CCNC in vitro (Table 3).

TABLE 3

In vitro binding parameters for CA to CDK8/CCNC.
CDK8/CCNC: CA Interaction

| | |
|---|---|
| $K_d$ | 195 ± 15.8 pM |
| $k_{off}$ | $6.35 \times 10^{-5} \pm 8.15 \times 10^{-6}$ s$^{-1}$ |
| $k_{on}$ | $3.26 \times 10^5 \pm 1.54 \times 10^4$ s$^{-1}$M$^{-1}$ |
| residence time | 262 ± 34 min |

Together, these results demonstrate that CA is a highly selective inhibitor of Mediator kinases with slow binding kinetics.

Figure 8:
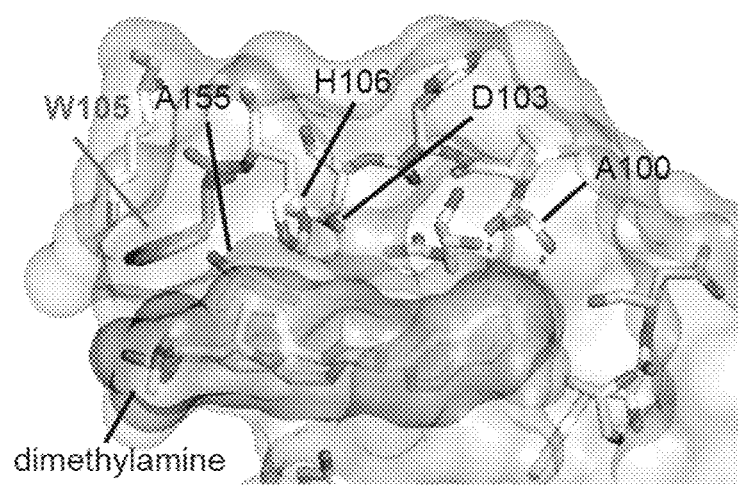
FIG. 8 illustrates a portion of the CA-CDK8-CCNC crystal structure showing the CA binding pocket of CDK8 (semi-transparent surface; CA in dark grey, CDK8 in grey) with certain residues and CA in stick representation. The dotted lines indicate H-bonds.

To understand how CA inhibits CDK8, a high-resolution (2.4 Å) crystal structure of a CA/CDK8/CCNC ternary complex was obtained (FIG. 8 and FIG. 29). CA exhibits exquisite shape complementarity with the ATP-binding pocket of CDK8. In particular, the isoquinoline of CA forms N—H and CH—O hydrogen bonds with Ala 100 (Pierce, A. C., Sandretto, K. L. & Bemis, G. W. Kinase inhibitors and the case for CH.O hydrogen bonds in protein-ligand binding. Proteins 49, 567-576 (2002)), the C5-C9 ethano bridge and the C13-methyl group of CA occupy deep hydrophobic crevices in the ATP-binding site, and the C3 N,N-dimethylamine of CA, which is protonated at physiological pH, engages in an apparent cation-π interaction with Trp 105 (Zacharias, N. & Dougherty, D. A. Cation-π interactions in ligand recognition and catalysis. Trends Pharmacol. Sci. 23, 281-287 (2002)).

The antiproliferative activity of CA was investigated and it was observed that CA potently inhibited proliferation of myeloid, mixed-lineage, and megakaryoblastic leukemia cell lines harboring diverse oncogenic drivers (10-day treatment; $GI_{50}$<10 nM, Table 4 and FIG. 34 and FIGS. 35A-35C).

TABLE 4

Mean 50% growth inhibition (GI50) of human cell lines by CA & I-BET151 after 10 and 3 days, respectively and of HCT116 cells after 7 days.

| Cell Line | Malignancy | Mutation | $GI_{50}$ (nM) CA | I-BET151 |
|---|---|---|---|---|
| SKNO-1 | AML | AML1-ETO | 1 | 50 |
| RS4;11 | B-ALL | MLL-AF4 | 3 | 200 |
| SET-2 | AML/MPN | JAK2V617F | 4 | 245 |
| MOLM-14 | AML | MLL-AF9 | 5 | 18 |
| MV4;11 | AML | MLL-AF4 | 6 | 20 |
| UKE-1 | AML/MPN | JAK2V617F | 7 | |
| MEG-01 | CML/AMKL | BCR-ABL | 9 | 375 |
| TF-1 | AML/Erythroleukemia | EpoR | 350 | 163 |
| HEL | AML/Erythroleukemia | JAK2V617F | >1,000 | 200 |
| K562 | CML/Erythroleukemia | BCR-ABL | >1,000 | 750 |
| HCT116 | Colorectal | β-catenin | >1,000 | |

Figure 9:
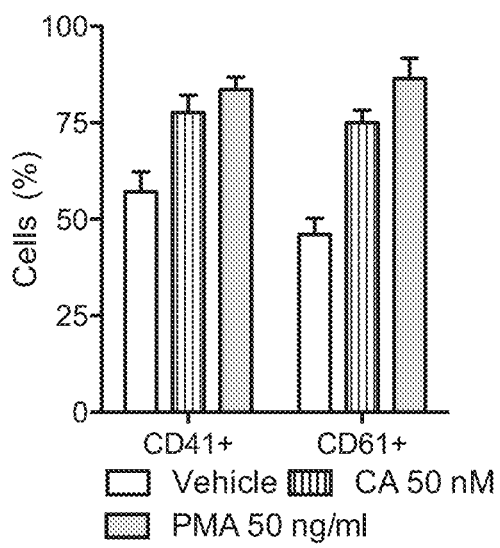
FIG. 9 is a bar graph showing CD41 and CD61 (vehicle vs. CA, p=0.04 and 0.005, respectively, two-tailed t-test) on SET-2 cells (Cells (%)) after 3 days of indicated treatment (mean±s.e.m., n=3). Phorbol 12-myristate 13-acetate (PMA) was used as a positive control.
Figure 10:
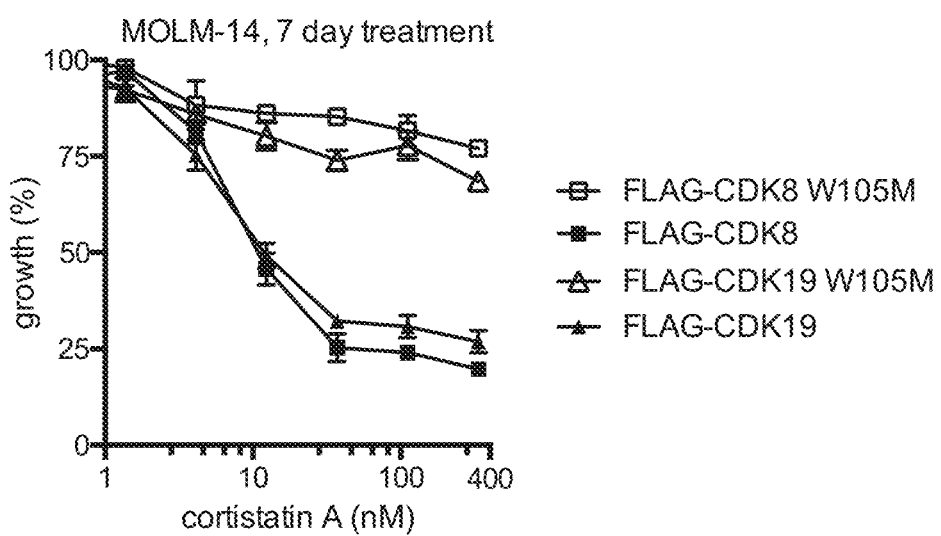
FIG. 10 is a line graph showing the sensitivity (growth (%)) of MOLM-14 cells to CA (nM) upon expression of FLAG-CDK8, FLAG-CDK19, FLAG-CDK8 W105M or FLAG-CDK19 W105M (mean±s.e.m., n=3). Expression of CDK8 W105M or CDK19 W105M prevented the antiproliferative activity of CA, supporting CDK8 and CDK19 as the cellular targets of CA responsible for its antiproliferative activity.

CA inhibited CDK8 kinase activity in both sensitive and insensitive cell lines with similar potency and did not alter Mediator kinase (CDK8 or CDK19) protein levels (FIGS. 37A-37G and FIG. 43). Of note, although SET-2 and HEL cell lines harbor the JAK2V617F oncogenic driver mutation and MEG-01 and K562 harbor the BCR-ABL translocation, only SET-2 and MEG-01 cells were sensitive to CA. SET-2 and MEG-01 were derived from megakaryoblastic leukemias whereas HEL and K562 were derived from erythroleukemias, suggesting that cell lineage may be a contributing determinant of CA sensitivity (Table 4) (Garraway, L. A. & Sellers, W. R. Lineage dependency and lineage-survival oncogenes in human cancer. Nat. Rev. Cancer 6, 593-602 (2006)). The phenotypic effects of CA were largely cell line-dependent. CA treatment increased megakaryocyte markers CD41 and CD61 on SET-2 cells (FIG. 9), whereas CA treatment of MOLM-14, MV4; 11, and SKNO-1 cells increased cleaved PARP levels, the sub-G1 cell population and Annexin V staining, consistent with apoptosis (FIGS. 38A-38D and FIGS. 39-42).

To determine whether Mediator kinase inhibition accounts for the antiproliferative activity of CA (i.e., that CDK8 and CDK19 are the relevant cellular targets of CA), point mutations were identified in CDK8 that would not disrupt its catalytic activity but would abrogate CA binding and confer resistance to CA-sensitive cells. The point mutations to CDK8 residues lining the CA binding pocket: Ala155, His106, Asp103, and Trp105 were evaluated (FIG. 8). Expression of CDK8 A155I, A155F, A155Q, H106K and D103E in MOLM-14 cells afforded only modest desensitization to CA (FIGS. 44A-44E). In contrast, expression of CDK8 W105M strongly desensitized MOLM-14, MV4; 11 and SKNO-1 cells to growth inhibition by CA but not antiproliferative agents (paclitaxel or doxorubicin) that do not target CDK8 (FIG. 10 and FIGS. 45-47, 48A-48B, 49A-49B, 50A-50B, and 51C-51D).

Similar results were obtained with CDK19 W105M (FIG. 10 and FIGS. 45-47, 48A-48B, 49A-49B, 50A-50B, and 51C-51D). CDK8 or CDK19 W105M mutants retained catalytic activity but were refractory to CA inhibition in cells and in vitro (FIGS. 11A-11B). Notably, CDK8 and CDK19 are the only mammalian CDKs with Trp (or any aromatic amino acid) at residue 105 (FIG. 52), highlighting the importance of Trp 105 and its cation-π interactions with CA. Collectively, these studies indicated that Mediator kinases (CDK8 and CDK19) mediate the antiproliferative activity of CA, although some involvement of other targets cannot be excluded.

Figure 17A:
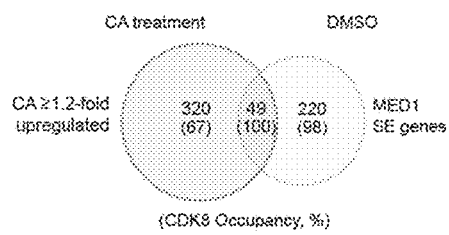
FIG. 17A is a Venn diagram showing the overlap between SE genes and genes upregulated ≥1.2-fold upon 3 h CA treatment in MOLM-14 cells ("CA upregulated genes").

Next, CA was used to investigate whether Mediator kinase activity regulates SE-associated gene expression in AML cells and if so, whether such regulation might contribute to AML cell proliferation. Global gene expression profiling in MOLM-14 cells treated with CA for 3 or 24 hours revealed that CA treatment had limited effects on transcription genome-wide (470 genes differentially expressed ≥1.2-fold at 3 hours and 414 genes ≥1.5-fold at 24 hours). Gene-set enrichment analysis (GSEA) (Subramanian, A. et al. Gene set enrichment analysis: a knowledge-based approach for interpreting genome-wide expression profiles. Proc. Natl. Acad. Sci. USA 102, 15545-15550 (2005)) revealed that genes upregulated by CA at 3 hours were highly enriched for association with SEs, identified by BRD4, H3K27ac, MED1, and CDK8 occupancy (FIGS. 12-13, FIGS. 17A-17B, and FIGS. 53A-53D). These SE-associated gene sets ranked among the most significantly enriched compared to all other signatures in the Molecular Signatures Database (MSigDb) C2 collection (FIG. 14). Genes upregulated by CA were disproportionately associated with SEs in MOLM-14 cells (49/251, 20%) compared to regular enhancers (173/5034, 3%) (FIG. 4b, Fisher's exact test, $p<2.2\times10^{-16}$). In contrast, of the 102 genes downregulated (≥1.2-fold) by 3-hour CA treatment, only three were identified as SE-associated (3/251, 1%). Additionally, the association between CA upregulated genes and SE-associated genes correlated with CDK8 occupancy (Fisher's exact test, $p=2.5\times10^{-8}$), consistent with the notion that in AML cells, SEs are direct targets of CA treatment (FIG. 17A).

Because SE-associated genes are on average more highly expressed compared to regular enhancer-associated genes, it was determined whether genes upregulated by CA had actively elongating RNA pol II and reduced traveling ratios (TR)(Adelman, K. & Lis, J. T. Promoter-proximal pausing of RNA polymerase II: emerging roles in metazoans, Nat Rev Genet 13, 720-731 (2012)), ratio of RNA pol II ChIP-seq reads in the proximal promoter versus the gene body). Indeed, CA upregulated genes exhibited reduced baseline TR (2.40-fold, $p<2.2\times10^{-16}$, FIG. 14 and FIGS. 54-55), consistent with CA upregulating active genes, including those associated with SEs. CA treatment further reduced the TR of these "CA upregulated" genes to a level similar to all SE-associated genes (yellow curve), in agreement with their increased expression after CA treatment (1.48-fold, $p=7.6\times10^{-4}$, FIG. 14). This effect is specific to upregulated genes, as those downregulated by CA experienced insignificant changes in TR (FIG. 56A). Furthermore, global effects of CA on RNA pol II TR, RNA pol II CTD phosphorylation, and mRNA and total RNA levels were modest or negligible (FIGS. 56B, 57A-57B, and 58).

Figure 16:
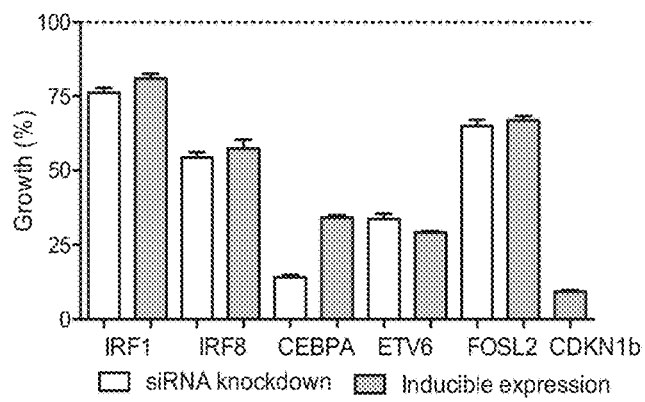
FIG. 16 is a bar graph showing the effect of change in expression of selected SE genes on MOLM-14 cell growth (mean±s.e.m., with n=6 for siIRF8, siIRF1, and siCEBPA, n=3 for siETV6 and siFOSL2, n=24 for FLAG-CEBPA, n=12 for FLAG-IRF1, FLAG-IRF8, FLAG-ETV6, and FLAG-FOSL2).
Figure 17B:
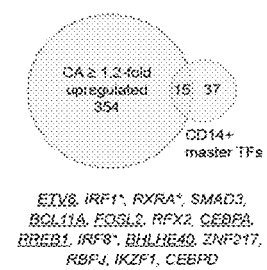
FIG. 17B is a Venn diagram showing overlap between CA upregulated genes and CD14+ master TFs. Overlapping genes are listed; SE-associated genes identified by one (*) or more (underlined) marks in MOLM-14 are indicated.
Figure 18:
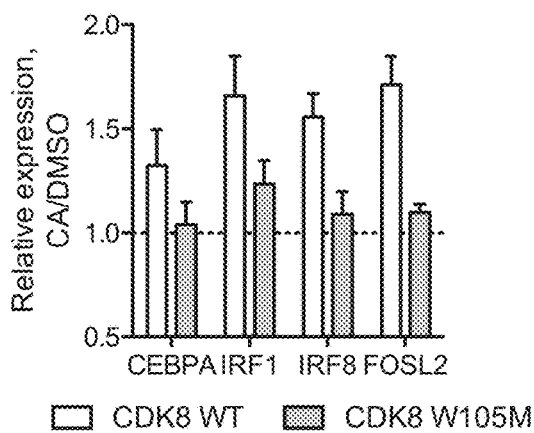
FIG. 18 is a bar graph showing the effect of 3 h treatment with 25 nM CA on mRNA levels of indicated genes in MOLM-14 cells expressing FLAG-CDK8 or FLAG-CDK8 W105M (mean±s.e.m., n=3).

Next, it was investigated whether upregulation of SE-associated genes might contribute to the antiproliferative activity of CA. SE-associated genes upregulated by CA were enriched in lineage-controlling master TFs identified in related CD14+ monocytes (Hnisz, D. et al. Super-enhancers in the control of cell identity and disease. Cell 155, 934-947 (2013)), including tumor suppressors IRF1, IRF8, CEBPA, and ETV6 (FIG. 15, FIG. 17B, and FIG. 59). Increased expression of these genes individually, as well as SE-associated genes FOSL2 and CDKN1B, inhibited the proliferation of MOLM14 cells (FIG. 16, FIGS. 60A-60E, and FIG. 61). CDK8 is present at each gene's nearby SE (shown for CEBPA, FIG. 5; and ETV6 and FOSL2, FIGS. 63A-63B). Furthermore, expression of W105M mutant CDK8 (conferring resistance to CA), prevented upregulation of SE-associated genes by CA (FIG. 18). These results suggest that upregulation of SE-associated genes contributes to the antiproliferative activity of CA in AML cells, and that CA's effects are dependent upon Mediator kinase activity. Furthermore, these results are consistent with the observation that sensitivity to CA is dependent upon hematopoietic cell lineage.

Figure 19:
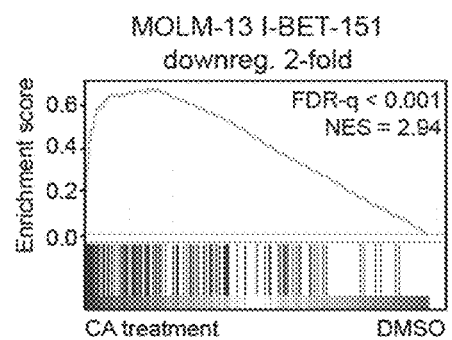
FIG. 19 is a GSEA plot showing significant positive enrichment of genes downregulated by IBET-151 ≥2-fold in MOLM-13 cells in 3 h CA differential gene expression in MOLM-14 cells.
Figure 20A:
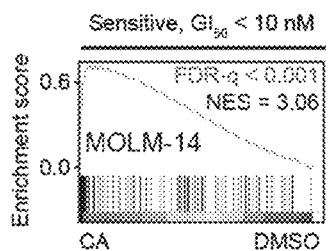
FIGS. 20A-20E: GSEA plots of MOLM-14 (FIG. 20A), SET-2 (FIG. 20B), MV;411 (FIG. 20C), HCT116 (FIG. 20D), or K562 (FIG. 20E) differential gene expression with CA. Regions of CDK8 and H3K27ac co-enrichment identify SE genes in each cell line. Specifically, cell lines sensitive to CA show significant positive enrichment of SE genes whereas insensitive lines do not.
Figure 20B:
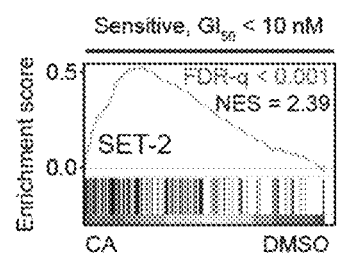
Figure 20C:
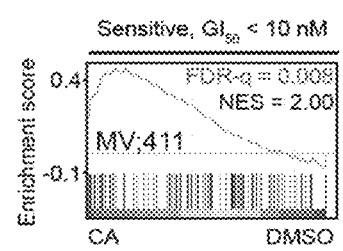
Figure 20D:
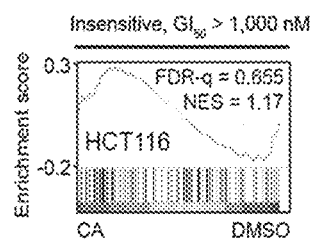
Figure 20E:
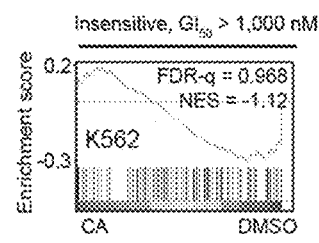
Figure 21:
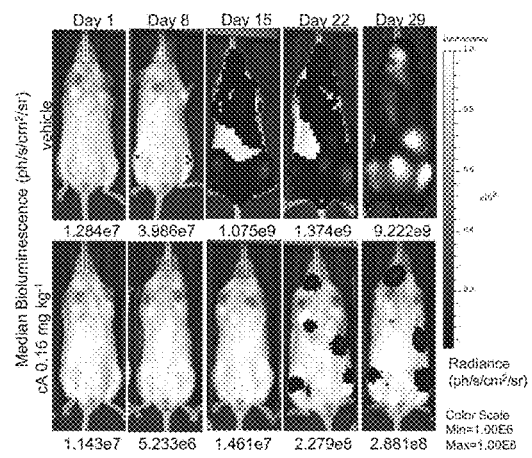
FIG. 21 are bioluminescent images of mice bearing MV4; 11 luciferase-expressing leukemia cells with the median bioluminescence indicated for each timepoint and treated as in FIG. 22.
Figure 22:
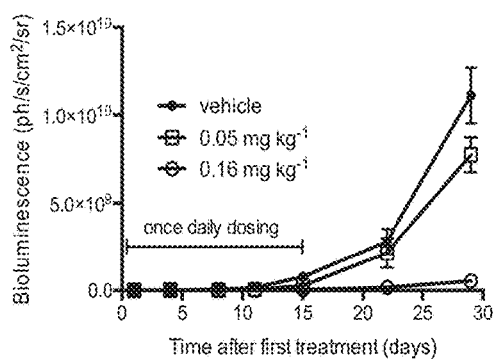
FIG. 22 is a line graph showing mean bioluminescence±s.e.m., n=11/group; p<0.0001, two-way analysis of variance (ANOVA).

Growth of several AML cell lines was sensitive to CA and the BRD4 inhibitor I-BET151 (Table 4 and FIG. 34, FIGS. 35A-35C, and FIGS. 36A-36C). However, these compounds have largely opposing effects on transcription, especially at SE-associated genes (FIG. 15, FIG. 19, and FIG. 59). This suggests that AML cell growth might be dependent on a precise "dosage" of SE-associated genes. Indeed, MOLM-14 cell growth was inhibited by either reduced or increased expression of the same SE-associated genes, many of which were upregulated by CA and downregulated by I-BET151 (FIGS. 15-16 and FIGS. 60A-60E and FIGS. 61-62).

Although CA and I-BET151 have opposing effects on transcription of many SE-associated genes, co-treatment of cells with both compounds did not normalize transcription. Instead, I-BET151-induced transcriptional effects dominated, suggesting a dependence on BRD4 for CA-induced transcription (FIG. 15 and FIG. 59). Consistent with this, I-BET151 caused a reduction of BRD4 and CDK8 on enhancer regions, and co-treatment of MOLM-14 cells with I-BET151 and CA resulted in inhibition of growth (FIGS. 64-65).

The gene expression and SE analysis were extended to additional cell lines that were sensitive (SET-2 and MV4; 11) and insensitive (HCT116 and K562) to CA and it was found that only the sensitive cell lines MOLM-14, MV4; 11 and SET-2 showed statistically significant enrichment of SE-associated genes among those upregulated by CA (FIGS. 20A-20E and Table 5).

TABLE 5

| $GI_{50}$ of cell lines by CA. | |
| --- | --- |
| Cell Line | $GI_{50}$ (nM) |
| MOLM-14 | 5 |
| SET2 | 4 |
| MV4;11 | 6 |
| HCT116 | >1,000 |
| K562 | >1,000 |

This result is consistent with upregulation of SE-associated genes contributing to the antiproliferative effects of CA. However, the contribution of non-SE related effects of inhibiting Mediator kinases cannot be excluded.

Figure 23:
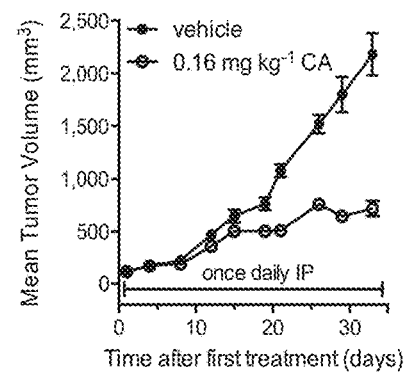
FIG. 23 is a line graph showing mean tumor volume ($mm^3$) in SCID beige mice (n=10/group) harboring SET-2 AML xenograft tumors with IP dosing of CA daily for 33 days.
Figure 24:
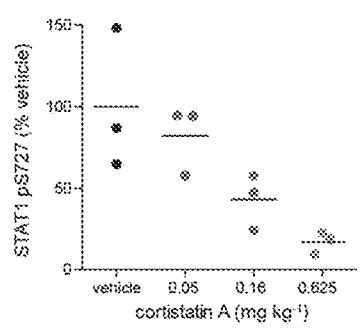
FIG. 24 is a dot plot showing densitometric analysis of STAT1 pS727 (% vehicle) in natural killer cells isolated from the spleen of C57BL/6 mice treated with CA or vehicle (n=3/group), STAT1-pS727 normalized to actin, P=0.011 for 0.625 mg/kg, one-way ANOVA.

Finally, it was investigated whether the anti-leukemic activity of CA observed in cells would translate to in vivo models of AML. It was determined that CA had acceptable pharmacokinetic properties in mice for once-daily intraperitoneal (IP) dosing (FIG. 66) and its efficacy was measured in a xenotransplant model of disseminated human AML using luciferase-expressing MV4; 11 cells (Etchin, J. et al. Antileukemic activity of nuclear export inhibitors that spare normal hematopoietic cells. Leukemia 27, 66-74 (2013)). CA afforded a dose-dependent reduction in disease progression as measured by bioluminescence (p<0.0001), spleen weight, leukemia cell burden, and survival (29.5-day median extension in survival, p<0.0001, FIGS. 21-22, FIG. 67, FIGS. 68A-68C, and FIGS. 69-72). In a second mouse xenotransplant model using subcutaneously implanted SET-2 cells, CA afforded a 71% tumor volume reduction, also with no loss in body weight (FIG. 23). The fact that CA inhibited CDK8 was confirmed in vivo by observing a dose-dependent reduction in STAT1 S727 phosphorylation in NK cells, which have CDK8-dependent constitutively phosphorylated STAT1 S727 (FIG. 31) (Putz, E. M. et al. CDK8-Mediated STAT1-S727 Phosphorylation Restrains NK Cell Cytotoxicity and Tumor Surveillance. Cell Rep. 4, 437-444 (2013)).

Although SE-associated genes are expressed at high levels, these results show that they are restrained from even higher expression by the enzymatic activity of Mediator kinases in human leukemia cells, thereby revealing a new facet to how these key controllers of cell identity and disease states are regulated. These studies also show that AML is highly sensitive to changes in the dosage of SE-associated genes. Perturbation of these genes from their optimal expression levels, either by downregulation (as has been shown for BRD4 inhibition) or upregulation (by inhibition of Mediator kinases) is a therapeutic approach to AML. CA's specificity, potency and favorable pharmacokinetics make it a useful in vitro and in vivo probe of Mediator kinases.

Methods

Cell Culture. All media was supplemented with 100 U/mL penicillin and 100 µg/mL streptomycin. Human cancer cell lines were grown in the following media: MV4; 11, RS4; 11, K562, HEL, MOLM-14, MEG-01 in RPMI-1640, 10% FBS; SET-2 in RPMI-1640, 20% FBS; UKE-1 in RPMI-1640, 10% FBS, 10% horse serum and 1 µM hydrocortisone; SKNO-1 and TF-1 in RPMI-1640, 10% FBS, and 10 or 2 ng/mL GM-CSF, respectively; HaCaT in DMEM, 10% FBS; and HCT116 in McCoy's 5 A, 10% FBS (proliferation assay) or DMEM, 10% FBS (gene expression study). HepG2, MV4;11, RS4;11, MEG-01, TF-1, HCT116 and K562 were from ATCC. SKNO-1 was from DSMZ. HEL, UKE-1, and SET-2 were provided by Ross L. Levine and HaCaT, MV4;11-mCLP, and MOLM-14 by Van Wilson, Andrew L. Kung, and Scott A. Armstrong, respectively. MOLM-14 cells were authenticated by STR profiling and flow cytometry and all cell lines were routinely tested and found to be negative for *mycoplasma*.

Reagents. Compounds were stored under argon at −80° C. in 100% DMSO. Vehicle represents 0.1% DMSO unless otherwise specified. Sources: IFN-γ (PHC4031, Life Technologies), TGF-β1 (R&D Systems), paclitaxel (LC Laboratories), I-BET151 (Tocris), PMA (Calbiochem), and doxorubicin and puromycin (Sigma-Aldrich). Immunoblot antibodies: anti-FLAG (F1804), anti-Actin (A5060) and anti-CDK19 (HPA007053) from Sigma-Aldrich; anti-Smad2/3 (8685), anti-Smad2 pTail (3108), anti-STAT1 (9172), anti-phospho-STAT1 Tyr701 (9170) and anti-phospho-STAT1 Ser727 (9177), anti-CEBPA (2843), anti-ROCK1 (4035), anti-ROCK2 (9029), anti-CDK8 (4101), anti-caspase-3 (9662) anti-PARP (9532) and anti-CDK9 (2316) from Cell Signaling Technology (CST); anti-phospho-Smad2/3 T220/T179 (600-401-C48) from Rockland; anti-CDK12 (NB 100-87012) and anti-CDK13 (NB 100-68268) from Novus; and anti-CDK8 (A302-501A) and anti-Haspin (A302-241A) from Bethyl. ChIP antibodies: RNA pol II (Rpb1 N terminus, sc-899X lot B2713) from Santa Cruz; MED1 (A300-793A lot A300-793A-2), BRD4

(A301-985A lot A301-985A50-3), and CDK8 (A302-500A lot A302-500A-1) from Bethyl; and H3K4me3 (ab8580 lot 1308511), H3K27Ac (ab4729 lot GR104852-1), and H3K4me1 (ab8895 lot GR61306-1) from Abcam.

Kinase Assays. Data was quantified with ImageJ and plotted and fitted with GraphPad Prism 6.0. For STAT1 transactivation domain (TAD), 750 ng of GST-STAT1 TAD (residues 639-750) was incubated with ~50 ng recombinant CDK8 module at 30° C. for 8 min in kinase buffer (25 mM Tris pH 8, 2 mM DTT, 100 µM cold ATP, 100 mM KCl, 10 mM $MgCl_2$ and 2.5 µCi [$\gamma$-$^{32}$P] ATP (Perkin Elmer) per reaction). The assay included 2.5% DMSO, which did not inhibit kinase activity. 12% SDS-PAGE gels were subsequently silver stained, exposed for 18 h on a Phosphor Screen and imaged (Typhoon 9400, GE Life Sciences). For pol II CTD, 400 ng of GST-CTD (murine sequence) was incubated with ~40 ng recombinant CDK8 module, 25 ng TFIIH, or 40 ng P-TEFb at 30° C. for 60 min in kinase buffer. Kinase amounts were chosen to give similar total pol II CTD signal. 9% SDS-PAGE gels were silver stained and exposed as above. In vitro FLAG-CDK8 kinase assays used ~40 ng kinase and 500 ng GST-CTD. For STAT1 or Smad2/3, cells were treated with compound for 1 h followed by IFN-$\gamma$ or TGF-$\beta$1 for 1 h, then washed twice with cold PBS, and lysed (RIPA buffer with inhibitors R0278, P8340, P0044, P5762 Sigma-Aldrich). Standard immunoblotting was then performed with one immunoblot shown. All experiments were performed twice.

Protein Purification. Buffers for purification and elution of recombinant proteins included 0.25 mM PMSF, 1 mM DTT, 1 mM benzamidine, and 1 mM sodium metabisulfite. TFIIH was captured from HeLa nuclear extract using a monoclonal antibody for the p89 subunit immobilized to Protein A Sepharose (GE). Final purification of peptide-eluted TFIIH was performed on a 1 mL HiTrap Heparin HP (GE) resulting in 0.1-0.2 µM TFIIH. P-TEFb was purified as described (Tahirov, T. H. et al. Crystal structure of HIV-1 Tat complexed with human P-TEFb. Nature 465, 747-751 (2010)) with a Superdex 200 polishing resulting in ~0.5 µM P-TEFb. For kinase assays, recombinant CDK8 module was purified as described Error! Bookmark not defined. with omission of the glycerol gradient. STAT1 TAD and pol II CTD were expressed as N-terminal GST fusion proteins in E. coli BL21-CodonPlus cells to $OD_{600}$ 0.5, then induced with 0.5 mM IPTG for 4 h at 30° C. and batch affinity purified with Glutathione Sepharose 4B (GE). Cells were lysed in H/E buffer (50 mM Tris pH 7.9, 0.5 M NaCl, 0.5 mM EDTA, 10% glycerol, 0.5% NP-40), immobilized on Glutathione Sepharose 4B in H/E buffer for 3 h at 4° C., washed with ~100 column volumes (CV's) of High Salt Buffer (50 mM Tris pH 7.9, 1 M NaCl, 0.5 mM EDTA, 0.5% NP-40, 8 mM CHAPS), 0.5 M HEGN (20 mM HEPES pH 7.6, 0.5 M KCl, 0.1 mM EDTA, 10% glycerol, 0.02% NP-40) and 0.15M HEGN (20 mM HEPES pH 7.6, 0.15 M KCl, 0.1 mM EDTA, 10% glycerol, 0.02% NP-40). Fusion proteins were eluted in 2×CV's of 30 mM reduced L-glutathione in GSH elution buffer (80 mM Tris pH 7.9, 0.15 M KCl, 0.1 mM EDTA, 10% glycerol, 0.02% NP-40). The GST-pol II-CTD was further purified by Superdex 200 polishing. FLAG-CDK8 WT and W105M mutants were expressed in MOLM-14 cells, captured using anti-FLAG M2 affinity resin (Sigma-Aldrich), and eluted with 1 mg/mL FLAG peptide in 0.15 M HEGN in 1×CV twice. FLAG peptide elutions were then stained with SYPRO Ruby to standardize kinase amounts. Purifications contained Cyclin C but not MED12 or MED13 (data not shown).

Native Kinase Capture Immunoblot and Native Kinome-Wide Profiling. Experiments were performed as previously described (Okerberg, E. et al. Profiling native kinases by immuno-assisted activity-based profiling. Curr. Protoc. Chem. Biol. 5, 213-226 (2013) and Patricelli, M. P. et al. In Situ Kinase Profiling Reveals Functionally Relevant Properties of Native Kinases. Chem. Biol. 18, 699-710 (2011)). $5 \times 10^8$ MOLM-14 cells were washed twice with 10 mL cold PBS and resuspended in 1 mL cold kinase buffer (20 mM HEPES pH 7.4, 150 mM NaCl, 0.5% Triton X-100, with inhibitors 11697498001, Roche and P5726, Sigma). Cells were lysed by sonication (2×10 s pulses with a 30 s break) and centrifuged (16,000×g, 10 min). The supernatant was desalted through a column (732-2010, Biorad) and the eluted lysate was diluted to 5 mg/ml with kinase buffer. For each treatment, 475 µL of the lysate was pre-incubated with 10 µL $MnCl_2$ (1 M) and 5 µL compound to the desired concentration at room temperature for 30 min. Uninhibited kinases were captured with 10 µL ActivX desthiobiotin-ATP probe (0.25 mM; 88311, Pierce) at room temperature for 10 min. Samples were mixed with 500 µL urea (8 M; 818710, Millipore) and 50 µL streptavidin agarose (20359, Thermo) for 60 min at room temperature on a nutator. Beads were washed twice with a 1:1 mixture of kinase buffer and 8 M urea, and collected by centrifugation (1,000×g, 1 min). Proteins were eluted from the beads with 100 µL 2×LDS sample buffer (NP0007, Life) at 95° C. for 10 min. Samples were analysed by standard immunoblotting followed by HRP detection. Experiment was performed twice with one immunoblot shown. Native kinome profiling was performed with MOLM-14 cell lysate according to KiNativ Method by ActivX Biosciences. For each peptide quantitated, the change in MS signal for the treated samples relative the MS signal for the control samples was expressed as percentage inhibition. The results correspond to one experiment of duplicates for each CA concentration. The percentage changes in MS signal reported are statistically significant (Student T-test score <0.04).

Recombinant Kinome-Wide Selectivity Profiling and $IC_{50}$ Determination. A radiometric protein kinase assay was used (PanQinase activity assay; performed by ProQinase GmbH) as described (Hutterer, C. et al. A Novel CDK7 Inhibitor of the Pyrazolotriazine Class Exerts Broad-Spectrum Antiviral Activity at Nanomolar Concentrations. Antimicrob. Agents Chemother. 59, 2062-2071 (2015)). $IC_{50}$ determination for CDK8/CCNC (8.3 µM with 1.0 M ATP and 1.0 µg/50 uL of substrate RBER-IRStide) was performed as duplicate measurements and $IC_{50}$ was calculated using Prism 5.04 with sigmoidal response, top fixed at 100% and bottom at 0% with least-squares fitting.

Binding and Kinetics. Measurements were made using the Proteros reporter displacement assay (performed by Proteros) as previously described (Neumann, L., Ritscher, A., Miller, G. & Hafenbradl, D. Fragment-based lead generation: identification of seed fragments by a highly efficient fragment screening technology. J. Comput. Aided Mol. Des. 23, 501-511 (2009) and Schneider, E. V., Bottcher, J., Huber, R., Maskos, K. & Neumann, L. Structure-kinetic relationship study of CDK8/CycC specific compounds. Proc. Natl. Acad. Sci. 110, 8081-8086 (2013)). Experiment was performed once.

Crystallization, Data Collection, and Refinement. Human CDK8/CCNC were expressed and purified as previously described (Schneider, E. V., et al. The structure of CDK8/CycC implicates specificity in the CDK/Cyclin family and reveals interaction with a deep pocket binder. J. Mol. Biol. 412, 251-266 (2011)). Co-crystals at a protein concentration of 11.3 mg/ml with 1 mM CA were obtained in 20% PEG 3350 and 0.20 M sodium formate at 20° C. and shock-frozen with 25% ethylene glycol as cryoprotectant. Diffraction data were collected at the SWISS LIGHT SOURCE (SLS, Villigen, Switzerland), beamline X06SA with a wavelength of 1.00004 Å at 100 K, and processed using XDS and XSCALE (Kabsch, W. Integration, scaling, space-group assignment and post-refinement. Acta Cryst. D66, 133-144 (2010)). The structure was solved by molecular replacement (Vagin, A. A. & Teplyakov, A. Molecular replacement with MOLREP. Acta Cryst. D66, 22-25 (2010)), subsequent model building and refinement (including TLS refinement) was performed with COOT (Emsley, P. & Cowtan, K. Coot: model-building tools for molecular graphics. Acta Cryst. D60, 2126-2132 (2004)) and CCP4 (Dodson, E. J., Winn, M. & Ralph, A. Collaborative Computational Project, number 4: providing programs for protein crystallography. Meth. Enzymol. 277, 620-633 (1997) and Vagin, A. A. et al. REFMAC5 dictionary: organization of prior chemical knowledge and guidelines for its use. Acta Cryst. D60, 2184-2195 (2004)). The $R_{free}$ validation was based on a subset of about 3.4% of the reflections omitted during refinement. Waters were included at stereochemically reasonable sites. Final refinement cycles led to a model with $R_{work}$ value 21.7% and $R_{free}$ value 26.6%. All main-chain angles of non-glycine residues fall into the conformationally most favored (93.2%), additionally allowed (6.6%) or generously allowed (0.2%) regions of the Ramachandran plot. Graphical figures were prepared using PyMOL (The PyMOL molecular graphics system (Schrödinger, New York)). Values in parenthesis in Table 6 refer to the highest resolution-shell.

TABLE 6

Data collection and refinement statistics (Molecular Replacement).

| | CDK8/CycC/CA |
|---|---|
| Data collection | |
| Space group | P $2_1 2_1 2_1$ |
| Cell dimensions | |
| a, b, c (Å) | 70.5, 71.3, 171.3 |
| α, β, γ (°) | 90.0, 90.0, 90.0 |
| Resolution (Å) | 85.62 (2.40)* |
| $R_{sym}$ | 7.4 (44.8) |
| I/σI | 10.99 (2.66) |
| Completeness (%) | 94.9 (98.6) |
| Redundancy | 2.8 (2.8) |
| Refinement | |
| Resolution (Å) | 85.62 (2.40) |
| No. reflections | 32875 (8656) |
| $R_{work}/R_{free}$ | 21.7%/26.6% |
| No. atoms | |
| Protein | 5017 |
| Ligand/ion | 50 |
| Water | 104 |
| B-factors | |
| Protein | 32.3 |
| Ligand/ion | 56.3 |
| Water | 47.5 |
| R.m.s deviations | |
| Bond lengths (Å) | 0.009 |
| Bond angles (°) | 1.13 |

*Highest resolution shell is shown in parenthesis.

Crystal Structure Data. The atomic coordinates of CDK8/CCNC in complex with cortistatin A was deposited in the Protein Data Bank with accession number 4crl. MIAME-compliant microarray data as well as aligned and raw ChIP-seq data were deposited to the Gene Expression Omnibus (GEO) with accession GSE65161 (www.ncbi.nlm.nih-.gov/geo/), the entire contents of these deposits are incorporated herein by reference.

Cell Growth Assay. All leukemia cells were plated (96-well) in triplicate at 5,000 to 30,000 cells/well with treatments. Viable cell number was estimated after 3, 7, and 10 days by counting viable cells from one vehicle well, generating a cell dilution series, transferring 20 μL/well in duplicate to a 384-well plate, and performing a linear regression to CellTiter-Glo (Promega) response (SPECTRAmax M3, Molecular Devices). Cells from all wells were also 4-fold diluted in media and transferred in duplicate for CellTiter-Glo measurement. On days 3 and 7, an equal volume for all wells were split-back with fresh media and compound, such that the resulting cell density for the vehicle well matched the initial seeding density. For days 7 and 10, estimated cell number represents the split-adjusted theoretical cell number. HCT116 were plated (96-well) in triplicate at 250 cells/well. Cells were incubated in the presence of vehicle, 1 μM paclitaxel, or compound. On day 7, CellTiter-Blue (Promega) response was measured and values were normalized to vehicle (100% growth) and paclitaxel (0% growth). For growth assays with inhibitors, n=3 for each concentration with two independent experiments, averaged for FIG. 2g, and one experiment shown for graphs of percent growth vs. concentration and time.

Flow Cytometric Analysis. Cells were plated (6-well) in triplicate at 150,000 cells/mL for 1-day, 2-day, and 3-day timepoints. For the 6-day timepoint, cells were plated at 35,000 cells/mL and diluted to 150,000 cells/mL with media and compound on day 4. For cell cycle, cells were washed twice with PBS, fixed with 70% ethanol at 4° C. overnight, washed with PBS, and stained with 50 μg/mL propidium iodide (eBioscience) for 1 h at 37° C. For Annexin V, we used Annexin V-FITC Apoptosis Detection Kit (BD Pharmingen) and 7-AAD (Miltenyi Biotec) staining. Samples were acquired on a BD LSR II and analysed using FlowJo v7.6.5. For the SET-2 differentiation assay, cells were cultured in triplicate with either 50 nM CA, 50 ng/mL PMA (positive control), or vehicle for three days. Cell pellets were collected at 4° C., washed three times with cold PBS, and stained with anti-CD61-PE (ab91128) or anti-CD41-PerCP (ab134373). For each experiment, n=3 with two independent experiments and one shown.

Plasmids, Mutagenesis, Packaging, Transduction, Selection, and siRNA. 5'-FLAG-tagged CDK8 was cloned from pBabe.puro.CDK8.flag (Addgene; Firestein, R. et al. CDK8 is a colorectal cancer oncogene that regulates β-catenin activity. Nature 455, 547-551 (2008)) into pLVX-EF1alpha-IRES-mCherry (Clontech) and transformed into E. coli (One Shot Stbl3, Invitrogen). Point mutations were introduced by whole plasmid PCR (QuikChange II XL Site-Directed Mutagenesis Kit, Agilent). pLVX lentiviral vectors were co-transfected with psPASx and pMD2.G (Addgene) in 293T cells. After 48 h, viral supernatants were collected and passed through a 0.45 m filter (Millipore). For transductions, 24-well plates were coated with 500 μL of 20 μg/ml RetroNectin (Clontech) at 4° C. overnight, blocked with 2% BSA for 30 minutes, washed with PBS, and 300-500 μL of viral supernatant was added. The plates were centrifuged (2000×g, 1.5 h) and then set in an incubator. After 2 h, viral supernatant was removed and 500 μL/well of 200,000 cells/ mL was added. After 1-3 days, the cells were expanded and isolated by FACS. FLAG-CEBPA, FLAG-IRF1, FLAG- IRF8, ETV6-Myc-FLAG, CDKN1b-Myc-FLAG, and FOSL2-Myc-FLAG were cloned into the Tet-On inducible system pLVX-TRE3G-mCherry or pLVX-TRE3G-ZsGreen (Clontech), transformed into *E. coli* (Stellar Competent Cells, Clontech), packaged into lentiviral vectors and cotransduced with regulator vector pLVX-EF1a-Tet3G. After one week of selection with puromycin (1 µg/ml) and G418 (400 µg/ml), cells were plated in the presence of 100 ng/mL doxycycline to assess 3-day growth via Cell-Titer Glo. SiRNA against CEBPA (Ambion s2888), IRF1 (Ambion s7501), ETV6 (Ambion s4867 and s4866), FOSL2 (Ambion s5345), and IRF8 (Ambion s7098) or scrambled control (Ambion 4390843) were introduced into cells by electroporation (Amaxa Nucleofector II, Program T-019). After 24 hours, cells were plated to assess 3 or 4-day growth via Cell-Titer Glo. Knockdown efficiency was assessed after 24 hours by immunoblot or after 48 hours by qRT-PCR. Results shown in FIG. 16 represent a single transduction or a single electroporation. SiRNA electroporation and inducible expression cell growth assays were performed twice. For ETV6, two siRNAs were tested once each, with data for siRNA s4867 shown in the figures.

Gene Expression, Gene Ontology and GSEA. Leukemia cells were plated (12-well) in triplicate at 500,000 to 800,000 cells/mL and incubated in the presence of vehicle or CA (25 nM 3 h for K562, MOLM-14 and MV4;11; 10 nM 24 h for MOLM-14; 25 nM 4 h for SET-2, n=3 for each cell line). Cells were then washed twice with cold PBS, and snap frozen. RNA was isolated (RNeasy Plus Microkit, Qiagen or TRIzol, Life Technologies), processed, and, for K562, MOLM-14, and MV4;11, hybridized to the Human U133 Plus 2.0 microarray (Affymetrix). Microarrays were processed with Bioconductor packages affyQCReport (Gentleman, R. et al. Bioconductor: open software development for computational biology and bioinformatics. Genome Biol. 5, R80 (2004)) for quality control and affy for background correction, summarization, and normalization using rma (Rafael, R. A. et al. Summaries of Affymetrix GeneChip probe level data. Nucleic Acids Research 31, e15 (2003)). Probe sets present in at least 1 sample (based on affy mas5call) and for which the interquartile range was >log 2(1.2) were retained for further analysis. The limma Bioconductor package (Johnson, W. E., Li, C. & Rabinovic, A. Adjusting batch effects in microarray expression data using empirical Bayes methods. Biostatistics 8, 118-127 (2007)) was used for differential expression (DE) analysis of CA-treated vs DMSO control samples (Benjamini-Hochberg adjusted p-value <0.05 (Benjamini, Y. & Hochberg, Y. J. R. Stat. Soc., B 57, 289-300 (1995))). SET-2 and HCT116 gene expression was measured by RNA-seq. SET-2 RNA-seq libraries were prepared and processed using the Ion Torrent workflow. Merged alignments from two-pass read mapping, first with rnaStar [ref and details] then BWA for unmapped reads, were counted using htseq-count (-s yes -m intersection-strict). The Bioconductor package DESeq was used for DE analysis (FDR <0.05 and 2-fold change) and normalization. HCT116 cells were grown to approximately 80% confluence and were treated with either 100 nM CA or DMSO for 3 h (n=3). Cells were then washed twice with cold PBS and scraped into TRIzol reagent (Life Technologies). After harvesting the RNA, it was further purified using an RNeasy mini kit (Qiagen) with an on-column DNase I digestion. Libraries for Illumina sequencing were generated via the Illumina TruSEQ stranded mRNA prep kit. Samples were run in a single lane on an Illumina HiSEQ 2000 sequencer with a single read flow cell using 1×50 bp reads and a 6-cycle index read. Reads were mapped to the hg19 reference genome using Tophat2 v. 2.0.6 with custom settings including the setting of—library-type fr-firststrand to appropriately account for the stranded nature of the protocol. HTSeq v. 0.6.1 was used to obtain read counts over annotated genes and differentially expressed genes were called by DESeq v. 1.10.1 with a padj value of less than 0.01. Counts were normalized for GSEA using the limma voom function (Law, C. W., Chen, Y., Shi, W. & Smyth, G. K. voom: Precision weights unlock linear model analysis tools for RNA-seq read counts. Genome Biol. 15(2):R29 (2014)). Expression data for the I-BET151 comparison were downloaded from ArrayExpress (https://www.ebi.ac.uk/arrayexpress/, accession:E-MTAB-774) and processed files used as is. Gene lists were submitted to the DAVID web server (http://david.abcc.ncifcrf.gov) for functional annotation (Huang, D. W., Sherman, B. T. & Lempicki, R. A. Systematic and integrative analysis of large gene lists using DAVID bioinformatics resources. Nat Protoc 4, 44-57 (2009)). GSEA version 2.09 (Subramanian, A. et al. Gene set enrichment analysis: a knowledge-based approach for interpreting genome-wide expression profiles. Proc. Natl. Acad. Sci. USA 102, 15545-15550 (2005)) was carried out using signal-to-noise on natural values as the metric. Signatures included curated gene sets (C2, v.3) downloaded from the Broad's MSigDB as well as signatures curated from in-house and published data sets.

ChIP-seq. Untreated cells or cells treated with CA (25 nM, 6 h), iBET-151 (500 nM, 6 h) or vehicle were cross-linked for 10 min at room temperature by addition of one-tenth of the volume of formaldehyde solution (11% formaldehyde, 50 mM HEPES pH 7.4, 100 mM NaCl, 1 mM EDTA, 0.5 mM EGTA) to the media followed by 5 min quenching with 125 mM glycine. For CDK8 and MED1 ChIPs, cells were instead centrifuged, resuspended in serum-free media, and crosslinked at room temperature by addition of an equal volume of 2% formaldehyde in serum-free media for 10 min followed by quenching with 125 mM glycine for 5 min. Cells were then washed twice with cold PBS and snap frozen. ChIP was performed essentially as previously described. Briefly, cells were lysed with lysis buffer 1 (50 mM HEPES pH 7.4, 140 mM NaCl, 1 mM EDTA, 10% glycerol, 0.5% NP-40, and 25% Triton X-100) and washed with lysis buffer 2 (10 mM Tris-HCl pH 8.0, 200 mM NaCl, 1 mM EDTA, and 0.5 mM EGTA). For H3K4me3, H3K27me3, H3K27Ac, H3K4me1, and pol II, the nuclei were resuspended in 10 mM Tris-HCl pH 8.0, 100 mM NaCl, 1 mM EDTA pH 8.0, 0.5 mM EGTA, 0.1% Na-deoxycholate, and 0.2% SDS, sheared for 2 min (Branson S220D sonifier, pulse, 0.7 s on, 1.3 s off, 12-14 watts) on wet ice, and then Triton X-100 was added to 1% v/v. For MED1 and CDK8, the nuclei were resuspended in 50 mM Tris-HCl pH 7.5, 140 mM NaCl, 1 mM EDTA, 1 mM EGTA, 0.1% SDS, and 1% Triton X-100 then sheared for 4 min (pulse, 0.7 s on, 1.3 s off, 10-12 watts) on wet ice. Sonicated lysates were cleared and incubated overnight at 4° C. with Protein G magnetic Dynal beads (50 µL) pre-bound with the indicated antibodies (5 µg). Beads were washed with sonication buffer, sonication buffer with 500 mM NaCl, LiCl wash buffer (20 mM Tris-HCl pH 8.0, 1 mM EDTA, 250 mM LiCl, 0.5% NP-40, 0.5% sodium deoxycholate) and TE. Bound complexes were eluted with 50 mM Tris-HCl pH 8.0, 10 mM EDTA, 1% SDS at 65° C. and reverse cross-linked at 65° C. RNA and protein were digested using RNAse A and proteinase K, respectively, and DNA was purified using Qiagen MinElute columns. Libraries for Illumina sequencing were prepared using the Illumina TruSeq ChIP Sample Preparation kit with the following exceptions.

After end-repair and A-tailing, ChIP DNA or whole cell extract DNA was ligated to Illumina RNA adaptors with unique indices. Alternatively, libraries were prepared using the KAPA Hyper Prep Kit for Illumina and ligated to unique Bioo Scientific NEXTflex barcode adaptors. Following ligation, libraries were amplified with 16-18 cycles of PCR and were then size-selected using a 2% gel cassette in the Pippin Prep System from Sage Science. For histone modifications and RNA pol II, DNA fragments of size 200-500 bp were captured. For CDK8 and MED1, DNA fragments of size 200-450 bp were captured. Libraries were quantified by qPCR utilizing the KAPA Biosystems Illumina Library Quantification kit. Libraries with distinct indexes were then combined in equimolar ratios and run together in a lane on the Illumina HiSeq 2500 for 40 bases in single read mode.

ChIP-seq Data Analysis. ChIP-seq data sets were aligned using Bowtie (v0.12.8) (Langmead, B., Trapnell, C., Pop, M. & Salzberg, S. L. Genome Biol. 10, R25 (2009)) to build version NCBI37/HG19 of the human genome (-n 1-m 1--best --strata). Duplicate reads were removed using Picard tools (version 1.88). For CDK8, peaks were called with both SPP (Kharchenko, P. V., Tolstorukov, M. Y., & Park, P. J. Design and analysis of ChIP-seq experiments for DNA-binding proteins. Nat. Biotechnol. 26, 1351-1359 (2008)) and MACS version 1.4 (Zhang, Y. et al. Model-based analysis of ChIP-Seq (MACS). Genome Biol. 9, R137 (2008)) using default significance cut-off values. SPP cross-correlation analysis was used for both quality control (Landt, S. G. et al. ChIP-seq guidelines and practices of the ENCODE and modENCODE consortia. Genome Res. 22, 1813-1831 (2012)) and to set the strand shift parameter for MACS. Regions of interest identified by both peak callers were retained and merged. Regions overlapping >70% with RepeatMasker regions (downloaded Nov. 16, 2012 from UCSC) were excluded from further analysis. Retained regions were annotated by overlap with RefSeq genes (genomic coordinates downloaded from UCSC refgene table Apr. 26, 2013) using bedtools (Quinlan, A. R. & Hall, I. M. BEDTools: a flexible suite of utilities for comparing genomic features. Bioinformatics 26, 841-842 (2010)). Retained regions were assigned to one of the following categories: (1) promoter=TSS-500 bp to TSS+200 bp, (2) body=TSS+201 bp to TES, (3) proximal enhancer=TSS-5 kb to TSS-501 bp, and (4) 3' UTR=TES+1 bp to TES+5 kb. All other regions were termed "desert" hits. Any gene satisfying the overlap criteria was included in the corresponding category. Traveling ratios were calculated essentially as described (Rahl, P. B. et al. c-Myc Regulates Transcriptional Pause Release. Cell 141, 432-445 (2010)). Briefly, mapped read coordinates were first extended 3' to 200 bases to capture the full fragment coverage. The RefSeq coordinates used for annotation were then used to count extended pol II reads falling in the range of TSS-30 bp to TSS+300 bp and those falling in the remainder of the gene body (TSS+301 to TES). Very short transcripts (<630 bp) were excluded, as were cases with very low counts in both regions. Input reads were subtracted and counts were scaled to reads per kilobase. Transcripts sharing identical TSS and TES coordinates were represented a single time in the count statistics. ChIP-seq tracks were smoothed by calculating the density per million mapped reads in 300 bp bins at 50 bp intervals and were visualized using Integrative Genomics Viewer. ChIP-seq density maps were generated using ngsplot (v2.08) (Shen, L., Shao, N., Liu, X. & Nestler, E. ngs.plot: An easy-to-use global visualization tool for next-generation sequencing data. Icahn School of Medicine at Mount Sinai, N.Y. (2013)). Heatmap of semi-supervised clustering in FIG. 11a of total signal on CDK8 positive regions was carried out as follows: (1) peaks were individually identified for each of the 6 ChIPs using MACS2 at default p-value cutoff; (2) all peaks were combined and merged into non-redundant regions using mergeBed (-d 0); (3) within each unique region, ChIP reads were counted and matched input reads were subtracted after scaling each to million mapped reads; (4) clusters were grouped by ChIPs represented in a given region into 64 categories in the following order: H3K4me1, H3K27ac, Pol II, MED1, and BRD4; (5) each group was ordered by decreasing CDK8 signal per region; and (6) ChIP samples were clustered by Euclidean distance of ChIP signal per region after median centring and normalization. A similar approach was used for BRD4 and CDK8 ChIPs in MOLM-14 cells treated with DMSO or I-BET151. In this case, non-promoter-associated regions in which I-BET151 treatment reduced BRD4 signal >2-fold were ordered by log 2 fold-change.

Irreproducibility Discovery Rate (IDR) Analysis. Reproducibility of two independent H3K27Ac ChIP-seq experiments carried out in cells treated with either DMSO or CA for 3 hrs was assessed according to the pipeline developed for the ENCODE project (https://sites.google.com/site/anshulkundaje/projects/idr)(Li Q, Brown J B, Huang H, Bickel P J. Measuring reproducibility of high-throughput experiments. Ann. Appl. Stat. 5, 1752-1779 (2011)). IDR was determined as recommended on peaks called by SPPError! Bookmark not defined. at FDR<0.5. At this threshold, SPP reported between 180,000 and 300,000 peaks, depending on the exact combination of sample and input, most of which are expected to be noise. Under both treatment conditions, the number of high-confidence peaks (IDR threshold <0.01 for true replicates and pseudo-replicate self-consistency tests and <0.0025 for pseudo-replicate pooled-consistency analysis) identified based on signal value in the replicates and pseudo-replicates was within the recommended 2-fold range, indicating good reproducibility. The number of peaks with IDR <0.01 in the true replicates was used to make the final selection of distinct, non-chrM pooled replicate peaks. Regions within 200 nt of each other were merged to generate the final peaks list. The same approach was used to determine reproducible peaks in two independent BRD4 and CDK8 ChIP experiments in MOLM-14 cells treated with DMSO or I-BET151.

Identification of SEs. MED 1 signal was measured in active enhancers (i.e., regions enriched in both H3K4me1 and H3K27ac) after extending MED1 ChIP-seq reads 100 bases in a strand-aware fashion. Enhancer regions were sorted based on their MED1 signal and the inflection point of the curve determined. Enhancers with MED1 signal above the inflection point were retained as SEs. In a separate approach, using only the MED1 ChIP-seq data and the ROSE software from the Young laboratory, >80% agreement was found with the K4me1+/K27ac+MED1 SEs. ROSE was used thereafter to identify SEs using BRD4, H3K27ac (±CA, 3 h), and CDK8 ChIP-seq on peaks called by MACS 1.4. For K562 and HCT116, CDK8 ChIPs were performed in-house but H3K27ac ChIP samples and their matched inputs were downloaded from the ENCODE project repository at UCSC. SE-associated genes were assigned to the nearest expressed transcript, based on H3K27ac signal in a 500 nt window centered on the TSS Error! Bookmark not defined. For FIG. 1c, we normalized each experiment's signal (after adjusting to million mapped reads and subtracting input signal) to show values from independent ChIP-seq experiments on a common scale. Normalized signal for each enhancer, x, is thus (x−minimum)/(maximum−minimum).

Each ChIP-seq experiment yielded different numbers of enhancer regions so we mapped each experiment's enhancer ranks to [0,1] by calculating (rank-1)/(maximum rank-1).

RNA Levels, Digital Droplet PCR (ddPCR), and qRT-PCR. Total RNA was isolated from 500,000 MOLM-14 cells (RNeasy Plus Mini Kit, Qiagen) and quantified by Nanodrop. mRNA was subsequently isolated (Dynabeads mRNA Purification Kit, Life Technologies) and quantified by Nanodrop. For ddPCR, total RNA was reverse-transcribed into cDNA (High Capacity cDNA Reverse Transcriptase Kit, Applied Biosystems) and used (ddPCR Supermix for Probes, no dUTP, Bio-Rad 186-3024) with TaqMan FAM probes for genes of interest and ACTB (VIC) as the reference gene. Droplets were generated in the QX200 Droplet Generator, thermocycled, and read on the QX200 Droplet Reader. Total RNA per cell was measured by isolating total RNA from $10^6$ cells using the mirVana miRNA Isolation Kit (Life Technologies) and quantifying by Nanodrop. Copy numbers of specific mRNAs (FIG. 3g) were determined relative to copies of ACTB mRNA per cell. Probes used (Life Technologies): CEBPA (Hs00269972_s1), ETV6 (Hs00231101_m1), IRF1 (Hs00971960_m1), IRF8 (Hs00175238_m1), RREB1 (Hs01002873_m1), CDKN1B (Hs01597588_m1), GFI1 (Hs00382207_m1), JARID2 (Hs01004460_m1), BHLHE40 (Hs01041212_m1), and ACTB (4325788). qRT-PCR for checking siRNA knockdown was performed with iTaq Universal Probes Supermix (Bio-Rad), n=3, or by ddPCR.

In Vivo Studies. Studies were performed at Charles River Laboratories (CRL) and Dana Farber Cancer Institute (DFCI) where indicated and approved by Harvard University and each institution's respective animal care and use committee. For pharmacokinetic studies, serial blood samples from 7 week old male CD-1 mice (n=3 per timepoint) were collected (no blinding) into $K_2$EDTA tubes, centrifuged, transferred into 96-well plates (matrix tubes), stored at $-20°$ C., and analysed by HPLC/MS/MS (in-life performed at CRL). Study size was determined by the need for three blood samples per timepoint with three blood samples collected per mouse. The MV4; 11 xenograft model were performed as previously described (Etchin, J. et al. Antileukemic activity of nuclear export inhibitors that spare normal hematopoietic cells. Leukemia 27, 66-74 (2013); in-life performed at DFCI) Two million MV4;11-mCLP cells were injected into the tail vein of 7-week-old female NOD-SCID-IL2Rc$\gamma^{null}$ (NSG) mice (The Jackson Laboratory) and tumor burden was assessed by bioluminescence imaging (BLI) using an IVIS Spectrum system (Caliper Life Sciences). 7 days post injection, leukemia establishment was documented by BLI and mice were assigned to groups to achieve a similar mean BLI and treated IP with vehicle (20% hydroxypropyl-3-cyclodextrin) or CA once daily for 15 days. After 30 days, blood counts were obtained (Hemavet 950 F, Drew Scientific) and spleen, femur, and peripheral blood cells were collected and analysed by flow cytometry (LSR Fortessa, BD Biosciences) from 3 mice/group. The mice and a portion of the spleen were preserved in bouins after body cavities were opened and visceral organs exposed. Samples from all organs were then dissected and placed in 9 cassettes/mouse. Tissues were paraffin embedded, sectioned at 6 microns and stained with haematoxylin and eosin. Survival was measured as the time from therapy initiation until moribund state. 11 mice per group were selected to match previous survival analysis in the model (n=8) (Etchin, J. et al. Antileukemic activity of nuclear export inhibitors that spare normal hematopoietic cells. Leukemia 27, 66-74 (2013)) and to have 3 additional mice per group for disease burden comparison. Blinding was only done for histopathology analysis. For the SET-2 xenograft model (in-life performed at CRL), 8 to 12 week old female SCID Beige mice (Charles River) were injected subcutaneously in the flank with $10^7$ SET-2 cells in 50% matrigel (0.2 mL/mouse). When tumors reached an average size of 80-120 mm$^3$, mice were assigned to groups to achieve a similar mean tumor size and treatment commenced without blinding. Tumor volumes were measured using calipers and calculated as (width$^2$×length)/2. Percent tumor growth inhibition was calculated as mean volumes of (vehicle-treatment)/(vehicle-initial)×100. 10 mice per group were selected to safeguard against the IACUC requirement to stop dosing a group if >10% mortality occurs. For safety testing (in-life performed at DFCI), 8 week old female CD-1 mice were treated once daily without blinding for 15 days and weighed daily. Two hours after the last dose, blood counts were obtained and blood chemistry was analysed. Three mice per group were selected as a minimum for comparison. For STAT1 pS727 inhibition, 6 to 10 week old female $C_{57}$BL/6 mice were treated once daily for two days (in-life at CRL, not blinded). One hour after the second dose, NK cells were isolated by dissociation of spleenocytes from isolated spleens, lysis of erythrocytes, and isolation of DX5+ cells (MiniMACS CD49b, Miltenyi Biotec) and analyzed by immunoblot and densitometry (ImageJ, STAT1 pS727 level normalized to beta-actin). 3 mice per group were selected as a minimum for comparison. Statistical analysis was performed using GraphPad Prism 6.0. Dotted purple lines were from the Mouse Phenome Database (The Jackson Laboratory).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula:

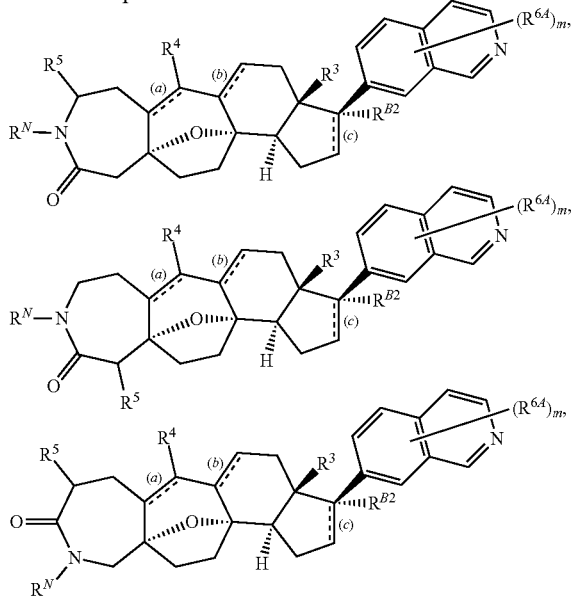

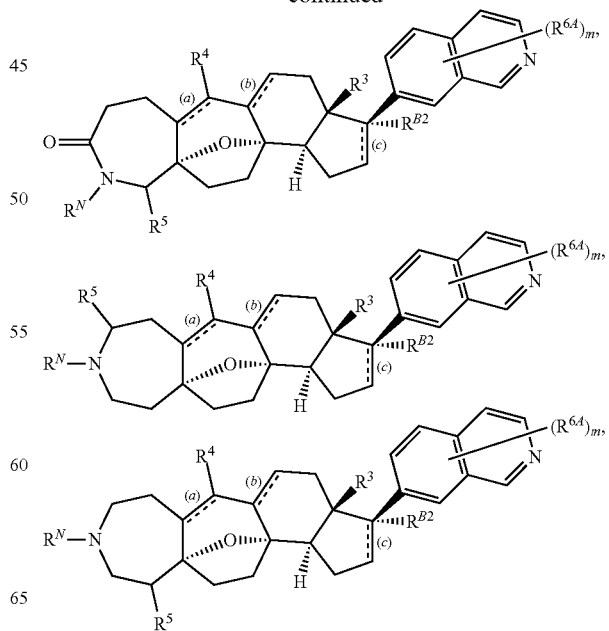

or a pharmaceutically acceptable salt thereof,
wherein:
  $R^N$ is hydrogen, alkyl, alkenyl, alkynyl, carbocyclyl, heterocyclyl, aryl, heteroaryl, —OR$^A$, —C(=O)R$^A$, —C(=O)OR$^A$, —C(=O)N(R$^A$)$_2$, —S(=O)$_2$R$^A$, or a nitrogen protecting group;
  $R^O$ is hydrogen, alkyl, alkenyl, alkynyl, carbocyclyl, heterocyclyl, aryl, heteroaryl, —C(=O)R$^A$, —C(=O)OR$^A$, —C(=O)N(R$^A$)$_2$, —S(=O)$_2$R$^A$, —Si(R$^A$)$_3$, —P(=O)(R$^A$)$_2$, —P(=O)(OR$^A$)$_2$, —P(=O)(NR$^A$)$_2$, —P(=O)$_2$R$^A$, —P(=O)$_2$(OR$^A$), —P(=O)$_2$(R$^A$)$_2$, or an oxygen protecting group;
  $R^3$ is hydrogen or alkyl;
  $R^4$ is hydrogen, halogen, alkyl, or —Si(R$^A$)$_3$;
  $R^5$ is hydrogen, halogen, alkyl, —OR$^A$, —OC(=O)R$^A$, —OC(=O)OR$^A$, —OC(=O)N(R$^A$)$_2$, —OS(=O)$_2$R$^A$, —N$_3$, —N(R$^A$)$_2$, —NR$^A$C(=O)R$^A$, —NR$^A$C(=O)OR$^A$, —NR$^A$C(=O)N(R$^A$)$_2$, —NR$^A$S(=O)$_2$R$^A$, or —C(R$^A$)$_3$;
  each instance of ⹀, designated as (a), (b), and (c), represents a single or double bond,
  provided that when ⹀ designated as (c) represents a double bond, then R$^{B2}$ is absent, and
  provided that when ⹀ designated as (c) represents a single bond, then R$^{B2}$ is present;
  $R^{B2}$ is hydrogen, -L$_1$-R$^{B3}$, or —X$^A$R$^A$;
  $X^A$ is —O—, —S—, or —N(R$^A$)—;
  $L_1$ is a bond, —CH(CH$_3$)(CH$_2$)$_2$—, —CH(CH$_3$)—CH=CH—, —C(=O)—, —C(=O)O—, —C(=O)S—, —C(=O)N(R$^L$)—, or —N(R$^L$)—(C(R$^{LL}$)$_2$)$_p$—;
  $R^L$ is hydrogen, alkyl, or a nitrogen protecting group;
  $R^{LL}$ is independently hydrogen, halogen, or alkyl;
  p is 0, 1, or 2;
  $R^{B3}$ is hydrogen, alkyl, alkenyl, alkynyl, carbocyclyl, heterocyclyl, aryl, or heteroaryl, provided that when Li is a bond, then R$^{B3}$ is not hydrogen;
  each instance of R$^{6A}$ is independently halogen, —NO$_2$, —CN, —OR$^{6C}$, SR$^{6C}$, N(R$^{6C}$)$_2$, —C(=O)R$^{6C}$, —C(=O)OR$^{6C}$, —C(=O)N(R$^{6C}$)$_2$alkyl, alkenyl, alkynyl, carbocyclyl, heterocyclyl, aryl, or heteroaryl;
  wherein each instance of R$^{6C}$ is independently hydrogen, alkyl, alkenyl, alkynyl, carbocyclyl, heterocyclyl, aryl, heteroaryl, an oxygen protecting group when attached to oxygen, a sulfur protecting group when attached to sulfur, or a nitrogen protecting group when attached to nitrogen, optionally when attached to N the two R$^{6C}$ groups may be joined to form an heterocyclyl or heteroaryl ring;
  m is 0, 1, 2, 3, or 4; and
  each instance of R$^A$ is independently hydrogen, alkyl, alkenyl, alkynyl, carbocyclyl, heterocyclyl, aryl, heteroaryl, carbonyl, silyl, an oxygen protecting group when attached to oxygen, a sulfur protecting group when attached to sulfur, or a nitrogen protecting group when attached to nitrogen, optionally when attached to N the two $R^4$ groups may be joined to form an heterocyclyl or heteroaryl ring.

2. The compound of claim 1, wherein $R^N$ is hydrogen.

3. The compound of claim 1, wherein $R^3$ is —CH$_3$.

4. The compound of claim 1, wherein $R^4$ is hydrogen.

5. The compound of claim 1, wherein $R^5$ is hydrogen.

6. The compound of claim 1, wherein each instance of ⩵ designated as (a) and (b) is a double bond.

7. The compound of claim 1, wherein ⩵ designated as (c) represents a single bond.

8. The compound of claim 1, wherein m is 0.

9. The compound of claim 1, wherein $R^O$ is hydrogen.

10. The compound of claim 1, wherein $R^O$ is —S(=O)$_2$R$^4$.

11. The compound of claim 1, wherein the compound is selected from the group consisting of:

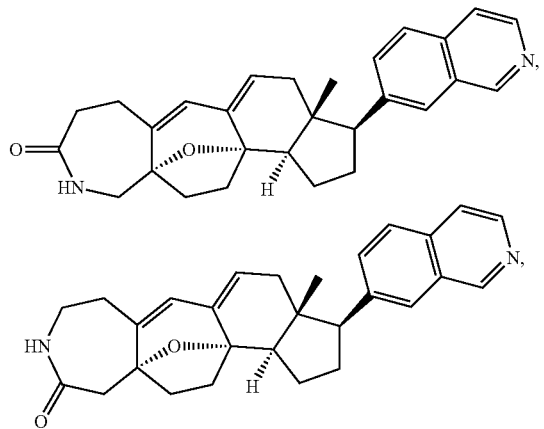

and pharmaceutically acceptable salts thereof.

12. The compound of claim 1, wherein the compound is selected from the group consisting of:

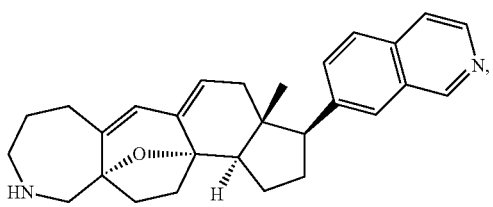

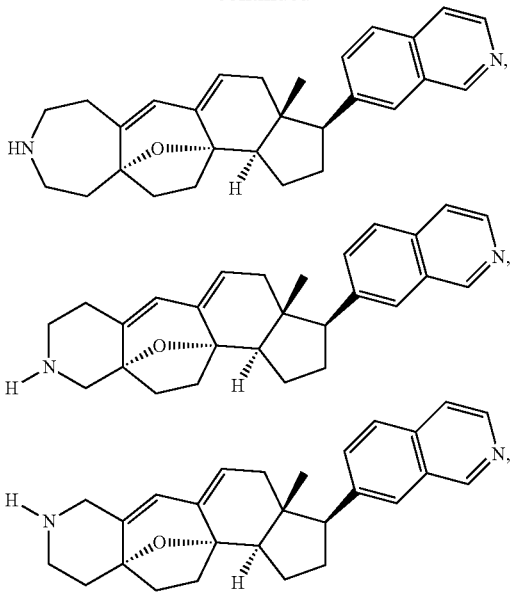

and pharmaceutically acceptable salts thereof.

13. A pharmaceutical composition comprising a compound according to claim 1, or a pharmaceutically acceptable salt thereof, and a pharmaceutically acceptable excipient.

14. The pharmaceutical composition of claim 13, wherein the composition is suitable for administration to a human.

15. The pharmaceutical composition of claim 14, wherein the composition is suitable for intravenous or oral delivery.

16. A method of treating a disease selected from acute myeloid leukemia (AML), myelodysplastic syndrome (MDS), acute lymphoblastic leukemia (ALL), chronic myelogenous leukemia (CML), chronic myelomonocytic leukemia (CMML), and multiple myeloma, comprising administering to a subject in need thereof a compound of claim 1 or a pharmaceutically acceptable salt thereof.

17. The method of claim 16, wherein the host is a human.

18. The method of claim 17, wherein the disease is acute myeloid leukemia (AML).

19. The method of claim 17, wherein the disease is myelodysplastic syndrome (MDS).

20. The method of claim 17, wherein the disease is acute lymphoblastic leukemia (ALL).

21. The method of claim 17, wherein the disease is chronic myelogenous leukemia (CML).

22. The method of claim 17, wherein the disease is chronic myelomonocytic leukemia (CMML).

23. The method of claim 17, wherein the disease is multiple myeloma.

* * * * *